(12) United States Patent
Moskowitz et al.

(10) Patent No.: US 11,980,432 B2
(45) Date of Patent: May 14, 2024

(54) SYSTEMS AND METHODS FOR AUTONOMOUS ROBOTIC SURGERY

(71) Applicant: Moskowitz Family LLC, Rockville, MD (US)

(72) Inventors: Mosheh T. Moskowitz, Rockville, MD (US); Nathan C. Moskowitz, Rockville, MD (US)

(73) Assignee: Moskowitz Family LLC, Rockville, MD (US)

( * ) Notice: Subject to any disclaimer, the term of this patent is extended or adjusted under 35 U.S.C. 154(b) by 859 days.

(21) Appl. No.: 16/673,806

(22) Filed: Nov. 4, 2019

(65) Prior Publication Data

US 2020/0281670 A1    Sep. 10, 2020

Related U.S. Application Data

(60) Provisional application No. 62/815,605, filed on Mar. 8, 2019.

(51) Int. Cl.
| | | |
|---|---|---|
| *A61B 34/32* | (2016.01) | |
| *A61B 17/00* | (2006.01) | |
| *A61B 90/00* | (2016.01) | |
| *A61B 90/10* | (2016.01) | |
| *A61B 90/50* | (2016.01) | |

(52) U.S. Cl.
CPC ........ *A61B 34/32* (2016.02); *A61B 17/00234* (2013.01); *A61B 90/10* (2016.02); *A61B 2090/374* (2016.02); *A61B 2090/376* (2016.02); *A61B 2090/3762* (2016.02); *A61B 2090/378* (2016.02); *A61B 2090/506* (2016.02)

(58) Field of Classification Search
CPC .......................................... A61B 34/30–34/37
See application file for complete search history.

(56) References Cited

U.S. PATENT DOCUMENTS

| | | |
|---|---|---|
| 4,976,582 A | 12/1990 | Clavel |
| 6,351,659 B1 | 2/2002 | Vilsmeier |
| 8,251,891 B2 | 8/2012 | Moskowitz |
| 8,498,744 B2 | 7/2013 | Odermatt |
| 8,992,580 B2 | 3/2015 | Bar |
| 8,996,429 B1 | 3/2015 | Francis |
| 9,051,043 B1 | 6/2015 | Peeters |
| 9,125,556 B2 | 9/2015 | Zehavi |
| 9,173,716 B2 | 11/2015 | Kasodekar |

(Continued)

OTHER PUBLICATIONS

Zwerdling, at VA Hospitals, Training and Technology Reduce Nurses' Injuries, NPR, Published Feb. 25, 2015, https://www.npr.org/2015/02/25/387298633/at-va-hospitals-training-and-technology-reduce-nurses-injuries (Year: 2015).*

(Continued)

*Primary Examiner* — Jonathan T Kuo
(74) *Attorney, Agent, or Firm* — Fish & Richardson P.C.

(57) ABSTRACT

Systems and methods are provided for autonomous robotic surgery which is preferably integrated with autonomous-assisted intraoperative real-time single modality and/or multi-modality fusion imaging/electrophysiological diagnostics. The robotic surgery systems and methods can be integrated with autonomous-assisted intraoperative body/limb positioning, and integrated with autonomous-assisted land and unmanned aerial vehicular patient transportation.

20 Claims, 109 Drawing Sheets

(56) References Cited

U.S. PATENT DOCUMENTS

| | | | |
|---|---|---|---|
| 9,489,852 | B1 | 11/2016 | Chambers |
| 9,492,241 | B2 | 11/2016 | Joskowicz |
| 9,573,684 | B2 | 2/2017 | Kimchi |
| 9,801,728 | B2 | 10/2017 | Moskowitz |
| 9,814,535 | B2 | 11/2017 | Bar |
| 9,872,733 | B2 | 1/2018 | Shoham |
| 10,299,871 | B2 * | 5/2019 | Zingaretti ............... A61B 5/448 |
| 10,842,699 | B2 * | 11/2020 | Mahoney ............... A61B 34/30 |
| 2003/0060810 | A1 * | 3/2003 | Syrowicz ............ A61B 18/203 606/9 |
| 2009/0110948 | A1 | 4/2009 | Buckel |
| 2009/0263634 | A1 | 10/2009 | Hyer |
| 2012/0190981 | A1 | 7/2012 | Harris |
| 2016/0324586 | A1 * | 11/2016 | Zingaretti .......... A61B 17/3468 |
| 2017/0069214 | A1 | 3/2017 | Dupray |
| 2017/0354470 | A1 * | 12/2017 | Farritor ................. A61B 34/77 |
| 2018/0000548 | A1 * | 1/2018 | Olds ...................... A61B 34/35 |
| 2019/0246882 | A1 * | 8/2019 | Graetzel ................ A61B 1/267 |
| 2019/0328599 | A1 * | 10/2019 | Mahoney ............... A61B 34/20 |
| 2020/0078097 | A1 * | 3/2020 | Gregerson ........... A61B 5/1127 |

OTHER PUBLICATIONS

Basso, Designing Control Loops for Linear and Switching Power Supplies: A Tutorial Guide, Artech House, 2012, pp. 252-253.

Bauer, et.al., "A soft future: From robots and sensor skin to energy harvesters," Adv. Mater., 2014, 26(1):149-162.

Canadinc, et al., "Ultra-high temperature multi-component shape memory alloys," Scripta Materialia, 2019, 158:83-87.

Kumar and Lagoudas, "Introduction to shape memory alloys," Shape Memory Alloys, Springer, Boston, MA, 2008.

McClintock, et. al., "The milliDelta: A high-bandwidth, high-precision, millimeter-scale Delta robot," Science Robotics, 2018, 3(14):eaar3018, 10 pages.

Nelson, et al., "The Pipeline Embolization Device for the Intracranial Treatment of Aneurysms Trial," American Journal of Neuroradiology, 2011, 32(1):34-40.

Nwe Nwe and Guest, "Topology Optimization of Truss Structures Considering Stress and Stability Constraints," Structures Congress, Apr. 2019, Orlando, Florida, pp. 49-58.

Ogawa, et al., "A lightweight shape-memory magnesium alloy," Science, 2016, 353:368-370.

Parmley, "10 Ways to Amplify Mechanical Movements," Machine Devices and Components Illustrated Sourcebook, 1st Ed., McGraw-Hill, 2004, pp. 1-6 to 1-7.

Romanishin, et al., "M-blocks: Momentum-driven, magnetic modular robots," IEEE/RSJ International Conference on Intelligent Robots and Systems, Nov. 2013, Tokyo, Japan, 8 pages.

Rubenstein, et al., "Programmable self-assembly in a thousand-robot swarm," Science, 2014, 345(6198):795-799.

Shademan, et al., "Supervised autonomous robotic soft tissue surgery," Science Translational Medicine, 2016, 8(337):337ra64, 9 pages.

Strelec and Lagoudas, "Design and Implementation of a Shape Memory Alloy Actuated Reconfigurable Airfoil," Journal of Intelligent Material System, 2003, 14(4-5), 27 pages.

Suhail, et al., "Potential Applications of Shape Memory Alloys in Seismic Retrofitting of an Exterior Reinforced Concrete Beam-column Joint," SECED 2015 Conference: Earthquake Risk and Engineering towards a Resilient World, Jul. 9-10, 2015, Cambridge UK, 11 pages.

Zhang, et al., "A high-impedance detector-array glove for magnetic resonance imaging of the hand," Nat. Biomed. Eng., 2018, 2:570-577.

* cited by examiner

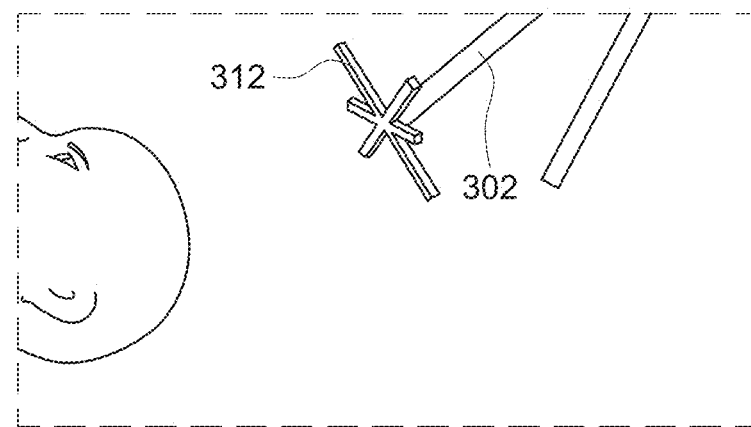
Scene 1
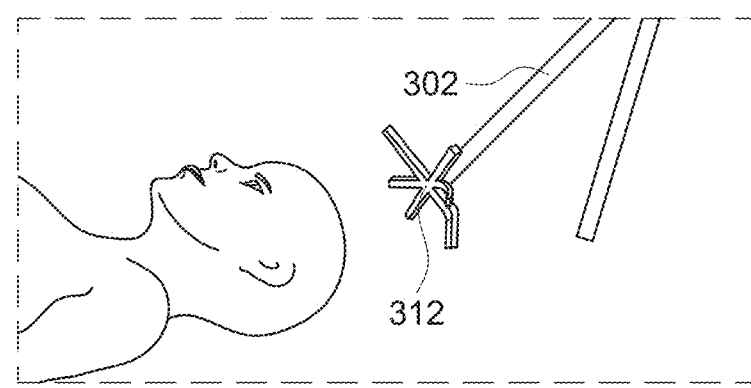
Scene 2
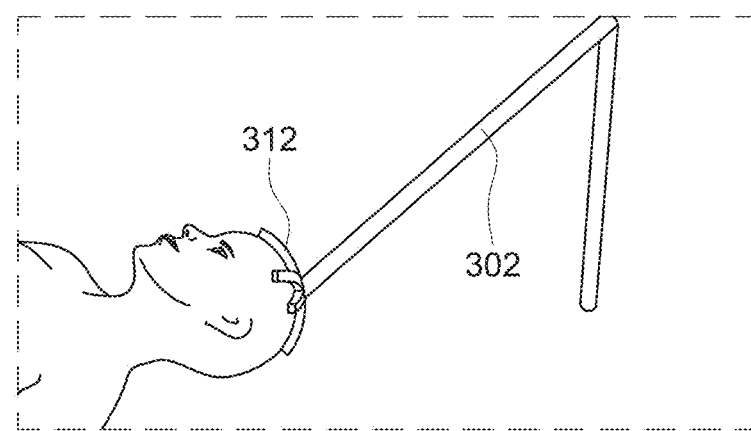
Scene 3
FIG. 7

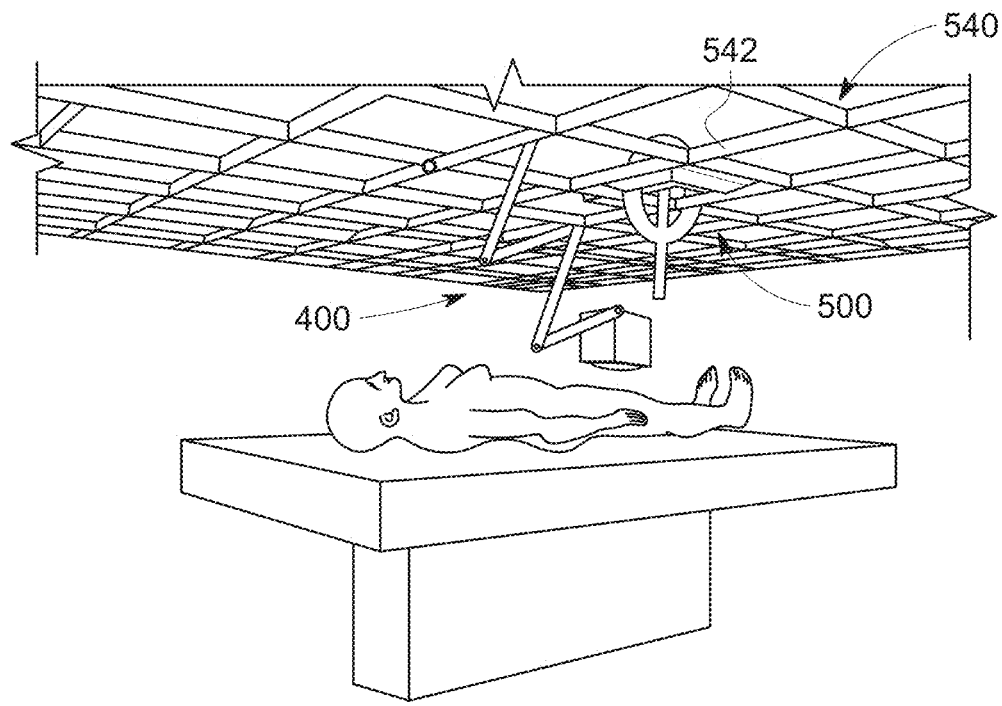
Scene 1
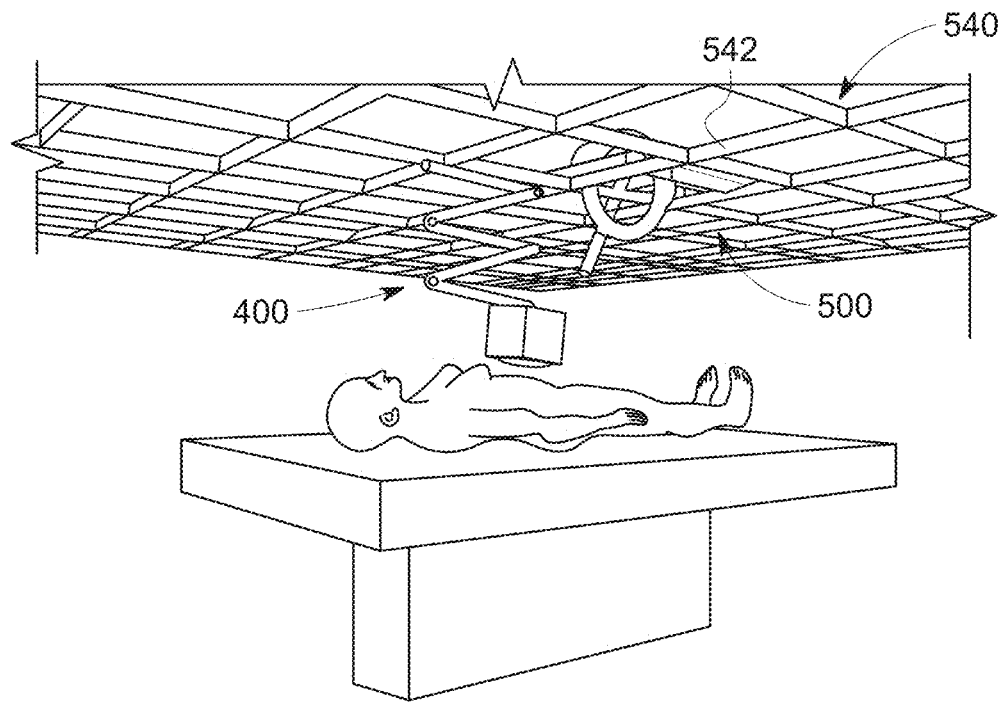
Scene 2
FIG. 15A-A

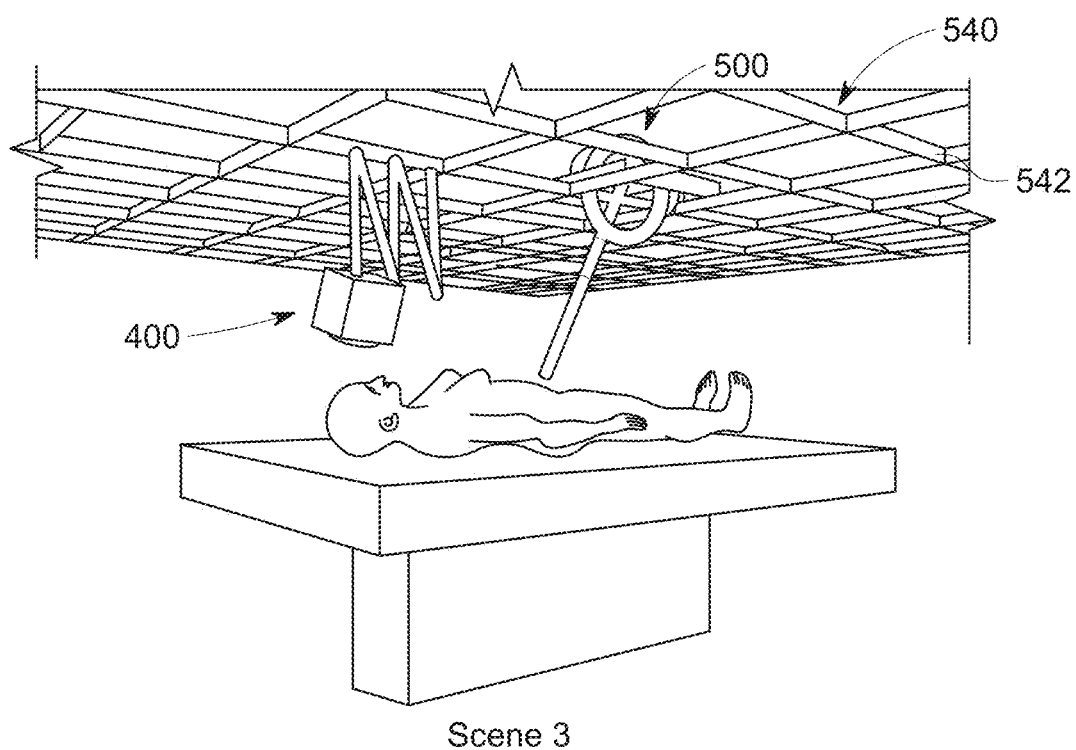
Scene 3
FIG. 15A-B

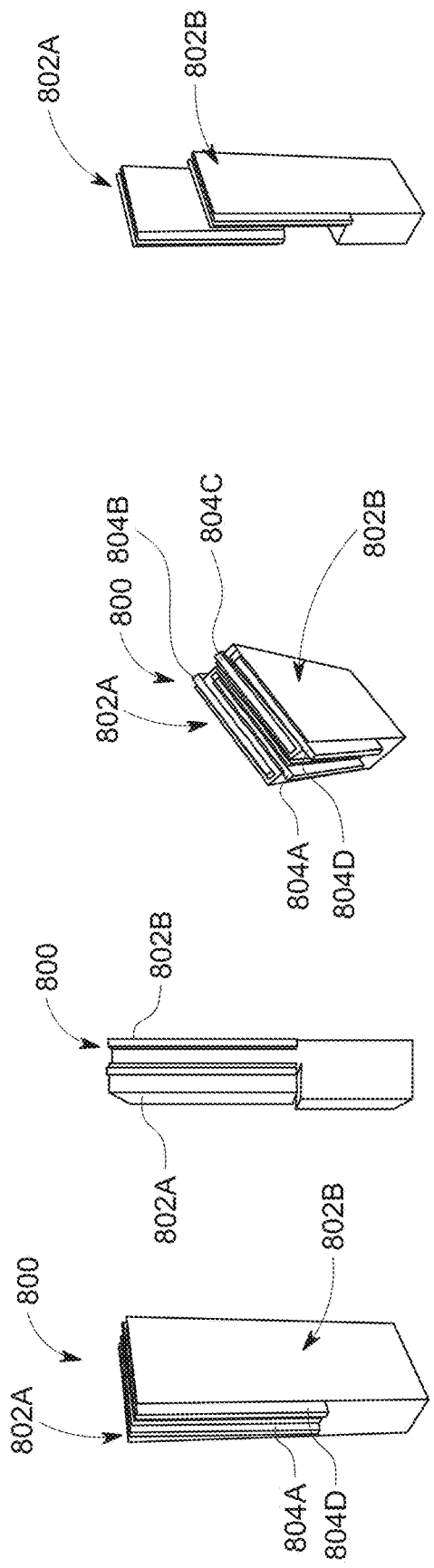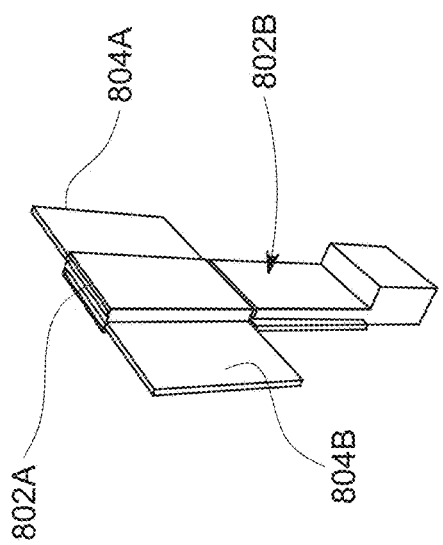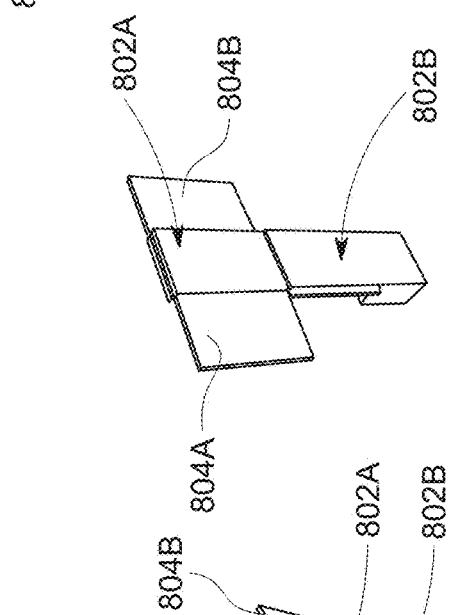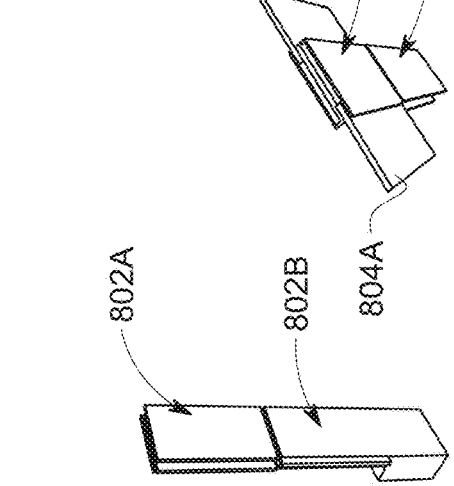
FIG. 20A FIG. 20B FIG. 20C FIG. 20D
FIG. 20E FIG. 20F FIG. 20G FIG. 20H

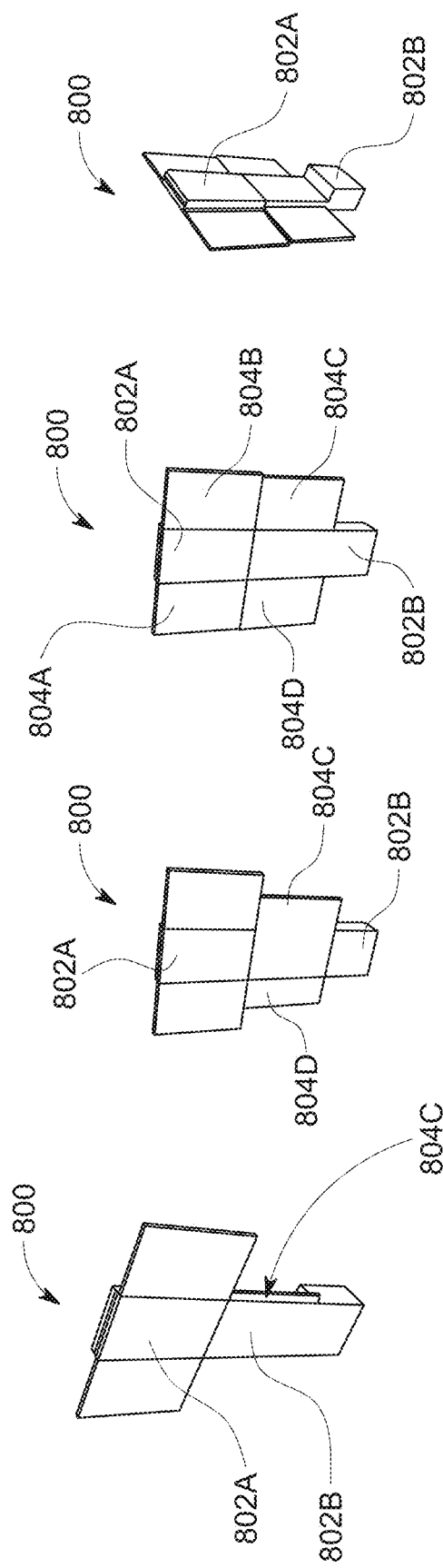
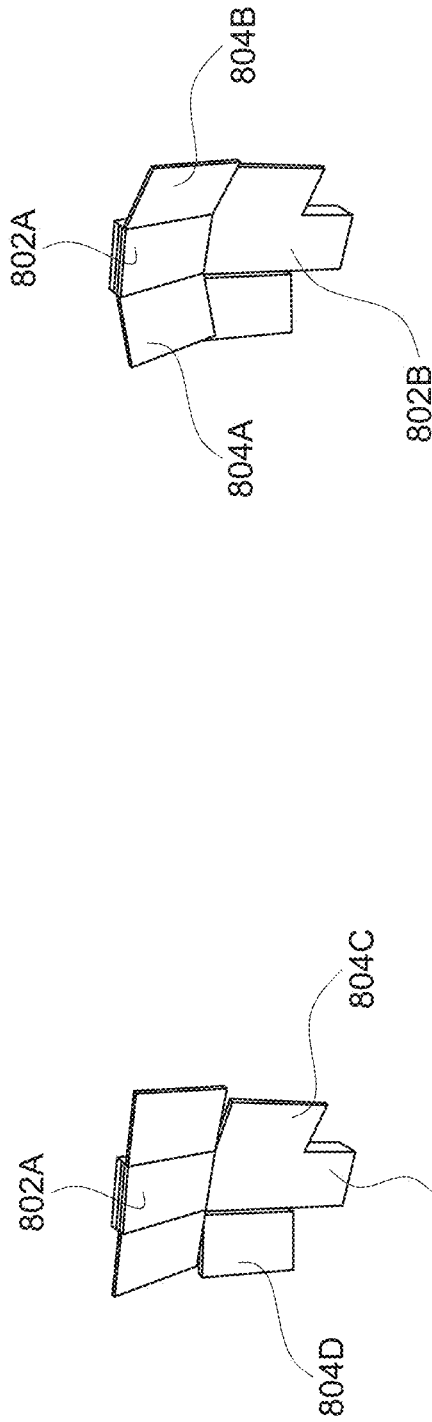
FIG. 21A FIG. 21B FIG. 21C FIG. 21D FIG. 21E FIG. 21F

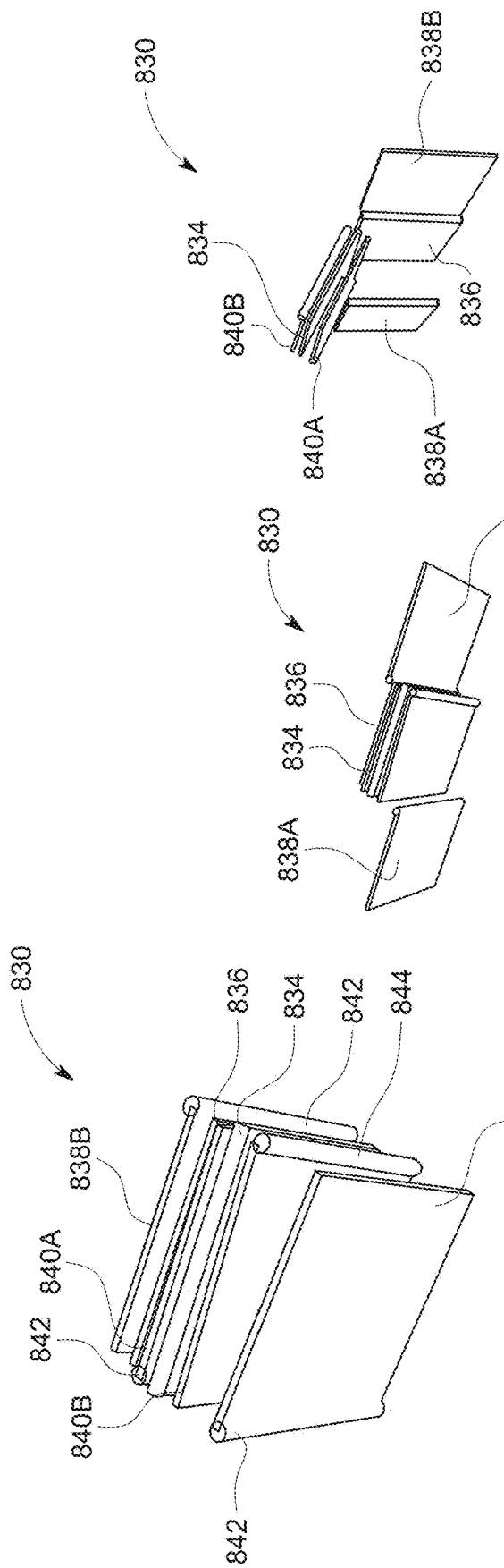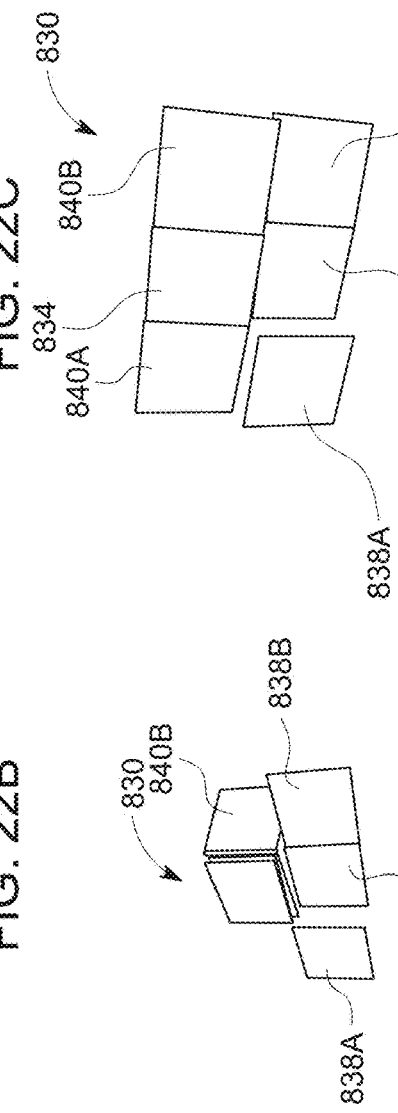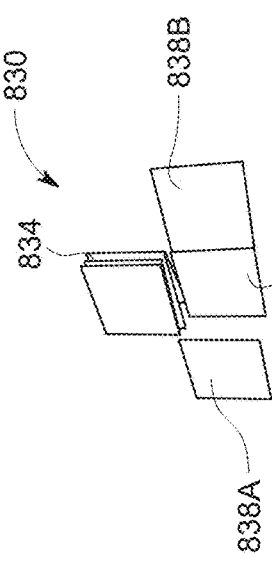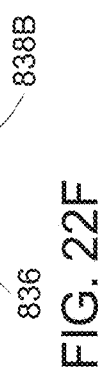
FIG. 22A
FIG. 22B
FIG. 22C
FIG. 22D
FIG. 22E
FIG. 22F

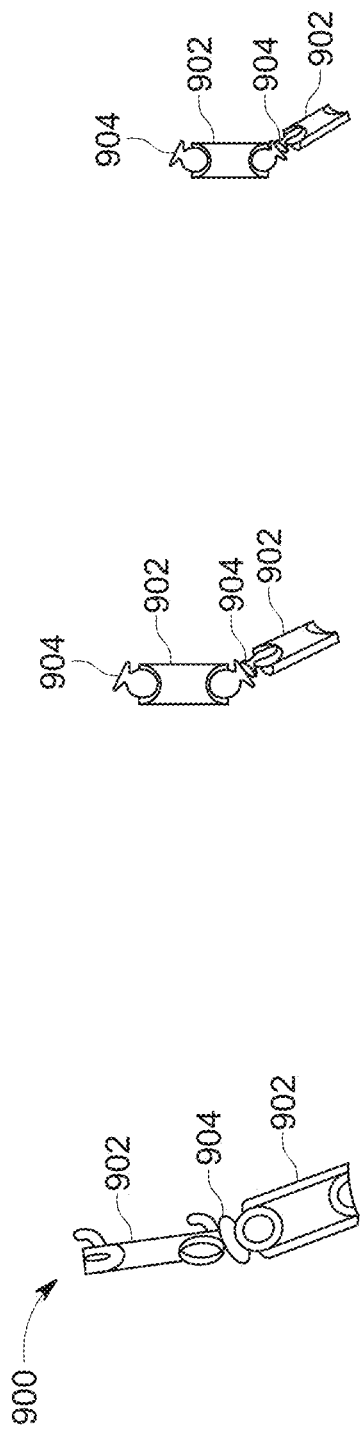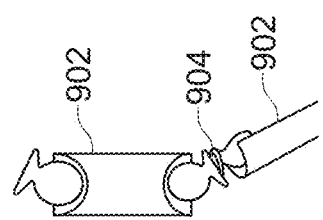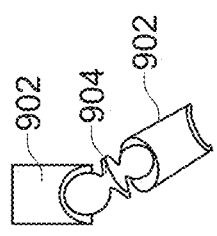

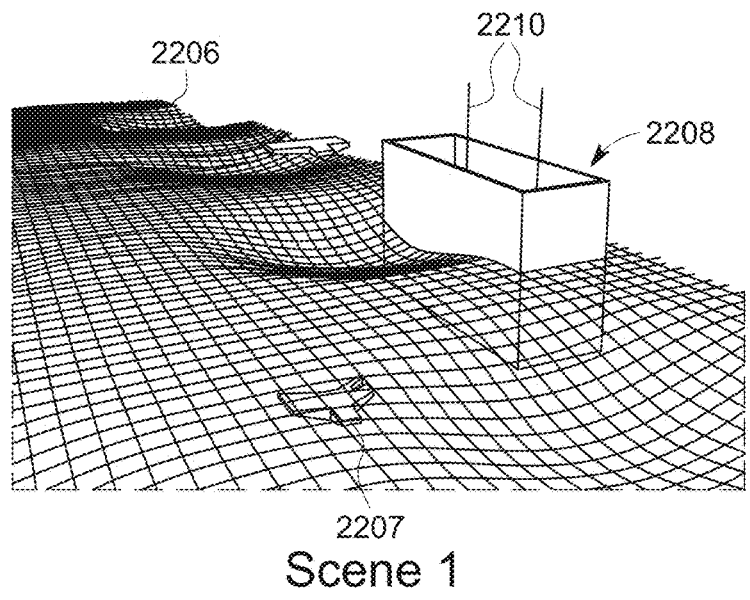
Scene 1
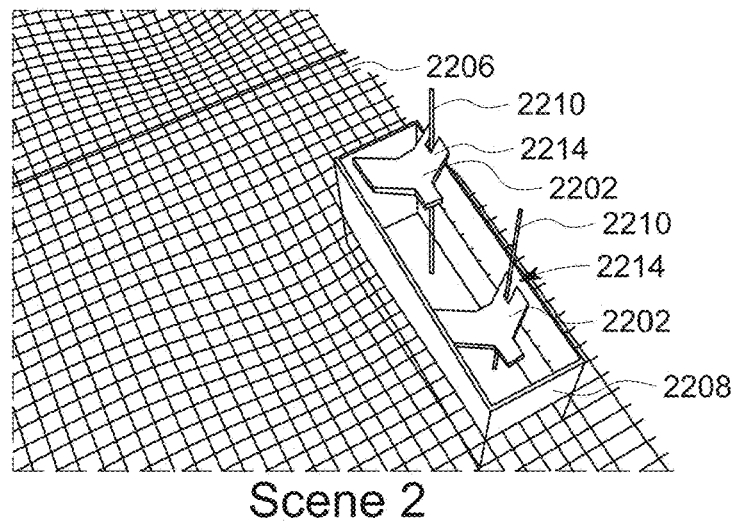
Scene 2
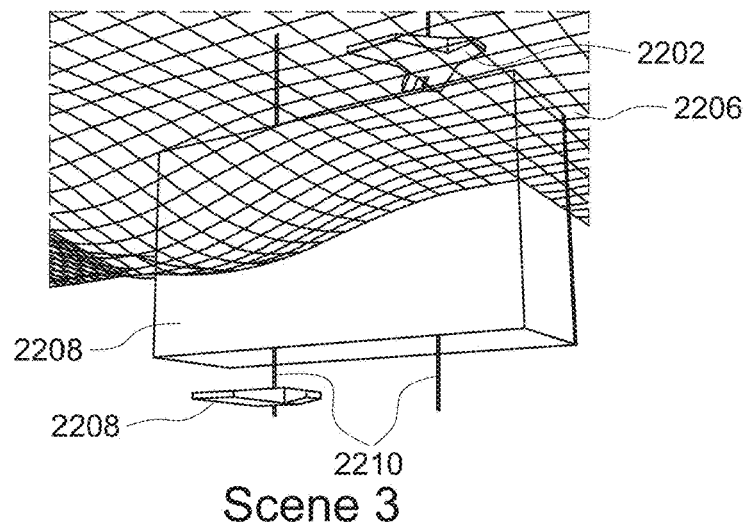
Scene 3
FIG. 43

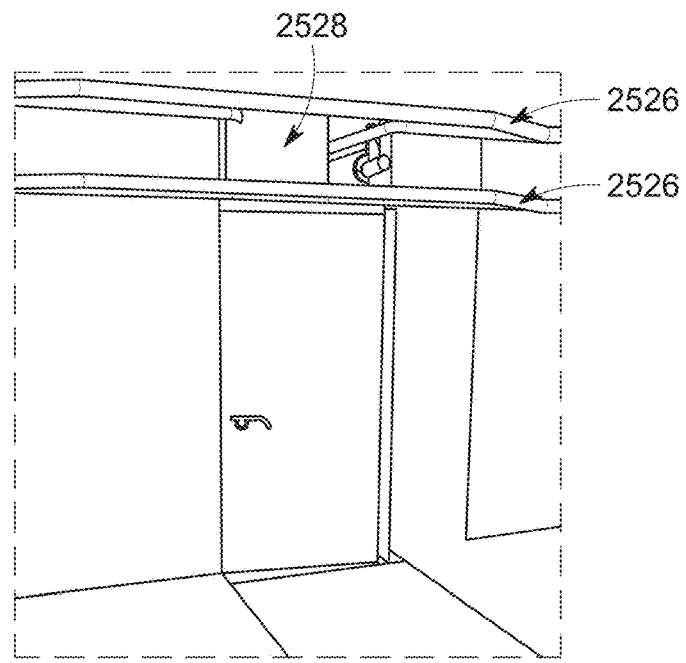
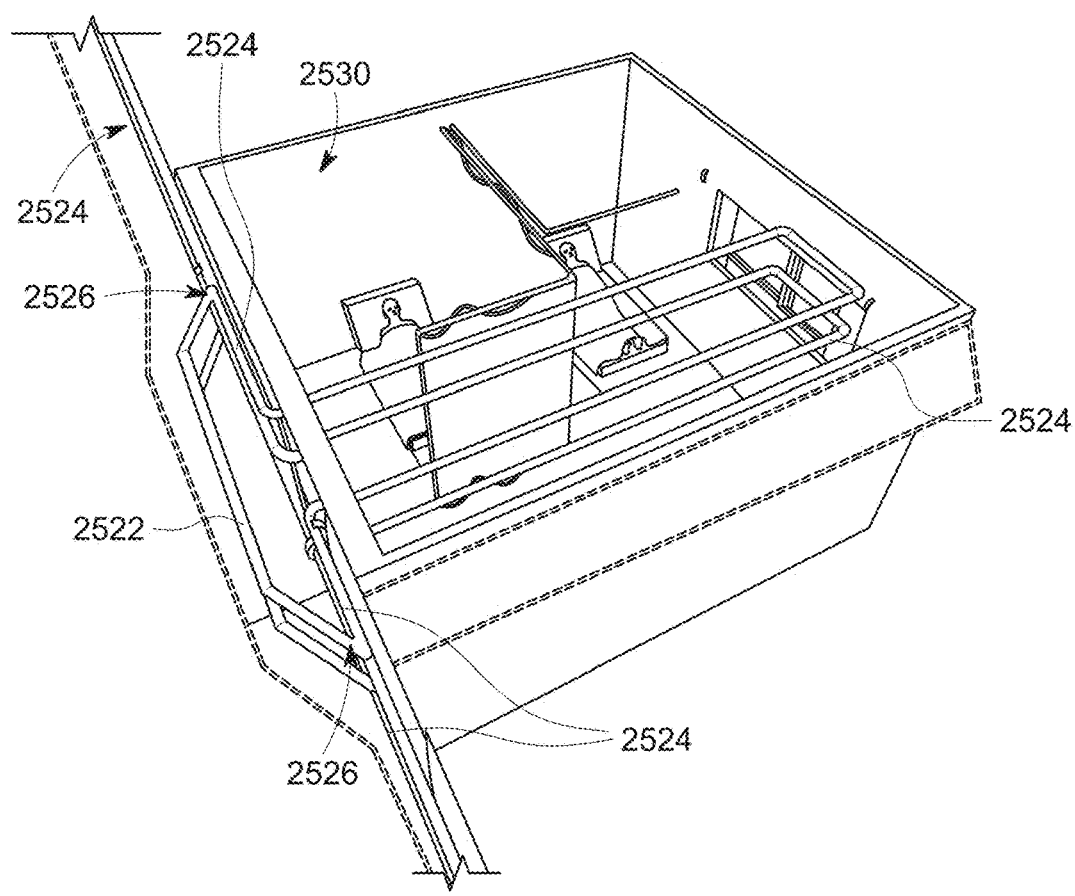
FIG. 50

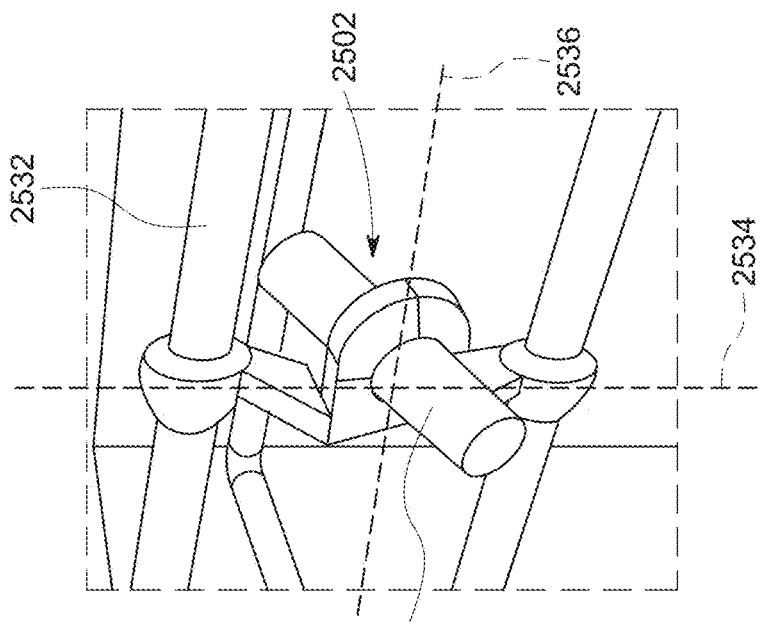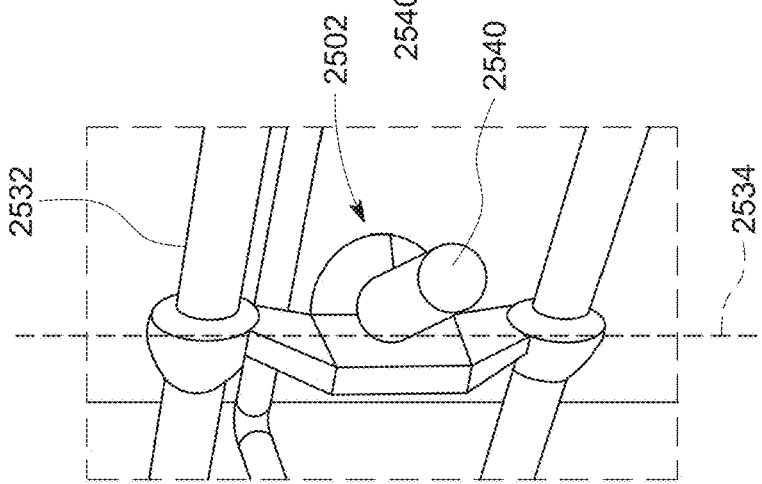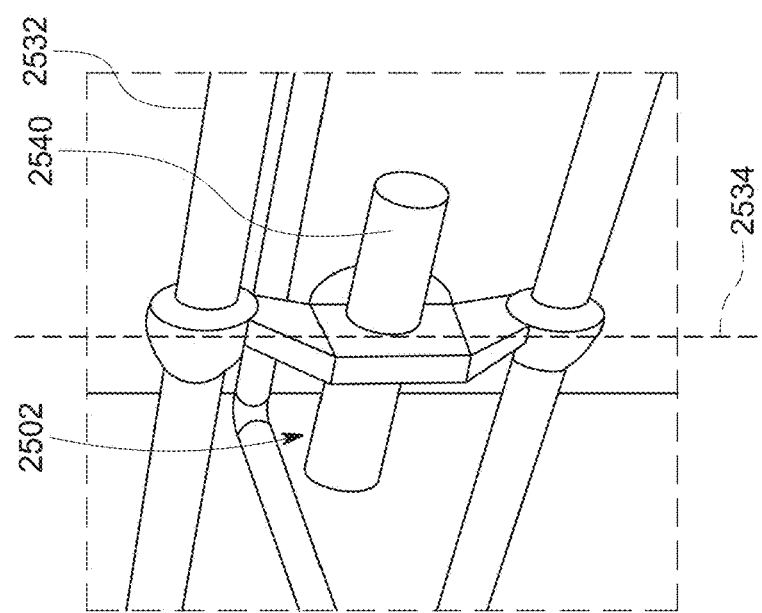
FIG. 53

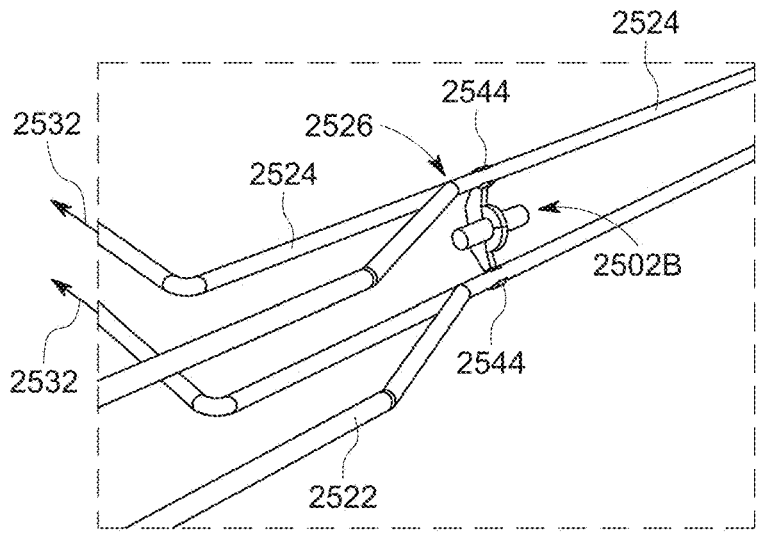
Scene 8
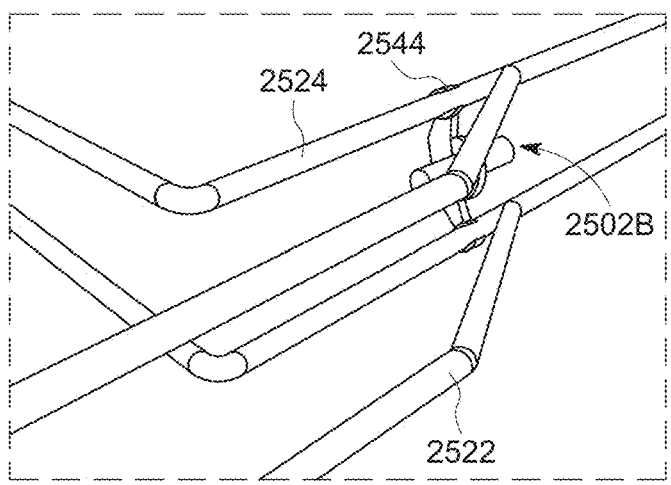
Scene 9
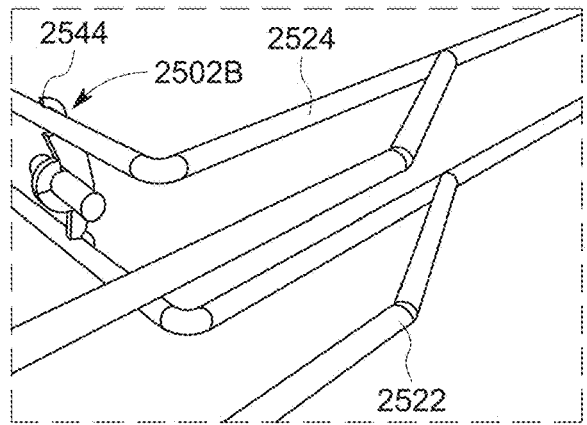
Scene 10
FIG. 55

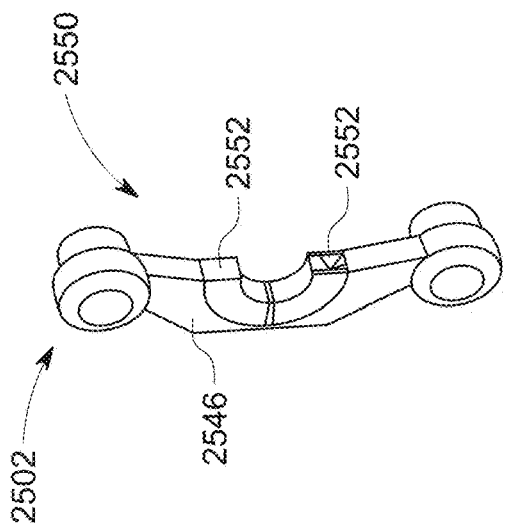
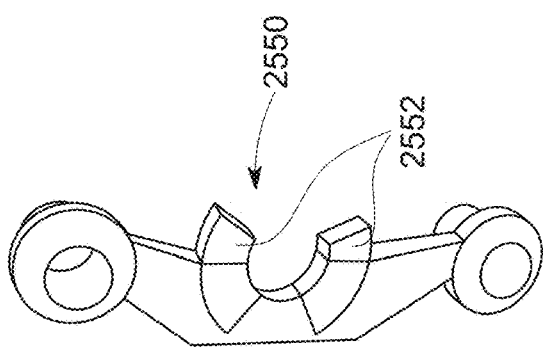
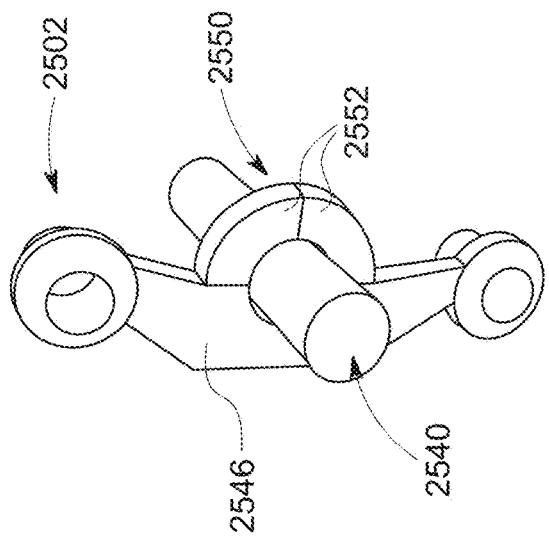
FIG. 58

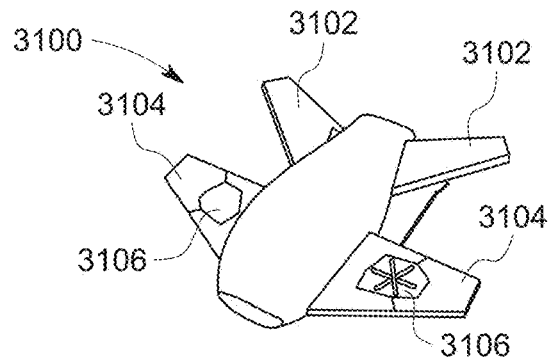
Scene 1
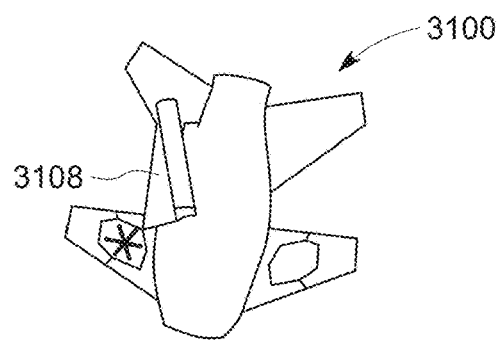
Scene 2
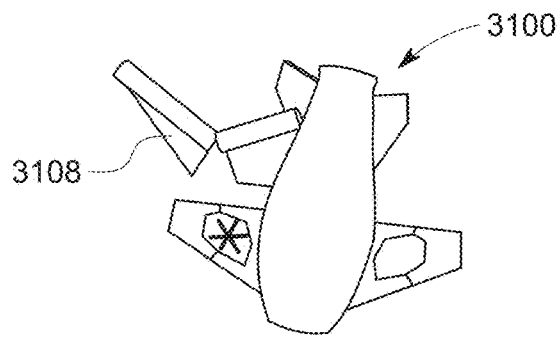
Scene 3
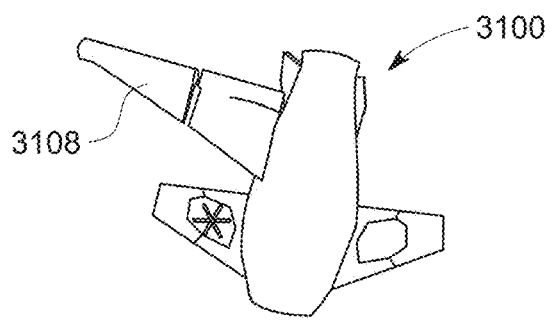
Scene 4
FIG. 64

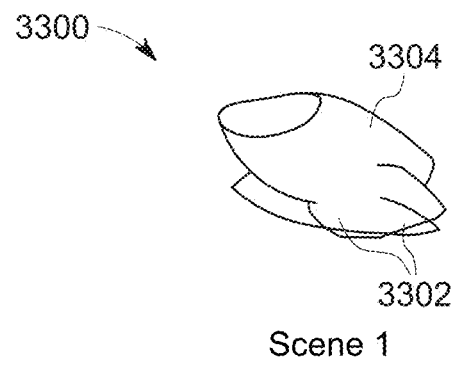
Scene 1
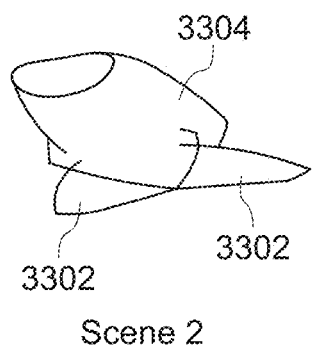
Scene 2
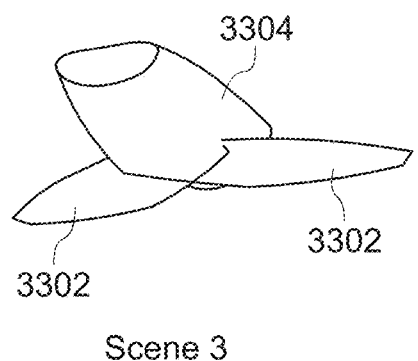
Scene 3
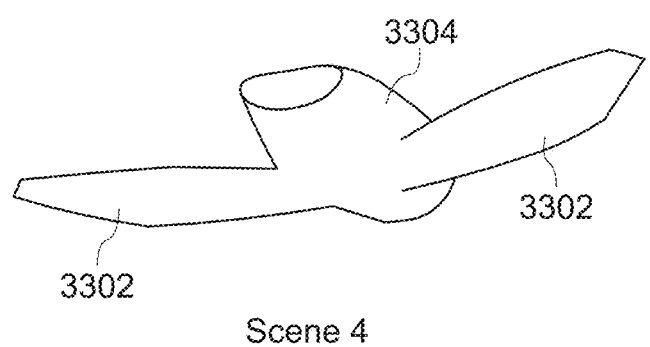
Scene 4
FIG. 66A

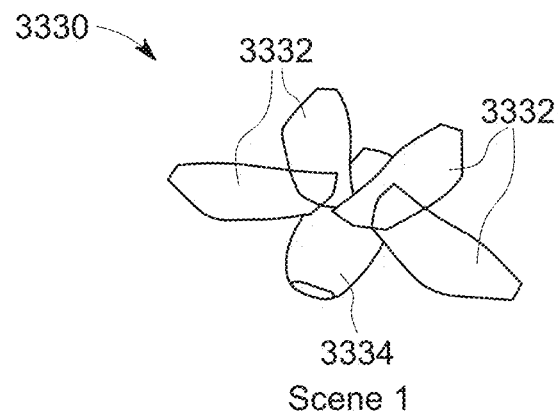
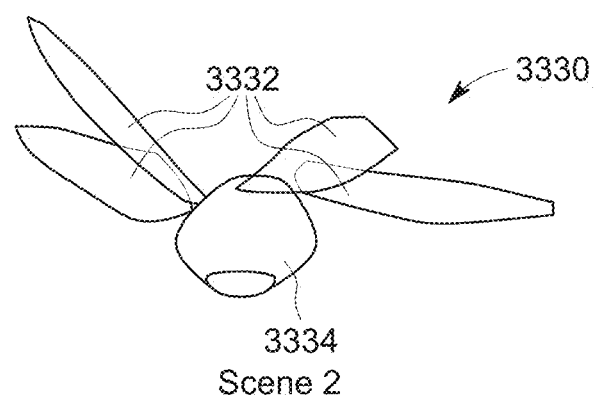
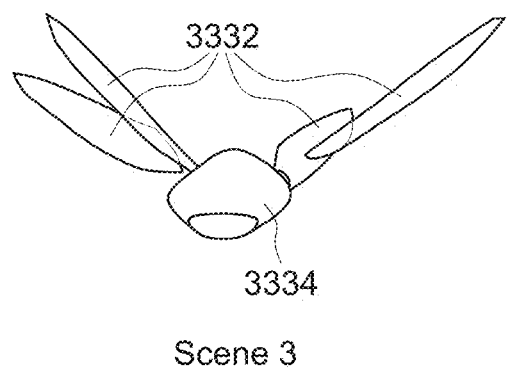
FIG. 66C

SYSTEMS AND METHODS FOR AUTONOMOUS ROBOTIC SURGERY

CROSS-REFERENCE TO RELATED APPLICATIONS

This application claims priority to U.S. Application Ser. No. 62/815,605, filed on Mar. 8, 2019. The disclosure of the prior application is considered part of the disclosure of this application, and is incorporated in its entirety into this application.

TECHNICAL FIELD

This document describes devices, systems, and methods related to robotic surgery, such as totally autonomous robotic surgery.

BACKGROUND

A number of robotic surgery concepts have been developed. For example, non-autonomous robotic surgical systems were developed to advance traditional surgery granting a greater degree of reliability and precision compared to the fallibility and fatigability of human hands. Some of the systems employ a surgeon's console, a 3-D vision system with articulating instruments allowing six degrees of freedom of motion. Such systems attempt to allow the surgeon to sit and look into this display throughout surgery while remotely manipulating 3-D intraoperative imagery. Those systems are examples of a non-autonomous robotic surgical system.

Other non-autonomous image-guided robotic systems are described, for example, in U.S. Pat. Nos. 9,872,733, 9,814,535, 8,992,580, and 9,492,241. Further, some robotic-guided endoscopy are described, for example, in U.S. Pat. No. 9,125,556. Some surgical robotics for orthopedics are which are described, for example, in U.S. Pat. Nos. 8,498,744 and 9,173,716.

In another known example, a manually supervised robot system has been developed. One example of a manually supervised smart tissue autonomous robot is described, for example, in Translational Medicine 4 May 2016: Vol. 8, Issue 337, pp. 337ra64. The system consists of a plenoptic three-dimensional and near-infrared fluorescent (NIRF) imaging system and an autonomous suturing algorithm. The computer program for this manually supervised system generated a plan to complete simple surgical tasks on soft tissue, such as suturing and intestinal anastomosis.

Another example of a robotic surgical system designed for simple tasks involves intravenous needle insertion described by Richard J. Harris, which is described, for example, in U.S. Patent Application Publication No. 2012/0190981 A1. This system combines infrared images with ultrasound images to highlight veins within these images based on shape, size, and orientation. According to that writing, the robot is capable of selecting the most suitable vein for needle insertion based on various parameters including, location within the arm, size, orientation, and probability of the selection being a vein.

Other robotic technologies were also developed for different applications. For example, a gimbal can include a pivoted support that allows the rotation of an object about a single axis. A set of three gimbals, one mounted on the other with orthogonal pivot axes, may be used to allow an object mounted on the innermost gimbal to remain independent of the rotation of its support. Their applications include rocket engines, imaging, film and video, marine chronometer and several others. Thus far, it is believed that no applications of such technology have been concretely applied to non-autonomous or autonomous surgery, or drone-patient rescue systems. In 2014 Rubenstein et al. published a description of a large-scale robotic self-assembly system that demonstrated programmable self-assembly of complex two-dimensional shapes with a thousand-robot swarm. The authors described autonomous robots designed to operate in large groups for non-surgical applications (e.g., shape building tasks) and to cooperate through local interactions. The authors described a collective algorithm for shape formation that was apparently robust to the variability and error characteristic of large-scale decentralized systems (described, for example, in Science 15 Aug. 2014: Vol. 345, Issue 6198, pp. 795-799). Thus far, it is believed that this assembly system has not been concretely applied to macro non-autonomous or totally autonomous medical robots enabling surgical applications. Others have also attempted to develop Artificial Intelligence robots capable of self-learning, which is described, for example, in U.S. Pat. No. 8,996,429.

Advances in image-guided, non-robotic surgery over the past years include angiography-guided endovascular surgery for the treatment of intracerebral vascular pathologies including for example, stent placements, coil embolization, pipeline embolization devices, as described, for example, in P. K. Nelson et. al., American Journal of Neuroradiology January 2011, 32 (1) 34-40, and other strategies.

Additional advances in non-robotic surgery also include image-guided surgery wherein the surgeon uses tracking surgical instruments in conjunction with preoperative X-Ray/CT/MM images in order to directly guide the surgeon to the particular anatomical location in 3-dimensional space. A hand-held surgical probe is an essential component of this system providing the surgeon with a map of the designated area. During the surgical procedure, the system tracks the probe position and displays the anatomy beneath it, for example, three orthogonal image slices on a workstation-based 3D imaging system. These images are relayed to computer monitors in the operating room. The tracking is performed on images recorded minutes or hours earlier (not in real-time upon surgical execution), and such images do not compensate for tissue movement during real-time surgery. This can be supplemented by having intraoperative MRIs in the surgical suite to periodically check on the progress of surgery, but because human beings are present in the OR, these procedures are not performed during real-time MM imaging, and therefore images are delayed (again, not in real-time), thereby adding time, adding costs, and losing precision. One example of a commercial application for such a non-robotic surgery is the neuro-navigation system developed by Brain Lab Med Computer system GmbH, which is described, for example, in Stefan Vilsmeier, U.S. Pat. No. 6,351,659 B1 Feb. 26, 2002.

Another surgical advance in real-time imaging over the past several decades is surgical endoscopy. Conventional endoscopy solutions in practice generally lack the advantage of image-guided surgery in that they cannot see below the surface of skin skull and bones. However, once the endoscope instrument reaches its desired destination, it can provide 3-dimensional visualization, and it can be manually guided by a surgeon to reach crevices navigating around surgical corridors etc. These conventional endoscope instruments are often wired systems. The inventors here have previously described wireless endoscopic systems in, for example, U.S. Pat. Nos. 9,801,728 and 8,251,891.

Others have described medical delivery usages for UAVs (unmanned aerial vehicles), such as drones for delivery of medical supplies in remote places and for emergencies, as described, for example, in U.S. Pat. Nos. 9,051,043, 9,489,852, 9,573,684 and U.S. Pub. No. US 2017/0069214. It is believed that these descriptions of UAVs are not integrated with autonomous robotic surgical systems and/or portable autonomous robotic surgical units.

Magnetic wallpaper, such as those described, for example, in U.S. Pub. Nos. US 2009/0263634 and US2009/0110948, has been described by others in applications different from those set forth below.

SUMMARY

Some embodiments described herein include systems and methods for autonomous robotic surgery which is preferably integrated with autonomous-assisted intraoperative real-time single modality and/or multi-modality fusion imaging/electrophysiological diagnostics. Additionally the robotic surgery concepts can be integrated with autonomous-assisted intraoperative body/limb positioning, and integrated with autonomous-assisted land and unmanned aerial vehicular patient transportation.

The technologies described herein include autonomous surgical systems that incorporate and integrate real-time imagery/diagnostics with autonomous smart robotic systems utilizing numerous or infinite degrees of motion, along with smart patient positioning, and intra-hospital, and extra- to intra-hospital autonomous transport systems.

Some embodiments described herein include totally autonomous robotic surgical (TARS) systems, which can be configured to execute complex and delicate surgical procedures with precision, including but not limited to tumor removal from the brain, from the spinal cord, and from other body cavities and parts.

In some implementations described here, the system can advantageously incorporate and integrate a combination of one, some or all of the several features. For example, the system can include one or more versions of stationery, and ambulatory non-self-configuring, and self-configuring intelligent robots with multiple arms and platforms which can navigate 3-dimensional space with infinite degrees of freedom. In addition or alternatively, the system can include one or more versions of real-time image generation including but not limited to two- or three-dimensional MRI, CAT, endoscopy, angiography, ultrasonography, fluoroscopy, Positron Emission Tomography, Single Photon Emission Computed Tomography (SPECT), and real-time electrophysiological diagnostics/monitoring including but not limited to electro-encephalography (EEG), Somatosensory evoked potentials (SSEPs), Motor evoked potentials (VEPs), and visual and auditory evoked potentials. These autonomous diagnostic modalities are operative throughout the duration of the entire surgery and function to precisely localize the operative target, and monitor in real-time the performance of the surgical task from start to finish. In addition or alternatively, the system can include a seamless integration of real-time imagery/diagnostics with totally autonomous robotic systems. In addition or alternatively, the system can include one or more versions of intelligent/autonomous operating room tables which can selectively position the patient's body and or limbs. In addition or alternatively, the system can include one or more versions of self-driving gurneys/carriages coupled to driverless autonomous self-driving land vehicles and/or one or more versions of unmanned aerial vehicles configured to provide transport systems (which can function independently or can be integrated with specifically designed complimentary hospital/clinic infrastructure including physical and electromagnetic rail-guidance systems). In addition or alternatively, the system can include one or more versions of drones engaging in multiple strategies of patient rescue, transportation and delivery to health care facilities.

Particular embodiments described herein include a robotic surgical system. The system includes one or more surgical robots, a plurality of arms movably coupled to the one or more surgical robots and configured to navigate three dimensional space, and one or more real-time imaging devices disposed in one or more of the plurality of arms and configured to provide real-time visual monitoring of the one or more surgical robots.

In some implementations, the system can optionally include one or more of the following features. The one or more surgical robots may be configured to be autonomously operated. The one or more surgical robots may be configured to provide autonomous robotic surgery. The one or more surgical robots may include integrated delta robots. The plurality of arms may include C-arms. The one or more surgical robots may include a base being autonomously movable and configured to operatively couple the plurality of arms. The plurality of arms may be coupled in humanoid form and including autonomous elements. The plurality of arms may be configured as a robotic articulated linkage arms array. The plurality of arms may include cylinder arms. The plurality of arms may include truss arms truss-arms. The plurality of arms may include arms movably coupled with an overhead support and movable along a surface of the overhead support above a patient. The plurality of arms may include a first arm assembly including autonomous elements coupled in humanoid form and supported by an autonomous movable base. The plurality of arms may further include a second arm assembly movably coupled with an overhead support and movable along a surface of the overhead support above a patient. The first arm assembly and the second arm assembly may operate to perform different phases of an operative preparation and procedure. The plurality of arms may include a gimbal-telescoping arm (GTA). The system may further include an autonomous limb positioner (ALP) including a robotic arm with a planar kinematic chain with linkages and configured to position an involuntary patient or limbs. The system may further include a plurality of autonomous robotic units (ARUs) and one or more double ball joints (DBJs). Each ARU may include a body and electronics contained in the body and configured to perform desired functionality. Each DBJ may be configured to movably interlock with an end of one ARU and an end of another ARU. The system may further include one or more operating room tables configured to be autonomously movable and selectively position a patient's body or limbs thereon. The system may further include one or more self-driving gurneys to provide transport for the patient. The system may further include one or more carriages coupled to driverless autonomous self-driving vehicles to provide transport for the patient. The system may further include one or more person rescue drones for transportation and delivery to a health care facility. The one or more person rescue drones may be configured to engage in multiple autonomous movements proximate to a targeted person. The system may further include patient carts can be automatically driven either independently or with a mobile table mover.

The devices, system, and techniques described herein may provide one or more of the following advantages. Some embodiments described herein include totally autonomous surgical systems which surpasses, in accuracy and safety, traditional non-autonomous systems that employ image-guided surgery (using, for example, MRI, CAT, or manual endoscopic imagery). For example, the systems described herein can achieve the incorporation and integration of real-time imagery/diagnostics with an autonomous smart robotic system utilizing numerous or infinite degrees of motion, along with smart patient positioning, and intra-hospital, and extra- to intra-hospital autonomous transport systems, thereby providing safe and precise autonomous surgery and patient surgery.

Furthermore, some embodiments described herein may incorporate smart learning programs into these systems to further enhance robotic independence. Also, some embodiments may employ driverless smart vehicles including gurneys, hospital beds ambulances and aerial drones for supplies, and aerial drones for patient rescue and transport, to provide benefits in terms of accuracy, safety, and efficiency for healthcare in general, and to surgery in particular.

Further, some embodiments of the systems can provide applications for increasing the safety and accuracy of hospital in-patient surgery and clinic out-patient surgery. Moreover, some embodiments of the systems can provide increased safety and accuracy for surgical applications in rural areas and in others locations where there may be a lack of trained human surgeons. In addition, some embodiments of the systems can be particularly beneficial in a military zone, aerospace, and surgical procedures performed during lengthy manned space flights, and on space stations or other colonized locations outside the reach of traditional medical hospitals.

The details of one or more implementations are set forth in the accompanying drawings and the description below. Other features and advantages will be apparent from the description and drawings, and from the claims.

BRIEF DESCRIPTION OF THE DRAWINGS

FIG. 7 illustrates an example linking arm of the system of FIGS. 6A-B, modified to perform simultaneous or sequential electrophysiological diagnostics.

FIGS. 15A-A, 15A-B, and 15B illustrate perspective views of another example TARS system employing the system of FIG. 14 with the system of FIGS. 11A-F.

FIGS. 20A-H illustrate perspective views of an example Unfoldable Endoscopic Screen (UES).

FIGS. 21A-F illustrate perspective views of other configurations of the UES of FIGS. 20A-H.

FIGS. 22A-F illustrate perspective views of another example Unfoldable Endoscopic Screen (UES).

FIGS. 27A-E illustrate partial cross-sectional views of a horizontal DBJ of FIGS. 26A-B and the ARU of FIG. 25.

FIG. 43 illustrates perspective views of an example UAV of FIG. 41 in a process of transferring from its safer travel lanes to the people/equipment lanes below.

FIG. 50 illustrates perspective views of example rail branching and rejoining for the rail guidance depicted in FIG. 49.

FIG. 53 illustrates perspective views of an example of a UAV positioned along the room's rail of FIG. 51 and then reorienting itself to interact with that area.

FIG. 55 illustrates additional perspective views of the second ACU of FIG. 54 following the opposing non-bypass route and entering the patient room.

FIG. 58 illustrates perspective views of the enlarged details of an ACU in clasping engagement with cargo.

FIG. 64 illustrates perspective views of an example aerial drone carrier with foldable wings.

FIGS. 66A-C illustrate perspective views of first and second drone vehicle embodiments with "nestled" wings, which can be compacted to above or below the vehicle body.

DETAILED DESCRIPTION OF ILLUSTRATIVE EMBODIMENTS

In general, the technologies described herein relate to robotic surgical systems and methods, and in some implementations, totally autonomous robotic surgery integrated with autonomous-assisted intraoperative real-time single modality and/or multi-modality fusion imaging/electrophysiological diagnostics, integrated with autonomous-assisted intraoperative body/limb positioning, and/or integrated with autonomous-assisted land or unmanned aerial vehicular transport systems (e.g., delivery drone systems) for patient delivery and rescue, equipment and supply delivery, etc.

Some embodiments of totally autonomous robotic surgery systems utilize artificial intelligence (AI). For example, the system can employ one or more of: Delta Robots, Mobile Robotic Doctors, Ceiling-Canopy mounted Robotic Accordioned Arms and Gimble-Telescoping arms, Robotic articulated linkage-arms arrays, non-compactable and compactable multi-functional interaction arches, autonomous limb positioners, autonomous electrophysiological diagnostics, autonomous unfoldable screens, Self-Organizing Modular Robots with self-organizing autonomous robotic units, automated gurneys/carts/undercarriage movers, automated vehicular land patient delivery systems and unmanned aerial vehicular delivery systems integrated with hospital guidance rails/granulated magnetic wall paper, and accompanying infrastructure. Further, some embodiments of the systems include patient rescue and delivery-drone systems employing various launching and rescue strategies.

Referring to FIGS. 1-31, example autonomous robotic surgery systems are described. Some example systems include multiple integrated delta robots (IDRs). The IDRs can include multiple C-arms. Other example systems include other types of arms, such gimbal-type arms, telescoping arms, etc.

Figure 1A:
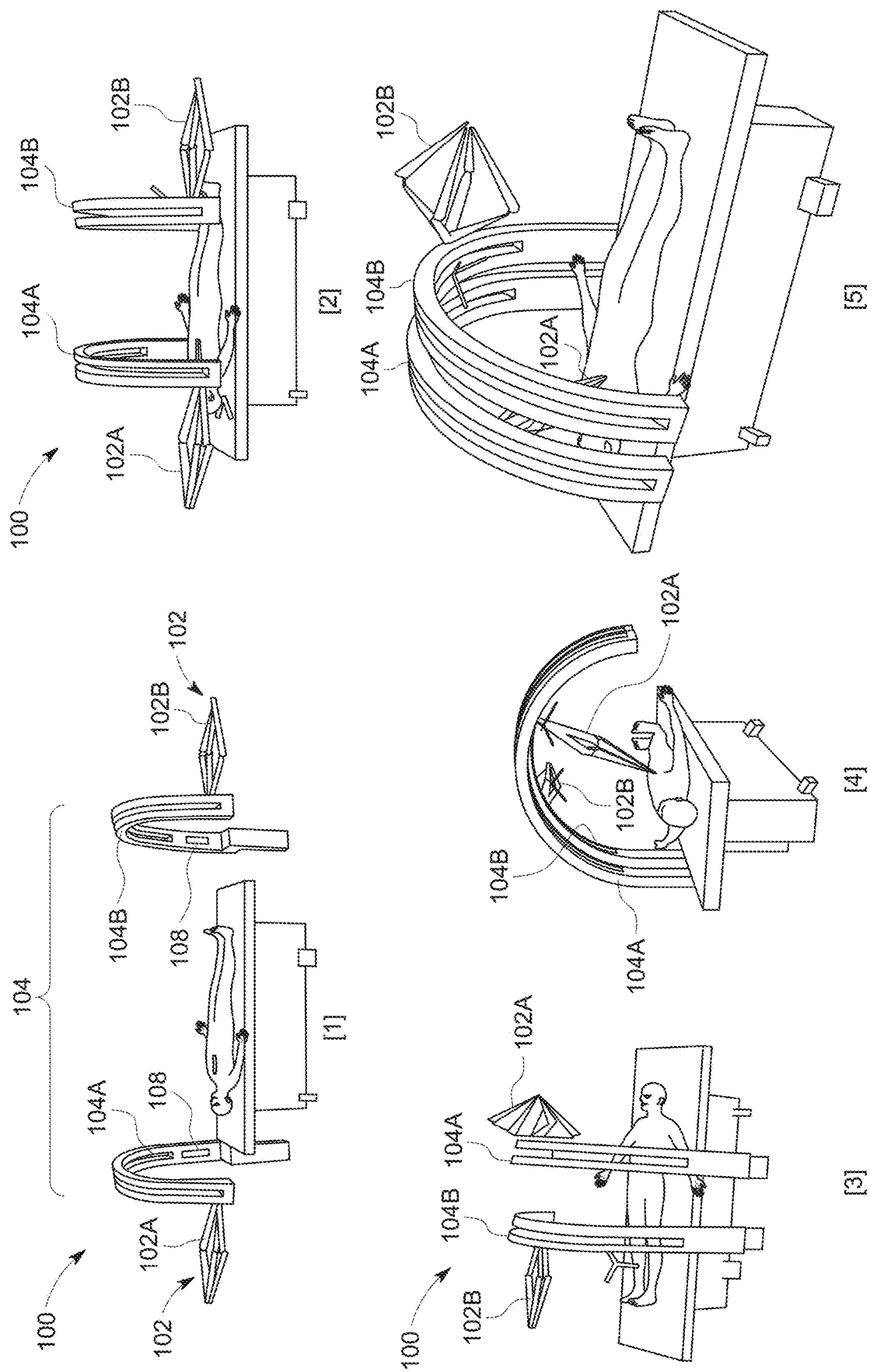
FIG. 1A illustrate an example Totally Autonomous Robotic Surgery (TARS) system.

FIG. 1A schematically illustrate an example operation of a Totally Autonomous Robotic Surgery (TARS) system 100. The system 100 includes one or more surgical robots 102 and one or more image scan devices 104 combined with the surgical robots 102 in a surgical environment. In this example, the surgical robots 102 are configured as parallel robots that use multiple computer-controlled serial chains to support an end effector arranged at the end and designed to interact with a patient or other objects in the environment. The surgical robots 102 can attach and automatically operate one or more surgical instruments, such as graspers, clamps, occluders, needle drivers, retractors, distractors, positioners, stereotactic devices, mechanical cutters (e.g., scalpels, lancets, drill bits, rasps, trocars, Ligasure, Harmonic scalpel, surgical scissors, rongeurs etc.), dilators, specula, suction tips, tubes, sealing devices (e.g., surgical staplers), irrigation and injection needles, tips and tubes, powered devices (e.g., drills, cranial drills and dermatomes), scopes and probes (e.g., fiber optic endoscopes and tactile probes), carriers and appliers, ultrasound tissue disruptors, cryotomes and cutting laser guides, measurement devices (e.g., rulers and calipers), and other suitable devices.

In some implementations, the surgical robots 102 include delta robots that include multiple arms (e.g., three arms) connected to universal joints at the base and configured to maintain the orientation of the end effector based on parallelograms in the arms. In other implementations, the surgical robots 102 can include other types of robots with multiple arms.

The image scan devices 104 are configured to scan images of a patient. For example, the image scan devices 104 include C-arm mobile machines. C-arms can be fluoroscopy machines (also referred to as image intensifiers), which may use an X-ray machine with an image intensifier. C-arms can be used to view live images to enable image-guide surgery. C-arms can be used either as a fixed piece of equipment in a dedicated screening room or as mobile equipment for use in an operating theatre. A mobile fluoroscopy unit can include two units, the X-ray generator and image detector (image intensifier) on a moveable C-arm, and a separate workstation unit used to store and manipulate the images. The patient is positioned between the two arms, for example on a radiolucent bed. Fixed systems may have a C-arm mounted to a ceiling gantry, with a separate control area. Most systems arranged as C-arms can have the image intensifier positioned above or below the patient (with the x-ray tube below or above respectively), although some static in room systems may have fixed orientations. In other implementations, smaller mobile C-arms can be available, primarily used to image extremities, for example for minor hand surgery.

In the illustrated example, the image scan devices 104 include two C-arms, such as a rostral C-arm 104A and a caudal C-arm 104B. Further, two surgical robots 102A and 102B are provided which are operatively coupled to the rostral and caudal C-arms 104A and 104B, respectively. For example, the C-arms 104 can provide two additional dimensions of control, such as the vertical axis along the bed and the cylindrical position surrounding the bed.

The C-arms 104 can be used for a multiplicity of designated functions including positioning and/or any designated implantable and programmable imaging modality. Each C arm can have separate integrated imaging modalities including but not limited to two- or three-dimensional MRI, CAT, EMG, endoscopy, angiography, ultrasonography, fluoroscopy, Positron Emission Tomography, Single Photon Emission Computed Tomography (SPECT). Each robot 102 (e.g., delta robot) can have different designated surgical functions, such as cutting, cautery, sewing, clipping etc. and/or stereotactic radiation/radio-surgical/ultrasonographic functions and many other modalities such as electrophysiological diagnostics including but not limited to Somatosensory Evoked Potential (SSEPs), Motor evoked potentials (MEPs), Visual and/or Auditory evoke potentials. Any number of C-arms and/or surgical robots can be utilized sequentially or simultaneously.

In some implementations, the surgical robots 102 (e.g., delta robots) can automatically move along the C-arms 104 while the C-arms can be positioned in different locations with respect to the bed or the patient thereon. The surgical robots 102 can be programmed to autonomously determine its positions and postures and control the end effector (e.g., surgical instruments attached thereto) as necessary to perform desired operations. The C-arms 104 can employ one or more various image technologies to obtain live images as the C-arms are at different locations with respect to the patient. The C-arms can transmit such image data to the surgical robots 102 in real time. The surgical robots 102 can receive the image data in real time and automatically determine any necessary operations based at least in part on the image data, and autonomously perform such operations with respect to the patient. The C-arms 104 can continuously feed live image data to the surgical robots 102. With such constant image feedback, the surgical robots 102 can automatically adjust their movement along the C-arms, their postures/positions/orientations (including the position and orientation of the end effector mounting one or more surgical instruments), and/or their performance of surgical and other operations without manual intervention.

Referring still to FIG. 1A, in an example operation, rostral and caudal C-arms 104 coupled with respective surgical robots 102 are in a contracted starting position (Operation [1]). The patient is illustrated on an operating room table. In this scenario, the C-arms have freedom along the bed/patient axis. The surgical robots have further freedom along a spherical coordinate system centered on its relative origin which is in turn bounded in this case to the semi-cylindrical coordinates of the c-arms.

The c-arms can be repositioned by moving to desired position (Operation [2]). The c-arms can be further repositioned and the surgical robots can be in action (Operation [3]). Both robot top-planes can be repositioned in the c-arms. The rostrally located robot has tool-end contracted. The caudal robot has the tool end in an opening position.

The rostral surgical robot operates to position the opened and elongated tool-end for action on patient (Operation [4]). The instrument attached to the robot (e.g., delta tool/sensor/imager) can interact with the patient. In the meantime, the caudal surgical robot operates to compact in preparation for positioning over patient (Operation [5]).

The system 100 further includes one or more controllers 108 provided in desired locations and configured to permit for the system 100 (or the components thereof) to autonomously perform desired surgical procedures. Such controllers 108 can run one or more software programs that are executed to cause the system 100 (or the components thereof) to perform various autonomous operations. In the illustrated example, the controllers 108 are provided in the C-arms. Other components in the system can include the controllers 108 in other implementations.

By way of example, the system 100 (as well as other embodiments of the systems described herein) can be used to perform surgery autonomously with real time images (e.g. MRI) as opposed to non-autonomous surgery performed by human practitioners (e.g., surgeons) in conjunction with intra-operative MRI. During the performance of intra-operative MRI, human practitioners should temporarily exit the operating room, hence there is a lag time between performing the MRI, obtaining the necessary imaging, and the execution of the surgical task during which there can be anatomical and fluid shifts rendering the imagery imprecise. The system 100 (as well as other embodiments of the system described herein) can provide robotic surgery that enables surgical operations with real time visual and/or physiological input (e.g. Pet/CT scan, MRI, etc.). For example, the illustrated C-arms can represent a construct of imagery which is constantly conveyed electronically computer to the end-effector robotic arms which are programmed algorithmically to perform particular surgeries based on visio-physiologic constant and real-time feedback. The C-Arms and the robot(s) function as a combined autonomous unit. For example the unit can be programmed to excise a tumor. The C-arms housing imagery units (e.g., MRI, CT, angiography etc.) can relay the constant real time information to the end effective organ of robot, which will incise, excise, coagulate, and execute other various operations from beginning to end based on an internalized preprogrammed algorithm written by a surgical team. In addition, the delta robots can swing about angularly around the C-arm with infinite degrees of motion, preprogrammed based on imagery and program written for them.

Figure 1B:
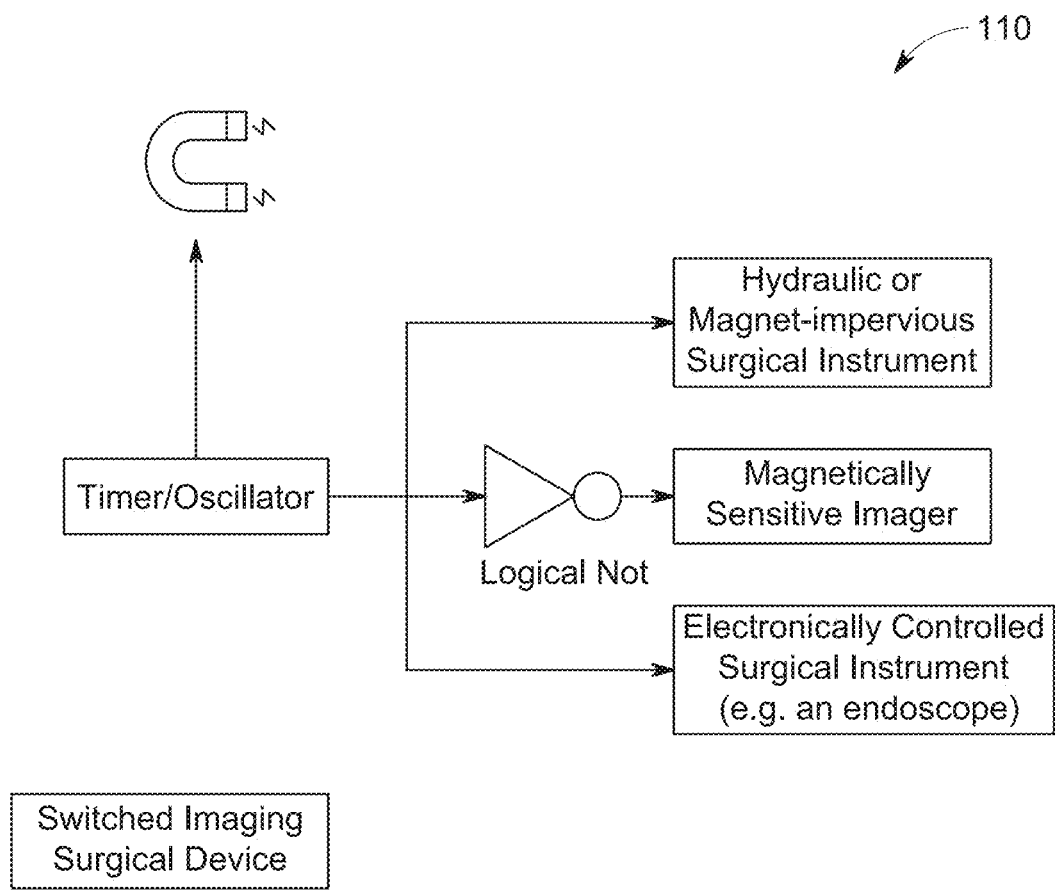
FIG. 1B schematically illustrates a subsystem for integrating MRIs with other electronic devices.

FIG. 1B is a block diagram 110 for illustrating an example TARS system 100 configured to integrate magnetic instrumentation (e.g., MRIs) with other electronic device (e.g., other surgical tools) so that the magnetic instrumentation can be used together with other electronic devices with reduced or no interruption. In the diagram, "Logical NOT" indicates reversal of an input value (e.g., yes=no and vice versa). In one embodiment of this scheme, electronic devices are disabled while magnetic equipment (e.g., MRI) is operational and vice versa, thereby reducing the likelihood of an error due to magnetic effects on magnetically sensitive tools. In another embodiment of this scheme, electronic or magnetically-sensitive devices are all-together reduced, eliminated or minimized. For example, magnetically impervious metals, or pneumatic systems, can be used to assume automated roles. In addition or alternatively, surface waves, acoustics or ultra-acoustics or line of site lasers can be used for communication.

Figure 2A:
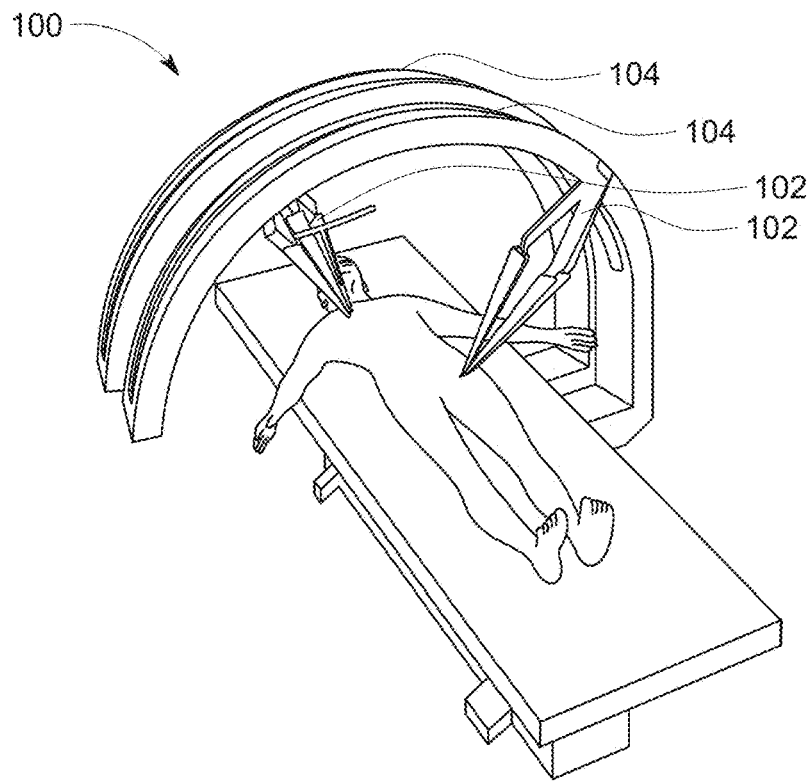
FIGS. 2A-B illustrate perspective views of another example TARS.
Figure 2B:
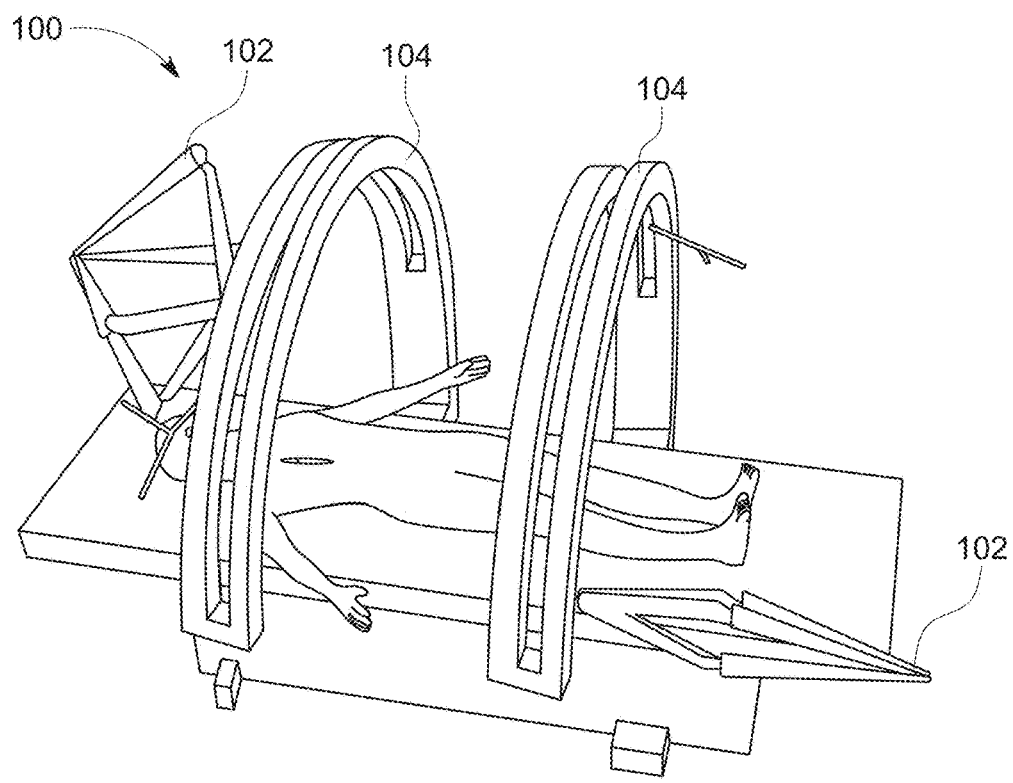

Referring to FIGS. 2-4, an exemplary embodiment of the TARS system 100 is further described. As described above, the system 100 can include one or more surgical robots 102 which can be movably coupled to respective movable image scan devices 104. FIG. 2A schematically illustrates that two surgical robots 102 perform simultaneous operations and interactions with a patient on a bed. FIG. 2B schematically illustrates the surgical robots 102 are in retracted positions from the patient. For example, the surgical robots 102 can be in retracted positions for preparation of interaction with a patient prior to operation or between operations.

In some implementations, the image scan devices 104 (e.g., C-arms) can be rigid in shape (e.g., configured in a single shape), such as a semi-circle as illustrated in FIGS. 2A-B. In other implementations, the image scan devices can be flexible in shape so that, for example, they can be altered from a semi-circle geometry to another shape.

The surgical robots 102 can include any type of modular element or elements not illustrated here. For example, elements or actions that may be conceived to be undertaken by the arch themselves can be the repositioning of patient limbs/anatomy such as the limb positioner shown in FIGS. 16 and 17 below.

The elements in the system 100, including the surgical robots 102 combined with the image scan devices 104, can be used to hold and/or position various instruments, such as imaging devices, sensors, surgical instruments, displays, respiration or suction tubing, to place draping, insert IV's and inject angiography dye and perform endovascular procedures, or to house non-robotic surgical instruments for use by surgical staff. The elements in the system 100 can also be used as automatic driving (steering/moving) elements for the patient-cart/gurney (e.g., those illustrated in FIGS. 9-10). In addition, they can steer themselves to deliver items or itself to a sterilization compartment.

Figure 3A:
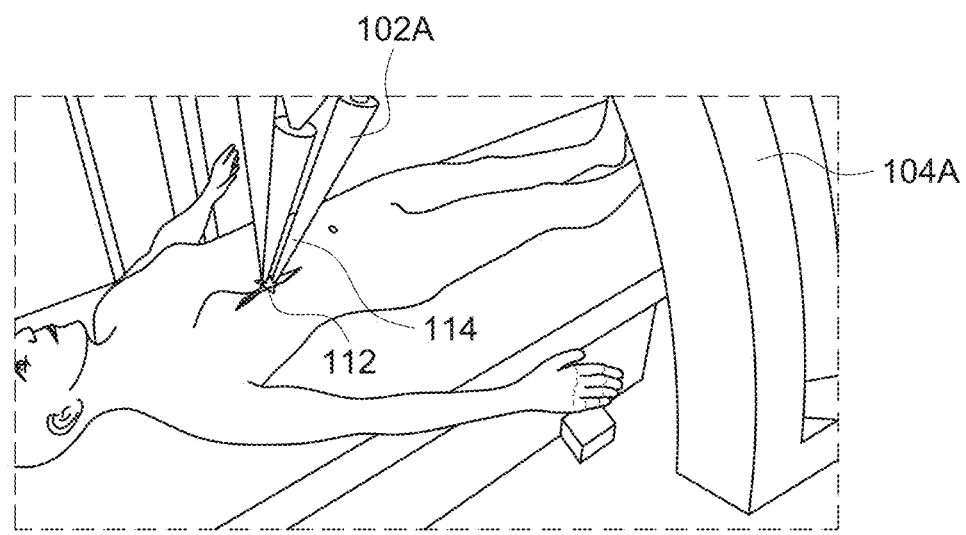
FIGS. 3A-B illustrates example robots depicted in FIGS. 2A-B performing simultaneous open surgery and closed imaging/radiation and other multiple functions.
Figure 3B:
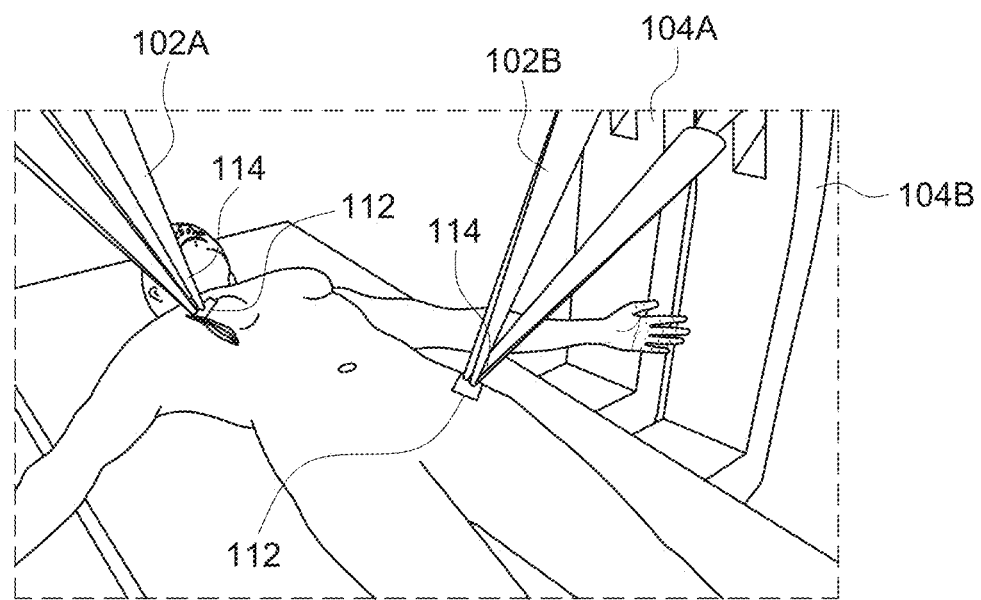

FIGS. 3A-B schematically illustrate the surgical robots 102 of FIGS. 2A-B performing multiple operations simultaneously, such as simultaneous open surgery and closed imaging/radiation. For example, two surgical robots 102A and 102B perform simultaneous actions including open surgery with an open incision illustrated beneath the extended action tool of the rostral surgical robot 102A and a closed surgical, radiation or imaging function of the caudal surgical robot 102B. The surgical robots 102 include surgical instrument ends 114 that attach instruments 112 for desired functionality. Illustrated are ample incision accomplished by robotically placed instruments 112, surgical instrument ends 114, and c-arms 104 (horizontal positioning arches).

FIGS. 4A-F schematically illustrate an example of the surgical robot 102 of FIGS. 2A-B in different positions. In some implementations, the surgical robot 102 is configured as a delta robot. As described herein, the surgical robot 102 can automatically change its positions (e.g., postures, orientations, etc.) in a plurality of configurations.

The surgical robot 102 can include parallel kinematic linkages 120. Adjacent linkages 120 can be pivotally connected and hinge relative to one another to permit for the surgical robot 102 to be in different configurations. The dimensions, geometry, and topology of the surgical robot 102 (and the linkages 120 thereof) can be optimized for it to be used as a precision instrument. For example, the arms (the linkages 120) of the surgical robot 102 can be controlled to cooperate with each other. In some implementations, the surgical robot 102 can be controlled in a closed control loop. An example of such a closed control loop is described in Basso, *Designing Control Loops for Linear and Switching Power Supplies: A Tutorial Guide*. Artech House. ISBN 978-1608075577, 2012, the disclosure of which is incorporated herein by reference. Other control schemes can be used for automatic operation of the surgical robot 102. In some implementations, the arms of the surgical robot 102 can perform multiple functions, such as dual functions as a sensor and positioner, an example of which is described in *Machine Devices and Components Illustrated Sourcebook 1st (first) edition* by Robert Parmley, McGraw-Hill Professional (2004), the disclosure of which is incorporated herein by reference. In addition, the arms of the surgical robot 102 can dually function as a sensor and positioner using a highly sensitive soft-sensor using an array of varying length, yet with miniscule spring-constant for organ or gross anatomy.

Figure 4A:
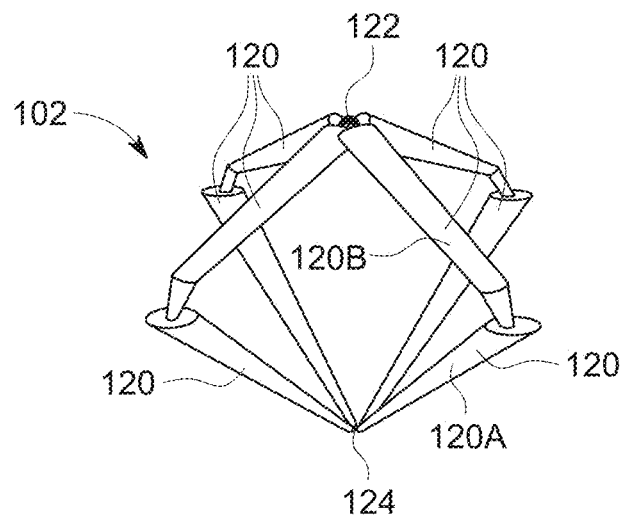
FIG. 4A-F illustrate example robots depicted in FIGS. 2A-B positioning themselves in multiple configurations.

Referring to FIG. 4A, the surgical robot 102 is in a first elongation configuration and normal to a component (e.g., the image scan device 104) to which the surgical robot 102 is coupled. The surgical robot 102 includes a top end 122 coupled (e.g., jointed) to a component, such as the image scan device 104 (e.g., a C-arm). The surgical robot 102 includes a bottom end 124 opposite to the top end 122 and configured as an effector end that attaches a surgical instrument. The linkages 120 are provided between the top end 122 and the bottom end 124. For example, the linkages 120 include lower linkages 120A and upper linkages 120B pivotally connected to the lower linkages 120A. The lower linkages 120A can be operatively coupled to provide the bottom end 124. The upper linkages 120B can be operatively coupled to provide the top end 122. In other example, the linkages 120 can have more than two levels (upper and lower) of linkages pivotally connected to one another. In some implementations, the linkages 120 can include one or more sensors and/or tools. For example, the linkages 120 can embed one or more sensors and/or tools therewithin, or mount such sensors and/or tools at the exterior (e.g., at their respective tips, or at the common tip (e.g., the bottom end 124)).

Figure 4B:
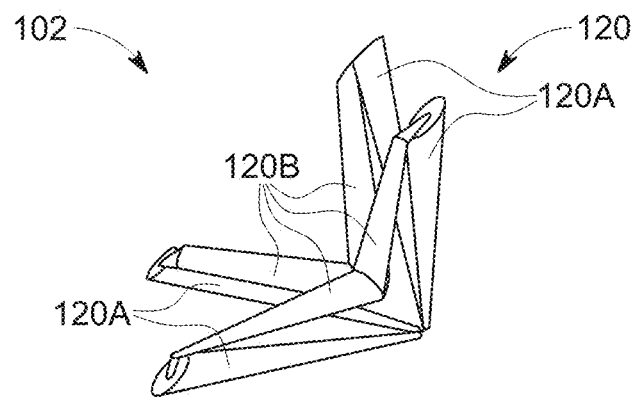

Referring to FIG. 4B, the surgical robot 102 is in an angled and length-compacted configuration relative to the component that couples the surgical robot 102. For example, the upper linkages 120B are pivoted relative to the lower linkages 120A and collapsed toward the lower linkages 120A so that the surgical robot 102 is in a compact profile.

Figure 4C:
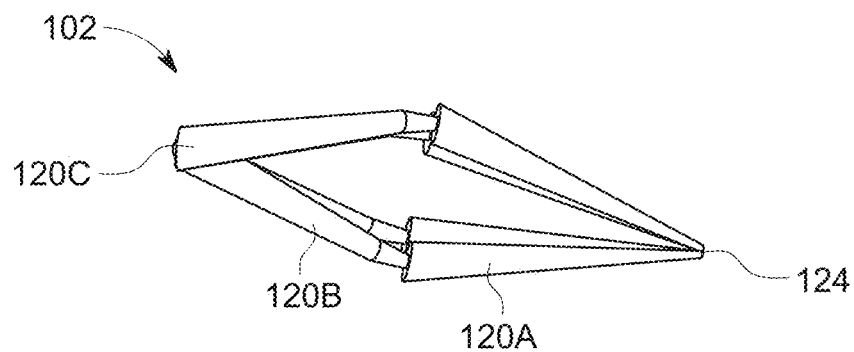

Referring to FIG. 4C, the surgical robot 102 is in an angle and outstretched configuration. For example, the lower linkages 120A are pivoted relative to the upper linkages 120B and moved away from the upper linkages 120B so that the surgical robot 102 is in a stretched position.

Figure 4D:
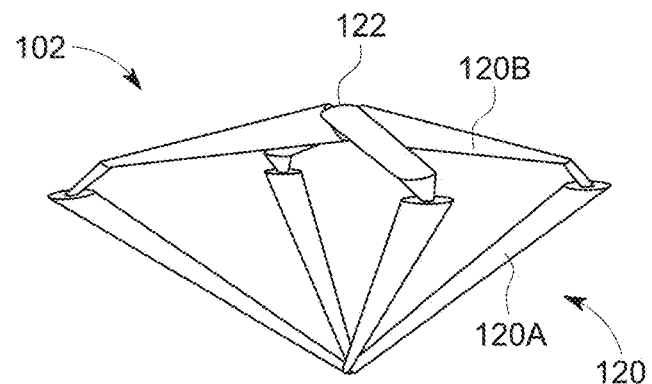
Figure 4E:
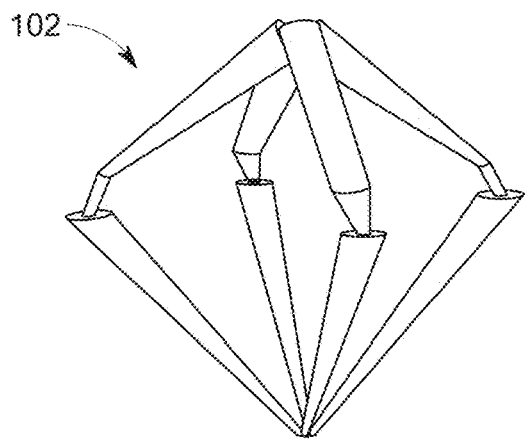
Figure 4F:
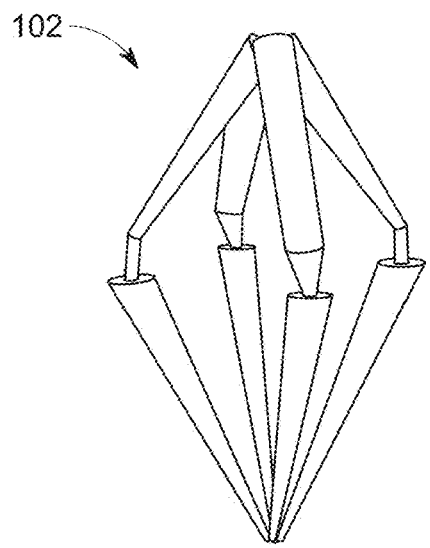

Referring to FIG. 4D, the surgical robot 102 is in a slightly compacted configuration where it is normal to the plane of the top end 122. Referring to FIG. 4E, the surgical robot 102 is in a slightly elongated configuration where the lower linkages 102A are stretched out relative to the upper linkages 102B. Referring to FIG. 4F, the surgical robot 102 is in a further elongated configuration where the lower linkages 102A are further stretched out relative to the upper linkages 120B.

The delta robots described herein can be in various configurations. In some implementations, a delta robot can include a parallel robot having multiple kinematic chains connecting the base with the end-effector. Such a robot may use parallelograms which restrict the movement of the end platform to translation movements in the X, Y or Z dimensions (three degrees of movement). Actuation of input links will move the triangular platform along the X, Y or Z direction. Actuation can be done with linear or rotational actuators, with or without direct drive. The moving parts of the delta robot may often have a small inertia. A few examples of delta robots are described, for example, in U.S. Pat. No. 4,976,582, the disclosure of which is incorporated herein by reference. The delta robot in this patent has four degrees of movement, three translations and one rotation and thus can manipulate small objects at a very high speed. Other example delta robots are miniaturized with piezoelectric actuators to 0.43 grams, as described, for example, in The milliDelta: A high-bandwidth, high-precision, millimeter-scale Delta robot, McClintock, et. al., Science Robotics 17 Jan. 2018: Vol. 3, Issue 14, eaar3018, the disclosure of which is incorporated herein by reference.

FIGS. 5A-E schematically illustrate another example operation of a TARS system 200. In this example, the TARS system 200 is configured as a Mobile Robotic Doctor (MRD) system that assumes different positions and engages in a variety of tasks. The system 200 can operate as an autonomous or semi-autonomous robot. In the illustrated example, the system 200 is configured in humanoid form and include a central root or base 202 and multiple (e.g., two) arms 204 extending from the base 202. The central base 202 is configured to automatically move on the ground. For example, the base 202 can stay at a rest location (e.g., a corner in the room) and automatically move toward a patient (or a bed supporting the patient). In some implementations, the arm 204 can include a plurality of autonomous elements 210 that are operatively coupled and pivotable to provide multiple degrees of freedom in operation. In the illustrated example, each arm 204 includes the autonomous elements 210 that are linearly jointed and pivotable so that the arm 204 can be in numerous configurations for different operations.

The autonomous element 210 can be configured in various shapes, such as cylindrical shape as illustrated. The autonomous element 210 can be configured as a self-organizing module as described with reference to FIGS. 24-31.

Each arm 204 has a distal end 220 configured to attach one or more instruments 230. Examples of the instrument 230 can include various surgical instruments, image scan devices (e.g., MRI, CAT, EMG, endoscopy, angiography, ultrasonography, fluoroscopy, Positron Emission Tomography, Single Photon Emission Computed Tomography (SPECT)), surgical robots (e.g., delta robots), and other suitable instruments that are controllable with the system 200.

The multiple arms 204 can cooperate and communicate with each other in a closed loop control scheme. For example, a first arm 204A mounts an image scan device (e.g., MRI) at its distal end 220, and a second arm 204B mounts a surgical robot (e.g., a delta robot) at its distal end 220. The first arm 204A can obtain live images using the image scan device, and transmit image data to the second arm 204B in real time. The second arm 204B can constantly receive the image data and perform desired operations with the surgical robot based on the image data feedback.

Although the system 200 is primarily described with two arms rooted from a central root, it is understood that the system 200 can be configured or reconfigured topologically/geometrically to be any conceivable form with generic segments, such as generalized as tall cylinders.

By way of example, the system 200 provides a delta robotic effector surgical end organ that is attached to a multi jointed robot enabling additional degrees of freedom in 3-dimensional space. The mobile arms may be cylindrical but can assume any desired shape. The joint movement is preprogrammed with respect to its multiple degrees of freedom including flexion, extension and rotation. This embodiment can be configured to be mobile with a planar mobilization component. This embodiment also has real-time feedback of imagery. Single or multiple imaging capabilities can be stored with the cylinders (e.g. MRI, CT, etc.) relayed to the end organ delta robots which perform the preprogrammed surgery.

Figure 5A:
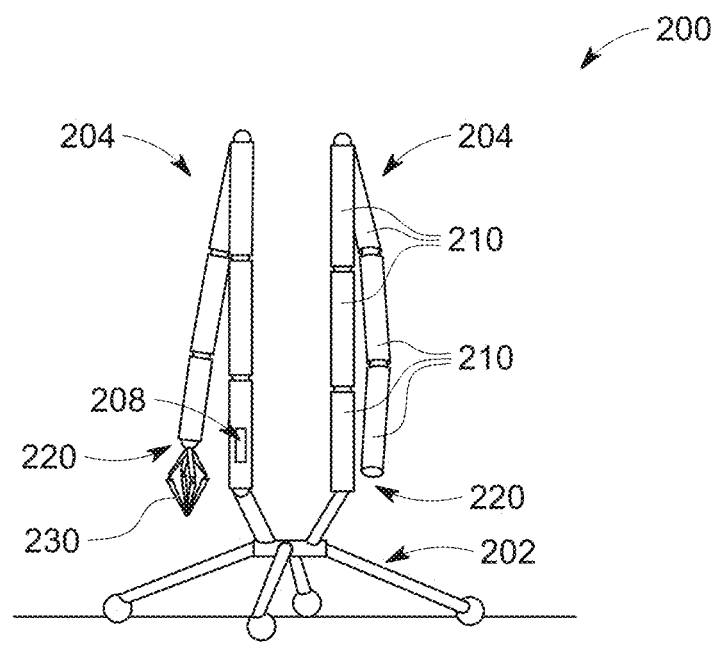
FIGS. 5A-E illustrate perspective views of another example TARS system.
Figure 5B:
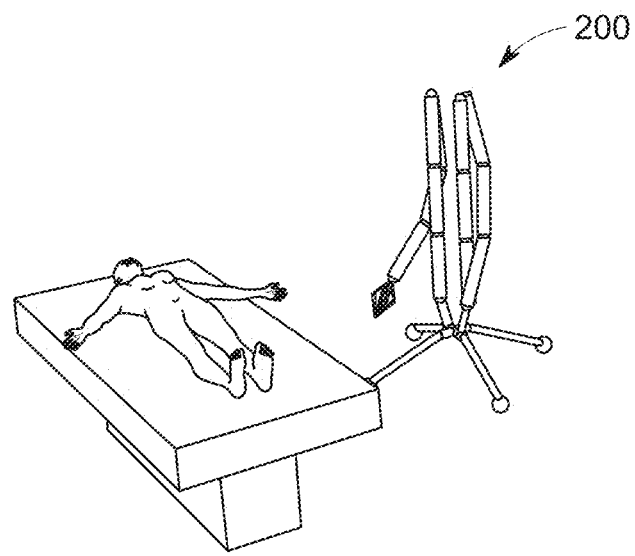
Figure 5C:
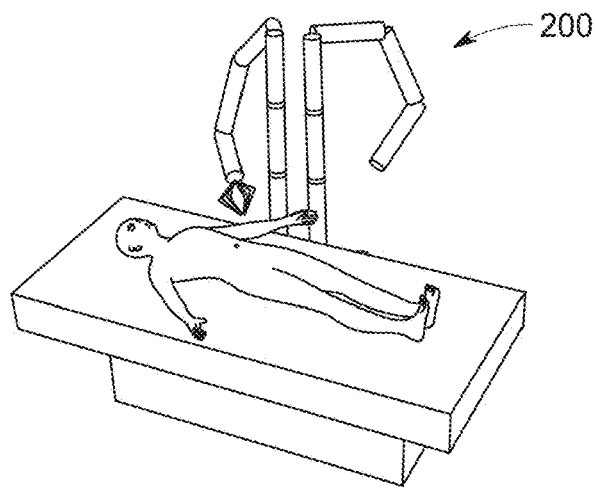
Figure 5D:
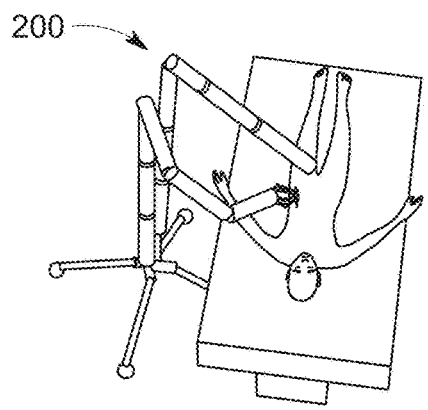
Figure 5E:
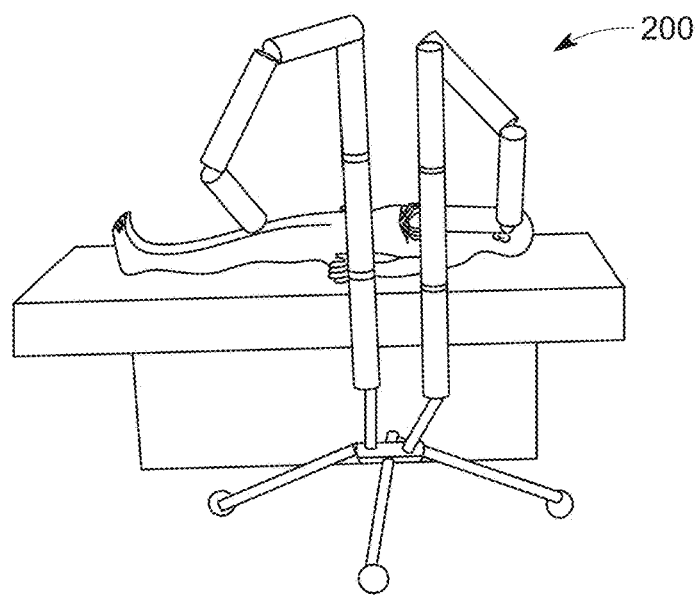

Referring to FIG. 5A, the system 200 is configured to be in a standing position and provide one arm 204 fitted with a precision delta robot manipulator hand. The base 202 is equipped with a planar mobilization component. Referring to FIG. 5B, the system 200 approaches the patient on an operating table. Referring to FIG. 5C, the system 200 is about to operate on the patient. Referring to FIG. 5D, the system 200 performs medical diagnosis and/or procedure identical or similar to procedures performed by the system 100 above. For example, one arm 204 is equipped with the delta hand manipulator whose function are similar or identical to those of the system 100. The other arm 204 can perform any of numerous imaging functions, for example real time imaging as those in the system 100 or other simultaneous surgical diagnostic procedures. FIG. 5E illustrates an enlarged posterior view of the system 200. In some implementations, the arms of the system 200 can be configured as generic reconfigurable arms that include cylindrical jointed elements. The base 202 of the system 200 can include a planar mobilization component allowing autonomous programmable movement.

The system 200 further includes one or more controllers 208 provided in desired locations and configured to permit for the system 200 (or the components thereof) to autonomously perform desired surgical procedures. Such controllers 208 can run one or more software programs that are executed to cause the system 200 (or the components thereof) to perform various autonomous operations. In the illustrated example, the controller 208 is provided in the arm 204. The controllers 208 can be arranged in other components in the system.

Referring to FIGS. 6-9, yet another example TARS system 300 is illustrated. FIGS. 6A-B schematically illustrate an example operation of the TARS system 300. The system 300 is configured as a robotic articulated linkage arms array (RALAA) system. The system 300 can be in a static state (FIG. 6A) or in an action/transition state (FIG. 6B).

The system 300 includes a plurality of arm assemblies 302 arranged in series. In the illustrated example, the system 300 include a series of 8 arm assemblies in a static linear array adjacent to a patient on an operating bed/rest platform. Each arm assembly 302 can include a plurality of linkages that are linearly coupled and pivotable to different configurations.

The system 300 can also include one or more guidance rails 304 configured to support the arm assemblies 302 and/or one or more arches 306. The arch 306 on the guidance rails 304 can assist arm stability, can aid in mobilizing heavier accessories, can contain other equipment such as imaging, delta-robot etc. and can act as guidance for other secondary or supplementary equipment.

The system 300 operates to interact with a patient. The arms 302 of the system 300 can be movable or stationary for different purposes. The arms 302 can be configured to be used for autonomous information gathering. The system 300 can include additional components which can be included in or attached to the arch 306 and the arms 302.

In some implementations, each arm 302 include a plurality of linkages which are automated. Alternatively, the linkages of the arm 302 can be semi-automated ("cooperative") such that the linkages can operate with limited human input or supervision. Alternatively, the linkages of the arm 302 can be predominantly controlled by human operators.

The system 300 can be operated in multiple modes. For example, the system 300 can be operated in a fully automated mode by employing, for example, artificial intelligent (AI), and/or cloud/knowledge base that is on-premise, remote, or a combination thereof. The system 300 can further be operated in a partially automatic mode where the system 300 is controlled with manual supervision. The system 300 can further be operated in an automatic and cooperative mode where the system 300 works with non-technical human staff without an operator controlling the arms. The system 300 can further be operated in a partially automatic and cooperative mode where the system 300 works with staff, and arms are overseen by a human operator.

The system 300 can be configured as a modular system such that an alternative array of linkages can work in conjunction with secondary arch. Further, the patient platform and the robotic system can be separated and rejoined for optimal resource efficiency.

The system 300 further includes one or more controllers 308 provided in desired locations and configured to permit for the system 300 (or the components thereof) to autonomously perform desired surgical procedures. Such controllers 308 can run one or more software programs that are executed to cause the system 300 (or the components thereof) to perform various autonomous operations. In the illustrated example, the controller 308 is provided in the arch assembly or rails. Alternatively, the controller 308 can be arranged in other components in the system.

In some implementations, the arch and respective arms can be configured to perform different operations and functions simultaneously or sequentially. For example, the arch and the arms can be configured to simultaneously or sequentially perform different types of image scans (e.g., MRI, CAT, EMG, endoscopy, angiography, ultrasonography, fluoroscopy, Positron Emission Tomography, Single Photon Emission Computed Tomography (SPECT)).

Figure 6A:
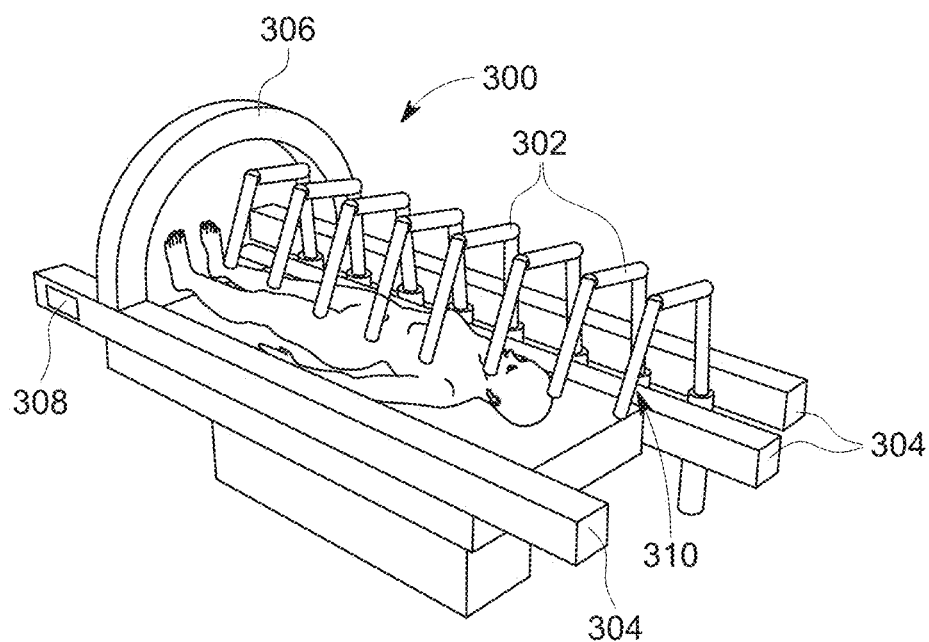
FIGS. 6A-B illustrate perspective views of another example TARS system.
Figure 6B:
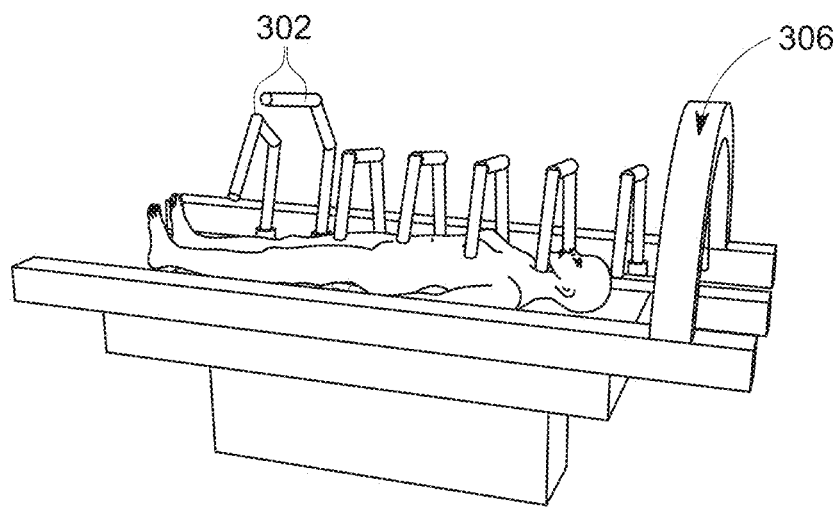

FIG. 7 schematically illustrates an example of the arm 302 of FIGS. 6A-B. In some implementations, the arm 302 can be configured to perform simultaneous or sequential electrophysiological diagnostics, for example.

The arm 302 has a distal end configured to attach one or more various instruments. For example, the arm 302 can mount an automated diagnostic element, such as a flexible neurological electroencephalogram (EEG) cap 312 configured to be autonomously applied to the top of patient's head conforming to the dimensions and contours of the top patient's skull. An example soft robotic technology, which can be used to implement the arm 302, is described in S. Bauer, et. al., *A soft future: From robots and sensor skin to energy harvesters*, Advanced Materials, Volume 26, Issue 1:149-162, Jan. 8, 2014, the disclosure of which is incorporated herein by reference in its entirety.

Referring to FIG. 7, an example process is illustrated for operating the arm 302. In Scene 1, the automatic linkage arm 302 can be autonomously moved to direct its distal neurological diagnostic (EEG) apparatus 312 towards the top of a patient's head. In Scene 2, the end-tool 312 (EEG apparatus) begins to dynamically deform to conform to the patient's head/skull geometry. In Scene 3, the end-tool 312 is in its final skull conformation state after further deforming to optimally contact head regions to perform an electrophysiological diagnostic exam, e.g. EEG.

In other examples, the arm 302 can mount other instruments, such as Somatosensory Evoked potentials (SSEPs) or Motor Evoked Potentials (MEPs), visual or auditory evoked potentials, with electrode application for each diagnostic performed by other linkage arms cooperating simultaneously or sequentially.

It is also understood that the diagnostic application described in FIG. 7 is not limited to the RALLA system 300, and based upon the teachings herein, it can be adapted to all the other embodiments of the system illustrated herein.

Figure 8:
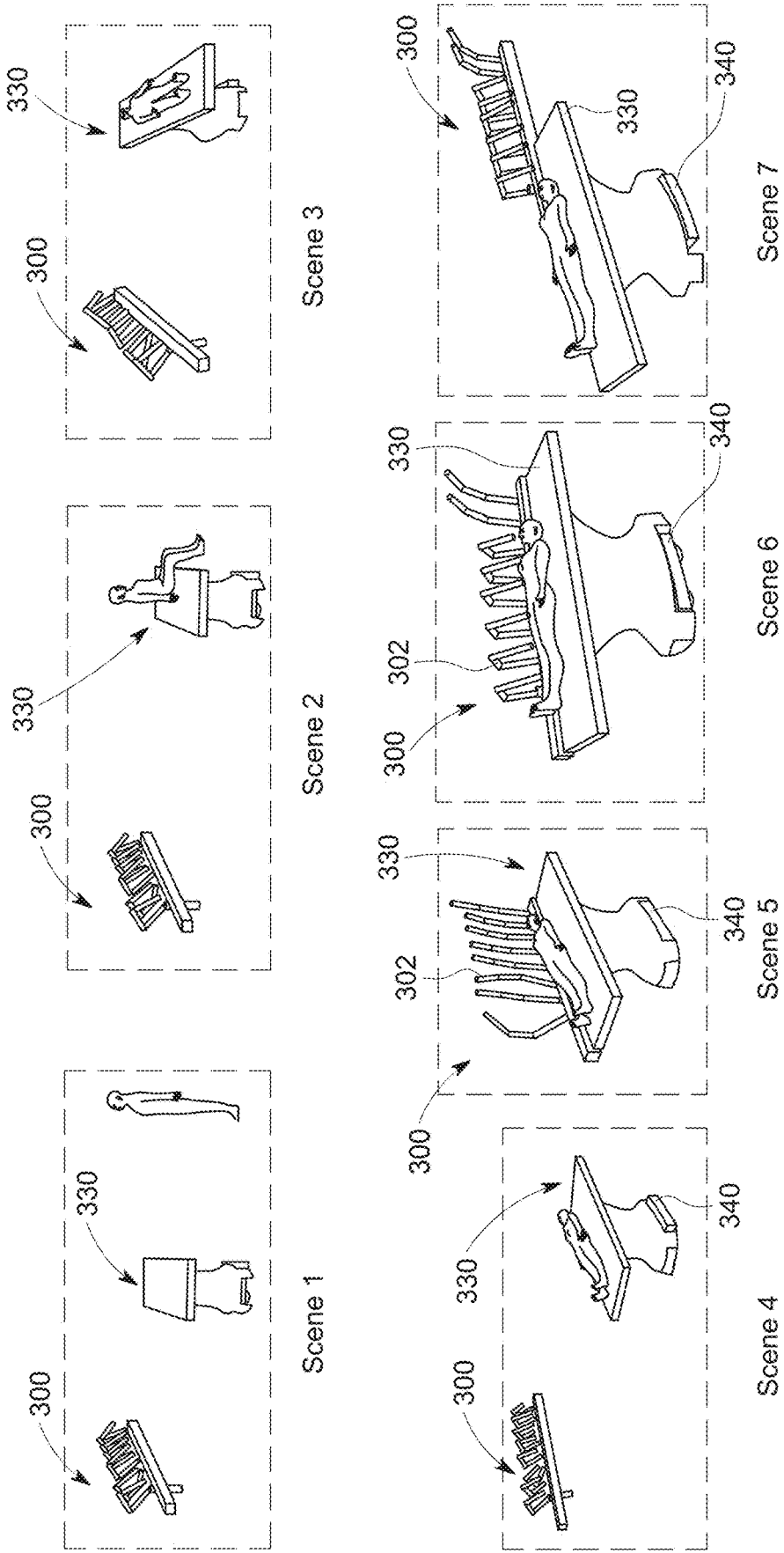
FIG. 8 illustrates an alternative truss-arm example for robotic cylinder arms in the embodiment depicted in FIGS. 5A-E or the embodiment depicted in FIGS. 6A-B.
Figure 9:
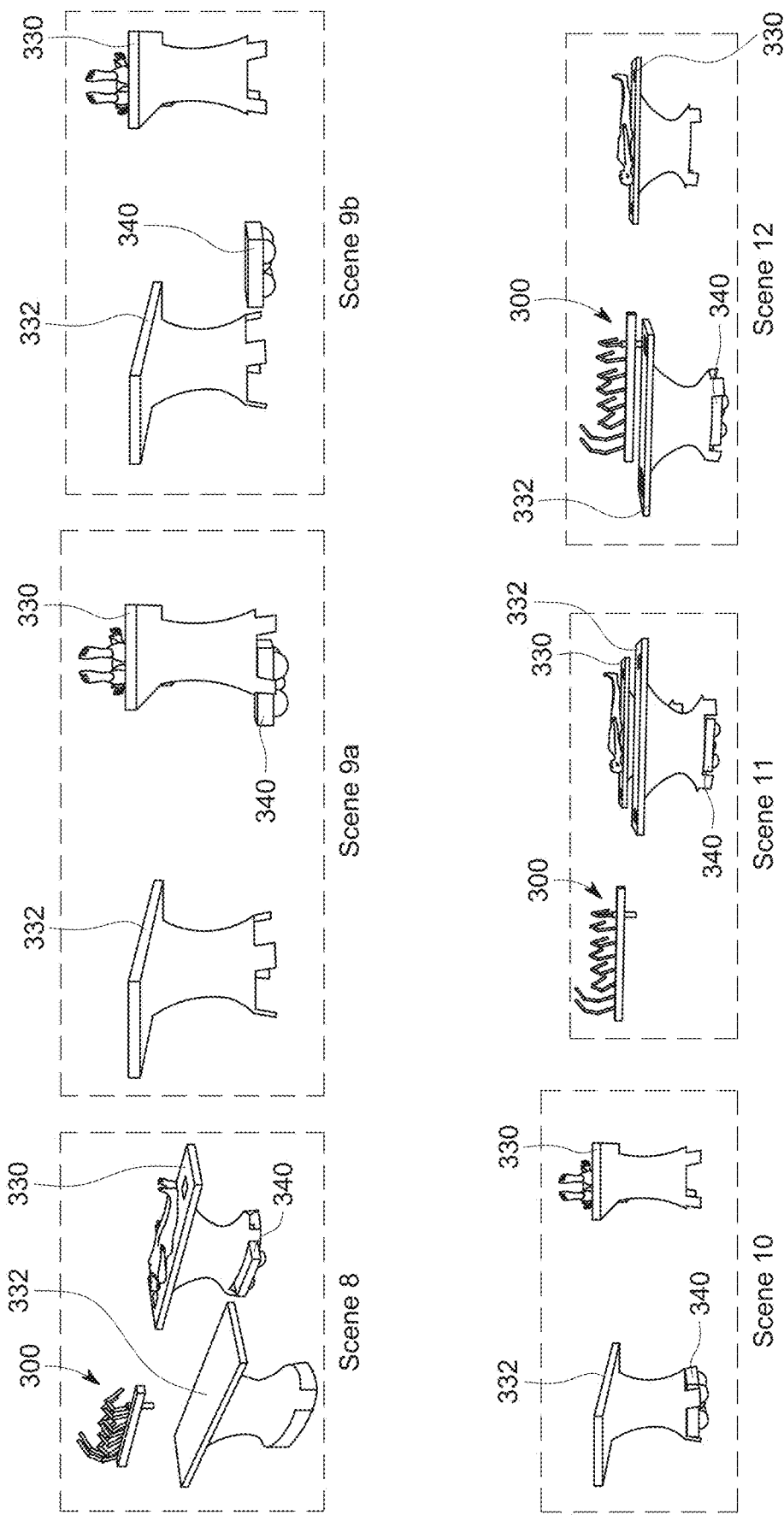
FIG. 9 illustrates perspective views of system modularity and patient intake using the embodiment depicted in FIGS. 6A-B.
Figure 10:
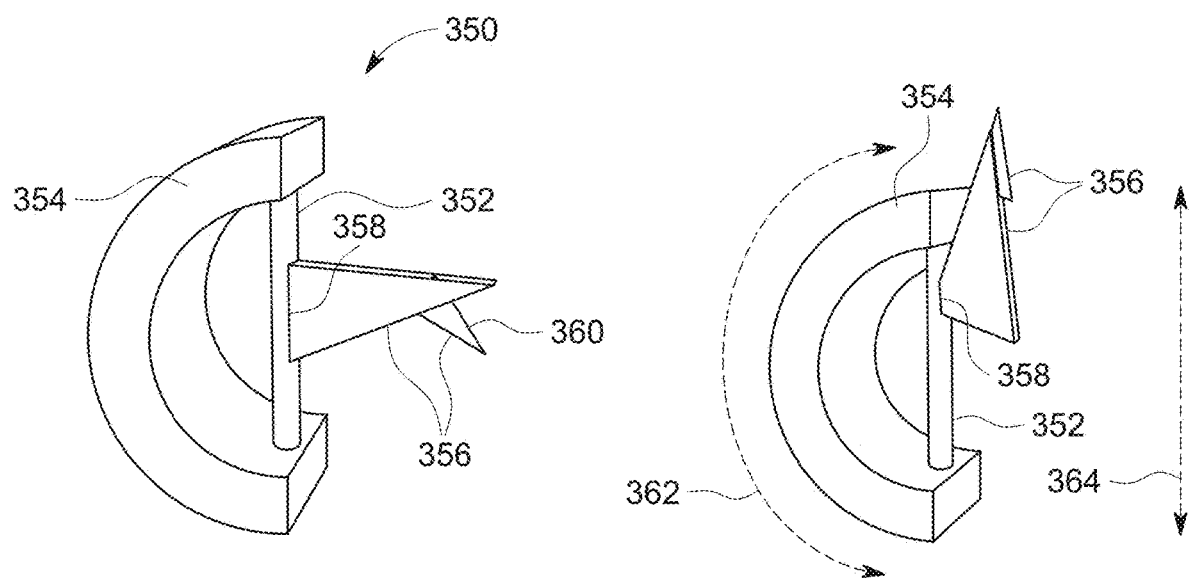
FIG. 10 illustrates additional perspective views of system modularity and patient intake using an example carriage mover of FIG. 9.

Referring to FIGS. 8-9, example operations with the system 300 are illustrated. FIG. 9 illustrates perspective views of system modularity and patient intake using the system 300 of FIGS. 6A-B. As described below, patient carts can be automatically driven either independently or with a mobile table mover. FIG. 9 illustrates additional perspective views of system modularity and patient intake using an example carriage mover of FIG. 8.

The system 300 can be used with one or more patient carts 330. The patient carts 330 can be automatically driven either independently or with a mobile table mover 340.

In FIGS. 8-9, a sequential scenario (Scenes 1-12) is illustrated to demonstrate an example operation of the system 300 with the cart 330, thereby providing a logistically efficient system for assessing, operating on, and transferring patients and equipment.

In Scene 1, a singular ambulatory patient is illustrated who stands by the patient cart 330 (table, gurney, etc.) and the system 300 (robotics assembly) that are remotely located. In Scene 2, the patient positions himself in a sitting position on the cart 330. In Scene 3, the patient positions himself in the supine position on the cart 330. In Scene 4, the mobile table mover 340 (under-carriage mover) operates to engage with the cart 330 to move the cart 330 with the patient. For example, the table mover 340 can move under the cart 330 (e.g., move into a space underneath the cart 330) to support the cart 330 for movement. The automated table mover 340 can be positioned to automatically transport/steer the cart with the patient.

In Scene 5, the under-carriage mover 340 has transported the cart 330 with the patient to the system 300. The system 300 has rearranged its individual arms 302 into an outstretched upright starting position so as not to yet interact with the patient. The cart 330 has been moved to procedure-arms, and information can be gathered automatically.

In Scene 6, the system 300 can perform various procedures on the patient. In some implementations, voice activated components can be incorporated with various functions with respect to the system 300, the cart 330, the mover 340, and other suitable components. Such different functions may be allowed/authorized based on authority level (i.e. doctor, nurse, patient etc.). Examples of such functions include a) triage: linguistic interaction (discussion with patient), blood pressure, b) further diagnostics: sensory (temperature), tactile (palpation), imaging (ultrasound, CT/X-ray/MRI/echo/sonar), electronic (EEG/ECG), auditory analysis (auscultation), respiratory analysis, etc., c) procedures: administering of physical adjustment, medication, topicals, invasive probing, etc., and d) stereotactic procedures, minimally invasive surgical procedures, respiration, full surgical procedures, outpatient procedures, various monitoring, etc.

In Scene 7, the system 300 has completed its medical interaction with the patient. It can now avail itself for further activities such as sterilization/self-sterilization, equipment-maintenance, equipment-modification, medical interactions with another patient or perform another hospital/medical oriented task.

In Scene 8, the cart 330 with the patient is moved by the undercarriage-mover 340 to either a planned or impromptu routed destination or simply away from the system 330. Conversely, in a non-illustrated embodiment, the system 300 can itself be moved, and from the cart 330 to its next destination. The undercarriage mover 340 has moved the cart 330 with patient and is clear of the system 300, allowing it to avail itself for other usage.

In Scenes 9a-b, the undercarriage mover 340 repositions itself from the cart 330 to another hospital object 332 (e.g., another cart/gurney/table). In Scene 9a, the undercarriage mover 340 is repositioning itself from the patient table 330 to another patient table 332. In Scene 9b, the undercarriage mover 340 is in the repositioning progress.

In Scene 10, the undercarriage mover 340 is engaged with the next object 332 (empty gurney). For example, the undercarriage mover 340 can secure itself to a different hospital object, such as another patient table in the illustrated example. In Scene 11, the undercarriage mover 340 transports the new patient table 332. In Scene 12, the new patient table 332 has been moved by the undercarriage mover 340 to a new desired location, such as adjacent the system 300. The new patient table 332 can contain or not contain a patient.

In some implementations, the objects being moved by the mover 340 can be delivered to an area of the hospital that AI or a human operator would determine can make the best use of it, such as an OR, cleaning facility or patient/emergency intake area. For example, the carts and the table movers carrying the carts can be real-time positionally tracked for route optimization (both automatically or operator assisted) and quality assurance. Once the cart is at its destination, the mobile table mover can join to a different cart for handling or moving.

FIGS. 10A-B illustrates another example arm 350 which can be used for robotic arms, such as the arm 204, 302. The arm 350 provides an alternative structure to the arm 204, 302 and is configured as a truss-arm structure. The arm 340 includes a plurality of robotic linkages that employ truss-geometry to improve stability and distribution of mechanical load/stresses. The truss-arm adjoining end can be elevated and depressed (electronically) and its housing arm can be rotated in-plane and translated along an axis, thereby providing emulated cylindrical coordinates. An example of stress and stability of truss structures can be found in M. Nwe Nwe, *Topology Optimization of Truss Structures Considering Stress and Stability Constraints*, Structures Congress 2019, April 2019, Orlando, Fla., the disclosure of which is incorporated herein by reference.

For example, the arm 350 includes an arch translational pole 352 secured to a base 354 (e.g., an arch). Arm linkages 356 may be pivotally coupled in series, and the assembly of the arm linkages 356 can have an adjoining end 358 that is pivotally coupled to the arch translational pole 354. Further, the assembly of the arm linkages 356 has an operational end 360 configured to mount an instrument (e.g. tool). As illustrated in FIG. 10B, the base 354 can rotate along arch rotation directions 362. Further, the arch translational pole 352 can be configured to move the arm linkages 356 therealong (e.g., elevating or lowering the arm linkage assembly along a longitudinal axis of the pole, or directions 364).

Referring to FIGS. 11-13, yet another example TARS system 400 is illustrated. FIGS. 11A-F schematically illustrate an example operation of the system 400 that may be in different positions. The system 400 is configured as a Robotic Accordion Arm (RAA) system. The system 400 includes an arm assembly 410 that can be movably coupled with an overhead support 420, such a ceiling, a canopy, or other suitable structure for supporting the arm assembly 410. For example, the arm assembly 410 can move along the surface of the overhead support 420 above a patient lying on a bed, so as to be positioned at different locations with respect to the patient. As illustrated in FIGS. 11A-F, the arm assembly 410 can be repositioned (programmatically or automatically) from an area above the patient by hanging on the overhead support 420 (e.g., ceiling or canopy). The arm assembly 410 can be autonomously repositioned on the overhead support 420. Alternatively or in addition, the arm assembly 410 can be programmed for automatic movement along the overhead support 420. Alternatively or in addition, the arm assembly 410 can be manually repositioned on the overhead support 420.

The arm assembly 410 has a distal end (e.g., tool end) configured to attach an instrument 430, such as one or more imaging devices, sensors, surgical instruments, etc. In the illustrated example, the arm assembly 410 mounts an imaging device at the distal end. In other examples, the distal end can hold other instruments, such as instruments that perform a variety of actions including radiation therapy or other interactions as described herein.

The arm assembly 410 is configured to receive a variety of inputs for operation. For example, the arm assembly 410 can receive an input for participating in an automatic surgery. In addition or alternatively, the arm assembly 410 can receive an input for cooperating with a human staff to position the arm assembly 410 to a desired anatomical region. In addition or alternatively, the arm assembly 410 can be configured to enable the arm assembly 410 to be manually repositioned. The arm assembly 410 can be configured to receive various types of human commands, such as physical inputs, verbal inputs, etc.

Figure 11A:
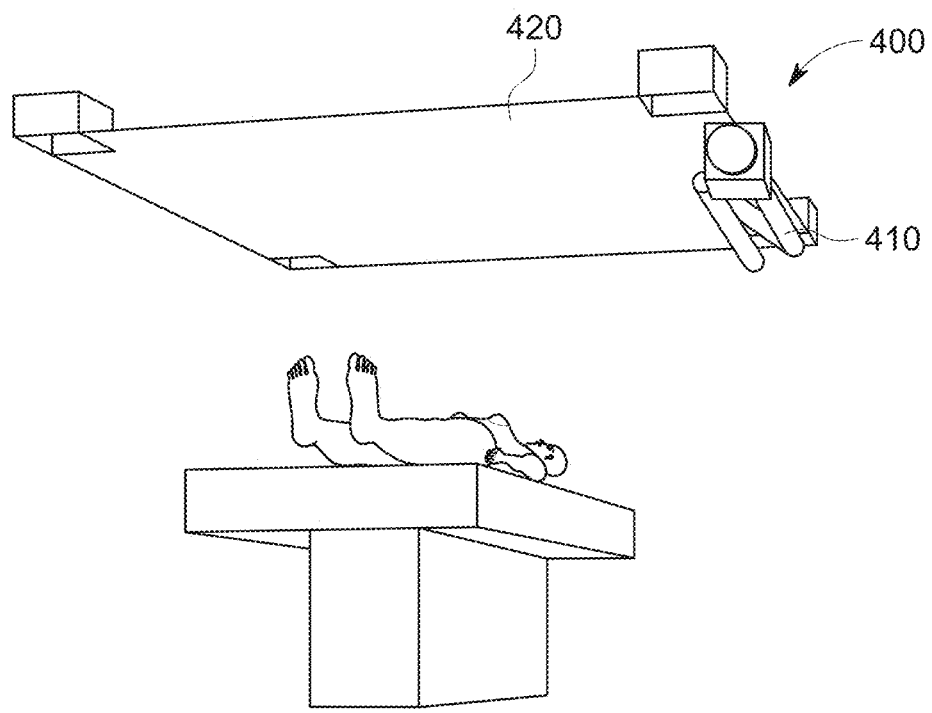
FIGS. 11A-F illustrate perspective views of another example TARS system.
Figure 11B:
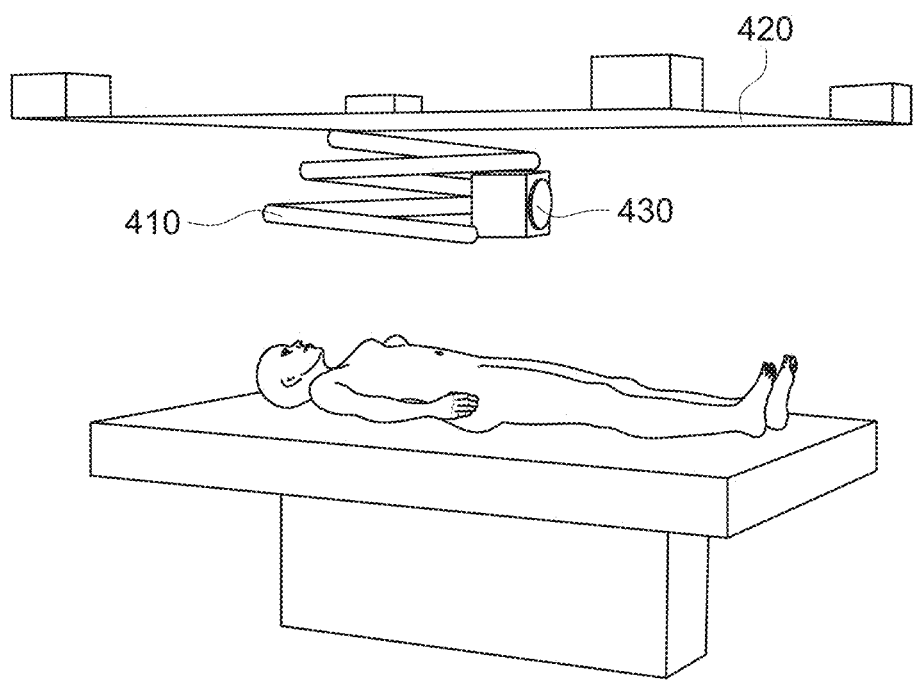
Figure 11C:
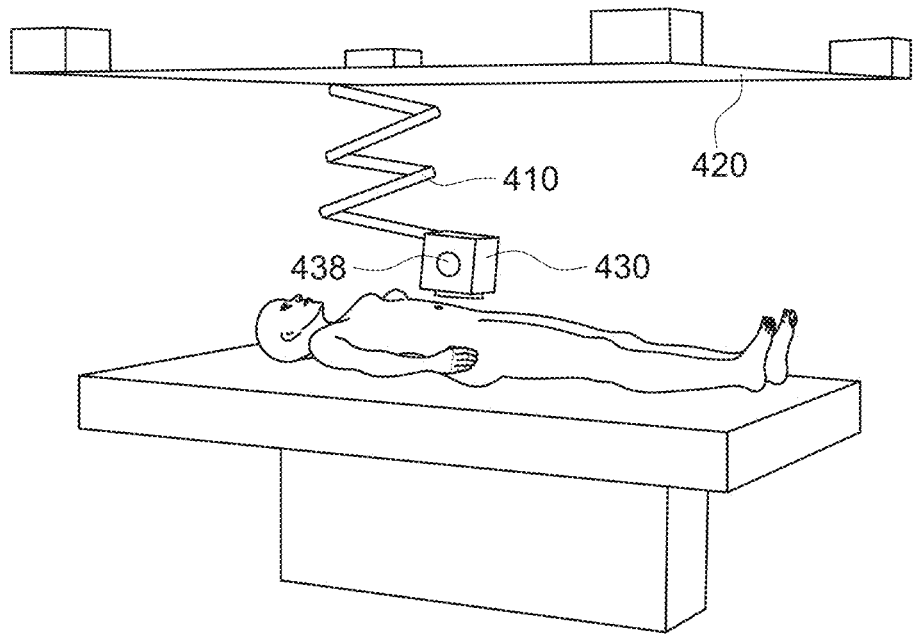
Figure 11D:
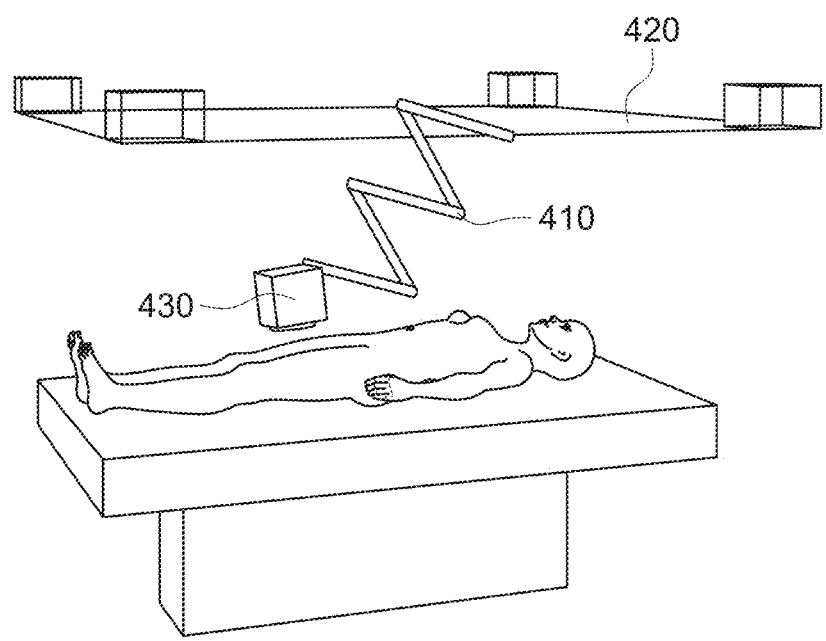
Figure 11E:
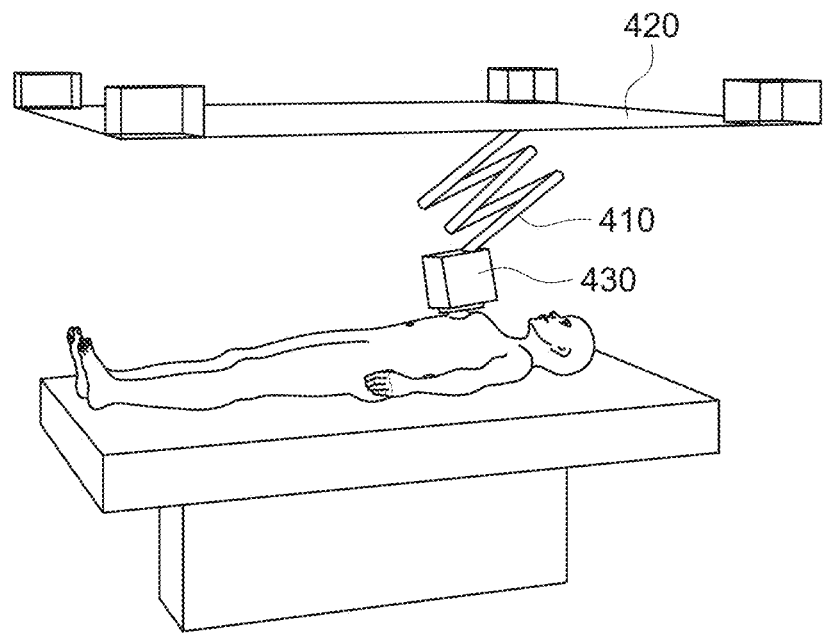
Figure 11F:
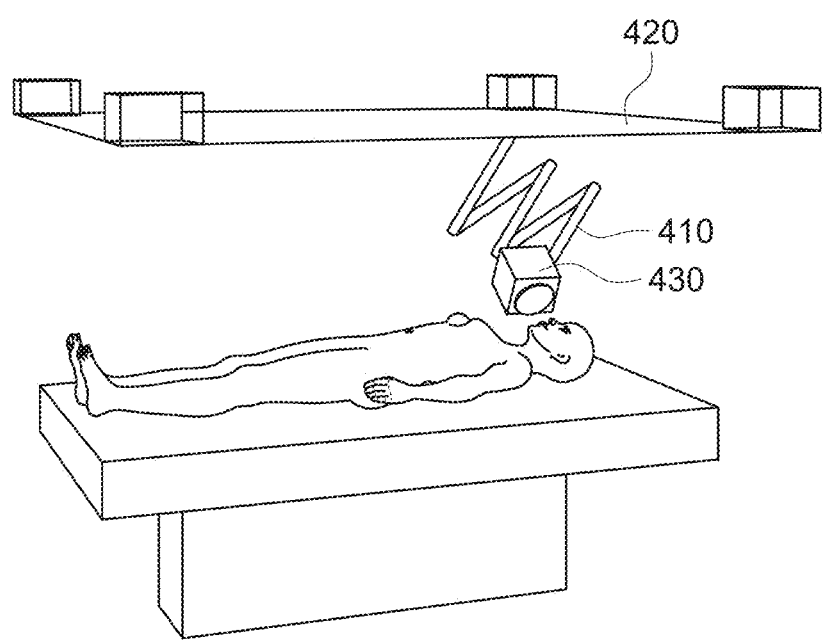

Referring to FIGS. 11A-F, the arm assembly 410 can be arranged at the edge of the ceiling canopy 420 above the patient on an operating room table (FIG. 11A). The arm assembly 410 can reposition to desired coordinates above the patient (FIG. 11B). The arm assembly 410 can extend to a desired position on the patient (FIG. 11C). The arm assembly 410 and/or the instrument 430 (e.g., image device) can reposition to different areas over the patient (FIGS. 11D-F). The arm assembly 410 and/or the instrument 430 can adjust their positions as appropriate. The operations of the arm assembly 410 and/or the instrument 430 can be performed autonomously, automatically as programmed or commanded, and/or manually.

The system 400 further includes one or more controllers 438 provided in desired locations and configured to permit for the system 400 (or the components thereof) to autonomously perform desired surgical procedures. Such controllers 438 can run one or more software programs that are executed to cause the system 400 (or the components thereof) to perform various autonomous operations. In the illustrated example, the controller 438 is provided with the instrument attached. Alternatively, the controller can be arranged in other components in the system.

Figure 12A:
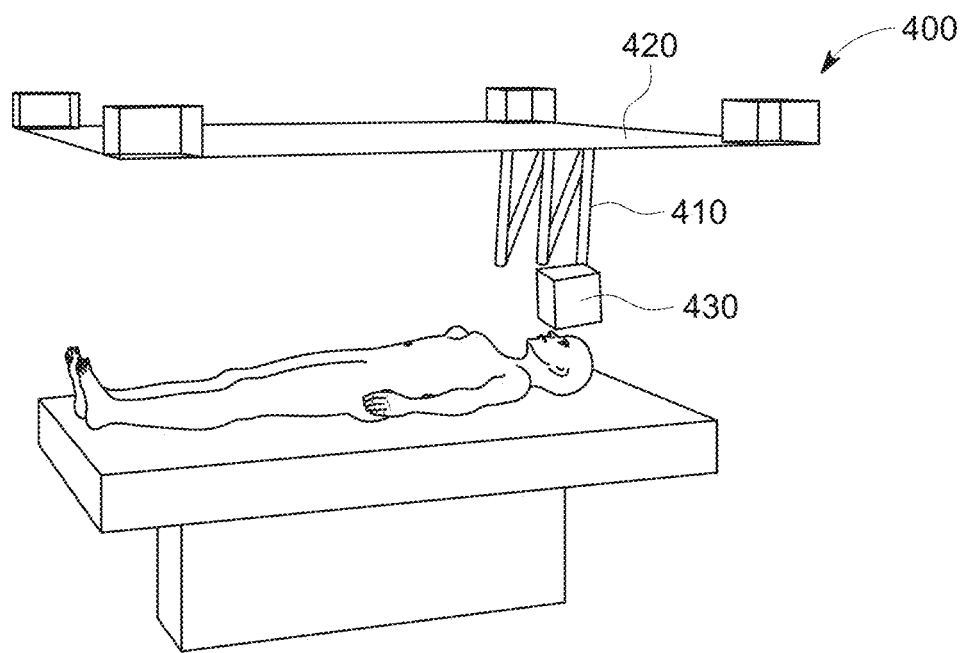
FIGS. 12A-B illustrates the system depicted in FIGS. 11A-F using dynamic positioning to rotate around a patient's head.
Figure 12B:
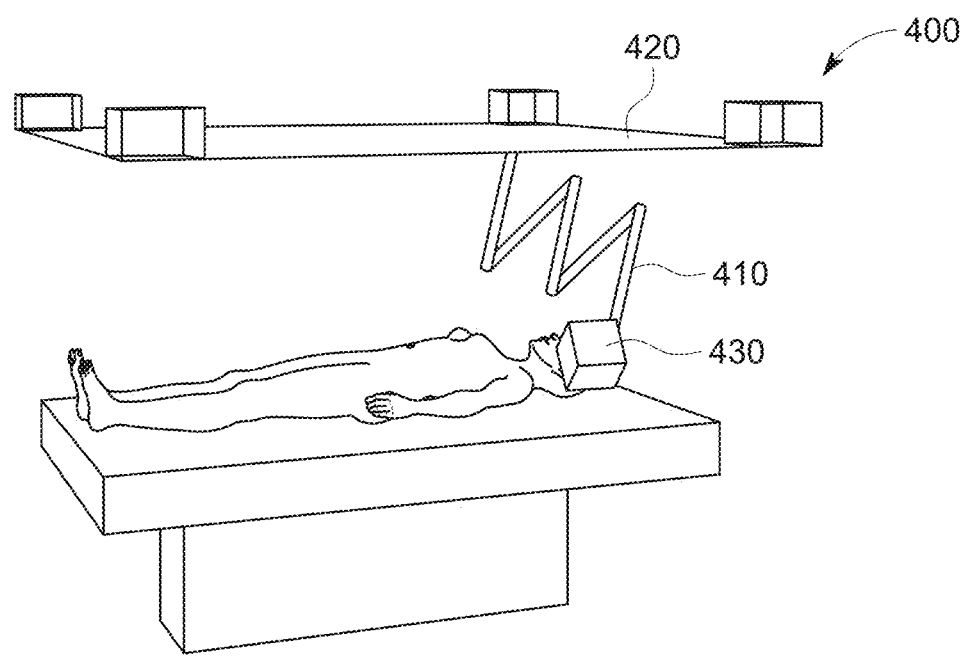

FIGS. 12A-B illustrate that the arm assembly 410 of FIGS. 11A-F dynamically reposition rotate around the patient's head. For example, the arm assembly 410 descends from the ceiling canopy and positions itself over the patient's head (FIG. 12A). The instrument at the distal end of the arm assembly 410 can be an imager, therapeutic radiation/ultrasound, robotic tools, and/or other suitable tools. The arm assembly 410 can be further extended and outstretched, and move (e.g., clockwise) around the patient's head (FIG. 12B).

Figure 13A:
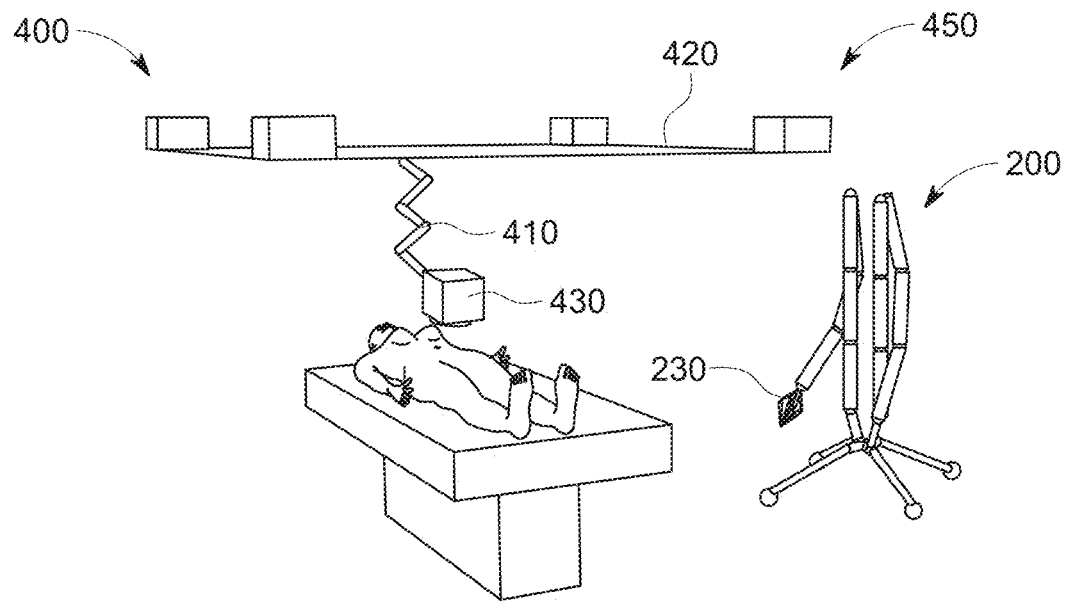
FIGS. 13A-E illustrates perspective views of another example TARS system employing the system of FIGS. 4A-F and the system of FIGS. 11A-F for performing different phases of an operative preparation and procedure.

FIGS. 13A-E schematically illustrate example operations of a combined system 450 employing the system 200 (MRD system) of FIGS. 5A-E and the system 400 (RAA system) of FIG. 11A-F, which provide cooperative and synergistic operations. The systems 200, 400 can perform different phases of an operative preparation and procedure. For example, as illustrated in FIG. 13A, the arm assembly 410 of the RAA system 400 descends from the ceiling canopy 420 above the patient as the MRD system 200 moves towards the patient. The MRD system 200 can be equipped with an instrument 230 (e.g., integrated delta robot as shown in the system 100).

Figure 13B:
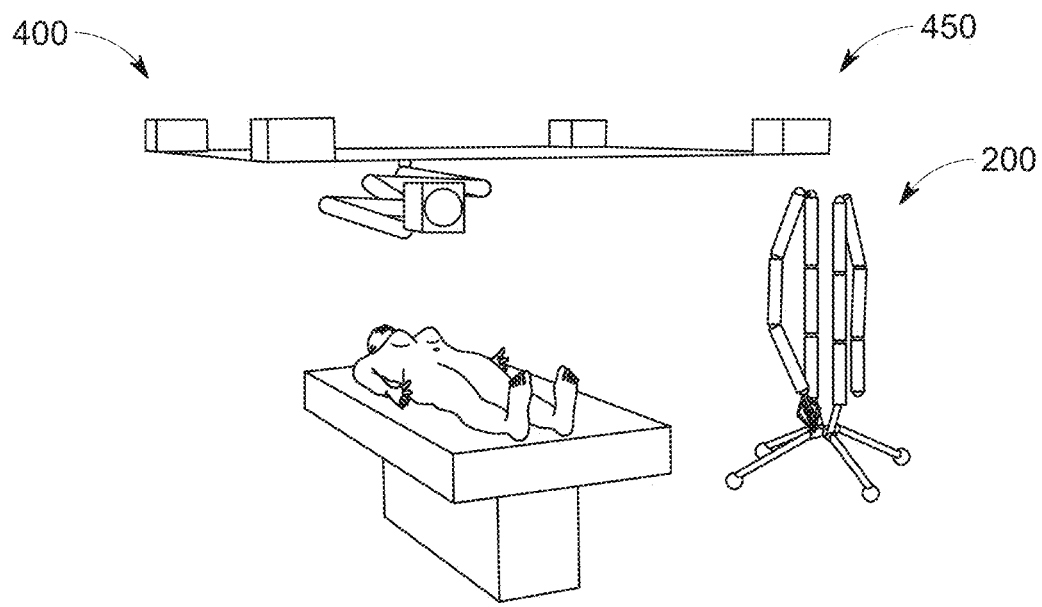
Figure 13C:
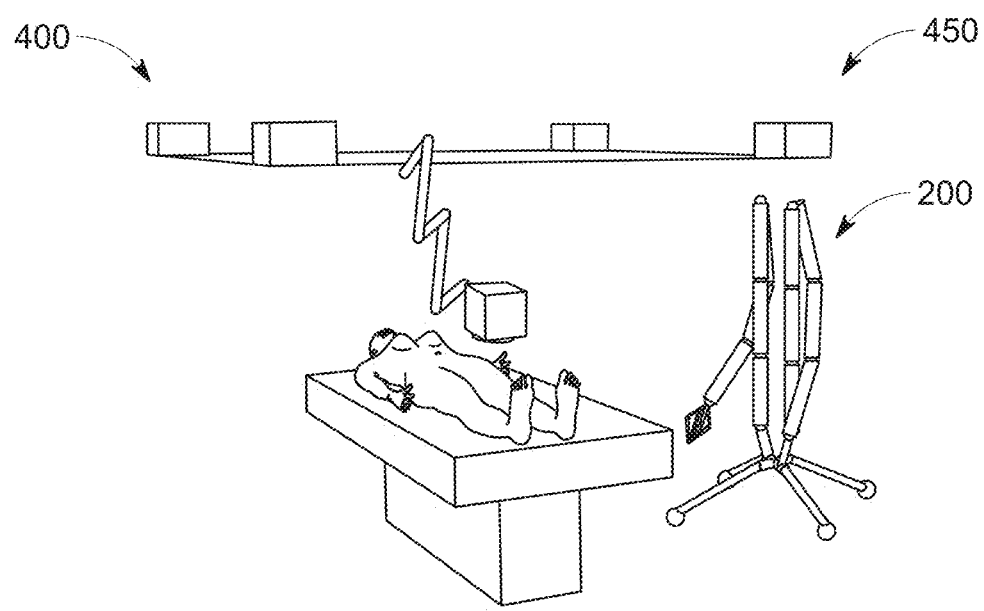
Figure 13D:
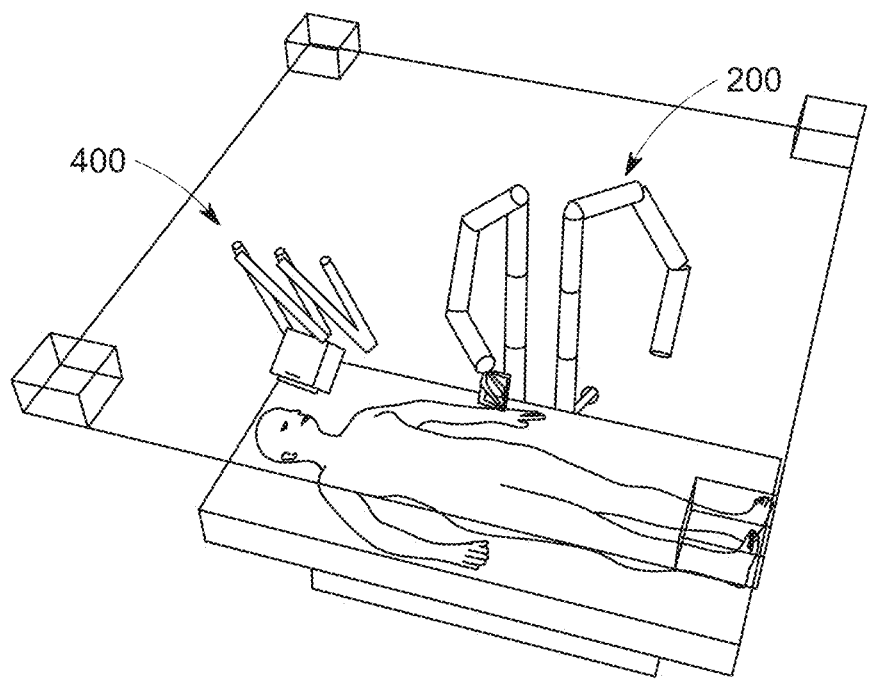
Figure 13E:
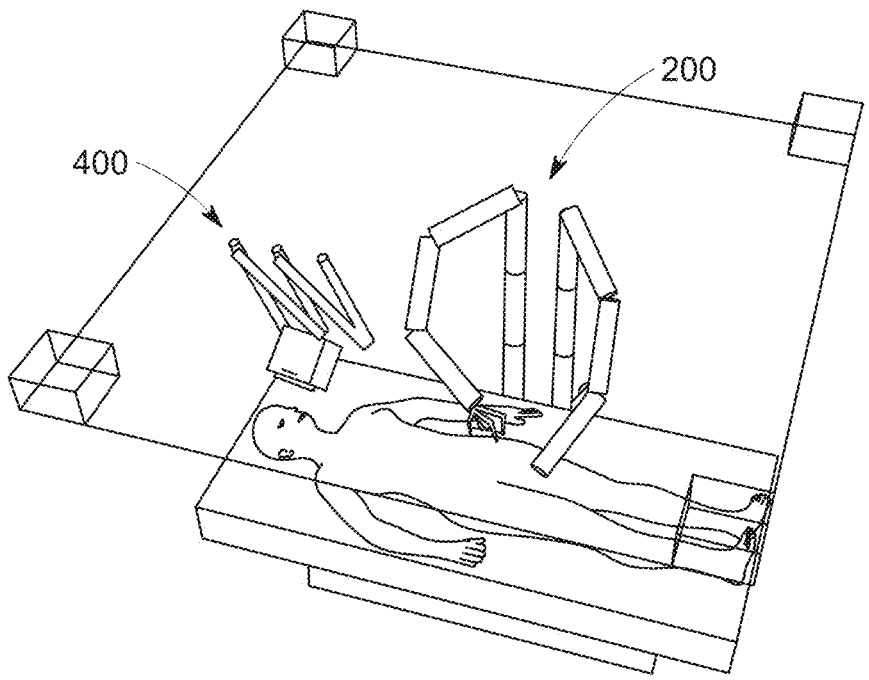

In FIG. 13B, the arm assembly 410 is contracted (nestled) to an overhead position, and the MRD system 200 with the delta robot 230 is in a resting position. In FIG. 13C, the arm assembly 410 is in an extended position positioning itself above the patient's torso. In FIG. 13D, the arm assembly 410 performs a desired operation (e.g., imagery or other assigned programmed functions) on the patient's head while the MRD system 200 is operating with the delta robot 230 on the patient's forearm. In FIG. 13E, three simultaneous procedures are being performed by the RAA system 400 and by the two arms of the MRD system 200. One arm is operating with the delta robot 230, and the other arm is using its cylindrical linked arm for imagery/surgery etc., thereby enhancing the efficiency and accuracy of the procedure.

In other examples, the combined system can include any combination of various systems, such as one or more of the systems described herein (e.g., the system 100, 200, 300, 400, 500, 900, etc.) and other suitable surgical systems. The combined system can provide cooperative and synergistic autonomous robotic surgery on the same or different body parts on a single patient, either sequentially or simultaneously.

Figure 13F:
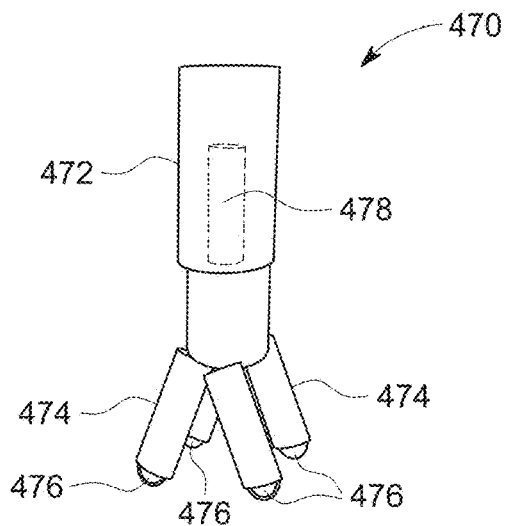
FIG. 13F-H illustrate example mobile bases.
Figure 13G:
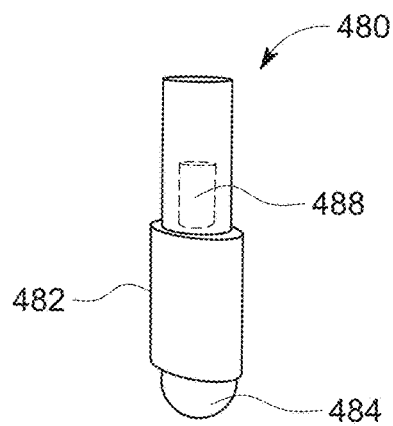
Figure 13H:
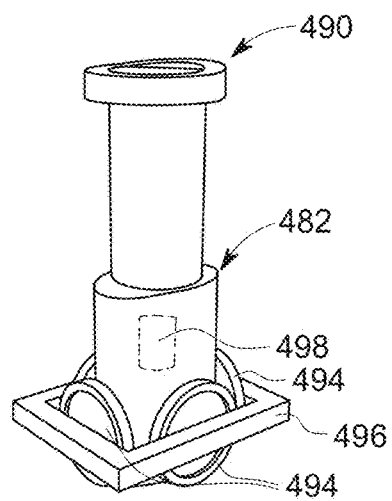

Referring to FIGS. 13F-H, various examples of a mobile base are illustrated which can be used to transport various components, devices, and systems that need to be moved, such as one or more of the systems described herein (e.g., the system 100, 200, 300, 400, 500, 900, etc.) and other suitable surgical systems. For example, the mobile base can be used to implement the base 202 of the system 200, the patient gurneys, carts or tables 330, 332, the table mover 340, or other suitable devices, components, or systems.

In FIG. 13F, an example mobile base 470 includes a body 472 with multiple legs 474 extending from the body 472, and wheels 476 movably mounted at the distal ends of the legs 474. The legs 474 are provided to stabilize the body 472 at rest and while moving. In some implementations, the body 472 is configured to telescope to adjust a vertical length. The wheels 476 can be configured to provide self-balancing and mobility of the mobile base 470 and other structures (e.g., instruments, arms, etc.) connected to the mobile base 470. Further the mobile base 470 includes sensors and/or electronics 478 configured to provide active counterweight and/or stabilization of the mobile base 470 and such other structures connected to the mobile base.

In FIG. 13G, another example mobile base 480 includes a body 482 and a single wheel 484 movably mounted at the distal end of the body 482. In some implementations, the body 482 is configured to telescope to adjust a vertical length. The wheel 484 is be configured to provide self-balancing and mobility of the mobile base 480 and other structures (e.g., instruments, arms, etc.) connected to the mobile base 480. For example, the wheel 484 can be a spherical ball. Further the mobile base 480 includes sensors and/or electronics 488 configured to provide active counterweight and/or stabilization of the mobile base and such other structures connected to the mobile base.

In FIG. 13H, yet another example mobile base 490 includes a body 492 with multiple wheels 494 movably attached around the body 492 at its distal end. For example, the mobile base 490 includes a skirt 496 that further supports the wheels 494 along with the body 492. In some implementations, the body 492 is configured to telescope to adjust a vertical length. The wheels 494 can be configured to provide self-balancing and mobility of the mobile base and other structures (e.g., instruments, arms, etc.) connected to the mobile base. Further the mobile base 490 includes sensors and/or electronics 498 configured to provide active counterweight and/or stabilization of the mobile base and such other structures connected to the mobile base.

Figure 13I:
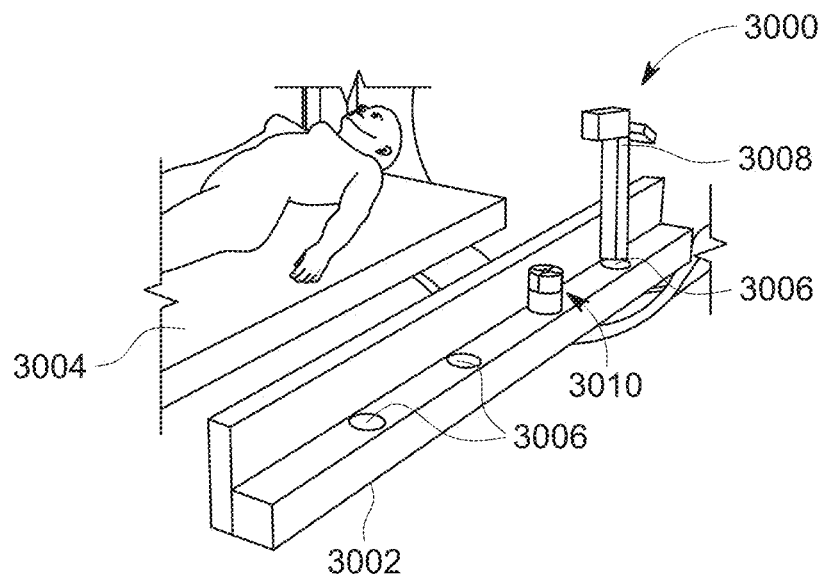
FIGS. 13I-K illustrate an example instrument support rail system for removably holstering and securing surgical instruments.
Figure 13J:
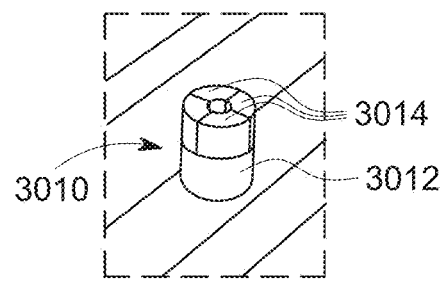
Figure 13K:
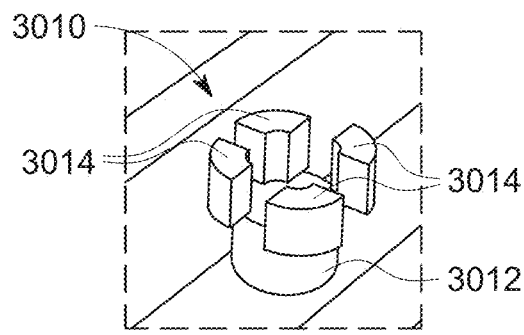

Referring to FIGS. 13I-K, an example instrument support rail system 3000 is illustrated which is configured to removably holster and secure surgical instruments. Instruments held at the rail system 300 can be accessible by practitioners and robots for whom the instruments can be interchanged. In some implementations, the instrument support rail system 3000 includes a longitudinal rail body 3002 which, for example, can be arranged adjacent a patient table 3004 for surgical operation. The rail body 3002 can include a plurality of instrument recesses 3006 each configured to receive and support at least a part of an instrument, such as a modular endoscope 3008 in the illustrated example.

The support rail system 3000 can further include a controllable instrument fastener 3010 configured to selectively engage and release an instrument. The instrument fastener 3010 can include a body 3012 and a plurality of gripping blocks 3014 movably coupled to the body 3012. The body 3012 can be configured to be inserted into the recesses 3006. The gripping blocks 3014 can be arranged to engage an instrument at or around a center of the body 3012. The gripping blocks 3014 can be controlled to move radially outwards relative to the body to open the center of the body to receive an instrument, and radially inwards to hold the instrument. An instrument held at the instrument fastener 3010 can be held until it is removed and conveyed to another manipulator.

Figure 14:
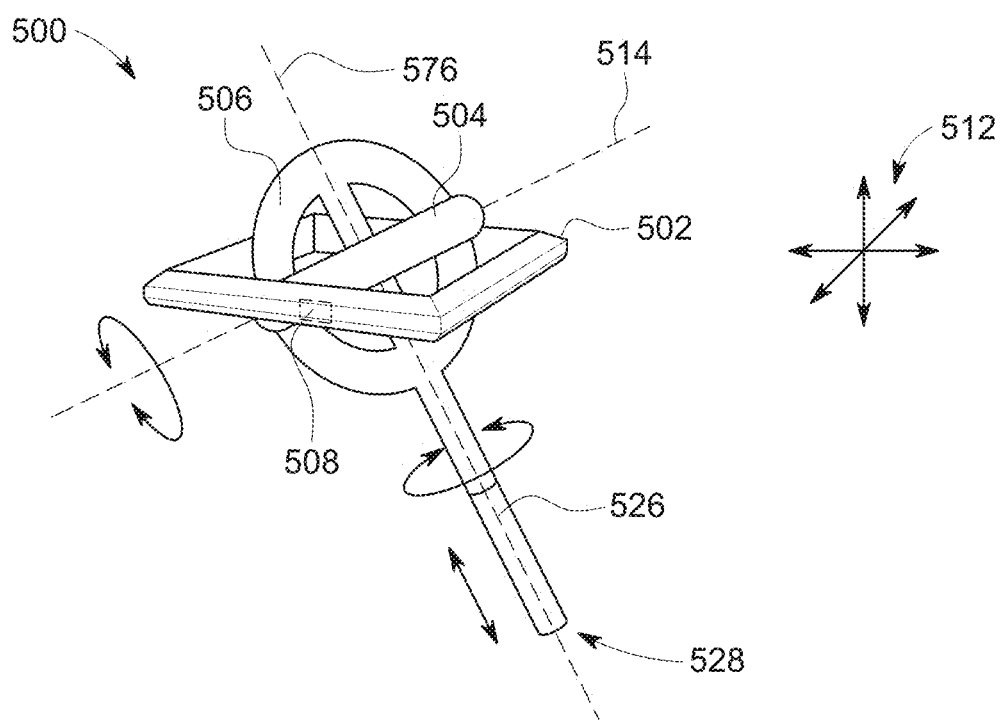
FIG. 14 illustrates a perspective view of another example TARS system including a Gimble-Telescoping arm (GTA).

Referring to FIGS. 14-15, yet another example TARS system 500 is illustrated. FIG. 14 is a schematic perspective view of a TARS system 500, which is configured as a Gimbal-Telescoping Arm (GTA) system. The system 500 is configured to provide a gimbal orientation, and includes a base 502 and two rotators 504 and 506. A first rotator 504 is coupled to the base 502 and rotatable along a first axis 514 with respect to the base 502. A second rotator 506 is coupled to the first rotator 504 and rotatable along a second axis 516 with respect to the first rotator 504. The base 502 can be movably mounted to a supporting structure, such as a ceiling, canopy, or other suitable structures, as illustrated in FIG. 15. The base 502 can displace with respect to such a supporting structure, for example along x-y-z axes 512.

In some implementations, the second rotator 506 includes an adjustable arm 526. For example, the arm 526 is configured to telescope to extend and retract its length. The arm 526 has a distal end (tool end) 528 configured to mount various instruments. The arm 526 can be configured to be straight. The arm 526 can be in other configurations, such as curved configurations. When the base 502 is mounted to a ceiling, the tool end 528 can be extended from the ceiling.

The base 520 is configured to be a guidance box that assists in rectilinearly positioning the system 500 along ceiling guidance rails (FIG. 15). The combination of these three positioning elements (the base 502 and the first and second rotators 504 and 506) can permit the system 500 to move along arbitrary spatial coordinates. The telescoping arm 526 is employed to reach the patient body and can have a tool affixed to it in order to provide a variety of functions identical to those mentioned for all the other embodiments.

The system 500 further includes one or more controllers 508 provided in desired locations and configured to permit for the system 500 (or the components thereof) to autonomously perform desired surgical procedures. Such controllers 508 can run one or more software programs that are executed to cause the system 500 (or the components thereof) to perform various autonomous operations. In the illustrated example, the controller 508 is provided in the base 502. Alternatively, the controller 508 can be arranged in other components in the system.

Referring FIGS. 15A (15A-A and 15A-B), the system 500 can be supported by a supporting structure 540, such as a ceiling canopy. FIG. 15A further illustrates the system 400 that is supported by the supporting structure 540, so that the GTA system 500 can be used together with the RAA system 400, thereby providing synergistic cooperation between the two systems. They can each perform a variety of functions, however there may be end tools more suitable to one embodiment than the other. Functions for either can include imaging, radiation, surgery, clamping/holding, device placement etc.

As illustrated in Scene 1, the system 500 is positioned on a guidance rail system 542 of the supporting structure 540 (e.g., a ceiling canopy). Further, the system 500 is positioned in close proximity from the RAA system 400 that is descending. The RAA system 400 is extending its arm hovering over the patient. In Scene 2, the RAA system 400 further moves rostrally, and the GTA system 500 orients its telescopic arm towards the patient. In Scene 3, the GTA system 500 further extends its telescopic arm to perform a function.

Figure 15B:
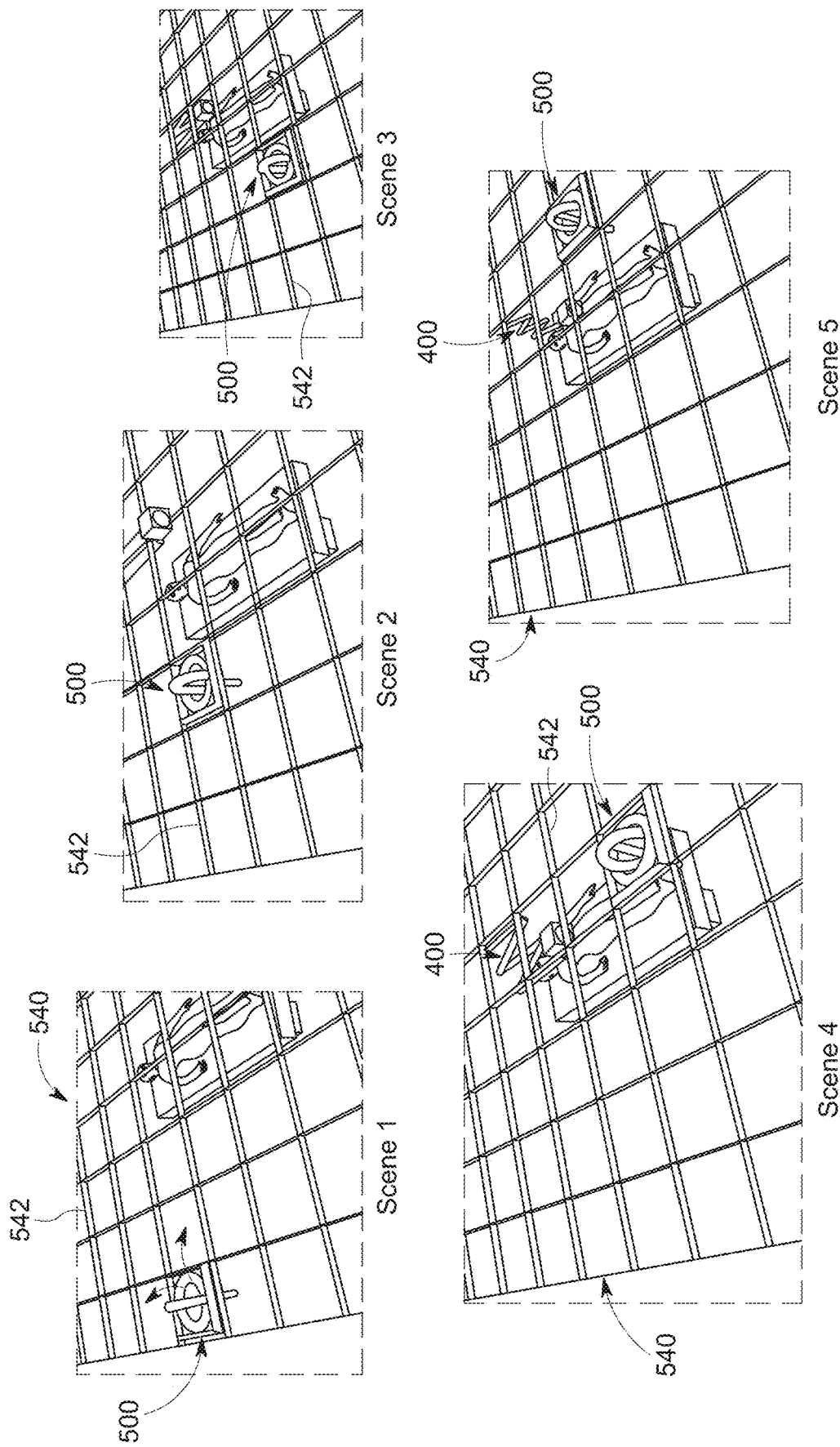

FIG. 15B is a schematic over-head view of the system of FIG. 15A. The ceiling structure is illustrated to be transparent for illustrative purposes here. As described herein, the supporting structure 540 can include a guidance rail system 542 configured to movably support the GTA system 500 and/or the RAA system 400. For example, the guidance rail system 540 provides rails to define cells in a gridded configuration, and the systems 400, 500 can move from one cell to another to change their locations.

Some example mechanisms are configured to actuate the motion of a GTA or instrument within the support rail rectangular (or based on non-rectangular coordinates such as polar, spherical, etc.) grid structure. In the most simple manner, small wheels of diameter close to matching the grid-rail thickness can be fit onto orthogonal sides of the GTA (e.g., a set of wheels that are actuated to accomplish motion in the X-direction and a set of wheels at an angle to that set (90 deg/orthogonal in the rectangular coordinate system) in the Y-direction. The force necessary to rotate these wheels can either arise from a stored-power within the GTA, or delivered by a wired or wireless connection to an external source through either the grid-rails or from another source that can either be mobile or fixed nearby—most simply vertically situated above the GTA (or instrument "farm"), however can be envisaged as a mobile battery unit that itself can be occasionally or permanently connected via wire or wirelessly transmitted power to a more reliable power source. In the same manner, in a rectangular grid system, other easily manufactured components can be affixed to the GTA and grid in order for them to both mate and deliver propulsion. One example can be a pneumatic tube system that can precisely control an internal mass by positive or negative pressures, this mass being coupled either mechanically or if safe, magnetically to the GTA. In a similarly derived manner, the requirements for pressure based locomotion can be replaced by an electric/magnetic motor system that controls the position of the mass that is coupled to the GTA. These "third rails" (i.e. power supple, the pneumatic tube or linear induction track) would be integrated with each grid line.

Figure 16A:
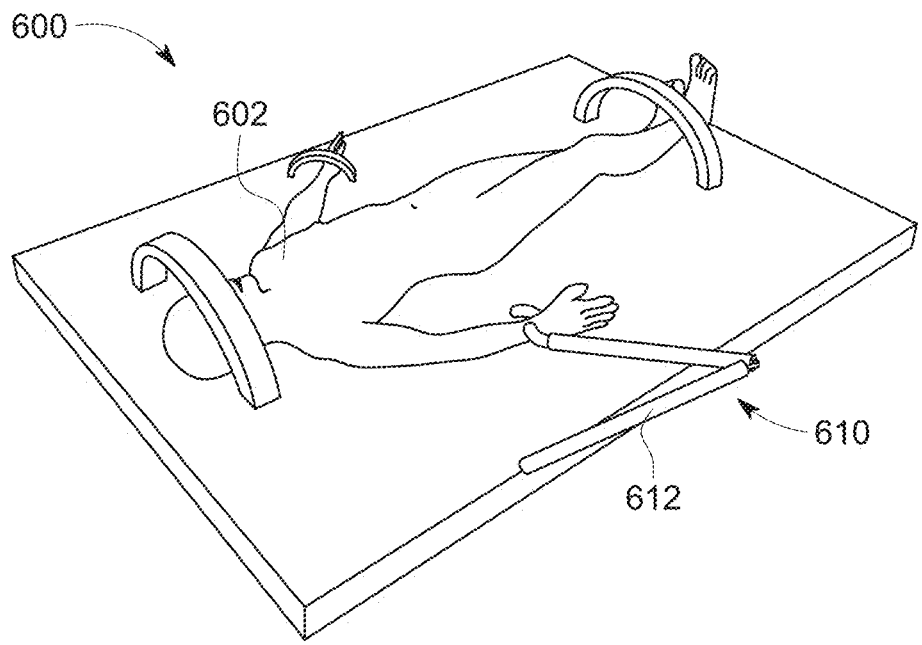
FIGS. 16A-C illustrate perspective views of an example autonomous limb positioner (ALP), which is configured for use with various embodiments of the TARS system described herein.
Figure 16B:
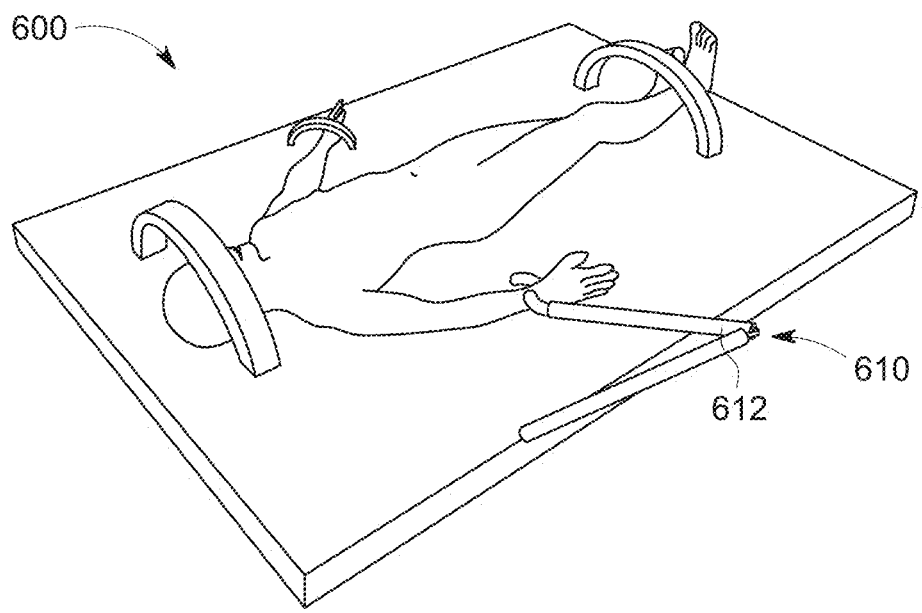
Figure 16C:
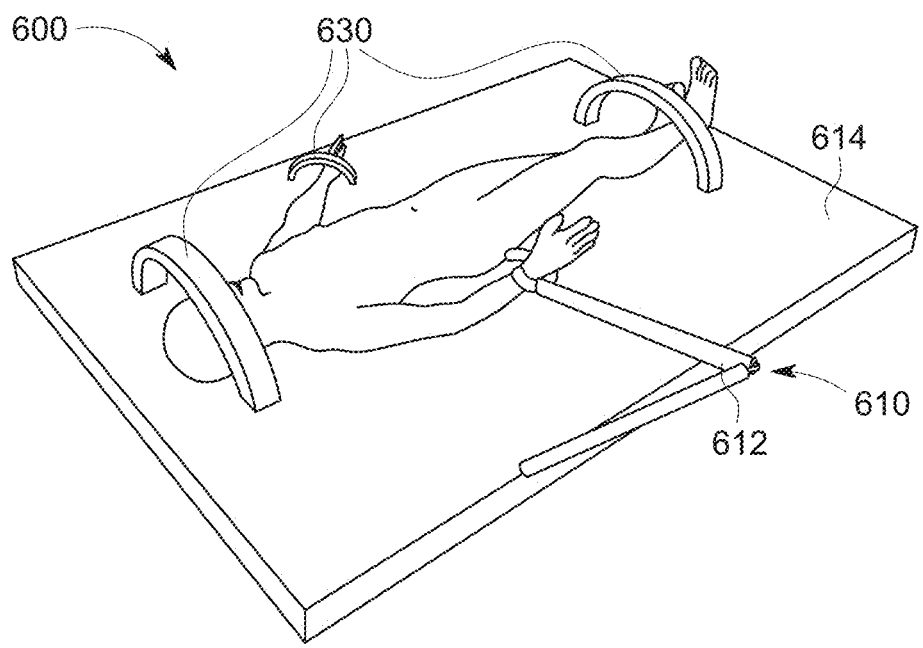

FIGS. 16A-C schematically illustrate an example autonomous limb positioner (ALP) 600, which may be used on its own or with various embodiments of TARS systems. For example, the autonomous limb positioner (ALP) can work synergistically with any of the TARS systems described herein (e.g., the system 100, 200, 300, 400, 500, 900, etc.).

The APL 600 is configured to position an involuntary patient or limbs in an assisted and automated manner. For example, the APL 600 can be used for an anesthetized patient 602. In some implementations, the APL 600 is configured as a robotic arm 610. The robotic arm 610 can include a planar kinematic chain 612 with a serial and/or parallel linkage. Alternatively, the robotic arm 610 can include a non-planner kinetic chain. The chain 612 can be movably coupled to a mobile or stationary base, such as a hospital bed 614.

The robotic arm 610 can support and control the position (and/or orientation) of a patient (or the patient's limb), or place it at rest. For example, the robotic arm 610 includes a limb support arch 620, which, for example, may be used to support the patient's wrist or forearm and adjust its position and angle, as illustrated in FIG. 16C.

The APL 600 can include one or more multi-functional arches 630 surrounding the forehead and various extremities of the patient (e.g., the forehead, ankles, wrists, etc.). The arches 630 can include one or more stationary or non-stationary components configured to perform various functions, such as imaging, miscellaneous treatments, etc., which can be applied to a patient at any time (triage, treatment, assessment, surgery, outpatient, etc.).

Figure 17A:
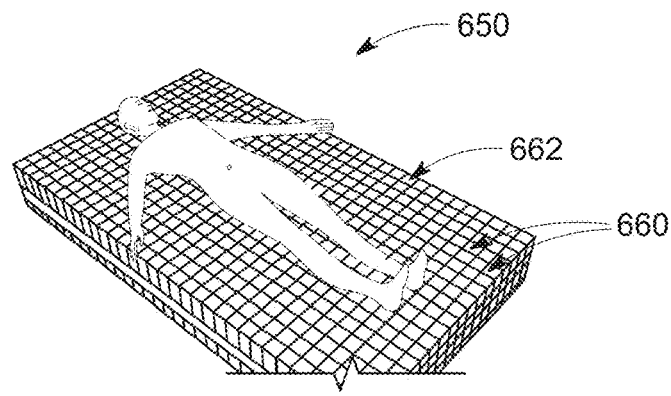
FIGS. 17A-C illustrate perspective views of another example autonomous limb positioner (ALP) utilizing voxelated sensor/actuator components.
Figure 17B:
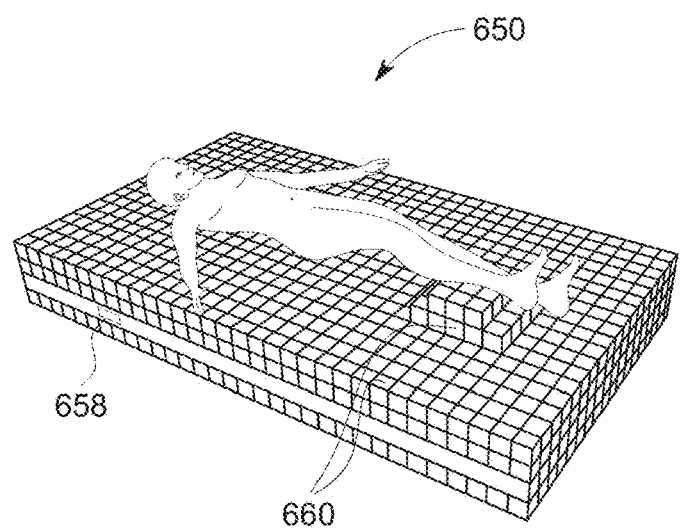
Figure 17C:
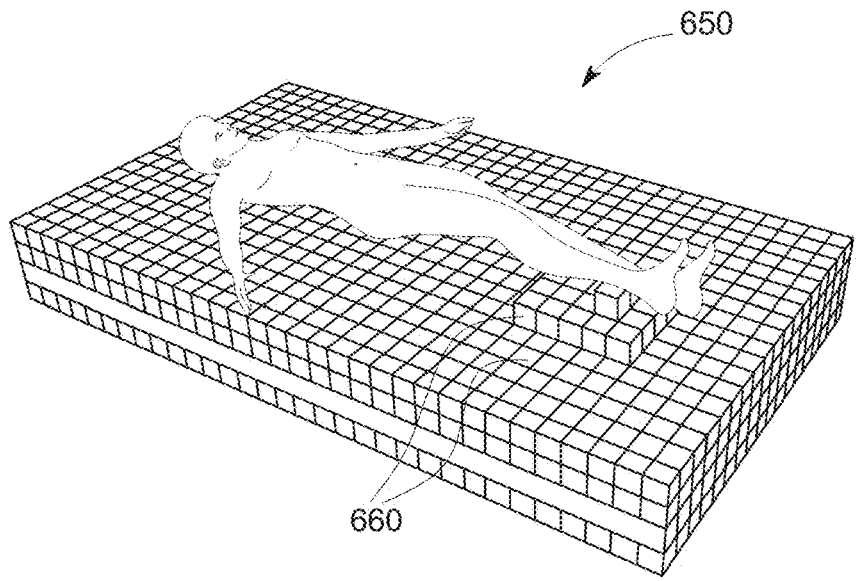

FIGS. 17A-C schematically illustrate another example autonomous limb positioner (ALP) 650, which may be used on its own or in conjunction with various embodiments of TARS system. For example, the autonomous limb positioner (ALP) 650 can work synergistically with any of the TARS systems described herein (e.g., the system 100, 200, 300, 400, 500, 900, etc.).

The ALP 650 includes a plurality of voxelated sensor/actuator components 660 that provide a subject rest surface 662. For example, the rest surface 662 for a subject can be partitioned with the sensor/actuator components 660 (for example, voxelated into cubic sensor/actuator components) that can autonomously sense the skeletal configuration of the subject supported on the rest surface. The components 660 can be adjusted electronically (simultaneously, in concert, or in succession) to raise or lower parts (e.g., limbs, extremities, head/neck/trunk sections, etc.) of the subject to a programmed position. The ALP 650 can be used to position a subject and further provide safeguards to reduce the probability of further injury.

In FIG. 17A, a patient is supported on a resting surface 662 of the ALP 650 that includes a plurality of voxelated sensor/actuator components 660. The components 660 can be programmed to automatically move themselves to provide desired positions of a subject whose posture and condition are detected on the resting surface 662. In FIG. 17B, the components 660 are automatically operated to raise or angle limbs in a manner that reduces the probability of further injury. FIG. 17C illustrates a different operation of the components 660 against a subject.

The system 650 further includes one or more controllers 658 provided in desired locations and configured to permit for the system 650 (or the components thereof) to autonomously perform desired surgical procedures. Such controllers 658 can run one or more software programs that are executed to cause the system 650 (or the components thereof) to perform various autonomous operations.

Referring to FIGS. 18-19, an example arch 700 is illustrated, which can be used for the C-arms and other arches described herein.

Figure 18A:
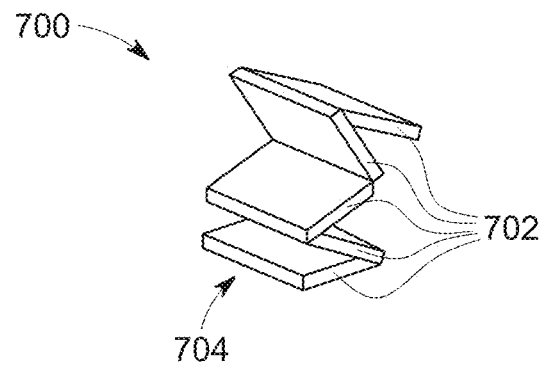
FIGS. 18A-C illustrate perspective views of an example Multi-Functional Compaction Arch (MFCA).
Figure 18B:
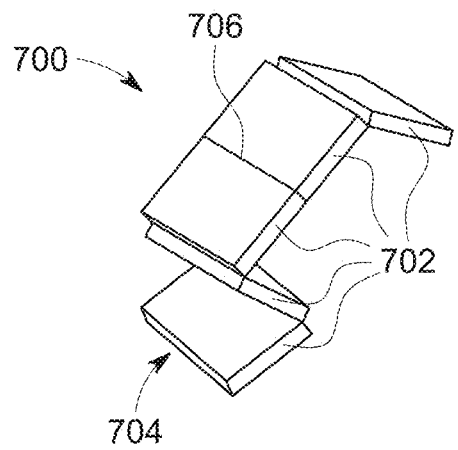
Figure 18C:
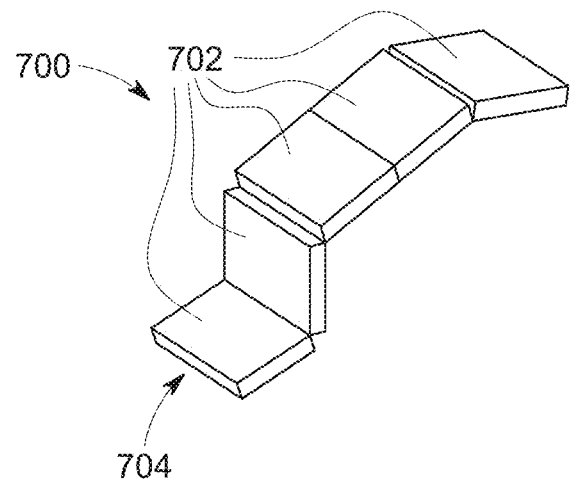

FIGS. 18A-C schematically illustrate a Multi-Functional Compaction Arch (MFCA) 700 in different stages of positioning. The arch 700 includes a plurality of actuation/manipulation components 702 that are coupled to be foldable. The components 702 can include transducers for various functions. The components 702 can be folded in stack to provide a compactable arch. The arch 700 can be attached to a stationary or mobile structure at one end (e.g., an end 704) so that the arch 700 can be folded and expanded with respect to the structure. Each of the components 702 can include one or more transducers and controllers that are programmed to perform various functions, such as non-invasive or invasive imaging, surgical operations, and assessments.

In FIG. 18A, the MFCA 700 is in or close to a compacted mode. In FIG. 18B, the MFCA 700 is expanded and partially opening. In FIG. 18C, the MFCA 700 is further opening.

The components 702 can be connected in a serial configuration. Adjacent components 702 can be pivotally coupled at a hinge portion 706. The hinge portion 706 can be configured in various manners, such as using various types (mechanical, electrical, etc.) of hinges, joints or other suitable mechanisms.

FIGS. 19A-E illustrate the MFCA 700 autonomously positions itself over a patient in a variety of stages. The advantages of the MFCA 700 is that it can easily be stowed while not in use, or be used as a mobile unit (e.g. emergency medical service, light surgery, diagnostics), making it ideal for a geometrically constrictive scenario such as a transport carriage. The MFCA 700 can further be configured to autonomously interact with a patient, permitting for a practitioner to remotely work from such autonomous operation (e.g., remote actions/imaging/surgery/diagnostics). Articulating elements are not depicted in FIGS. 19A-E, but various components described herein can be used with the MFCA 700.

Figure 19A:
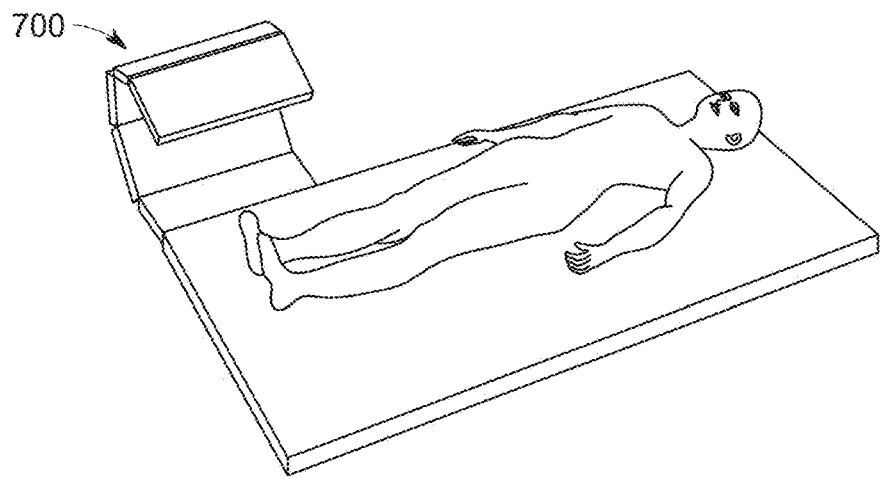
FIGS. 19A-E illustrates the example MFCA of FIGS. 18A-C autonomously positioning itself over a patient in a variety of stages.
Figure 19B:
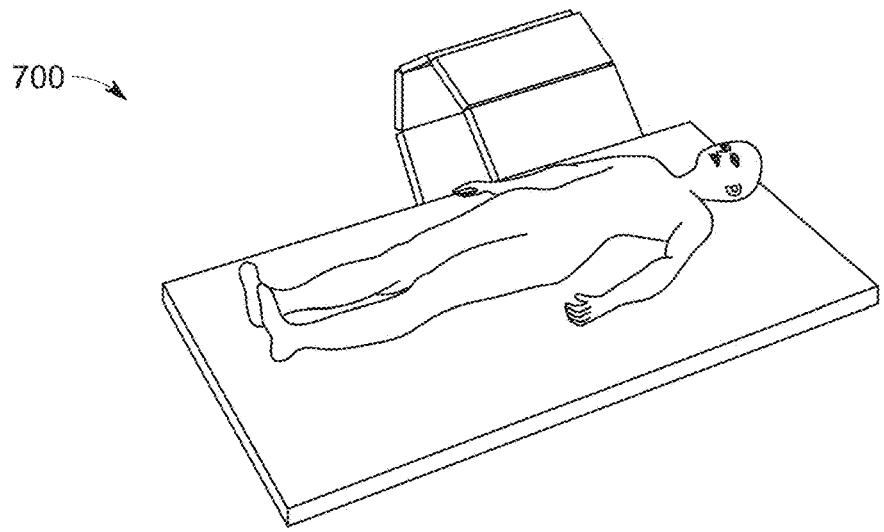
Figure 19C:
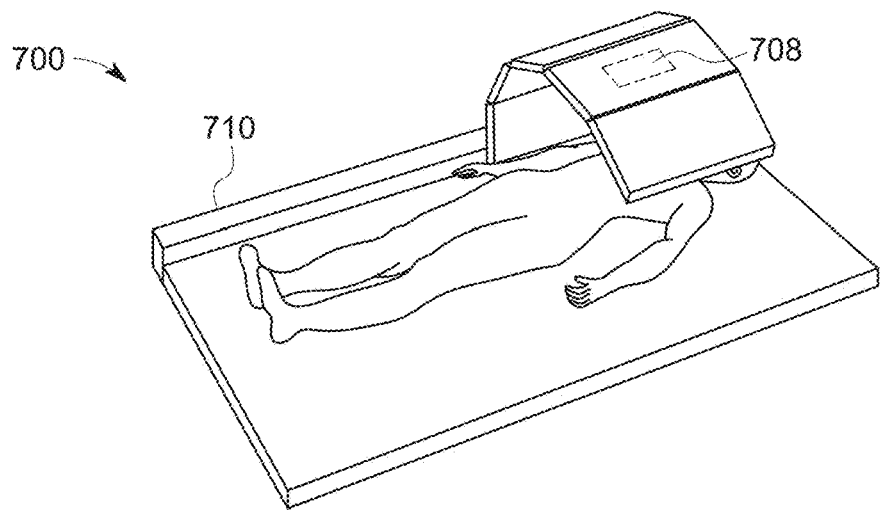
Figure 19D:
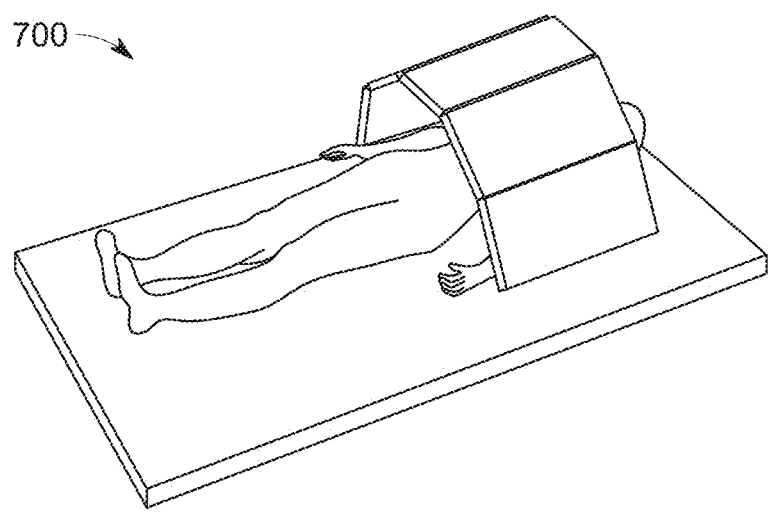
Figure 19E:
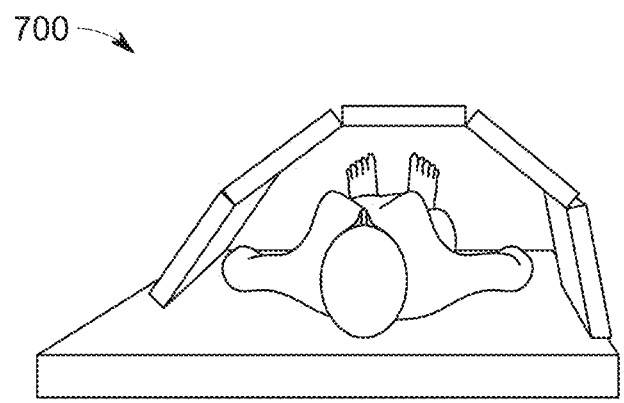

In FIG. 19A, the MFCA 700 is positioned relatively caudally with respect to the patient. In FIG. 19B, the MFCA 700 opens and begins to position itself over the patient. In FIG. 19 C, the MFCA 700 extends further around the patient. In FIG. 19D, the MFCA 700 is completely positioned over the patient. In FIG. 19E (an end-face view of the MFCA), The MFCA 700 is completely positioned over the patient. In some implementations, the arch 700 is movably connected to a ledge 710 provided to or adjacent the patient cart or table.

The system 700 further includes one or more controllers 708 provided in desired locations and configured to permit for the system 700 (or the components thereof) to autonomously perform desired surgical procedures. Such controllers 708 can run one or more software programs that are executed to cause the system 700 (or the components thereof) to perform various autonomous operations.

Referring to FIGS. 20-22, exemplary embodiments of screens are illustrated. FIG. 20A-H illustrate an example embodiment of a screen 800, which can be used as a video or image monitor. The screen 800 can be connected to an endoscope or other suitable viewing systems which may be used with any TARS systems described herein. In this example, the screen 800 is configured as an Unfoldable Endoscopic Screen (UES) system.

The screen 800 includes a plurality of screen surfaces that can be unfolded to provide a larger screen surface. The screen 800 can include a casing 802 and a plurality of segments 804 which can be expanded from the casing for viewing, and retracted into the casing for compact storage and transportation. The housing 802 can include multiple sub-casings, each configured to slidably support one or more segments 804.

In the illustrated example, the screen 800 includes two sub-casings 802A and 802B, and four segments 804, which provide six-fold screen areas. In FIGS. 20A-C, the screen 800 is in a compacted configuration (a perspective view in FIG. 20A, a side view in FIG. 20B, and a top view in FIG. 20C). A first (movable) sub-casing 802A is a back portion of the screen that can be raised relative to a front (fixed) sub-casing 802B that is fixed. The screen 800 includes an upper-left segment 804A that can extend from the first sub-casing 802A leftwards, and an upper-right segment 804B that can extend from the first sub-casing 802A rightwards. The screen 800 further includes a lower-right segment 804C that can extend from the second sub-casing 802B rightwards, and a lower-left segment 804D that can extend from the second sub-casing 802B leftwards.

In FIG. 20D, the movable sub-casing 802A is being extended upwards. In FIG. 20E, the movable sub-casing 802A is fully extended. In FIG. 20F, the upper left and right segments 804A and 804B are extended to provide upper screen sections. As illustrated in FIGS. 20G and 20F (a rear view of FIG. 20G), the exteriors of the upper left and right segments 804A and 804B and the movable sub-casing 802A provide an upper screen surface.

FIGS. 21A-F illustrate other variants of the screen 800. In FIG. 21A, the lower right segment 804C starts extending from the fixed sub-casing 802B. In FIG. 21B, the lower right and left segments 804C and 804D are extending from the fixed sub-casing 802B. In FIG. 21C, the lower right and left segments 804C and 804D are fully extended. FIG. 21D (a rear view of the screen) illustrates all screens fully extended to form six-fold flat screen viewing area.

In FIG. 21E, the movable sub-casing 802A is tilted relative to the fixed sub-casing 802B for different viewing screens. The movable sub-casing 802A can be manually or electronically tilted with respect to the fixed sub-casing 802B for different tilting angles. The movable sub-casing 802A can tiled inwards or outwards relative to the fixed sub-casing 802B.

In addition or alternatively, the segments 804A-D can be selected tilted relative to the associated sub-casings 802A-B either inwardly or outwardly. In FIG. 21E, the lower right and left segments 804C and 804D are tilted inwards relative to the fixed sub-casing 802B. In FIG. 21F, the upper right and left segments 804A and 804B are tilted inwards relative to the movable sub-casing 802A. The segments 804A-D can be manually or electronically controlled for different tilting angles.

FIGS. 22A-F illustrate another exemplary embodiment of a screen 830, which can be used as a video or image monitor. The screen 830 can be connected to an endoscope or other suitable viewing systems which may be used with any TARS systems described herein. In this example, the screen 830 is configured as an Unfoldable Endoscopic Screen (UES) system.

In this embodiments, the screen 830 includes a plurality of segments 832 each providing a part of a larger screen surface. The segments 832 are pivotally connected and unfolded to provide such a larger screen surface. For example, the screen 830 includes a first (upper) base segment 834 and a second (lower) base segment 836 pivotally connected to the first base segment 834. The screen 830 further includes a lower left segment 838A and a lower right segment 838B, which are pivotally coupled to the lower base segment 836. The lower left and right segments 838A-B can be connected to the lower base segment 836 at hinges 842. Further, the screen 830 includes an upper left segment 840A and an upper right segment 840B, which are pivotally coupled to the upper base segment 834. The upper left and right segments 840A-B can be connected to the upper base segment 834 at hinges 844. When unfolded, the segments 832 (including 834, 836, 838A-B, and 840A-B) provide a viewing area.

In FIG. 22A, the screen 830 is in a compacted (folded) position. In FIG. 22B, the screen 830 is partially unfolded so that the lower left and right segments 838A-B are unfolded. In FIG. 22C, the upper base segment 834 is unfolded upwards relative to the lower base segment 836. In FIG. 22D, the upper left and right segments 840A-B are being unfolded. In FIG. 22E, the upper left and right segments are further unfolded. In FIG. 22F, the screen 830 are fully unfolded with six segments providing an unfolded surface/viewing area.

Figure 23A:
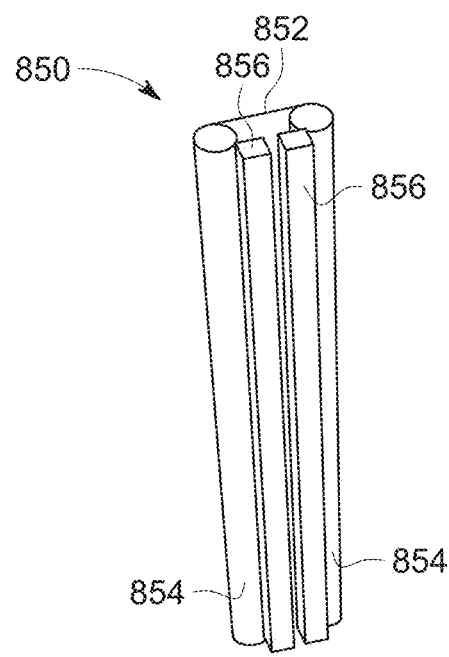
FIGS. 23A-B illustrate perspective views of another example Unfoldable Endoscopic Screen (UES).
Figure 23B:
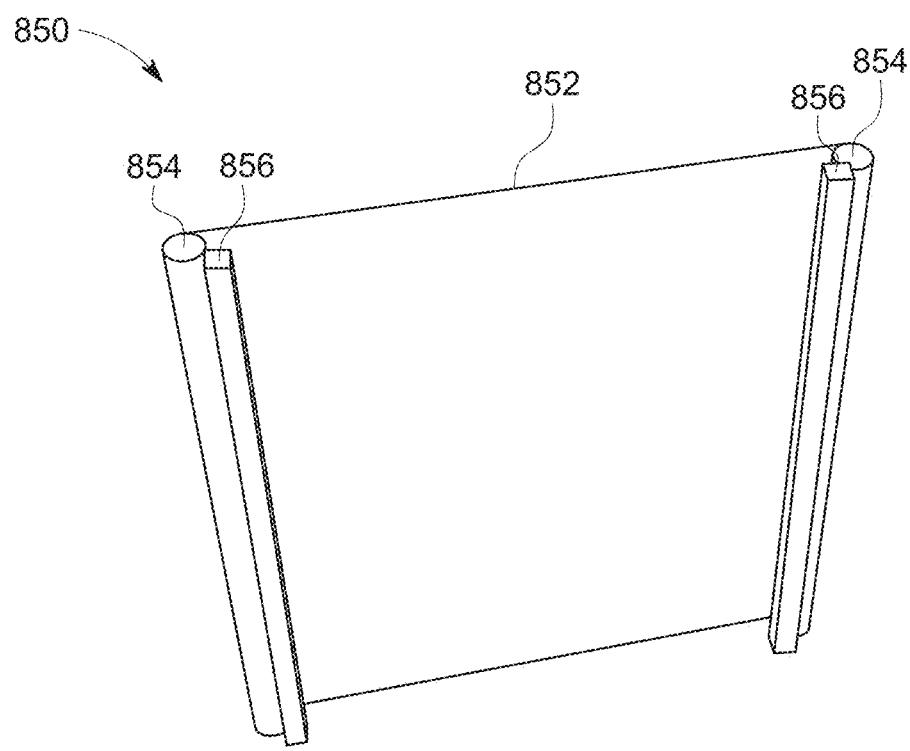

FIGS. 23A-B illustrate yet another exemplary embodiment of a screen 850, which can be used as a video or image monitor. The screen 850 can be connected to an endoscope or other suitable viewing systems which may be used with any TARS systems described herein. In this example, the screen 850 is configured as an Unfoldable Endoscopic Screen (UES) system.

The screen 850 is configured as a canvas 852 with opposite posts 854. The canvas 852 can be scrolled in and out one or more of the posts 854. The screen 850 further includes one or more image projectors 856 (e.g., short distance image projectors) arranged adjacent the posts 854 and configured to project images/videos onto the canvas 852 when unscrolled. For example, in FIG. 23A, the screen 850 is scrolled. In FIG. 23B, the screen 850 is unscrolled and an image is projected onto the canvas 852 from the projectors 856.

Referring now to FIGS. 24-31, yet another example TARS system 900 is illustrated. FIGS. 24A-D schematically illustrate an example structure and operation of the system 900 that may be in different positions. The system 900 is configured as a Self-Organizing Modular Robot (SOMR) system.

The system 900 can include a plurality of units 902 and one or more joints 904 configured to movably couple adjacent units 902. The units 902 are used as building blocks to provide the system 900. A limited number of units 902 coupled using the joints 904 can associate themselves in multiple fashions to produce desired robotic geometry. The robotic geometry can either be decided artificially through accumulated intelligence or with human supervision or human operators.

The units 902 can be autonomous robotic units (ARUs). Each unit 902 can be configured as a simple mechanical structure that contains electronics for autonomous robotic functionality. The joints 904 can be electronic double ball joints (DBJs), which may be configured to be similar to double-headed doorknobs. Each end of the joint 904 is configure to interlock with an end of the unit 902. In a simplest form, two units 902 that are coupled through a single joint 904 can provide a full joint chain of the system 900.

The interlocking between the unit 902 and the joint 904 can be provided with various mechanisms. For example, the unit 902 is coupled to the join 904 using unique rearrangeable magnetic patterns, which and can be controlled via multiple electronic feedback signals or an ad-hoc nervous-system-like signaling pervasive throughout the robot. Signals can be coupled from joint to joint via electronic to magnetic transmission at its attachment points to the joint.

The units 902 are configured to self-organize to pre-programmable implantable AI's. The system 900 with a plurality of coupled units 902 can self-transport with internal mechanisms, such as momentum producing, rolling, motors, etc. In some implementations, some units 902 are configured to transport other units 902 being coupled thereto via the joints 904 (e.g., DBJs).

Figure 24A:
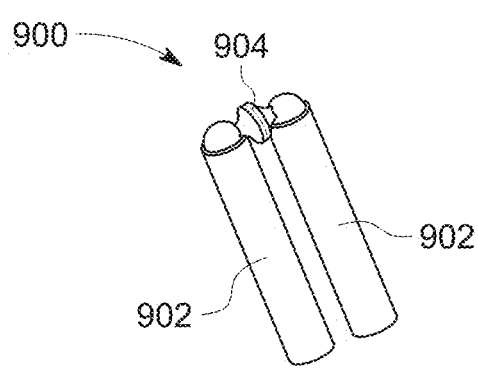
FIGS. 24A-D illustrates perspective views of another example TARS system including a Self-Organizing Modular Robot (SOMR).
Figure 24B:
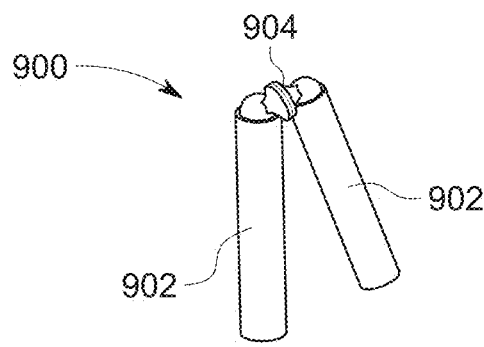
Figure 24C:
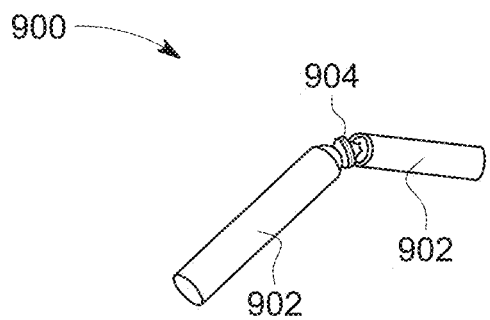
Figure 24D:
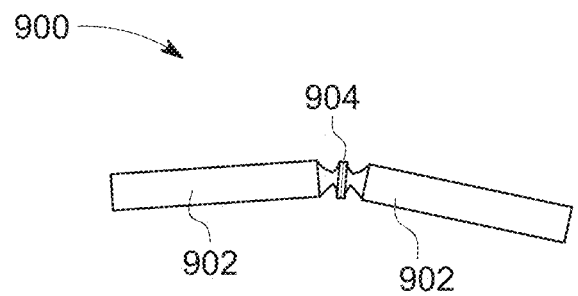

As illustrated, the units 902 can be autonomously arranged relative to each other to provide various relative angles between adjacent two units by their mutual intermediate joint 904. For example, in FIG. 24A, the ARUs 902 are maximally closed/adducted. The ARU's are almost parallel in this configuration. In FIG. 24B, the ARUs 902 are somewhat opened. In FIG. 24C, the ARUs 902 are further opened. In FIG. 24D, the ARUs are completely opened/aligned.

Figure 25:
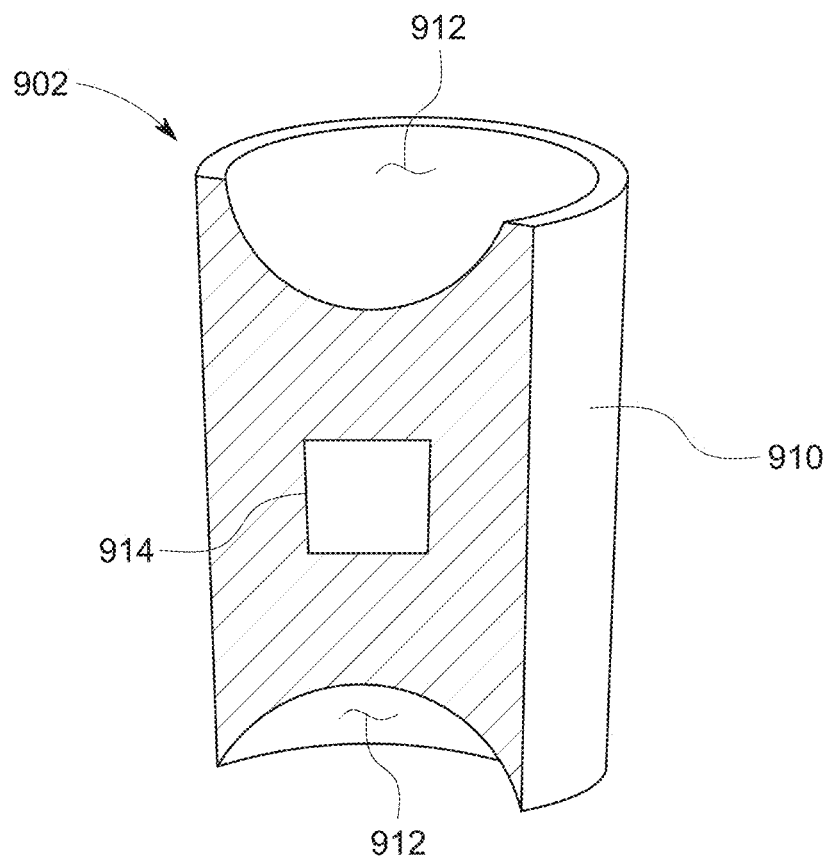
FIG. 25 illustrates a cross-sectional view of an Autonomous Robotic Unit (ARU) configured for use with the TARS system of FIGS. 24A-D.

FIG. 25 is a schematic cross-sectional view of the unit 902 of FIG. 24. In this example, the unit 902 has a housing 910 that is cylindrical. Other shapes of the housing 902 are also possible. The unit 902 includes one or more sockets 912 provided at the housing 910, such as opposite longitudinal ends of the housing 910. The socket 912 is configured to movably engage with the end of the joint 904 (e.g., mechanically, electrically, magnetically, electromagnetically, etc.). Each unit 902 can be configured in various sizes. For example, each unit 902 is sized similar to a bone (e.g., a long bone).

The unit 902 can include electronics 914 for operating the unit 902 as programmed or autonomously. The electronics 914 can be at least partially housed in the housing 910. In some implementations, the electronics 914 are configured to implement an artificial intelligent (AI) self-organizing unit. The electronics 914 can include at least some of the components as illustrated in FIG. 24, such as electronics components and/or systems including computation or processing systems, calculating or programmable solid-state, analog, digital or integrated components such as microprocessors, FPGAs, CPUs, GPUs located on either printed, pre-fabricated or modular circuit boards.

The unit 902 (e.g., the housing 910) can be made of one or more various materials, such as metal, alloy, polymer, plastic, wood, bio/organic materials, etc. The unit 902 can be made in various shapes. In some implementations, the unit 902 can be made to be rigid. Alternatively, the unit 902 can be made to be flexible. As described herein, the system 900 that is made of a plurality of units 902 and joints 904 can be in various configurations, with compressibility and/or extensibility, and/or with a degree of non-axial range of motion.

Figures 26A, 26B:
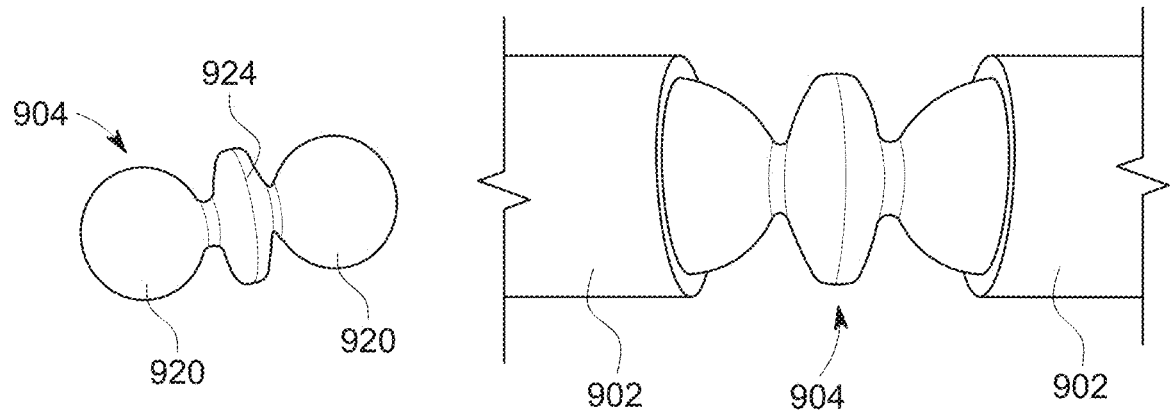
FIGS. 26A-B illustrate perspective views of an example double ball joint (DBJ) configured for used with components of the TARS system of FIGS. 24A-D.

FIGS. 26A and 26B are magnified views of the joint 904 of FIG. 24, which illustrates an example configuration of the joint 904. The joint 904 can be configured as a double ball joint (DBJ) and include balls or spheres 920 arranged at opposite ends. For example, the balls or spheres 920 can be axially mated at an interface 924 to allow for single-axis rotation. The balls or spheres 920 are configured to operatively mate with the sockets 912 of the units 902. The units 902 can freely (spherically) rotate around the mated ball or sphere 920 of the joint 904. In addition, the joint 904 can rotate axially (along its own axis extending through the balls or spheres 920). Alternatively or in addition, the joint 904 is configured to rotate about more than one axis.

In some implementations, the joint 904 can include electronics for operating the joint 904 as programmed or autonomously. Such electronics can be at least partially housed in the joint 904. In some implementations, the electronics are configured to implement an artificial intelligent (AI) self-organizing unit, similarly to the ARUs 902 described above. The joint 904 can be made of one or more various materials, such as metal, alloy, polymer, plastic, wood, bio/organic materials, etc. In some implementations, the joint 904 can be made to be rigid. Alternatively, the joint 904 can be made to be flexible.

FIGS. 27A-E schematically illustrate different geometric cross-sectional views of the assembly of the unit 902 and the joint 904. When assembled, the units 902 and the joint 904 can provide arm-like angulation within its kinematic space.

Figure 28A:
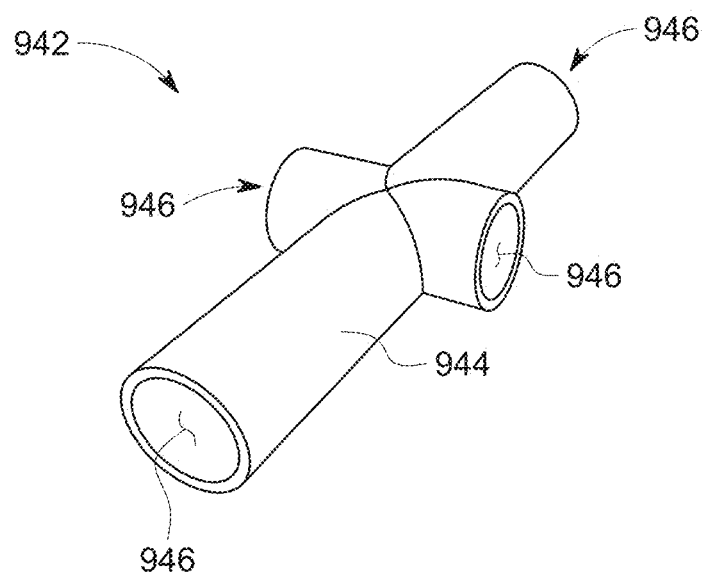
FIGS. 28A-B illustrate perspective and sectional views of an example T-jointed embodiment of an example ARU.
Figure 28B:
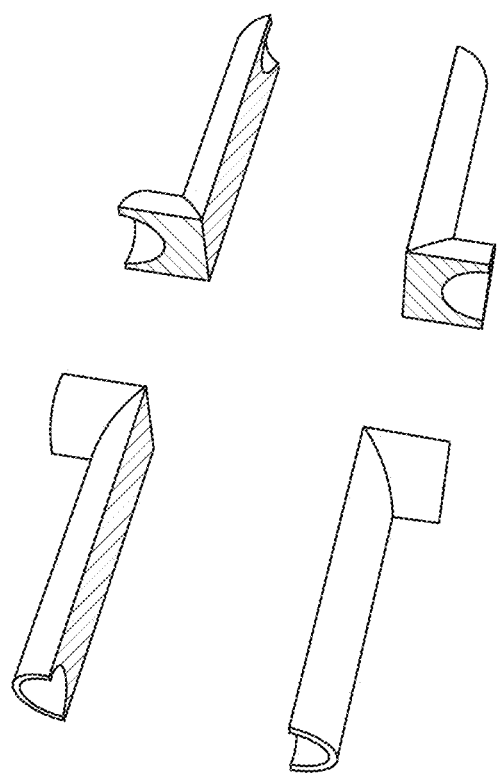

FIG. 28A-B schematically illustrate another example unit 942. The unit 942 is configured similarly to the unit 902 with some modifications. For example, the unit 942 is configured with a T-jointed housing 944 with four sockets 946 each for mating the joint 904. In this example, the unit 942 can be adjoined with four other units 902 and/or 942 through the joints 904.

The unit can have other example configurations of the housing that have geometry or topology for increasing or maximizing the joint connector sockets per strength requirements. Examples shapes can include a star shape, polygon with connectors on outside or other non-planar examples.

Figure 29A:
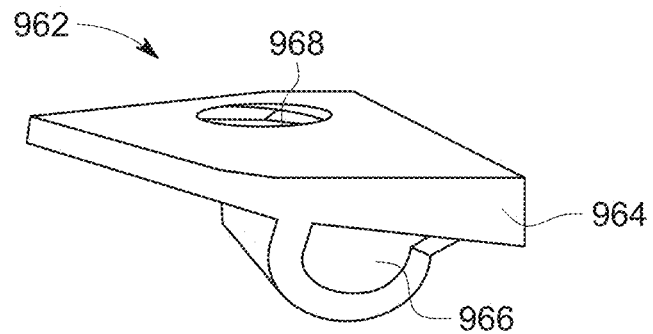
FIGS. 29A and B illustrate perspective views of an example wing-shaped ARUs capable of assisting non-ground locomotion or other propulsive mechanisms.
Figure 29B:
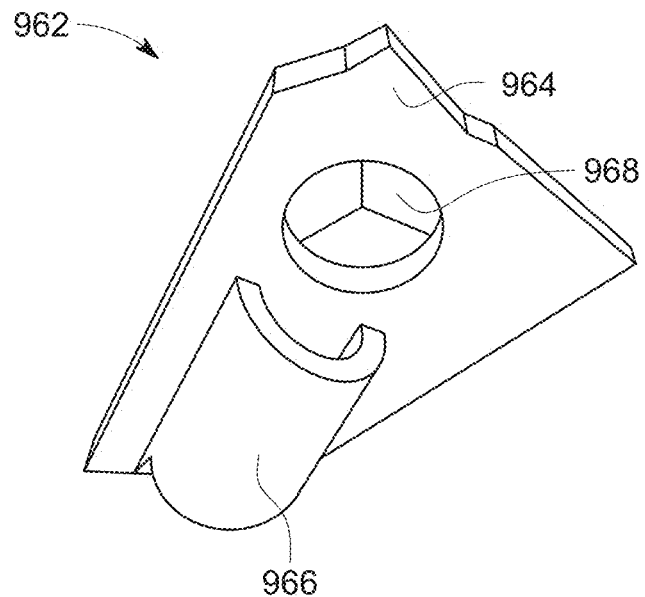

FIGS. 29A-B schematically illustrate yet another example unit 962. The unit 962 is configured similarly to the unit 902 with some modifications. For example, the unit 962 is configured as a wing-shaped ARU capable of assisting in non-ground locomotion or other propulsive mechanisms utilizing a propellant fan arrangement. The unit 962 includes a housing 964 and a propulsion fan 966 that can be horizontally oriented in the housing 962. The fan 966 can operate to propel the unit 962 horizontally. In addition, the unit 962 includes a vertical propeller 968 that is oriented vertically in the housing 964 and configured to be openable to optimally allow hovering or steep vertical lift and landing.

Referring to FIGS. 30A-F, various example configurations of the system 900 using multiple units 902, 942, 962 and joints 904 are illustrated. As illustrated, the system 900 can be autonomously configured into increasing complex re-configurable states. For clarity, in some of FIGS. 30A-F, the joints 904 are omitted from view. Each example configuration may be optimally suited for specified scenarios.

Figure 30A:
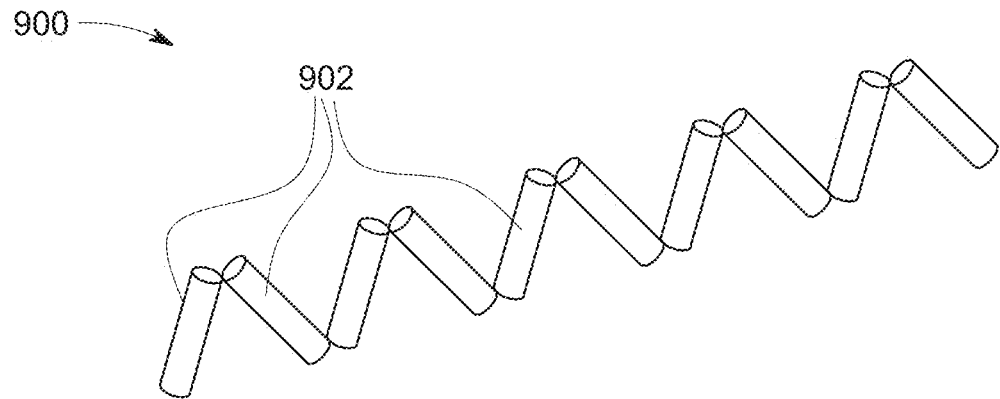
FIGS. 30A-F illustrate perspective views of examples of ARUs in variously complex re-configurable states (with the DBJs removed from view for illustrative purposes).
Figure 30B:
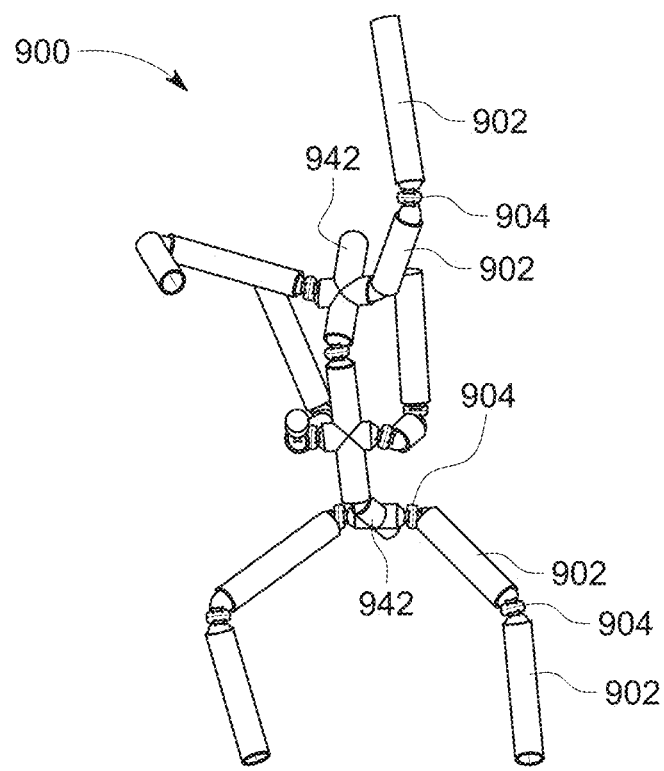
Figure 30C:
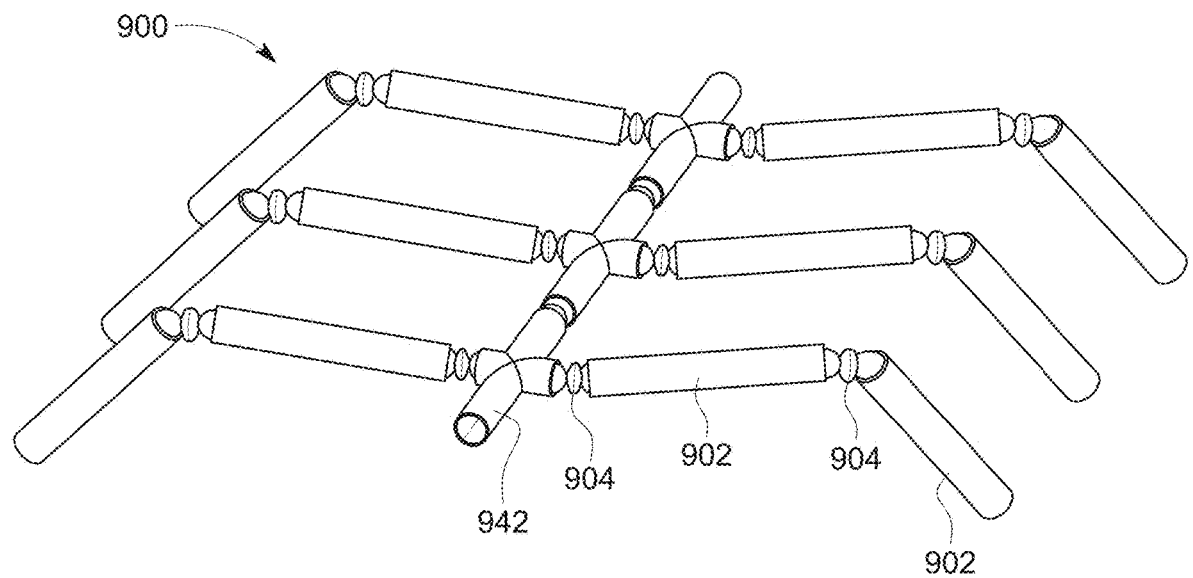
Figure 30D:
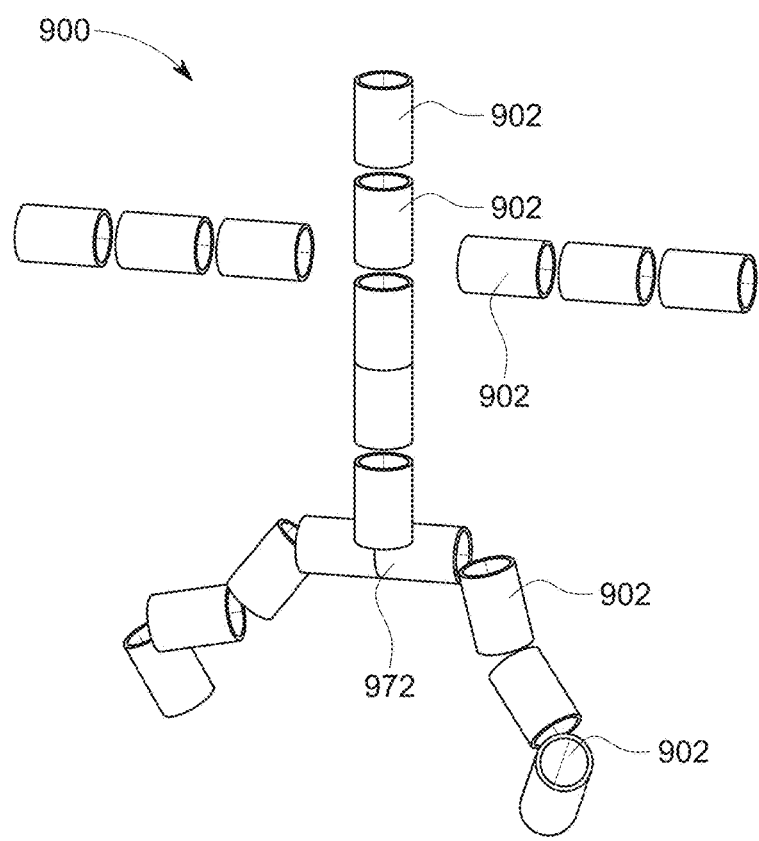
Figure 30E:
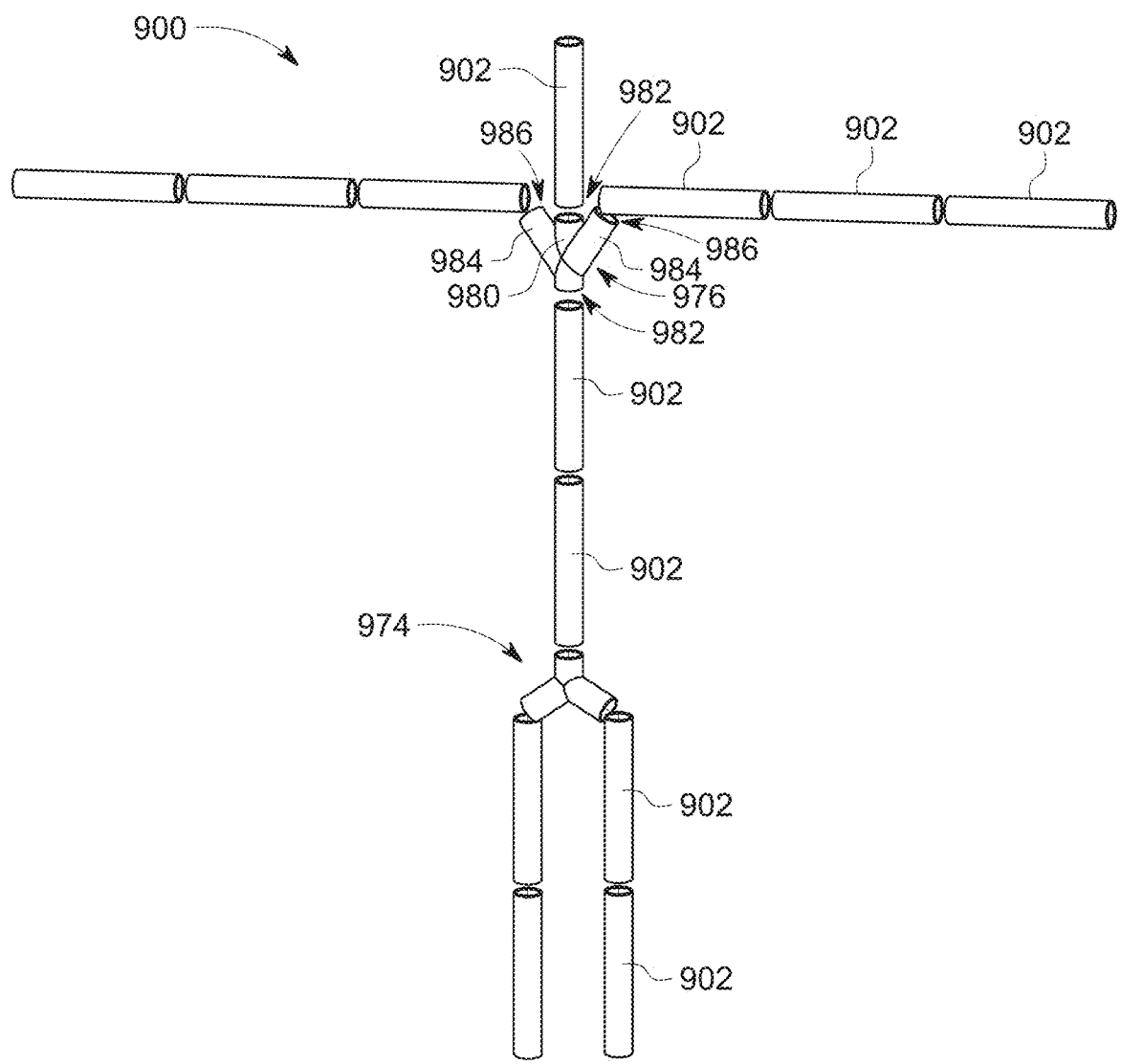
Figure 30F:
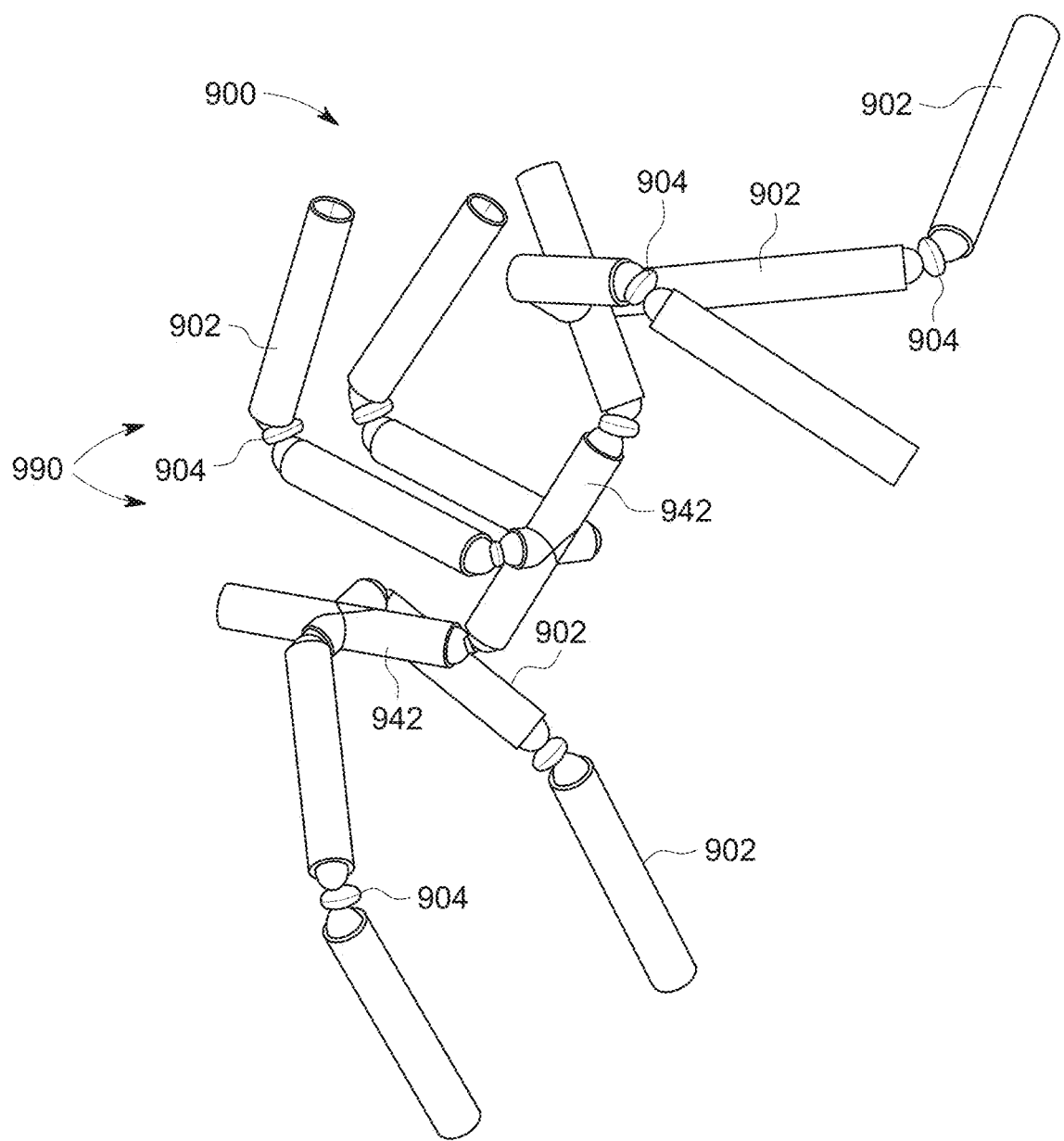

For example, in FIG. 30A, ARU units 902 are arranged to assume a snake like configuration. In FIG. 30B, ARUs 902, 942 are configured in a praying mantis configuration with back attachments. Multi-planed and joint configuration are optimized to suit specific task. In FIG. 30C, ARUs 902, 942 are configured in a spider/arachnoid configuration. In FIG. 30D, ARUs 902, 972 are arranged in a humanoid configuration with four major limbs and a head. In this example, a T-shaped ARU 972 is used and coupled with other ARUs 902. The T-shaped ARU 972 includes a T-shaped housing with three sockets configured to operatively mate with the joints 904. In FIG. 30E, ARUs 902, 974, 976 are arranged in another embodiment of a humanoid configuration. In this example, ARUs 902 of various lengths can be used to imitate human limbs. Further, a Y-shaped ARU 974, which has a Y-shaped housing with three sockets for mating with the joints 904, is used as a connector for connecting ARUs 902 for a body part and ARUs 902 for leg parts. Moreover, a V-shaped ARU 976 is provided as a connector for connecting one or more ARUs 902 for a head part, ARUs 902 for arm parts, and ARUs 902 for a body part. The V-shaped ARU 976 includes a main housing 980 with opposite sockets 982 for connecting ARUs for the head and body, and two branch housings 984 with respective sockets 986 for connecting ARUs for arms. In FIG. 30F, ARUs 902, 942 are arranged in yet another embodiment of a humanoid configuration (e.g., in praying mantis configuration). In this example, the system 900 includes additional ARUs 902 and joints 904 for back attachments 990. The system 900 further provides the arms, legs, body, and head.

Referring to FIGS. 31A-E, various example scenarios of operating the system 900, which is constructed, for example, in a humanoid configuration, are illustrated performing a variety of tasks. For example, in FIG. 31A, two systems 900 of different configurations are simultaneously used to assist in an injured person. One system 900 is in a humanoid configuration with a tool in hand and is working with another system 900 in a different configuration (e.g., unspecified ARU autonomous assistive device) responding to an injured person.

Figure 31A:
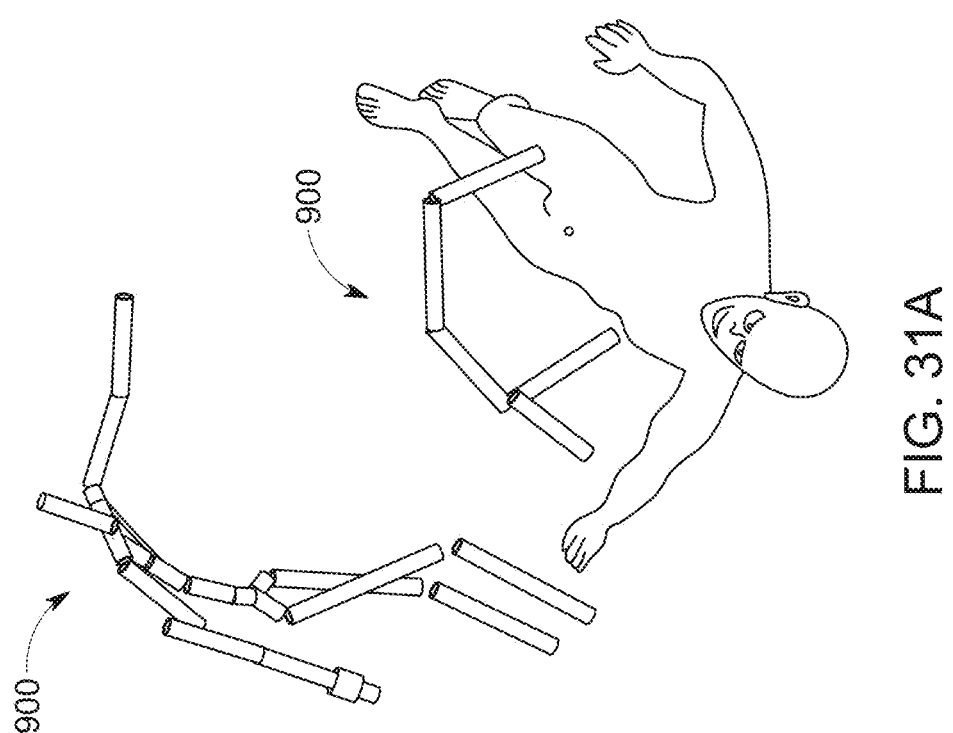
FIGS. 31A-E illustrate perspective views of examples of Humanoid ARUs performing a variety of tasks.
Figure 31B:
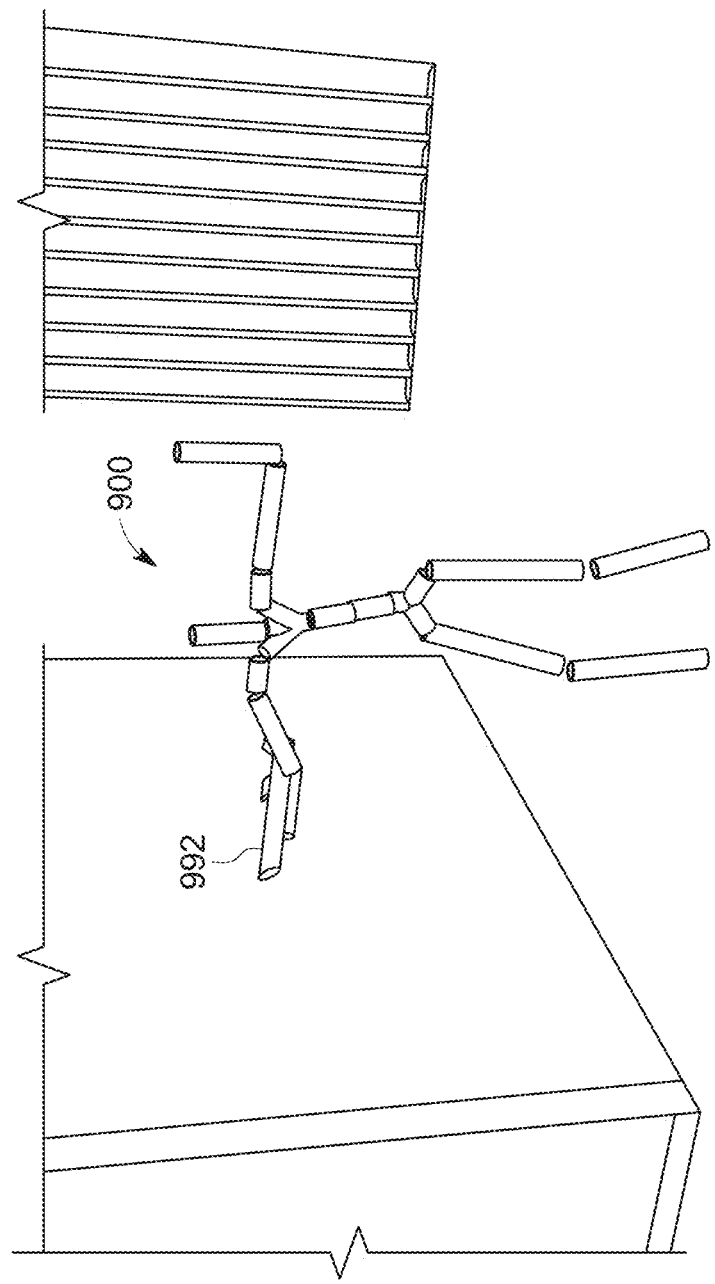
Figure 31C:
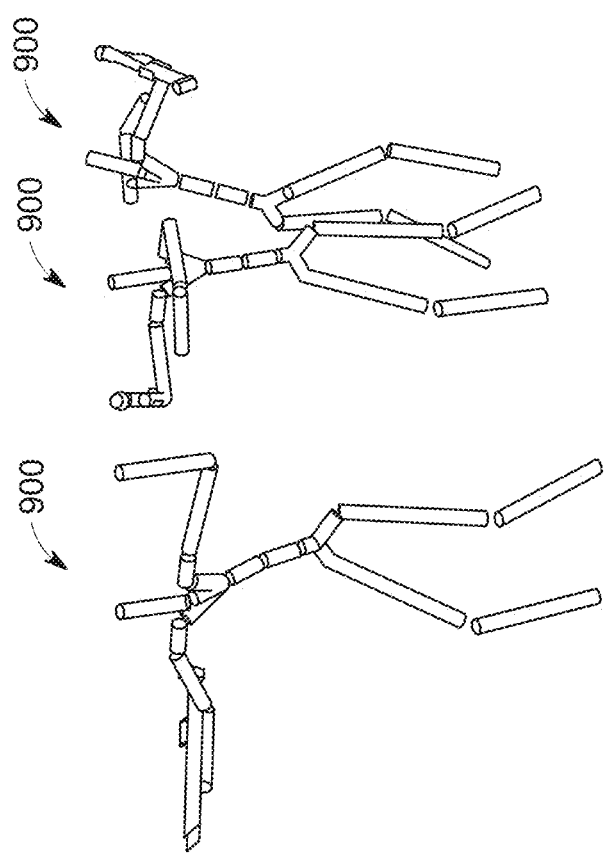
Figure 31D:
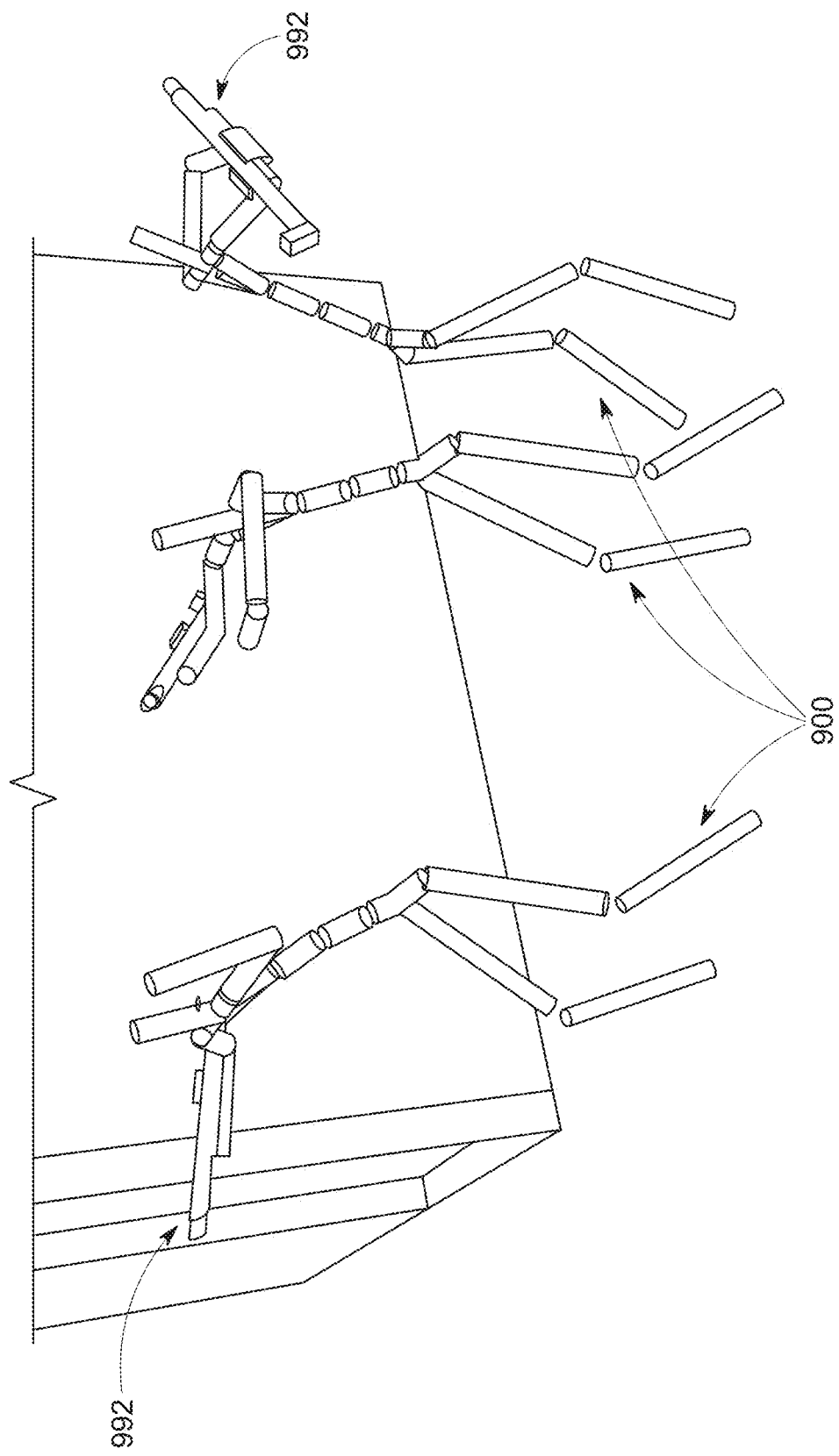
Figure 31E:
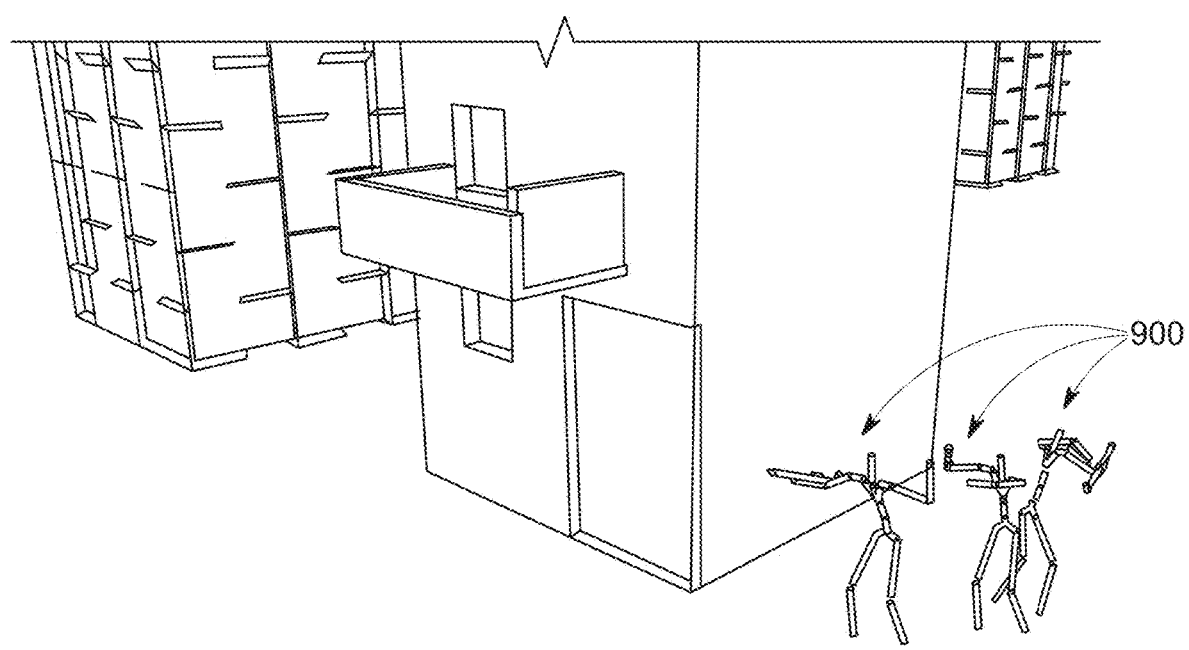

In FIG. 31B, a roving humanoid ARU system 900 is illustrated. The system 900 is holding a tool 992 in a hand part, readying a response. In FIG. 31C, three humanoid ARU systems 900 are working as a team. In FIG. 31D, three humanoid ARU systems 900 are holding tools 992 and working as a team at an outside environment, such as in front of a building, going in different directions, yet cooperating. In FIG. 31E, multiple humanoid ARU systems 900 are working on human scale environment.

Figure 32:
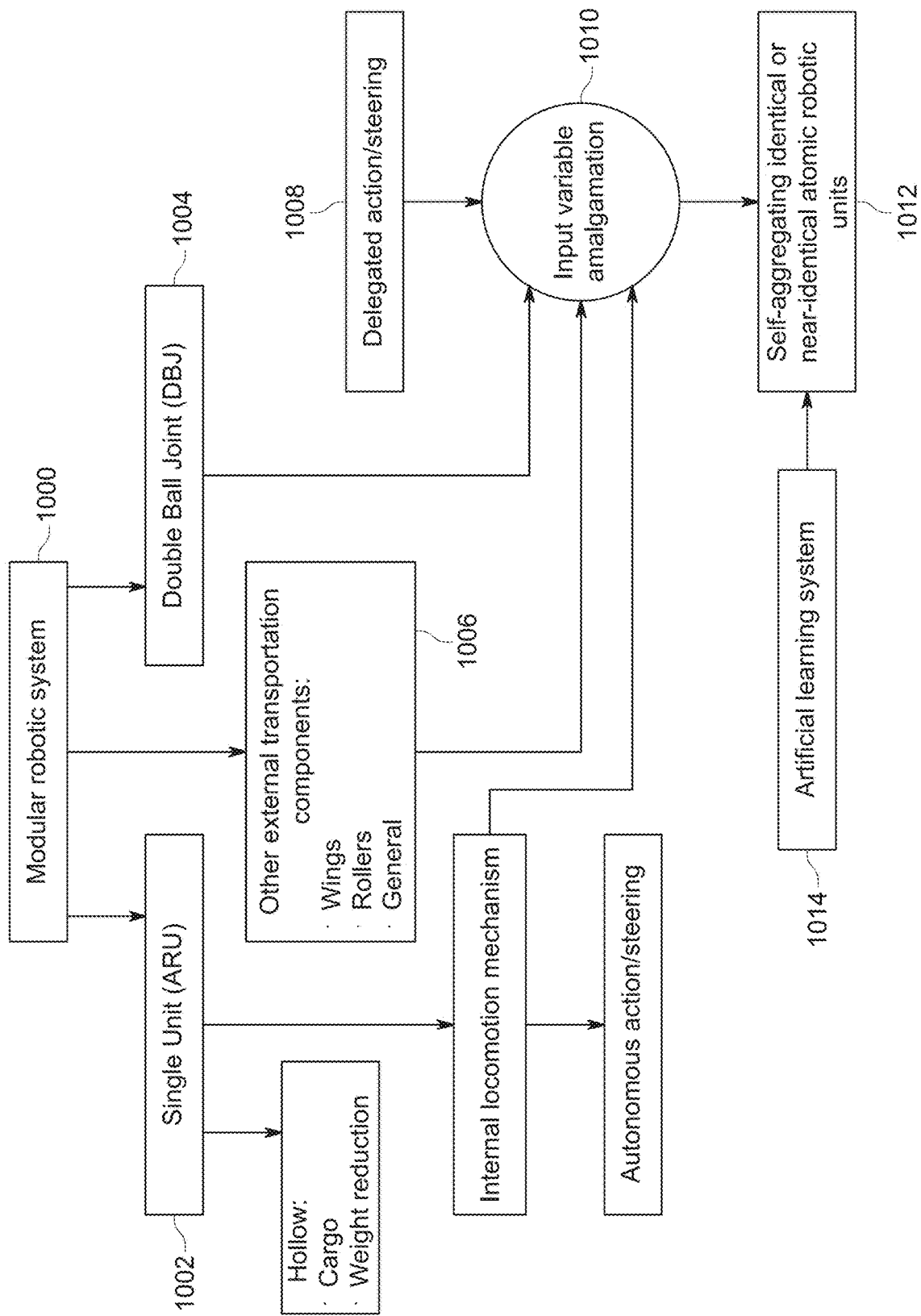
FIG. 32 illustrates a component diagram of a self-aggregation and learning system for a modular robotic system.

FIG. 32 is a block diagram that illustrates an example modular robotic system 1000. The modular robotic system 1000 is configured to provide a self-aggregation and learning system. For example, the modular robotic system 1000 includes one or more ARUs 1002 (e.g., the units 902, 942, 962, 972, 974, 976, etc.), one or more DBJ 1004, and one or more other external transportation components 1006 (e.g., drones described herein). The ARUs 1002, the DBJs 1004, the transportation components 1006 can organize, disassemble, and/or reassemble themselves for optimal configurations. The ARU 1002 can be made with a hollow body for cargo space and weight reduction. The ARU 1002 can include an internal locomotion mechanism to autonomously operate itself.

The modular robotic system 1000 can receive inputs from the ARUs 1002, the DBJs 1004, the other external transportation components 1006, and delegated operations 1008, and combine them (input variable amalgamation 1010). Such combined input variables can be used to permit for the ARUs 1002, the DBJs 1004, and the other components 1006 to operate as self-aggregating identical or near identical atomic robotic units 1012. In addition, an artificial learning system 1014 is used to improve the operation of the modular robotic system 1000 (e.g., the implementation of atomic robotic units 1012).

ARUs and other robotic units described herein can be configured to be self-assembled by autonomously arranging, climbing, rolling, leaping, attaching, and otherwise positioning themselves with respect to each other. ARUs and other robotic units described herein can be configured to communicate with each other using various technologies (e.g., Wi-Fi, NFC, RFID, barcode recognition, etc.) to identify each other. For example, ARUs and other robotic units described herein can be self-assembling and self-reconfiguring by using pivoting motions to change their intended geometry. An example of such self-assembling and self-reconfiguring robotic mechanisms is described in John W. Romanishin, et al., M-blocks: Momentum-driven, magnetic modular robots, 2013 IEEE/RSJ International Conference on Intelligent Robots and Systems, 4288-4295, November 2013, Tokyo, Japan, the disclosure of which is incorporated hereby in its entirety.

Referring now to FIGS. 33-37, various exemplary embodiments of an artificial intelligent (AI) system are illustrated which may be used with various devices, components, and systems described herein, such as the TARS systems described herein (e.g., the system 100, 200, 300, 400, 500, 900, etc.), the autonomous limb positioners 600, 650, the arches 700, the screens 800, 830, 850, and the modular robotic system 1000.

Figure 33:
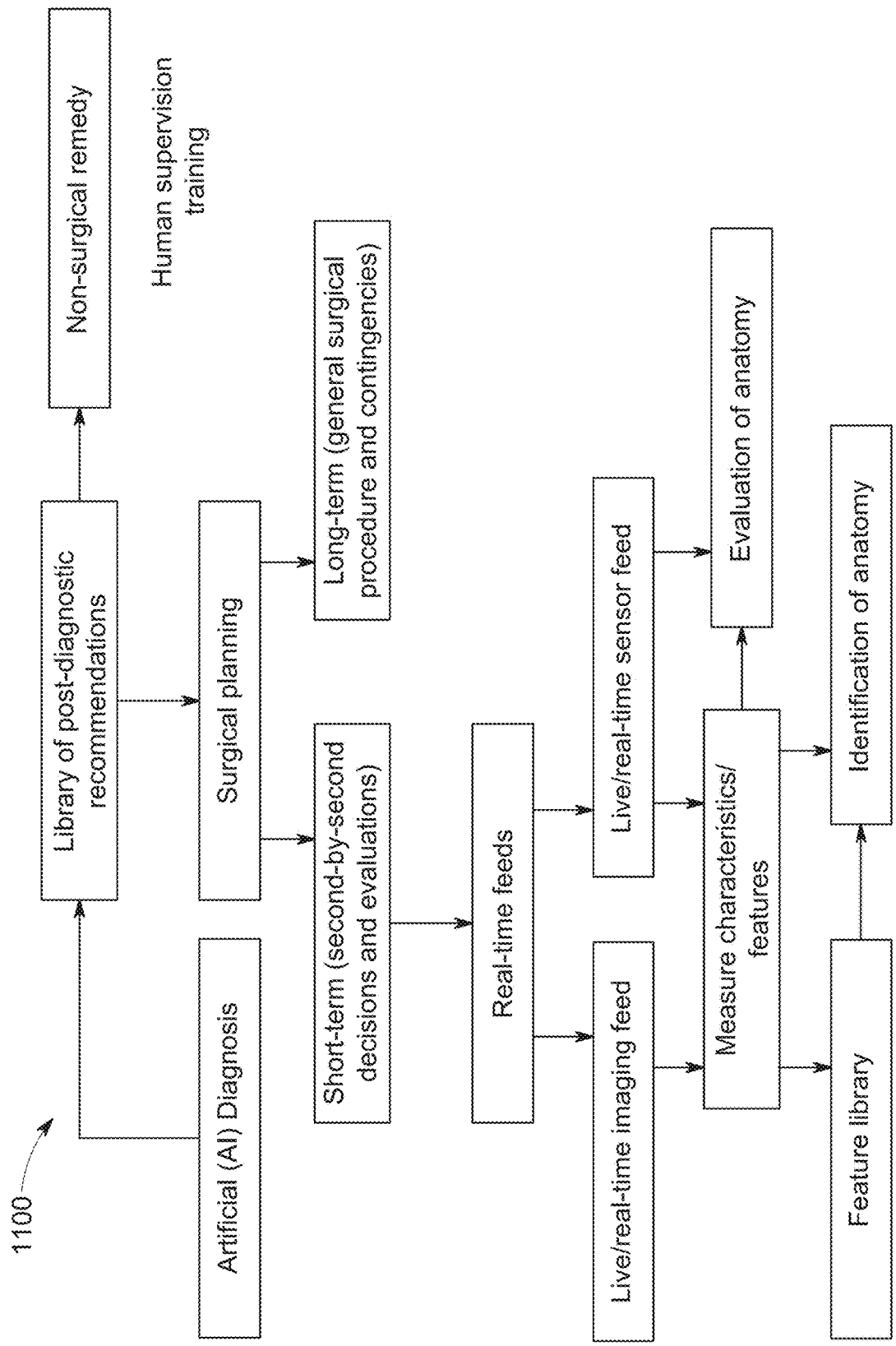
FIG. 33 illustrates a flow chart of an example process for an Artificial Intelligent (AI) system for diagnosis and surgical procedures.

FIG. 33 illustrates an example AI system 1100 for diagnosis and surgical procedure. This Figure presents a framework for start-to-finish medical care. Starting from the top left, an AI will interact with a patient, at which point it will decide a procedural route, either surgical or non-surgical. If surgical, it will act out appropriate preparations and perform the surgery either independently or cooperatively (with humans/tele-humans or another AI). The system would optimally improve over time as a central or distributed library gains experience from being trained either through video interpretation, knowledge expansion or supervision/correction by humans.

Figure 34:
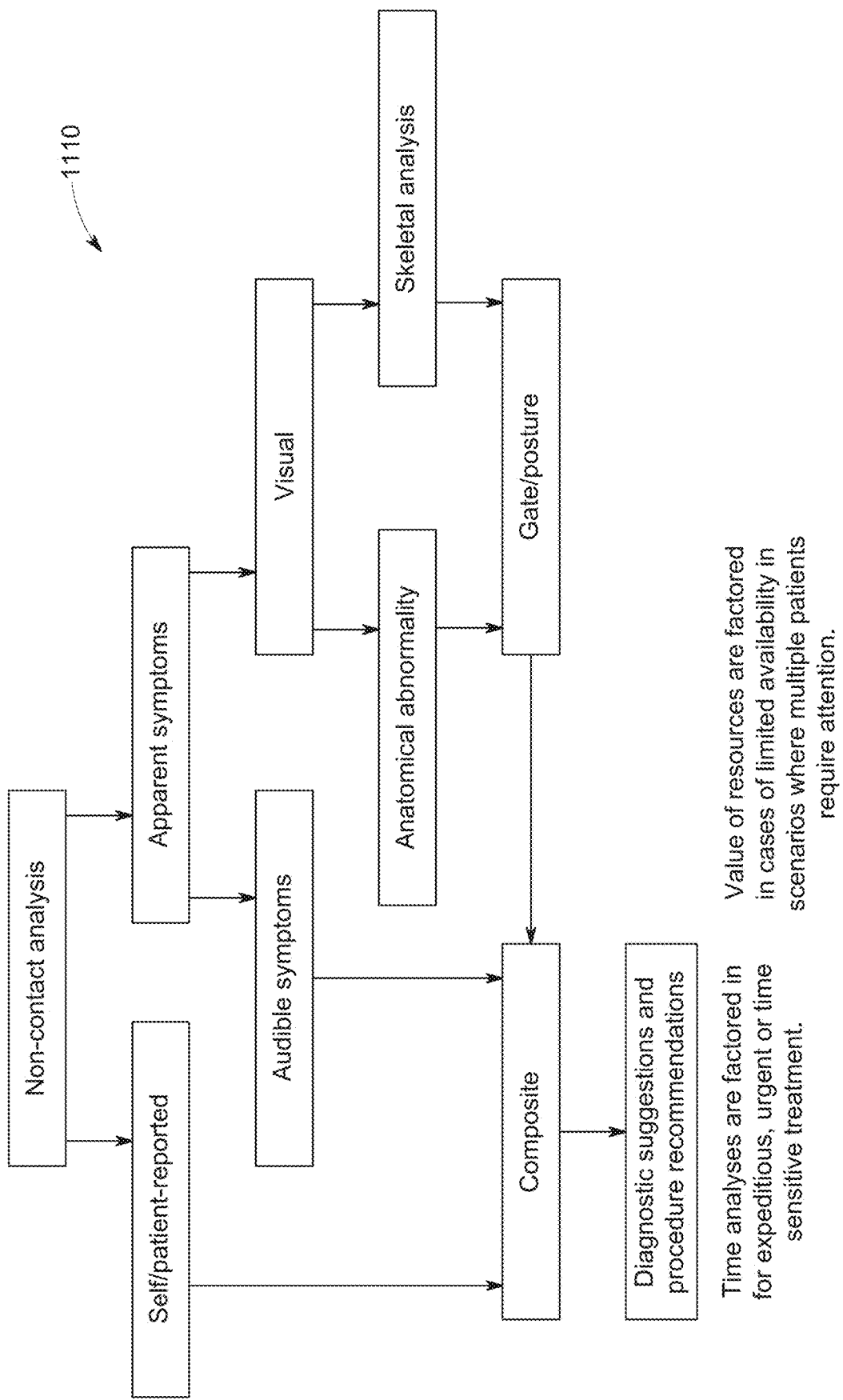
FIG. 34 illustrates a flow chart of an example process for an AI Robotic-based Diagnosis in accordance with particular embodiments of the TARS system described herein.

FIG. 34 illustrates an example AI Robotic based diagnosis 1110 based on only a few sensory (and in this example non-contact) cues, which would be an analogous diagnostic procedure for a doctor telephonically interacting with a patient. Visual and audio input would measure the state of a patient and their measured aberration from health (for example, limp, cough, discoloration etc.) and combine that with symptoms reported by the patient to assemble a recommendation.

Figure 35:
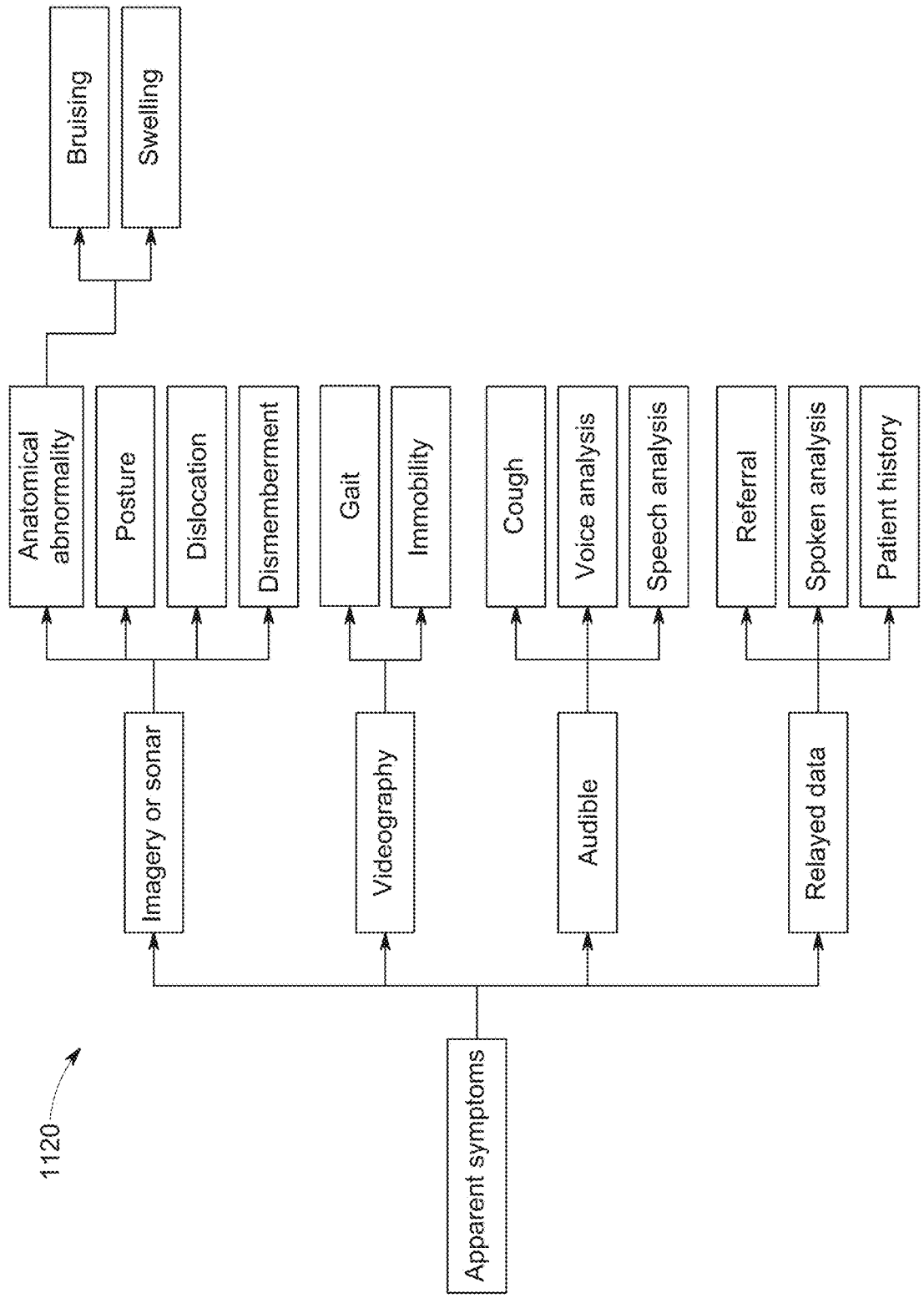
FIG. 35 illustrates a schematic of an example system for AI/Robotic diagnosis.

FIG. 35 illustrates another example of AI diagnostic routes 1120. Based on time/cost analysis these are adjustable as needed. For example, if a patient verbally reports symptoms that may more unequivocally represent a condition (such as a stroke), other time/cost consuming diagnostic elements may be bypassed or conducted in a rough or expedient manner.

Figure 36:
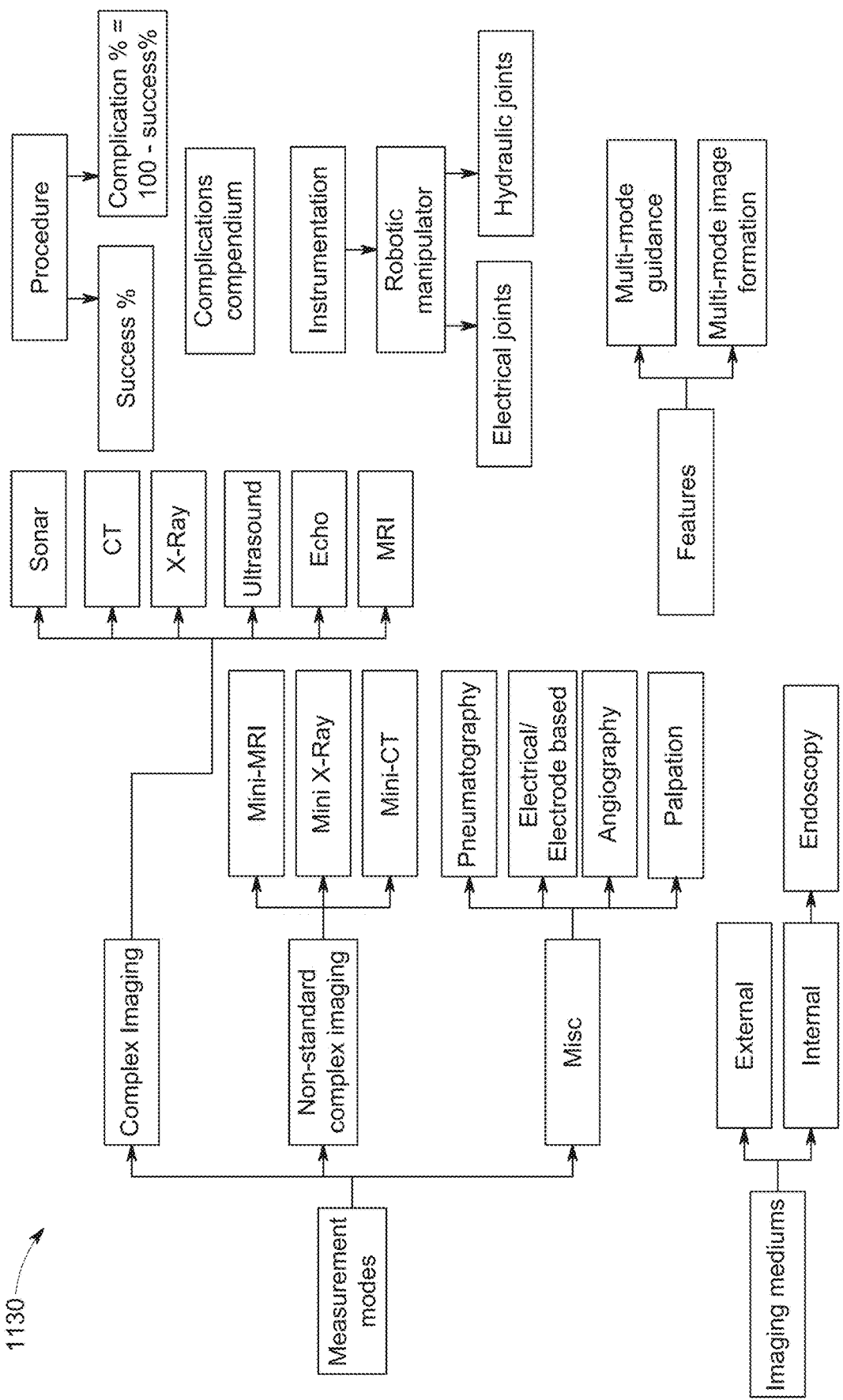
FIG. 36 illustrates a schematic an example system for an AI/Robotic algorithm.

FIG. 36 illustrates an example AI/Robotic algorithm 1130. This Figure demonstrates further decision making with regard to necessity benefits, cost and time when diagnosing a patient. This model would like the others also improve over the time with human modification/supervision/teaching.

Figure 37:
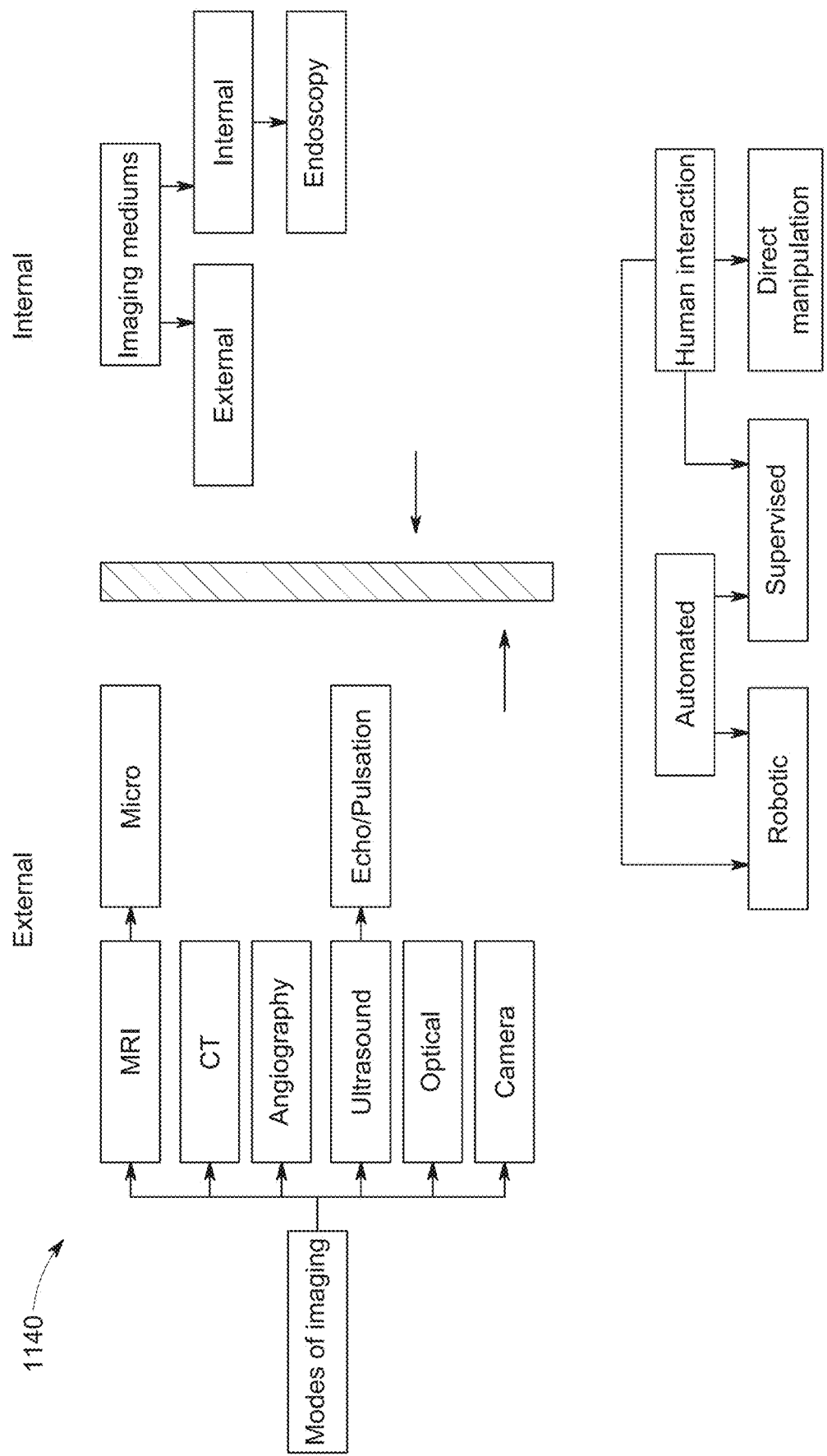
FIG. 37 illustrates a diagram of an example of diagnostic elements with AI and human interaction.

FIG. 37 illustrates various example diagnostic elements 1140 with AI and human interaction. This graph decomposes the diagnostic elements in an alternative matter as well as disclosing how humans may be involved. This graph roughly outlines an incomplete sampling of available diagnostic and monitoring resources. Each resource can be in turn associated with a number of other variables that can be optimized, minimized, or maximized, such as: risk (direct effects, such as invasiveness, unpredictable outcomes if incoming patient has unknown history and/or is unconscious), expense, availability, time-required. Combinations can include: switching-mode (alternate every x-seconds, x<10), MM-on/off, instrument-off/on, switching/alternating modes of imaging modes (e.g., MRI/CT, multiple simultaneous imaging (e.g., one arm can be an ultrasonic device), triple check on the robot (different imaging confirmation), human supervision observing with stop or assist modes—or computer can request supervision for risky segments of surgery, surgical pincers: anything miniaturized: Visualization, (surgical) instrumentation, radiosurgery, stereotactic radiation up-close (6 dof/motion), laser ablation, ultrasonic treatment and usual/typical manual surgical tools, suction irrigation, ability and checks to interact with the robot, also, smooth/easy transitions, fail-safes, sensors, feedbacks, micro/macro visualization modes of MRI/CT, endoscopic ultrasound, 6 dof. programming, learning from video, and connecting to an agglomerated database reference, human to personalize surgery, we could use a new computer language, SurgC, Preoperative computer planning and algorithms that are surgeon-friendly, choosing/executing the autonomous surgical program of choice.

Figure 38A:
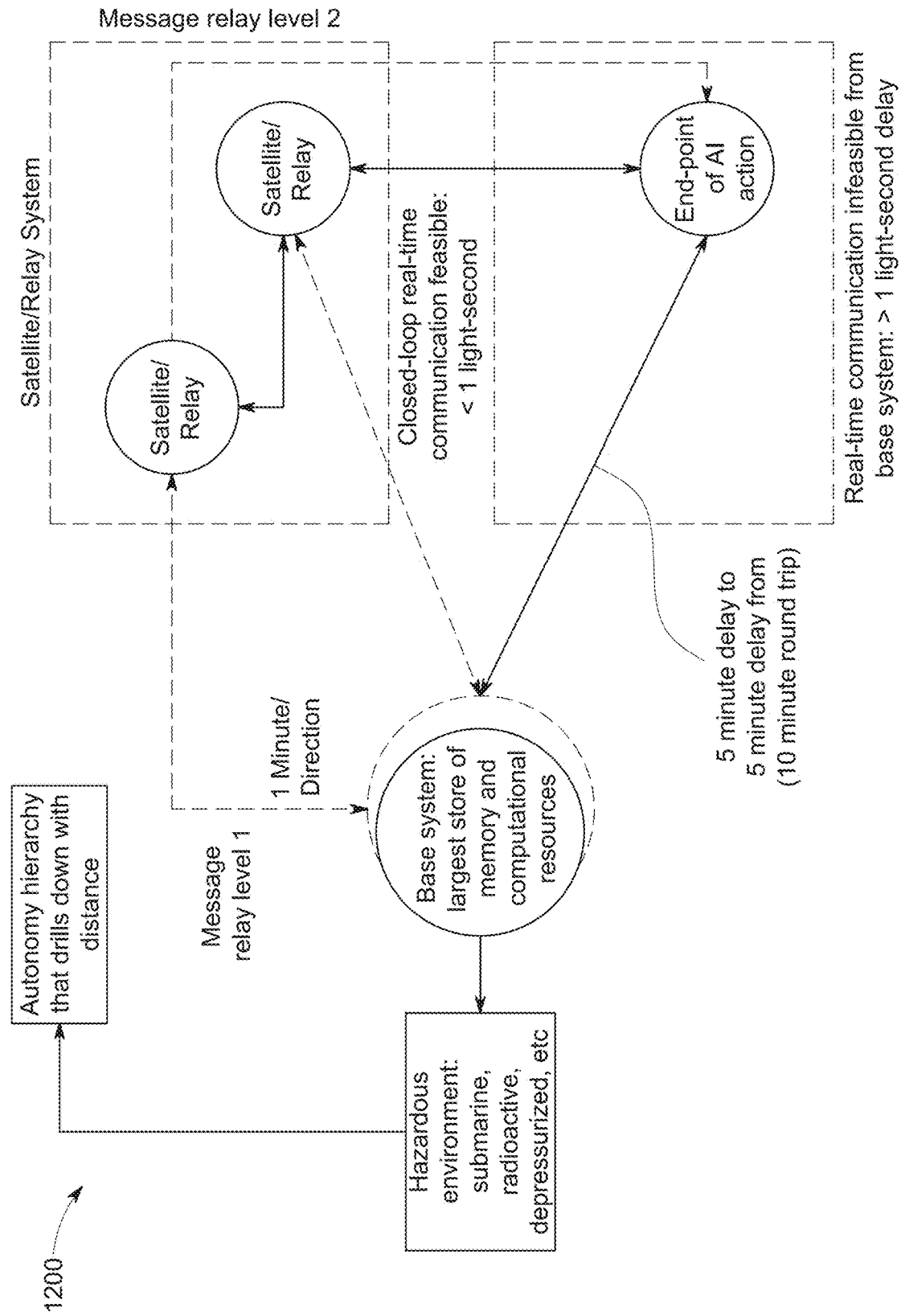
FIGS. 38A-B illustrate diagrams of example AI communication structures over distances.
Figure 38B:
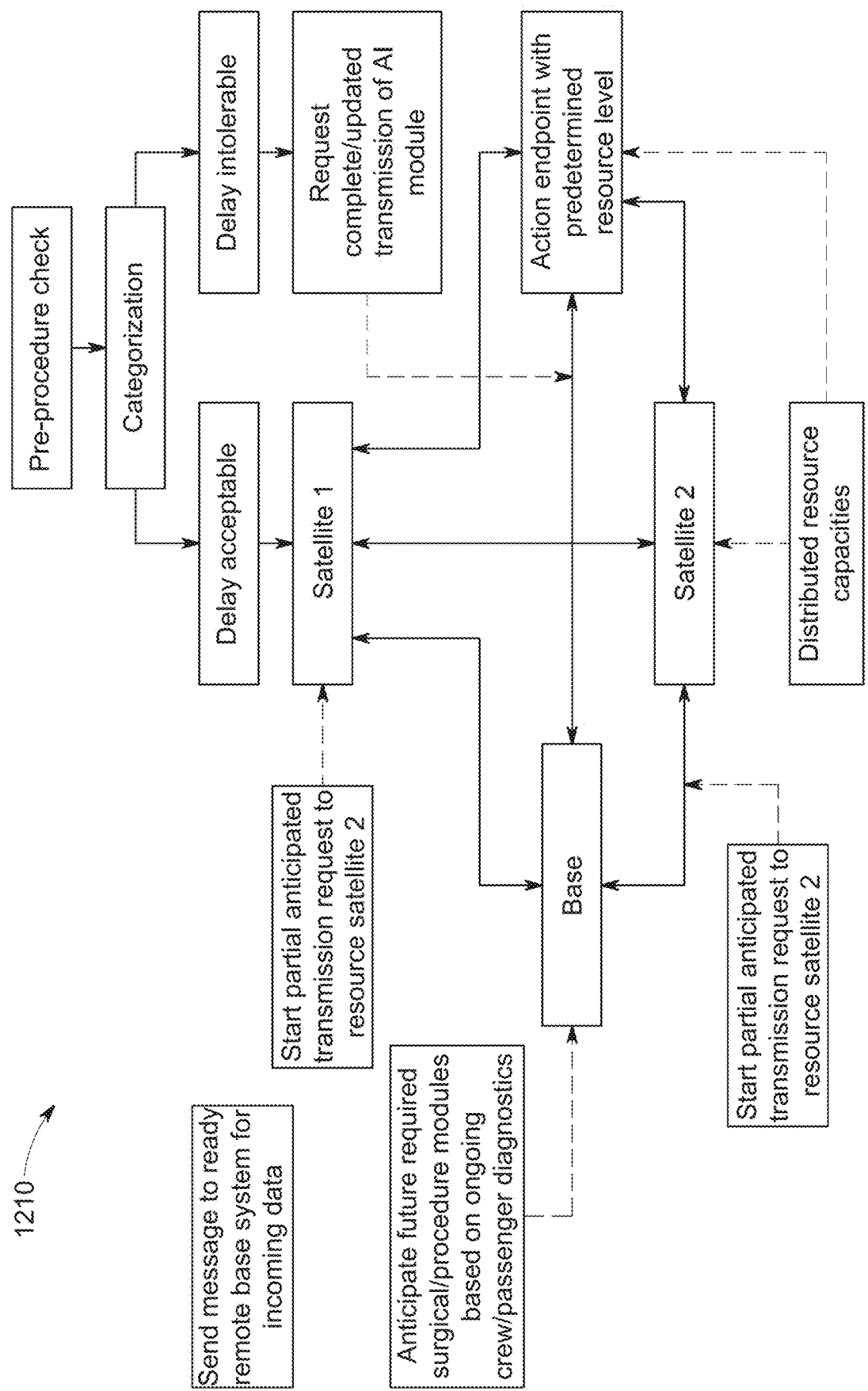

Referring now to FIGS. 38A-B, example AI communication structures are illustrated, which are over distances (FIG. 38A), and over time sensitivity (FIG. 38B).

FIG. 38A illustrates an example communication structure 1200 configured for not necessarily-determinate, lossy, or unreliable communication channels or distances. For example, the communication structure 1200 can be used for remote autonomous and/or automatic surgical operation at a long distance (e.g., a distance between Earth and Mars), especially when bi-directional communication times are greater than several tens of milliseconds and thus may cause significant delay and unreliability in remote autonomous and/or automatic surgical operation. The more distant an AI component is from a central processing system, the more self-reliant it need be, especially during delicate procedures that may have expensive, fatal, or injurious negative outcomes.

The communication structure 1200 can be implemented via satellite transmission. In some implementations, the communication structure 1200 is configured with an AI scheme acting in environments that are separated from base-stations by distances far greater than light-seconds (1 light second is close to 300,000 km), possibly light-minutes, or conceivably light-hours. For example, the distance between Earth and Mars is 54.6M-225M km (3-13 light-minutes, not including processing through relays). Notwithstanding techniques that may overcome lightspeed communication barriers, such as quantum entanglement, spatial expansion/contraction, for further reaches of space travel, this distance/time would vastly increase, making real-time 2-way communication for dynamic scenarios, such as surgery, and other less-predictable or on-the-fly scenarios unfeasible.

One example application of the communication structure 1200 is an autonomous doctor/surgical system that would behave as a surrogate for a hospital/surgical staff without requiring the resources to sustain humans fulfilling this role. An example of an environment in which resources may be limited and the overall well-being of system and humans would benefit from maximal efficiency and conservation would be in a small and isolated population such as characteristic of those in a voyage or remote colony.

The automated tasks can be categorized by their time sensitivity. For example, a diagnostic measure such as interpreting an MRI may be able to withstand a delay of minutes or an hour without substantially impacting the health of a patient. In contrast, a scenario during a surgical procedure during which there is an unexpected situation such as vast changes in respiration/blood-pressure or if there is a bleed, delays that are greater than a few seconds may cause permanent injury or be fatal to the patient.

As illustrated in FIG. 38A, the communication structure 1200 (e.g., an algorithm thereof) is configured to optimally maintain, cache and send or receive AI modules that may benefit from larger off-premise data-stores or parallel processing units. Example tasks include AI radiological/diagnostic image interpretation. During a learning phase, human intervention may be necessary or it is possible that human interpretation may present advantages over AI interpretation. However, during a procedure that is too remote for real-time communication, imaging references can use caching prior to a procedure to enable real-time interpretations by the AI. Another example scenario is that while a patient undergoes a surgical procedure, the resources in terms of real-time AI or equipment are not available. In this scenario, a mobile system can be sent merely to with a light-second proximity of the geographic location (such as entering into any type of orbit or a stationary/geo-sync orbit type) to interact in real time. In an undrawn system, physical equipment may be delivered from this mobile system.

Further, as illustrated in FIG. 38A, an example communication channel is provided to accomplish telerobotic over extended distances or in environments impenetrable by other humans. In some implementations, data can transmit through multiple satellite relays. Computation tasks can also be off put to satellites if the environment/vessel containing the AI is of a lower grade.

FIG. 38B illustrates that another example communication structure 1210. The communication structure 1210 can be configured to be non-location dependent (due to time insensitivity). In this structure, modules can be primed for transmission in an anticipatory manner based on ongoing monitoring or crew/passenger health. This monitoring can be silent and non-interactive. For example, the monitoring can be accomplished through either non-contact or not-specifically medical measurement systems. This can include surfaces that can measure pulse rate for example. Resource consuming data and computation can be distributed between the endpoint and a network of satellite systems as shown. The crew can also be trained by a doctor.

As described herein, MRIs can be configured to be compact and mobile, and fitted with various types of arms, arches, gimbals, and other suitable components described herein. An example method of incorporating MRI features into other components (e.g., arms, arches, gimbals, etc.) of small form factor is described in Zhang, B., Sodickson, D. K. & Cloos, M. A. A high-impedance detector-array glove for magnetic resonance imaging of the hand. *Nat Biomed Eng* 2, 570-577 (2018) doi:10.1038/s41551-018-0233-y, the disclosure of which is incorporated herein by reference.

Referring now to FIGS. 39-82, various examples of automated transportation systems are illustrated which are configured for delivery of various objects including patients.

Figure 39:
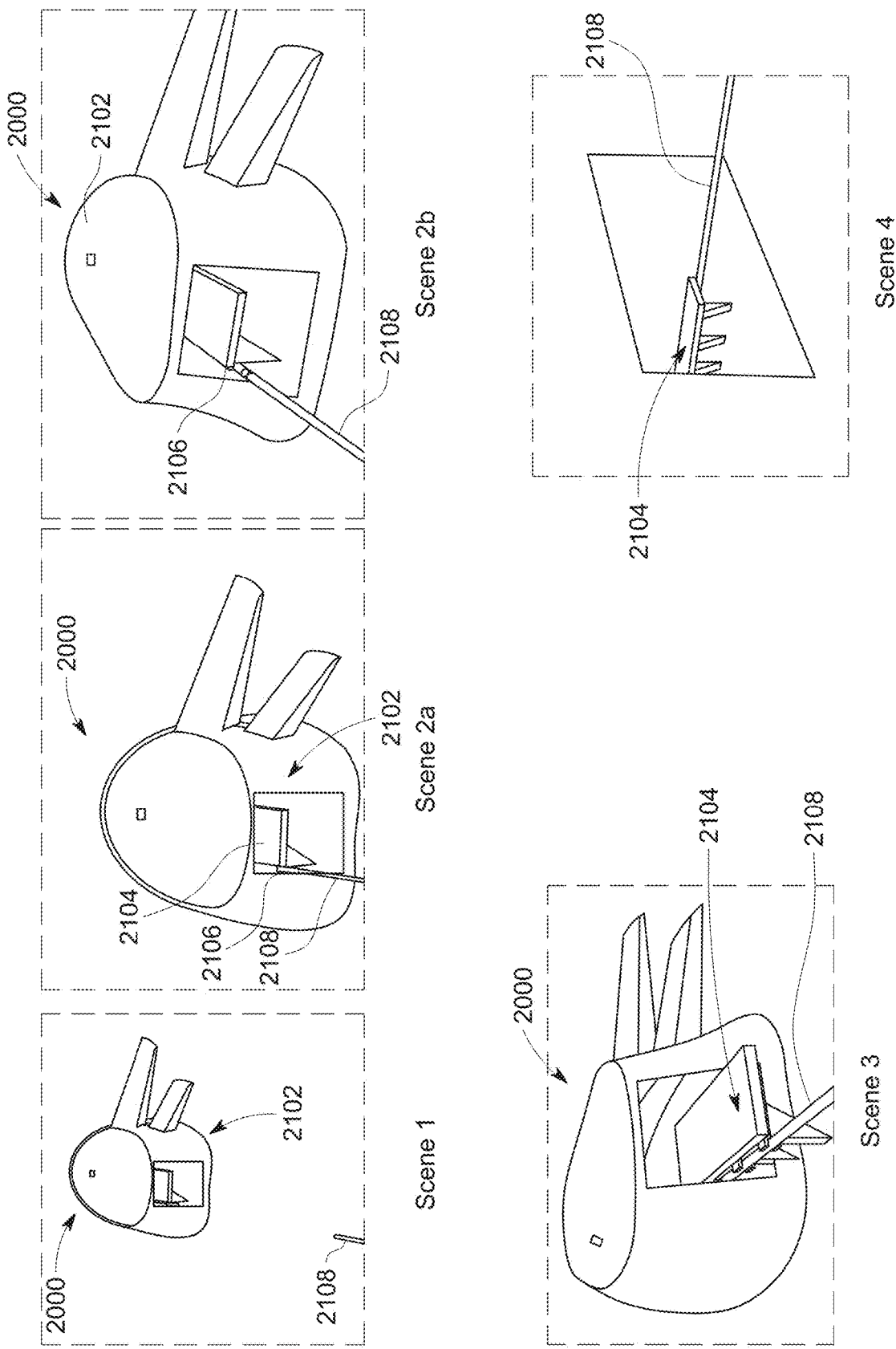
FIG. 39 illustrates perspective views of an example Automated Patient Delivery System (APDS) utilizing a transport carriage, in accordance with particular embodiments of the TARS system described herein.

FIG. 39 illustrates an example automated patient delivery system (APDS) 2100. An example sequence for transporting a patient with the system 200 is illustrated in Scenes 1-4. The system 2100 can include a transport carriage 2102, a patient gurney or cart 2104, a carriage rail 2106, and an intake rail 2018. The transport carriage 2102 can be configured as a vehicle which can be human-driven and/or autonomously driven.

The cart 2104 can be automatically delivered using one or more actuating mechanisms. For example, the cart 2104 can be propelled magnetically or mechanically through the mating rails (e.g., through the intake rail 2018 when mating with the carriage rail 2016) to a hospital or patient-center emergency intake. For example, in Scene 1, the transport carriage 2012 can position itself to mate with the intake rail 2018. In Scenes 2A and 2B, the carriage rail 2016 has mated with the intake rail 2018. In Scene 3, the patient cart 2014 is transported through the carriage rail 2016 and the intake rail 2018 that have been aligned. In Scene 4, the patient cart 2014 is transported along the intake rail 2018 into an inpatient area.

Referring to FIGS. 40-43, an example hospital environment 2200 is illustrated in which one or more unmanned aerial vehicles (UAVs) or drones 2202 are operated to aerially deliver patients and/or equipment to desired locations for treatment and surgery. The drones 2202 can be of various types, such as hybrid mass drones. The drones 2202 are configured to perform multiple functions, and can maneuver along a human right-of-way corridor 2204.

The environment 2200 can include a protective netting 2206 provided along the corridor 2204 so that drones 2202 can travel above the protective netting 2206 for safety of humans and equipment close to the floor. The protective netting 2206 can be arranged at a desired height relative to the floor. In some examples, the protective netting 2206 can be installed close to the ceiling of the corridor. People can walk, and equipment can be delivered along the corridor under the protective netting 2206.

For a drone to travel below the protective netting 2206, one or more drone transfer systems 2208 can be arranged along the corridor. For example, the drone transfer systems 2208 include ducts or elevators for ingress/egress of drones 2202 (with or without persons).

The environment 2200 can further include one or more guidance rails 2210 configured to permit drones 2202 to latch thereon for maintenance and repair (for a fail-safe). The guidance rails 2210 can be arranged in various locations, such as along the corridor below and/or above the protective netting 2206, and through the drone transfer systems 2208. In some implementations, the guidance rails 2210 can be used to perform the functions of the protective nettings 2206 by guiding the travel of drones therealong.

The guidance rails 2210 can include a magnetic or monorail type lock as an example fail-safe, which can be attached to the guidance rails 2210. Alternatively, the guidance rails 2210 are configured as monorail systems in which drones can use aerial propulsion systems provided by the guidance rails 2210 either instead of, or in conjunction to propulsion systems built in the drones. In case of failure of a drone, the drone is bound to the guidance rail 2210.

Figure 40:
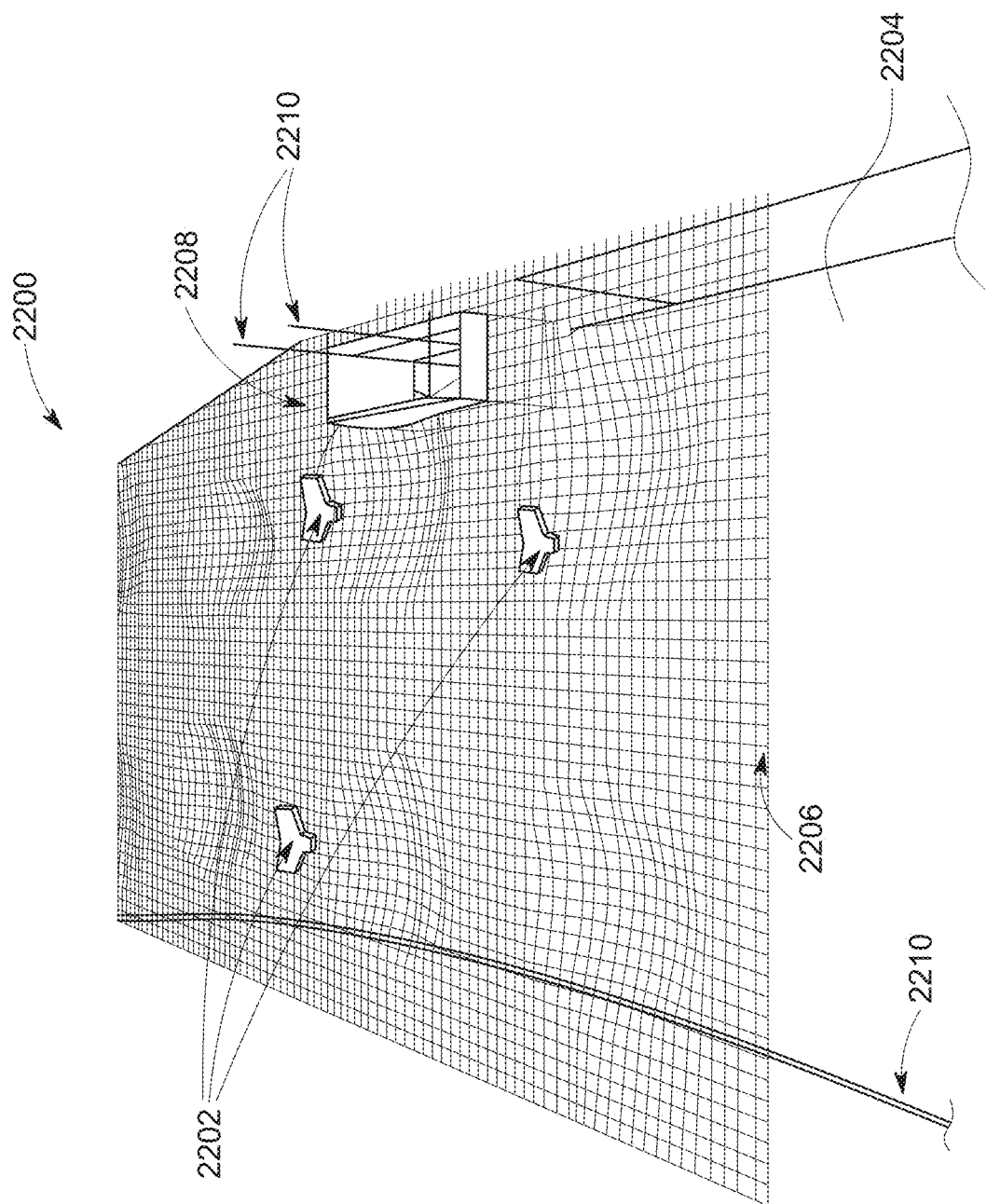
FIG. 40 illustrates a perspective view of an example system of UAVs configured for use in a hospital setting that can aerially deliver patients and or equipment to hospitals for treatment and surgery, in accordance with particular embodiments of the TARS system described herein.
Figure 41:
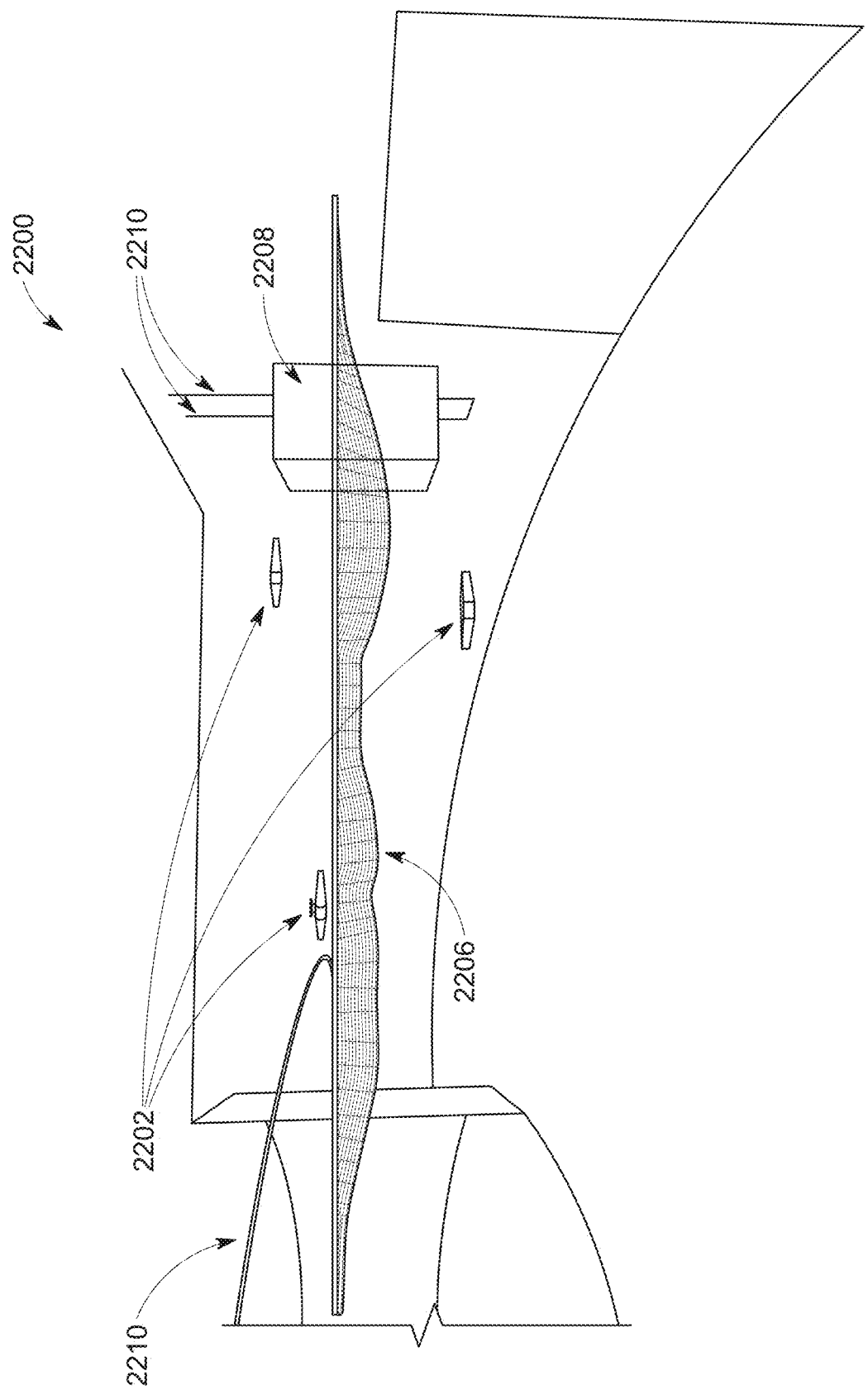
FIG. 41 illustrates a cross-sectional view of the system depicted in FIG. 40.

FIG. 41 illustrates a schematic front perspective view of the environment 2200 of FIG. 40. As illustrated, the guidance rails 2210 extending through the drone transfer system 2208 can further be used as a drone elevator or depressor.

Figure 42:
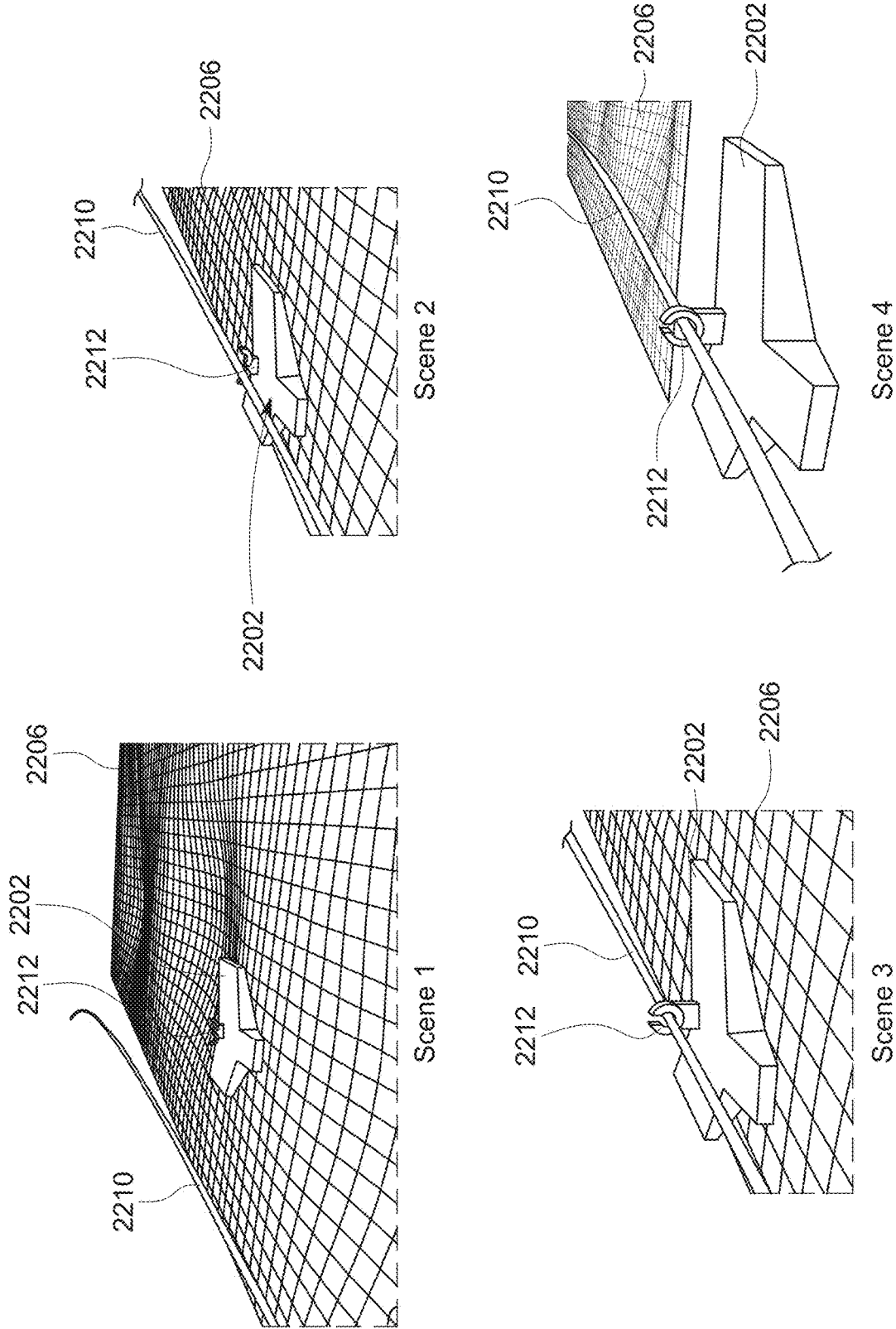
FIG. 42 illustrates perspective views of an example UAV latching on to the guidance rail of FIG. 41.

FIG. 42 illustrates an example process of a free-travelling drone 2202 that latches on to the guidance rail 2210. For example, in Scene 1, a drone 2202 travels in a default free-flying state. In this state, the drone 2202 has a latch structure 2212 that is in an opened position. Alternatively, the latch structure 2212 can be concealed from the exterior of the drone 2202 while the drone is in a free-flying state. In Scene 2, the drone 2202 can reposition itself to mate with the guidance rail 2210 by aligning the latch structure 2212 with the guidance rail 2210. In Scene 3, the latch structure 2212 of the drone 2202 operates to close around the guidance rail 2210. In Scene 4, the drone 2202 is fully latched to the guidance rail 2210. In some implementations, a preprogrammed AI can be used to operate the drone.

In addition, the latch structure 2212 can be configured to form a communication and/or power link with the guidance rail 2210 to serve a multitude of functions, such as charging, power delivery, unspecified propulsion, semi-hardwire (through magnetic link, NFC-near-filed-communication) communication with network. For example, if the drone 2202 powers down or fails, the latch structure 2212 can remain in its closed position, and a magnet can engage the drone 2202 to maintain its position. In some implementations, an additional system can be installed to recover, recuperate, or maintain drones that have malfunctioned for efficient re-use and to remove drones from traffic to prevent jams. Similarly, the guidance rail 2210 extending through the drone transfer system 2208 (e.g., drone elevator vertical pole) can further have multiple functions (charge, power, communication etc.) other than drone guidance.

FIG. 43 illustrates an example process of a drone transferring from two different levels of travel lanes (e.g., from an upper travel level or lane to a lower people/equipment level or lane). For example, in Scene 1, a drone 2202 starts to position itself towards a guidance rail 2210 (e.g., elevator rail) in the drone transfer system 2208 (e.g., duct). In Scenes 2A and 2B, drones 2202 raise or lower themselves through the duct 2208 using the guidance rails 2210. In some implementations, the drones 2202 include side latch structures 2214 configured to engage with the guidance rails 2210 and permit the drones 2202 to move up and down through the duct 2208 between the upper drone-only travel area/level (above the protective netting 2206) and the lower general travel area/level (below the protective netting 2206).

In some implementations, the latch structures 2214 can be arranged on the side of the drones 2202 so that the drones 2202 can position to easily enable the latch structures 2214 to engage with the guidance rails 2210. The guidance rails 2210 with the duct 2208 can be arranged on the side of the corridor. In some implementations, the guidance rails 2210 with the duct 2208 do not have to include fail-safe functionality in a non-netted environment because the drones are in a designated elevator area, much more restricted than the span of its travel lanes.

Figure 44:
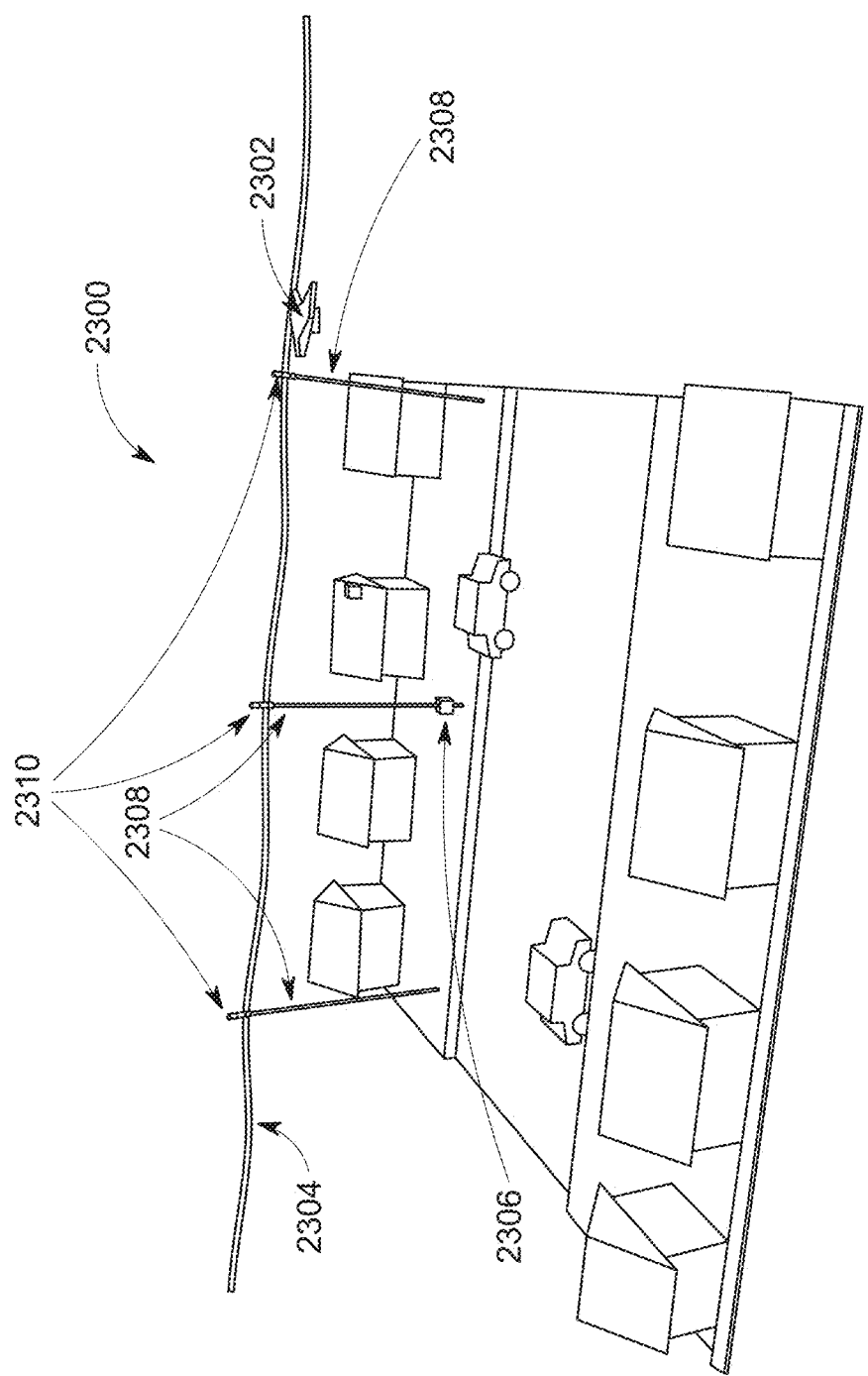
FIG. 44 illustrates a perspective view of an example UAV operating parallel to existing power with contraptions, for example, for purposes of charging or powering the UAV (wirelessly or wired).

FIG. 44 illustrates an example environment 2300, such as an existing street, in which aerial vehicles (drones) 2302 can operate with existing structures, such as other vehicles, houses, buildings, and other miscellaneous properties with or without structures. The drones 2302 can travel parallel to existing power delivery lines 2304. The drones 2302 can be physically engaged with the power delivery lines 2304 for electric connection, or wirelessly connected to the power delivery lines 2304 while traveling close to the lines 2304. The drones 2302 can be charged or supplied with electric power from the power delivery lines 2304.

In the environment 2300, the drones 2302 can operate along streets, thereby providing additional benefits of limiting low-fly drone exhaust/noise to street lanes where it may be additionally muffled by usual environmental noise (e.g., other non-electric locomotion devices requiring muffling such as cars/trucks etc.). Streetwise drones can obtain power from power lines, such as the existing power delivery lines 2304 (from existing power grids or systems).

In the environment 2300, one or more delivery receptacles 2306 can be provided and configured to move up and down along wire support structures 2308 which can be arranged (e.g., at intervals) along the street. One or more power delivery devices 2310, either wireless or wired, can be fixed to the wire support structures 2308 and configured to deliver electric power to the drones 2302.

Figure 45:
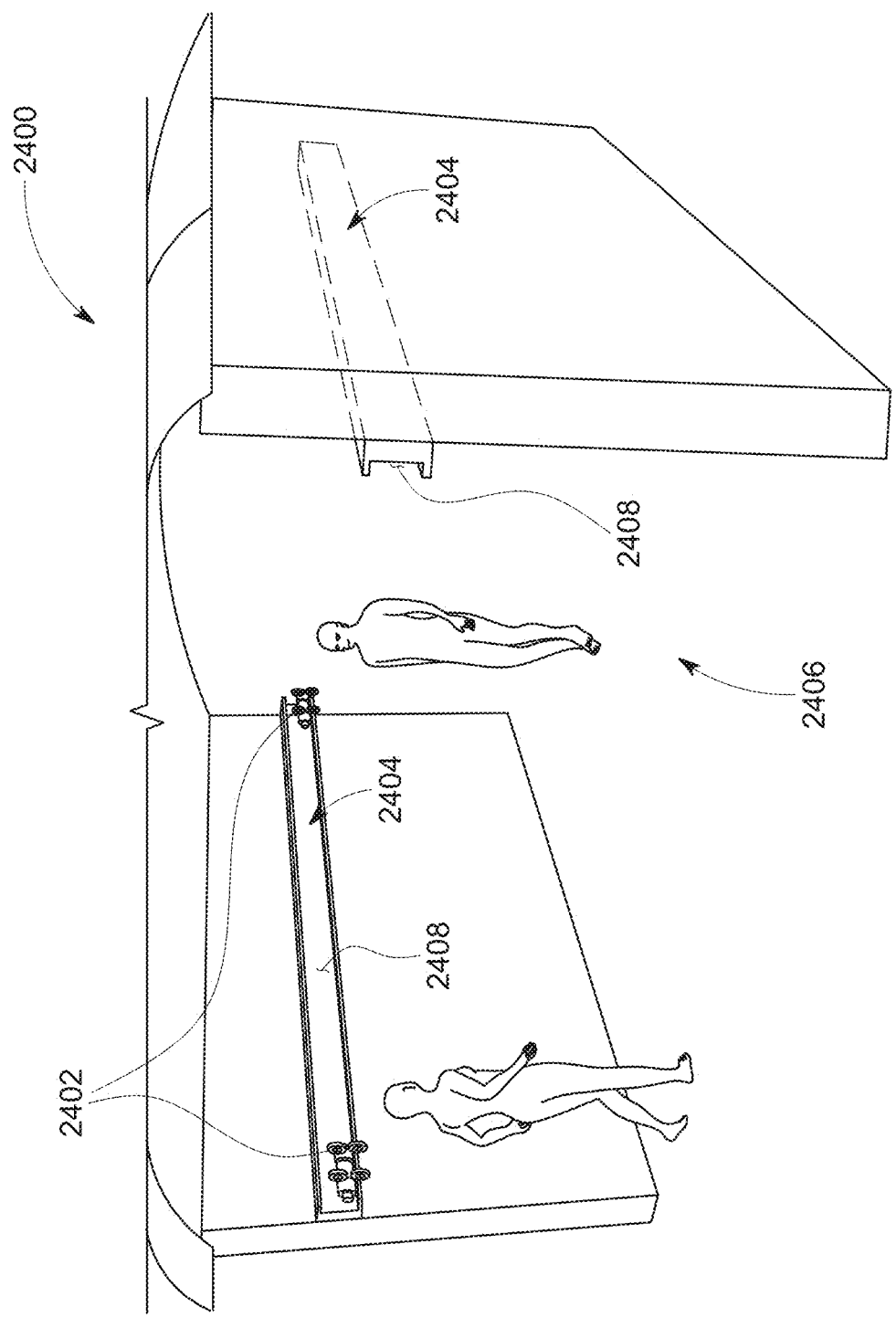
FIG. 45 illustrates a perspective view of an example hospital corridor having both UAV and human traffic, in which the UAVs are engaged with multi-purpose guidance rails.
Figure 46A:
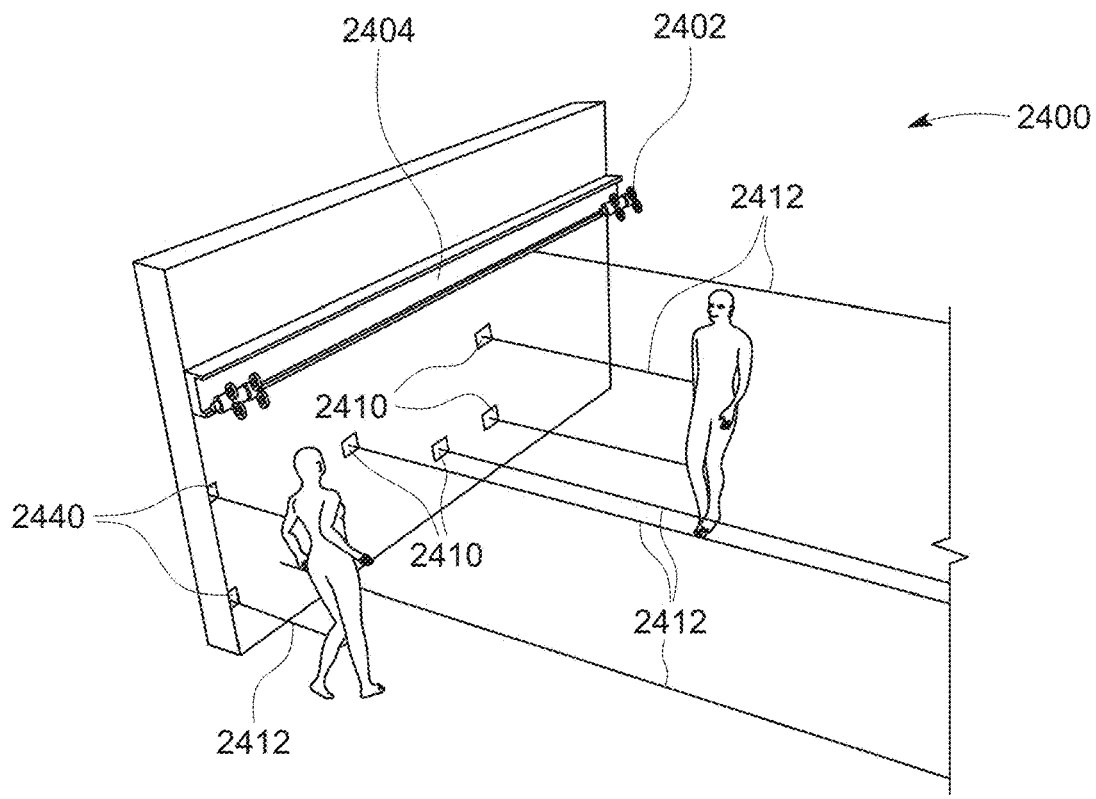
FIGS. 46A-B illustrate perspective views of an example Hybrid Drone Electromagnetic Guidance Rail/Propulsion System integrated into a hospital corridor.
Figure 46B:
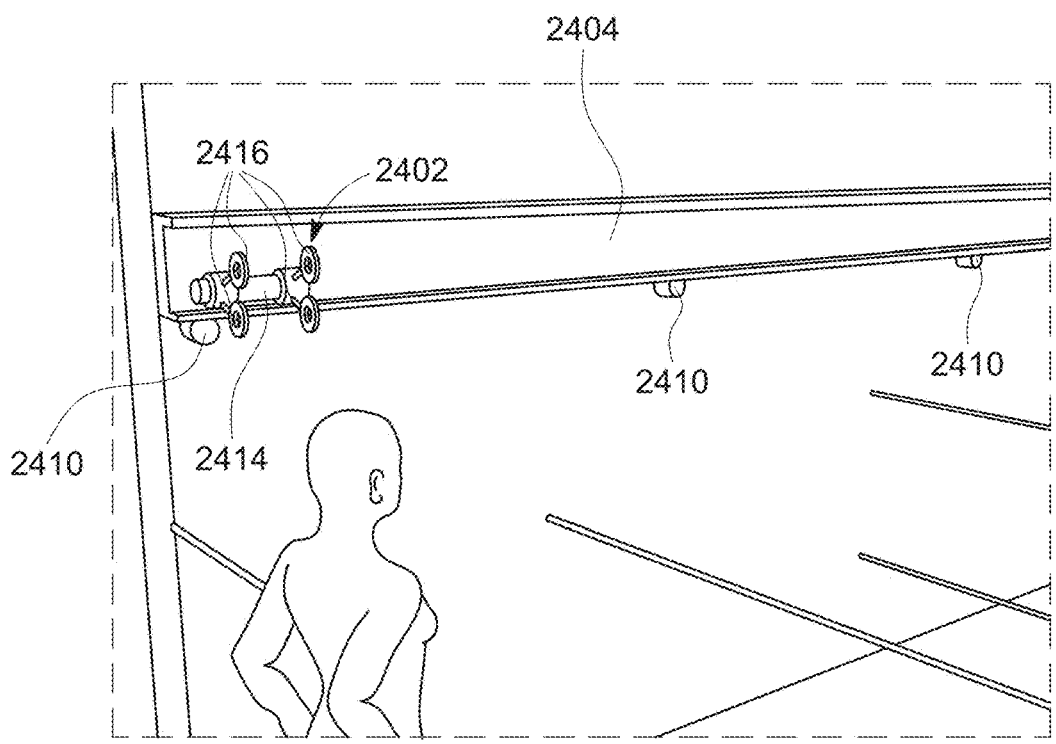
Figure 47:
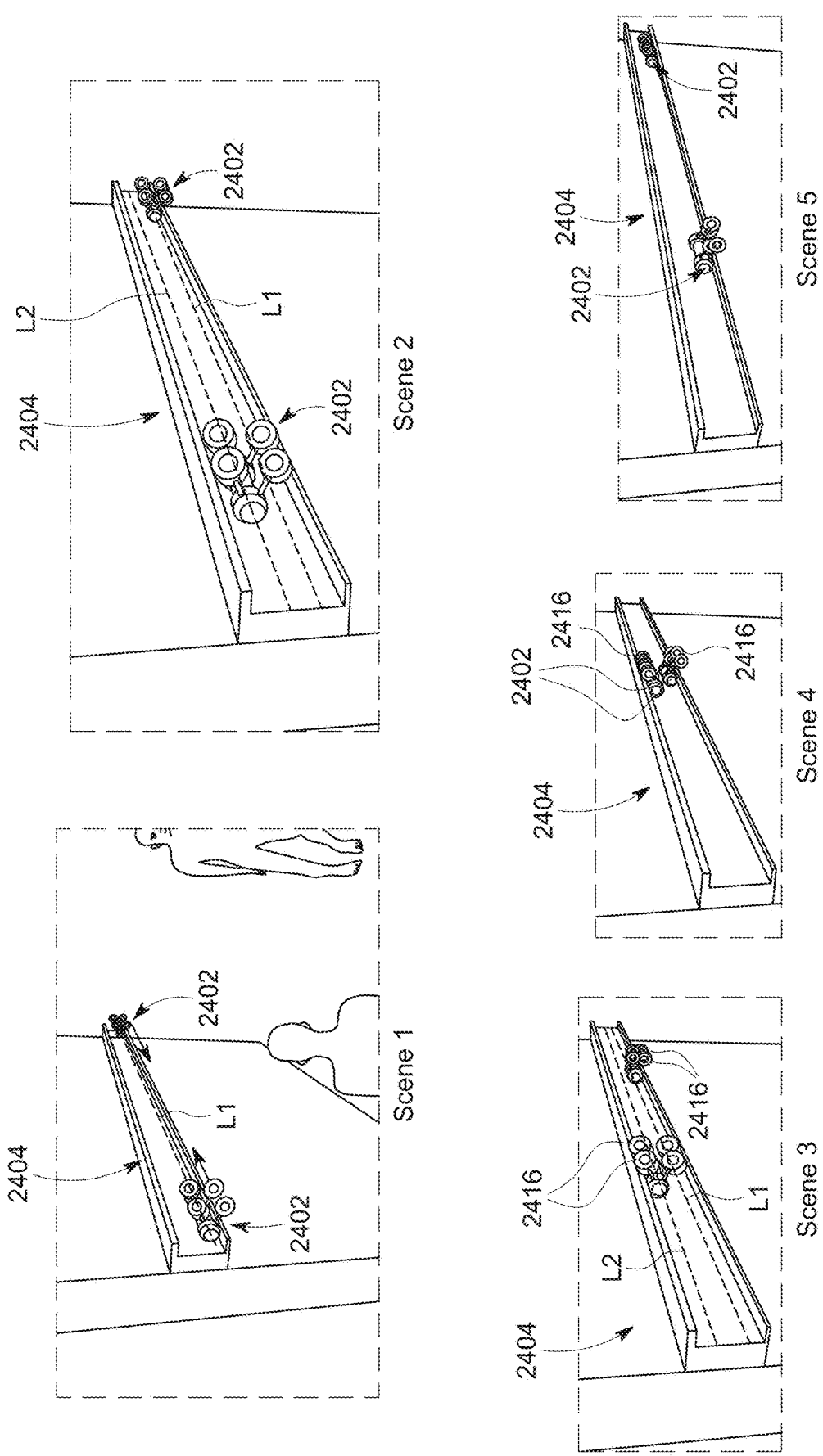
FIG. 47 illustrates perspective views of example drone traffic and collision avoidance of the Hybrid Drone Guidance and self-propulsion system.

Referring to FIGS. 45-47, an example environment 2400 is illustrated that safely integrates drones 2402 with human traffic (and other regular traffic of robots or other objects) within a corridor 2406 (e.g., a hospital corridor). For example, the environment 2400 includes one or more multi-purpose guidance rails 2404, which can be arranged above a general human height level.

As illustrated in FIG. 45, the guidance rails 2404 include tracks 2408 configured to engage the drones 2402. Although being able to free-fly, the drones 2402 can be generally relegated to the tracks 2408 that may be arranged above head-level to ensure free-flowing and non-obstructed human foot traffic.

FIGS. 46A-B further illustrate the environment 2400 of FIG. 45. The guidance rails 2404 can be configured as a hybrid drone electromagnetic guidance rail and propulsion system integrated into a hospital corridor.

In addition, as illustrated in FIG. 46A, the environment 2400 can include one or more randomized echo locator beam devices (e.g., sensors with emitters and receivers) 2410 which can be electrical (e.g., laser and/or photonic) or mechanical (e.g., sonar). The beams 2412 emitted from the devices 2410 can be reflected off from the presence of objects. As illustrated, some beams are reflected sooner than others indicating the presence of an object. The devices 2412 can be integrated with a wall in the corridor. The devices 2412 can be arranged in a predetermined pattern, or randomly arranged.

FIG. 46B is a partial enlargement of the drone 2402 of FIG. 46A. In this example, the drone 2402 can include a body 2414 configured as a cylindrical cargo for carrying one or more objects. The drone 2402 further includes one or more dynamic fans (with air propulsion bores) 2416 provided on the body 2414 and configured to propel the drone 2402. In addition, the environment 2400 can include an array of the beam devices or sensors 2410 that are adjacent to, and spaced along, the guidance rail 2402.

FIG. 47 illustrates an example operation for drone traffic and collision avoidance using the guidance rail 2402. As described herein, the drones 2402 are configured to be self-propelled, and the guidance rail 2402 is configured to prevent collision between multiple drones 2402 traveling along the guidance rail 2402. For example, in Scene 1, two drones 2402 are travelling in opposing directions and towards each other along the same virtual lane L1. Without collision avoidance, a collision would occur. In Scene 2, either or both of the drones 2402 can detect the other drone in the way and determine whether any of the drones 2402 should move and/or which drone will actively avoid the other. The drone that is determined to move can navigate to an alternative virtual lane L2 that does not overlap the lane L1 along which the other drone is still traveling. In alternative implementations, the determination can be performed at a remote computing device or server that communicates with the drones 2402. Further, in other implementations, both of the drones can move to shift their traveling lanes to avoid collision. In Scene 3, both drones 2402 can adjust their propulsive fans 2416 towards the direction of the nearest outer edge of the guidance rail 2404 to further avoid unintended contact. In Scene 4, the drones 2402 are traveling in different lanes L1 and L2 and passing each other without collision. In Scene 5, the drones 2402 have successfully passed each other. Further, the propulsive fans 2416 can return to their original (neutral) position. In addition, the drones 2402 can return to their original lanes that they had traveled prior to passing each other. In some implementations, magnetic-bumper collision can be provided to reduce possibility of derailment or otherwise damage.

Figure 48:
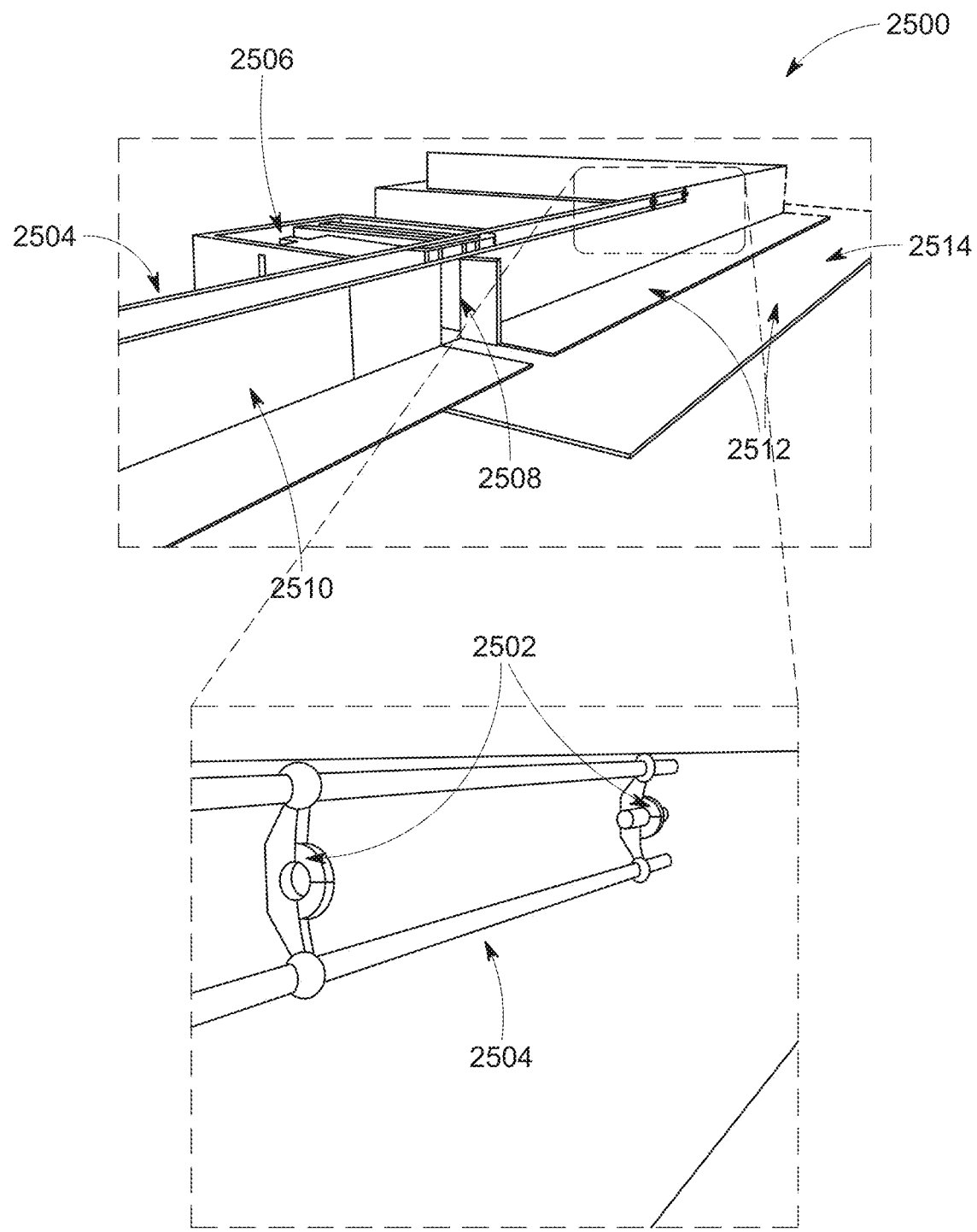
FIG. 48 illustrates perspective views of an example indoor-rail-based drone system as used in a hospital, for example, with wall rails for Accessory conveyance unit (ACU) guidance.

Referring now to FIGS. 48-56, an example indoor-rail-based drone system 2500 is illustrated. FIG. 48 schematically illustrates an overview of the indoor-rail-based drone system 2500 as used in a hospital for example. Illustrated are one or more drones 2502, a guidance rail system 2504, a patient examination/visitation room 2506, a patient-room door 2508, an outside room wall 2510, and a floor 2512 on a hospital corridor 2514. In this example, the drones 2502 are configured as Accessory Conveyance Units (ACUs).

Figure 49:
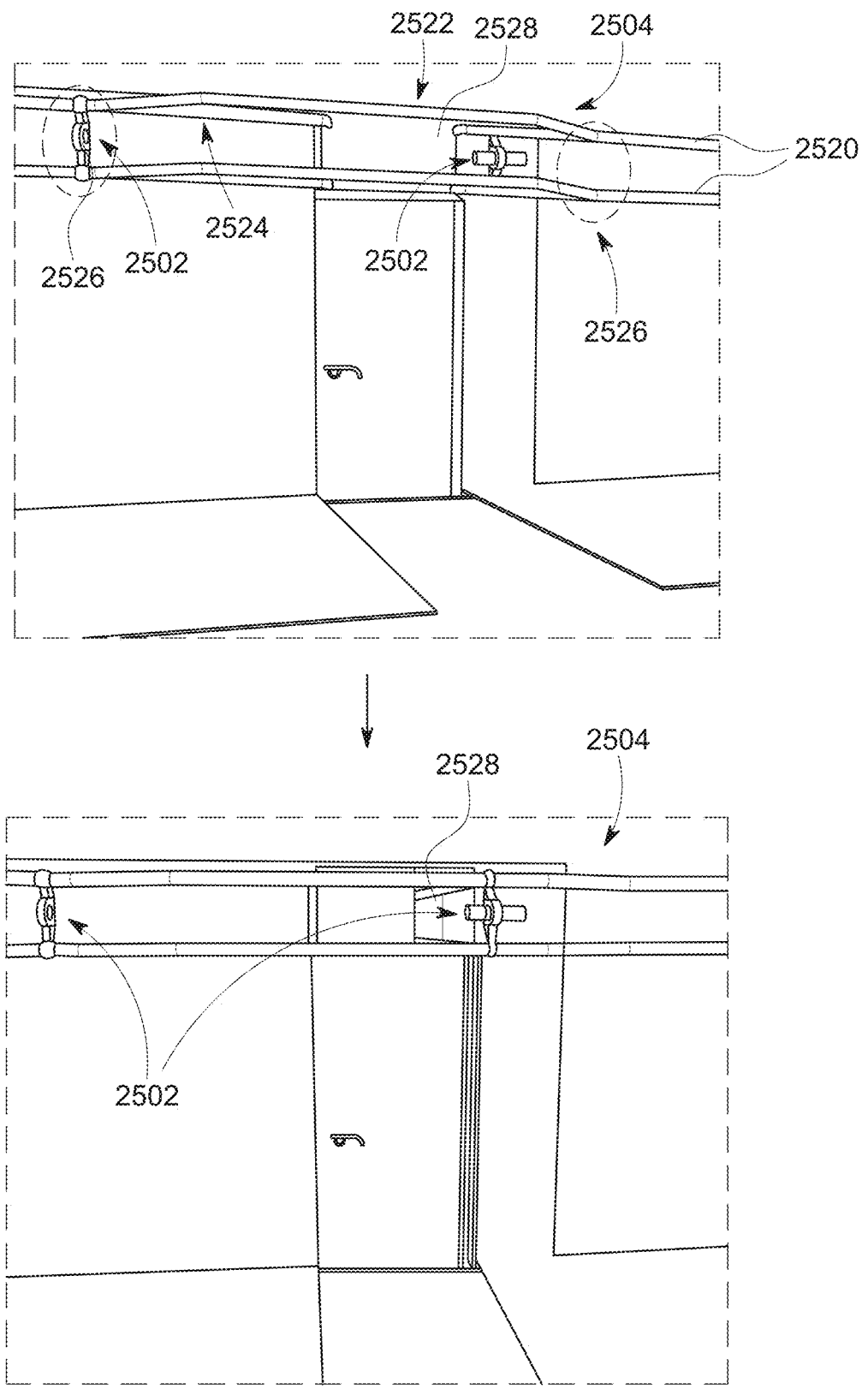
FIG. 49 illustrates perspective views of an alternative embodiment of ACUs with rail guidance and bypass capacities.

FIGS. 49-52 illustrate an example of the guidance rail system 2504 for the drones 2502. As illustrated in FIGS. 49-50, the guidance rail system 2504 can provide bypass capabilities.

In this example, the guidance rail system 2504 includes a pair of rail lines 2520 configured to guide drones 2502 therealong. The rail lines of the guidance rail system 2504 can physically engage (e.g., clasp, contact, etc.) with the drones for guidance. Alternatively or in addition, the guidance rail system 2504 is configured to provide virtual rails using various mechanisms (e.g., markers, electronic elements such as magnets, lasers etc.).

The guidance rail system 2504 can include a base rail 2524 extending along a corridor wall, and further include a bypass rail 2522 that branches out from, and rejoins back to, the base rail 2524 and are routed in parallel with a portion of the base rail 2524. The drones 2502 can selectively navigate along the base rail 2524 or the bypass rail 2522 that they can enter or return from through Y-shaped branches 2526. In the illustrated example, the base rail 2524 is routed into, and out from, a patient room 2530 while the bypass rail 2522 continues along the corridor wall. As described herein, the guidance rail system 2504 can be arranged above head level to minimally obstruct human traffic.

The base rail 2524 is routed into the room. As a drone 2502 navigates along the base rail 2524 and enters the room, a drone door 2528 (like a pet door) can be automatically opened by the drone 2502 (e.g., by wireless control from the drone 2520, or by the drone 2520 pushing the door).

Figure 51:
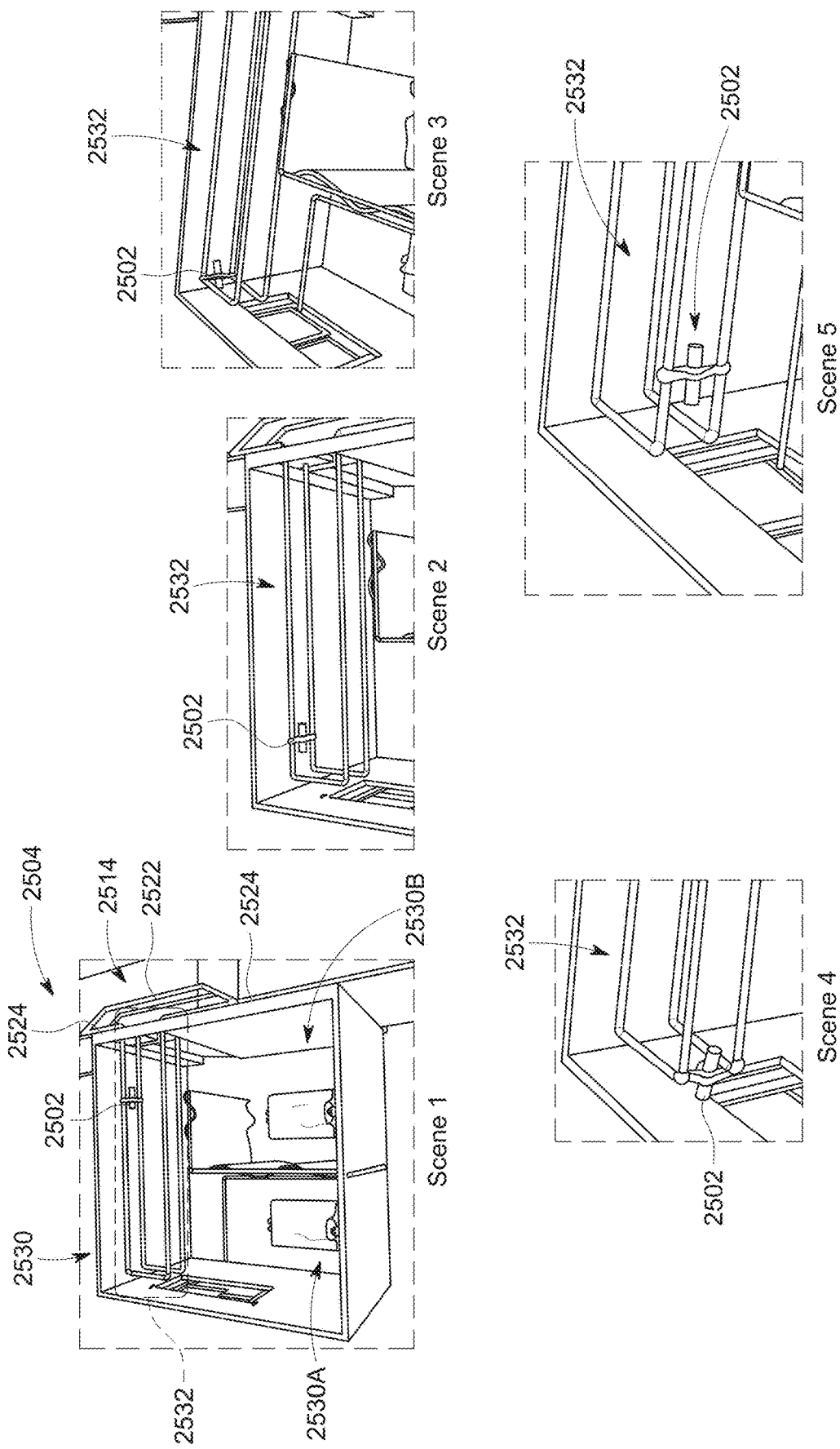
FIG. 51 illustrates perspective views of an example of an ACU entering a hospital room, and traversing an example U-shaped rail to access individual patient or doctor necessities on both sides of the room.
Figure 52:
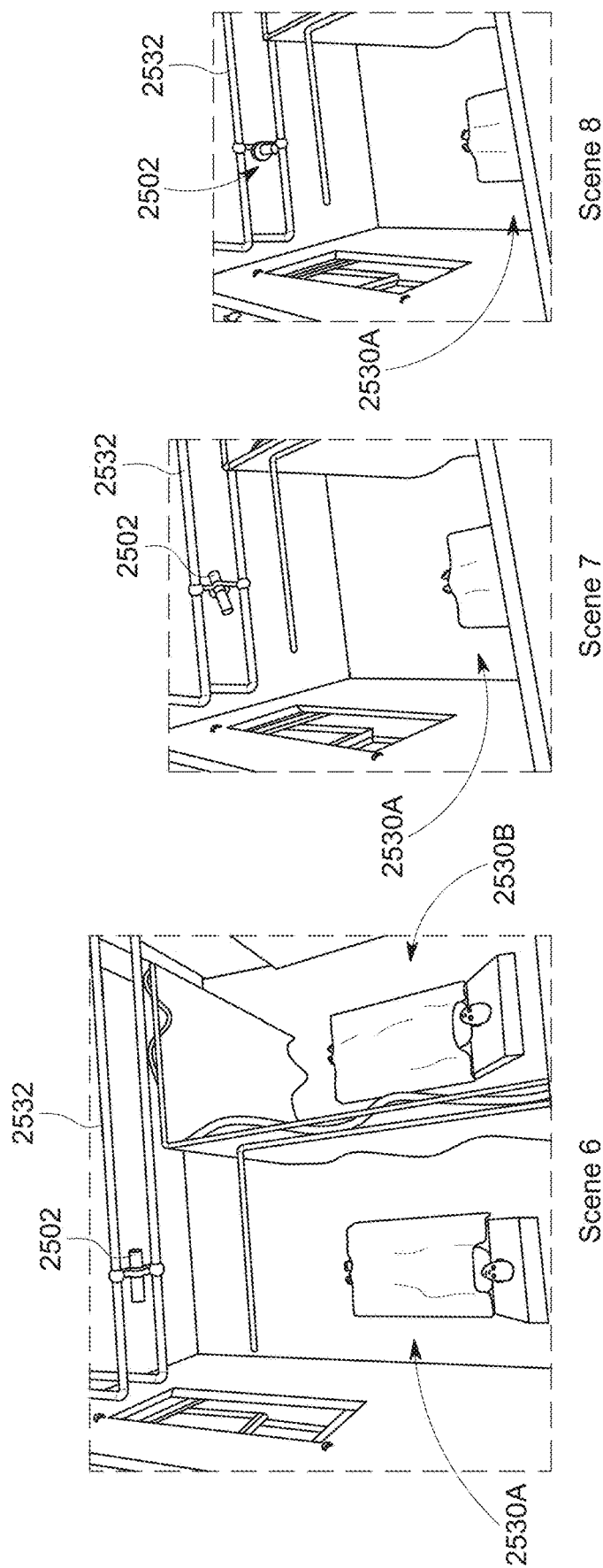
FIG. 52 illustrates additional perspective views of the example ACU of FIG. 51.

As illustrated in FIGS. 51-52, the guidance rail system 2504 is routed in a room 2530 from a corridor 2514. The guidance rail system 2504 includes a room rail 2532 that is connected to the base rail 2524. A drone 2502 traverses the room rail 2532 (e.g., U-shaped rail) to access individual patient or doctor necessities on both sides of the room. For example, in Scene 1, a drone 2502 is moving along the room rail 2532 after entering the room 2530. The room 2530 has multiple areas or sub-rooms, such as a first area 2530A and a second area 2530B. In Scene 2, the drone 2502 is about to make a turn along the room rail 2532. In Scene 3, the drone 2502 is making a sharp turn at a curved portion of the room rail 2532. In Scene 4, the drone 2502 is making a second sharp turn for return path along the room rail 2532. In Scene 5, the drone 2502 is now in position to interact with the first area 2530A in the room 2530. In Scene 6, the drone 2502 is in a position convenient for the first area 2530A. In Scene 7, the drone 2502 stays in the same location of the room rail 2532, while a cargo is repositioning to change its orientation to optimize its interaction relative to the first area 2530A. In Scene 8, the drone 2502 is further reoriented for interaction in the first area 2530A.

FIG. 53 illustrates example positions (including orientations) of a drone 2502 in the guidance rail system 2504. In the illustrated example, the drone 2502 is positioned along the room rail 2532 in the first area 2530A of the room 2530, and reorienting itself to interact with that area. For example, in Scene 1, the drone 2502 is in a neutral orientation. In Scene 2, the drone 2502 is rotating about a vertical axis 2534. In Scene 3, the drone 2502 is rotating relative to a horizontal axis 2536.

For example, the drone 2502 can include a cargo 2540 containing a sensor configured to detect a patient or other objects. As moving along the room rail 2532 and traversing multiple areas, the drone 2502 can monitor the statuses of multiple patients or other objects in the room and other rooms.

Figure 54:
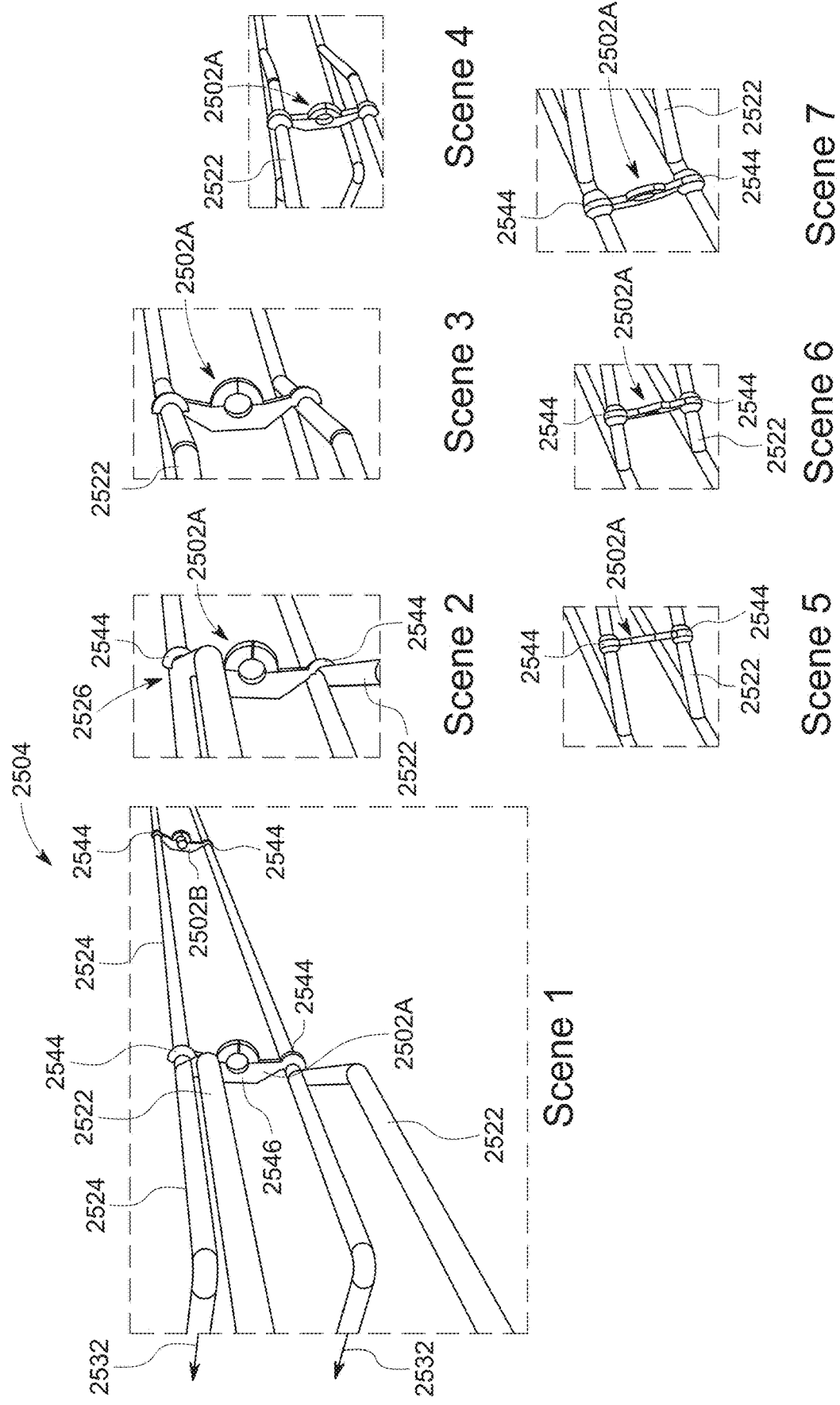
FIG. 54 illustrates perspective views of an example mechanism for first and second ACUs using a room bypass track.

Referring to FIGS. 54-55, an example operation of a drone 2502 is illustrated, which can travel along selectively a base rail or a bypass rail. FIG. 54 illustrates an example mechanism and operation of drones choosing a room bypass track 2522. In Scene 1, two drones 2502A-B (collectively 2502) are traveling in the same direction (towards the bottom-left of the scene). For example, each drone 2502 includes one or more claspers 2544 operatively coupled to a body 2546 of the drone 2502. The claspers 2544 are configured to engage the rails and change their orientations relative to the rails. The orientation of the claspers 2544 can determine which rail the drone follows (e.g., between the base rail 2524 and the bypass rail 2522) (whether the drone enters or passes the room).

For example, when moving along the base rail 2524 and reaching the location of the branch 2526, the claspers 2544 of a first drone 2502A can be oriented onto the side of the bypass rail 2522 (towards the bypass rail 2522). As described below, if the claspers 2544 are oriented onto the side of the base rail 2524 (e.g., opposite side to the side of the bypass rail 2522), the drone will follow the base rail 2524, not the bypass rail 2522. In Scenes 2-7, the drone 2502A are sequentially traversing along the bypass route 2522 in progressing stages.

A second drone 2502B has claspers 2544 reoriented to follow the base rail 2524 (the opposing non-bypass route) to enter a patient room. In Scene 8, the second drone 2502B has claspers 2544 oriented (or reoriented) at (or before) the branch 2526 so as to move toward the room along the base rail 2524. The second drone 2502B will enter the room and not bypass it. In Scenes 9-10, the drone 2502B are sequentially traveling on the base rail 2524 leading into the room.

Figure 56:
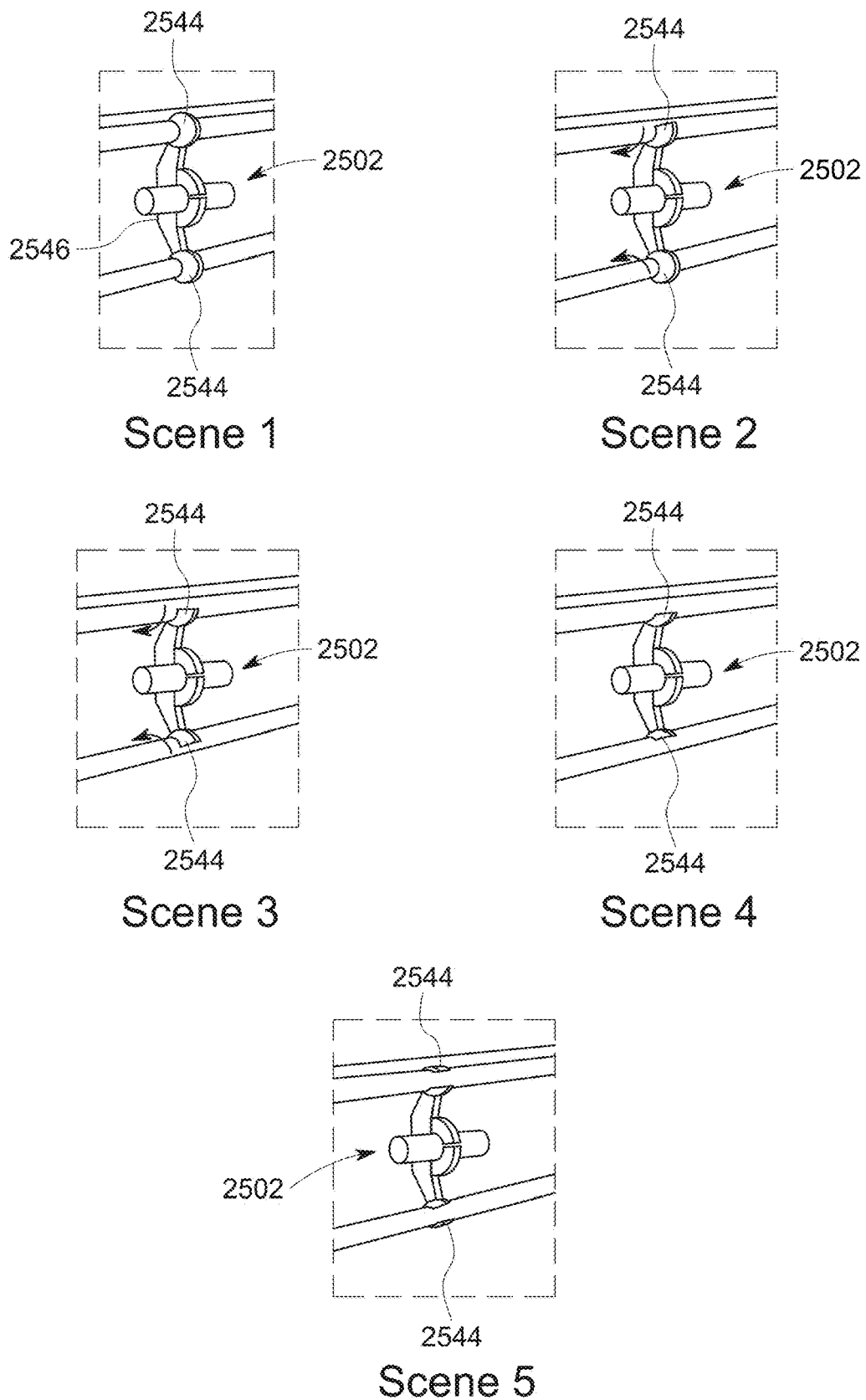
FIG. 56 illustrates perspective views of an example ACU in a process of altering rail-clasper orientation in preparation of alternating tracks.

FIG. 56 illustrates an example operation of a drone 2502 changing the orientation of claspers 2544 to alter tracks (rails) that it follows. For example, the claspers 2544 of the drone 2502 alter their orientation in order to determine a branch path (e.g., between the base rail 2524 and the bypass rail 2522). For example, in Scene 1, the claspers 2544 are in a first orientation (e.g., neutral orientation). In Scenes 2-4, the claspers 2544 are in process of changing orientation relative to the rail. In Scene 5, the claspers 2544 are fully reoriented.

The claspers 2544 can be reoriented relative to the body 2546 of the drone 2502 in various mechanisms. For example, the claspers 2544 include C-shaped gripping portions that are rotatably coupled to opposite ends of the body 2546. The C-shaped gripping portion is configured to rotate relative to the body 2546 and thus rotate around the associated rail while the body 2546 remains stationary. As it rotates, the open side of the C-shaped gripping portion faces different sides of the rail as illustrated in Scenes 1-5.

Figure 57:
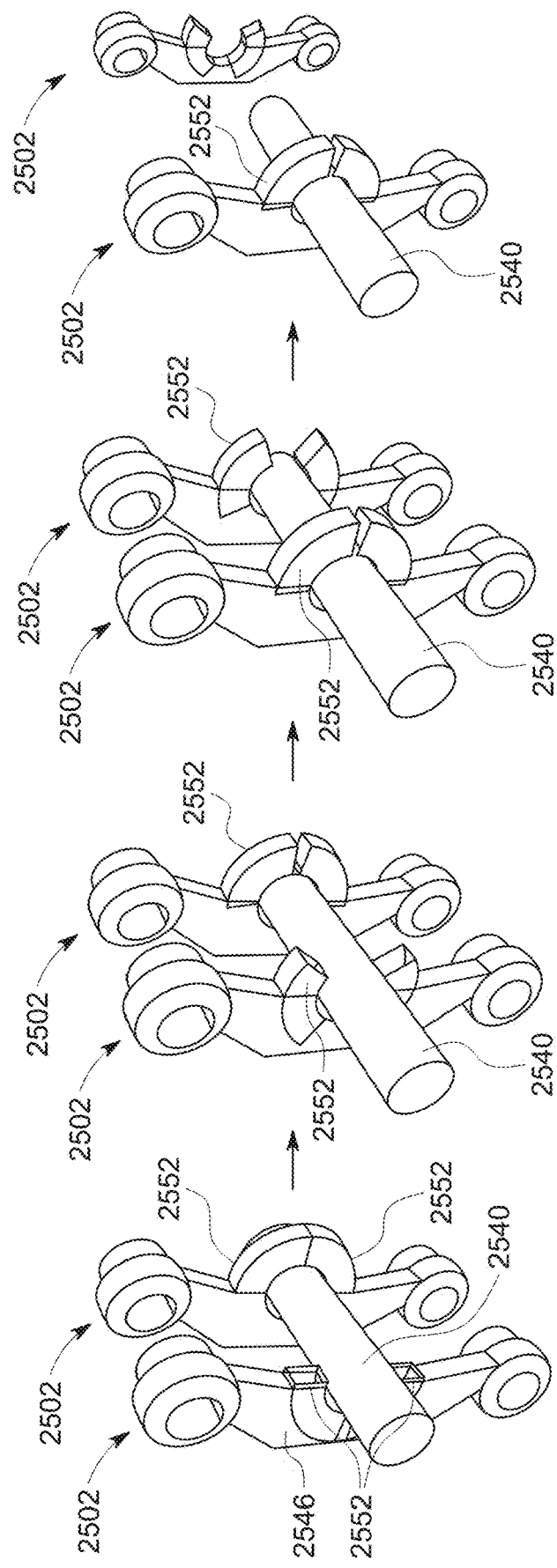
FIG. 57 illustrates perspective views of an example of an ACU-to-ACU handoff of cargo.

Referring to FIGS. 57-58, an example cargo gripping mechanism of the drone 2502 is described. FIG. 57 schematically illustrates an example operation of transferring a cargo from one drone to another. For example, the drone 2502 includes a cargo holding structure 2550 having a pair of mating grippers 2552 configured to hold a cargo 2540. The grippers 2552 can be retracted into and extended from the body 2546 of the drone 2502. For example, as shown in Scene 1, two drones 2502 come close and aligned (e.g., along a rail) so that a cargo 2540 held by the extended grippers 2552 of a first drone 2502 is arranged close to the retracted grippers 2552 of a second drone 2502. In Scenes 2 and 3, the grippers 2552 are gradually extended out from the body of the second drone 2502, while the grippers 2552 of the first drone 2502 may be gradually retracted into the body of the first drone 2502. In Scene 4, when the second drone 2502 finally holds the cargo, the first drone 2502 may hand off, and two drones may be moved away from each other.

FIG. 58 illustrates an example structure of the drone 2502 (as an accessory conveyance unit (ACU)) with the cargo holding structure 2550 for carrying a cargo 2540. The cargo 2540 can include equipment for use by a medical practitioner or patient. In Scene 1, the drone 2502 is in clasped engagement with the cargo. For example, the grippers 2552 (e.g., C-ring claspers) are in a closed position holding the cargo. In Scene 2, the grippers 2552 of the drone 2502 is in a partial closed/open position. In Scene 3, the grippers 2552 of the drone 2502 is in an open position. The drone 2502 can include a propulsion mechanism for driving the drone 2502. For example, the drone 2502 can include a pair of engines 2560 (with fans). The drone 2502 can be self-guided, or guided by the rails as described herein or by other mechanisms (e.g., magnetic wallpaper) with or without counterweight.

Figure 59A:
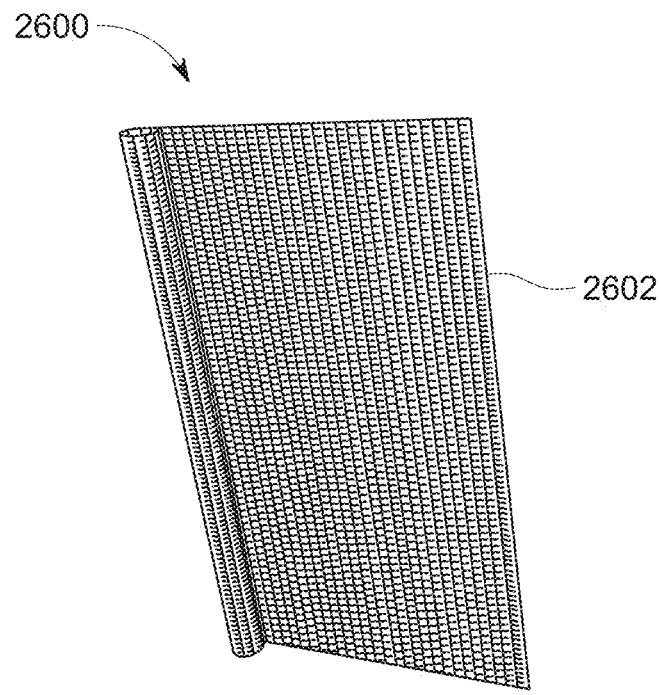
FIGS. 59A-B illustrate perspective views of example magnetic wallpaper (for indoor/outdoor usage) for guiding ACUs and other drone devices along a path.
Figure 59B:
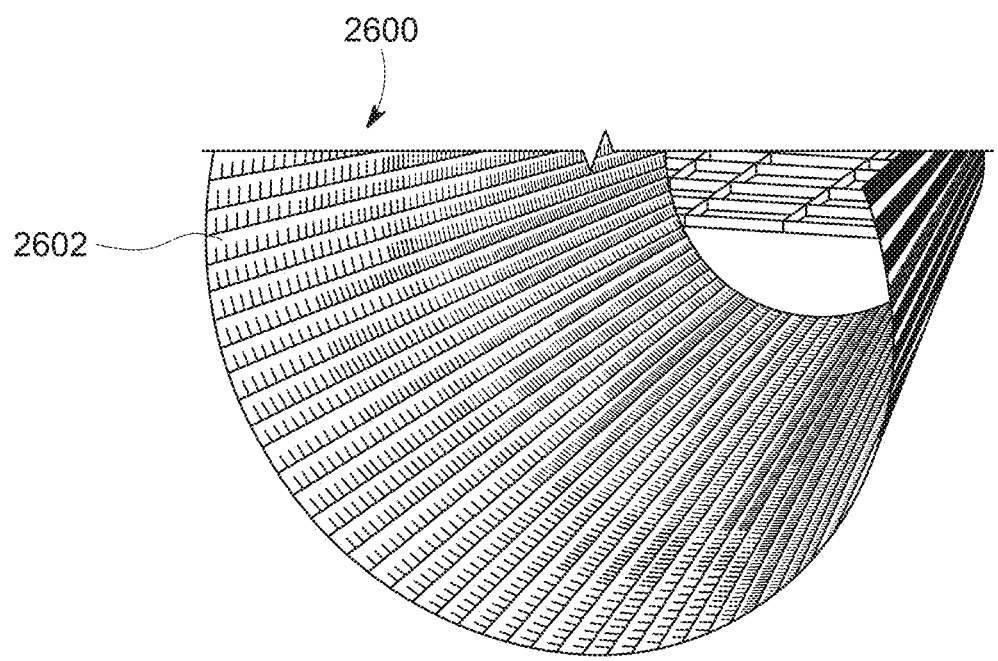

FIGS. 59A-B illustrate an example system 2600 for guiding drones or other objects (e.g., carts carrying patients) along a desired path. The system 2600 includes a granulated magnetic wallpaper 2602, which may be for indoor or outdoor usage. The system 2600 can replace, or be used along with, the guidance rail system described herein. The granulated magnetic wallpaper 2602 includes a plurality of sensors and/or markings that are sparsely positioned. Examples of the granulated magnetic wallpaper is described in U.S. Pub. Nos. US 2009/0263634 and US2009/0110948, the entirety of which are incorporated herein by reference.

The granulated magnetic wallpaper 2602 can be stored and/or potable in a rolled configuration. In FIG. 59A, a roll of the granulated magnetic wallpaper 2602 is being unrolled for usage. In FIG. 59B, the granulated magnetic wallpaper 2602 is arranged and installed in a desired configuration (e.g., a cylindrical shape along a path) for usage.

Figure 60:
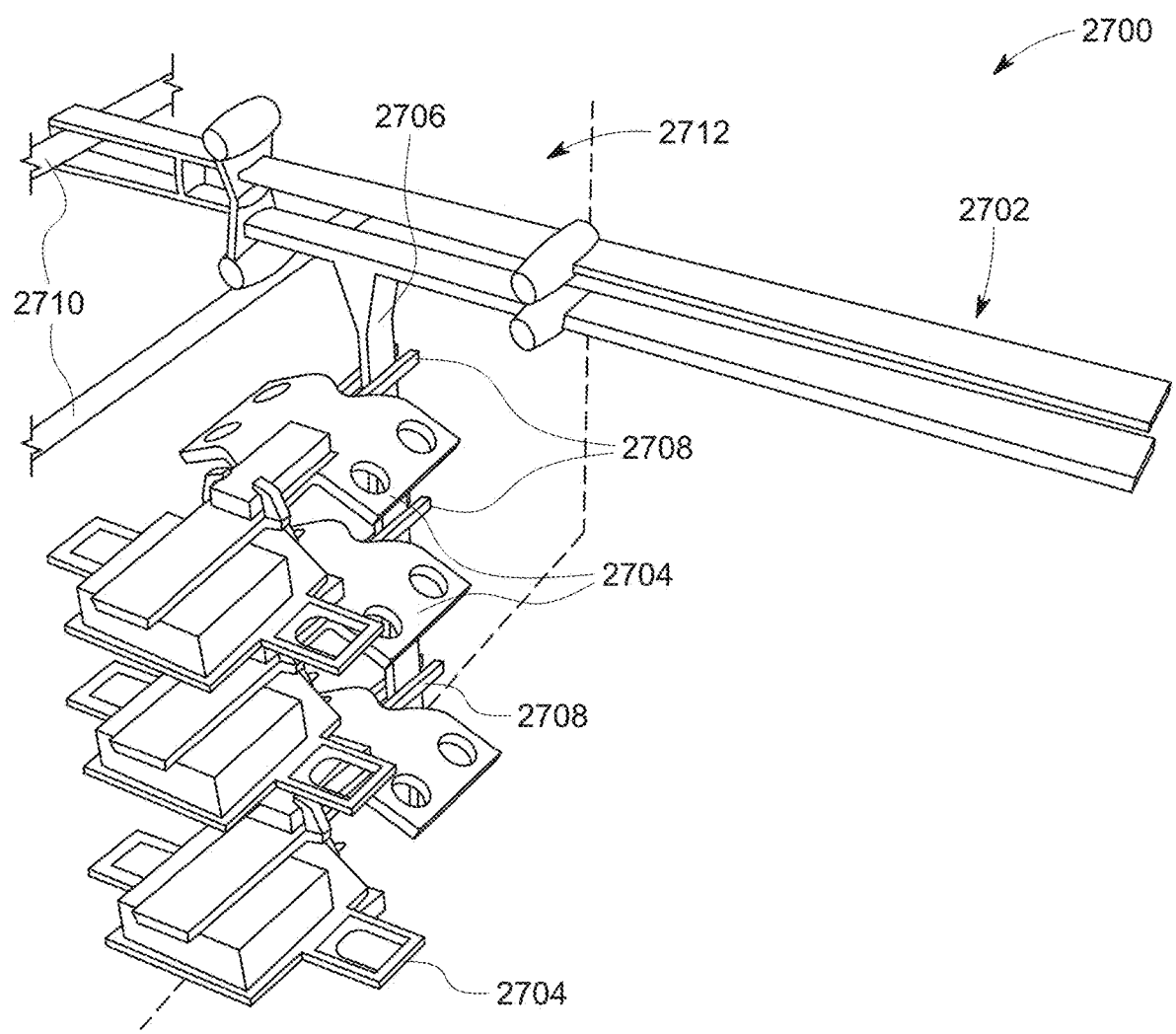
FIG. 60 illustrates a perspective view of another example aerial drone carrier with rail guidance for use, for example, in a hospital or medical environment.
Figure 61:
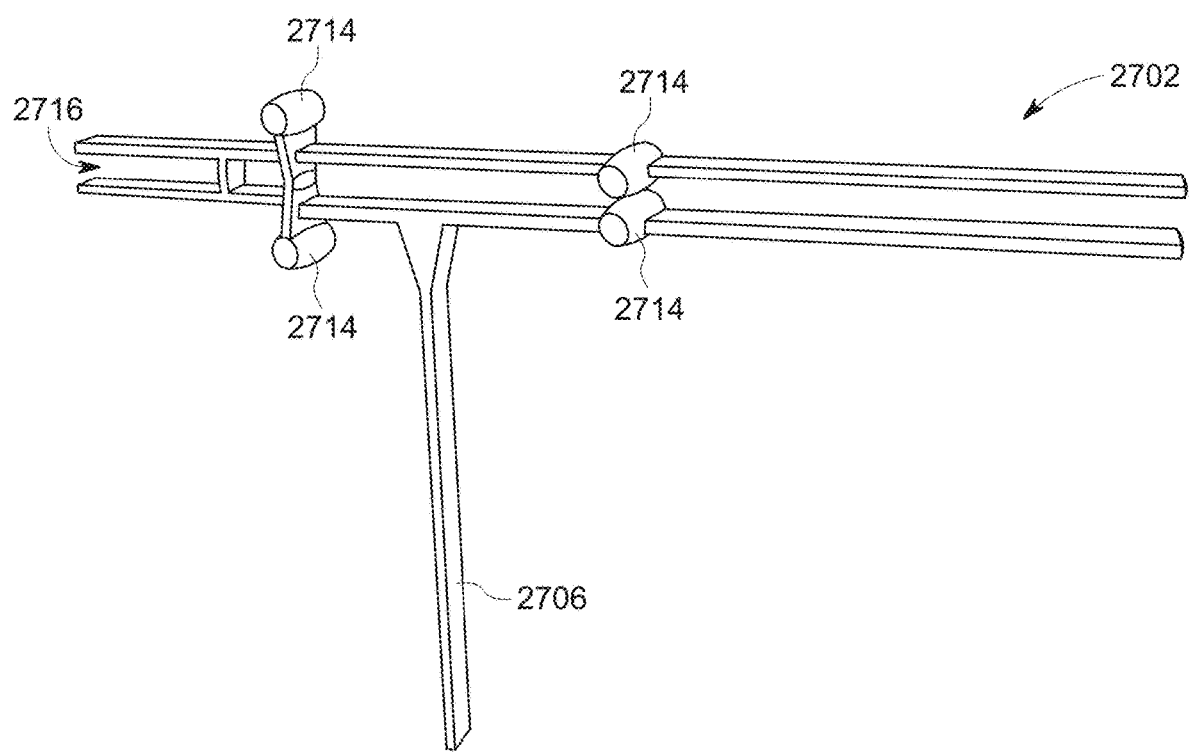
FIG. 61 illustrates another perspective view of the aerial drone carrier of FIG. 60.

Referring to FIGS. 60-61, an example aerial drone carrier system 2700 is described. The aerial drone carrier system 2700 includes a drone carrier 2702 configured to carry one or more drones 2704 of the same or different functionalities together. The drone carrier 2702 can be used to collect and transport multiple drones simultaneously for repurposing, recharging or for energy conservation of drone batteries (e.g., satellite drones batteries which may be consumed relatively quickly).

For example, the drone carrier 2702 includes a vertical docking extension 2706 with which drones 2704 engage. The vertical docking extension 2706 can be configured to pick up or mate with such drones 2704. For example, the drones 2704 include slots 2708 configured to engage the vertical docking extension 2706 of the drone carrier 2702. In some implementations, the drone carrier 2702 can be configured to provide additional functions to the drones 2704, such as charging, data communication, etc., through the connection between the vertical docking extension 2706 and the slots 2708.

The drone carrier 2702 can include one or more propulsion devices 2714 (e.g., engines with fans) for self-driving. In addition or alternatively, the drone carrier 2702 can be guided by a guidance rail system 2710 (e.g., the guidance rail system described herein) which can be fixed or not fixed to, for example, an upper area of a wall 2712. For example, the drone carrier 2702 includes a rail engaging section 2716 configured to slidably engage a rail line of the guidance rail system 2710.

Figure 62A:
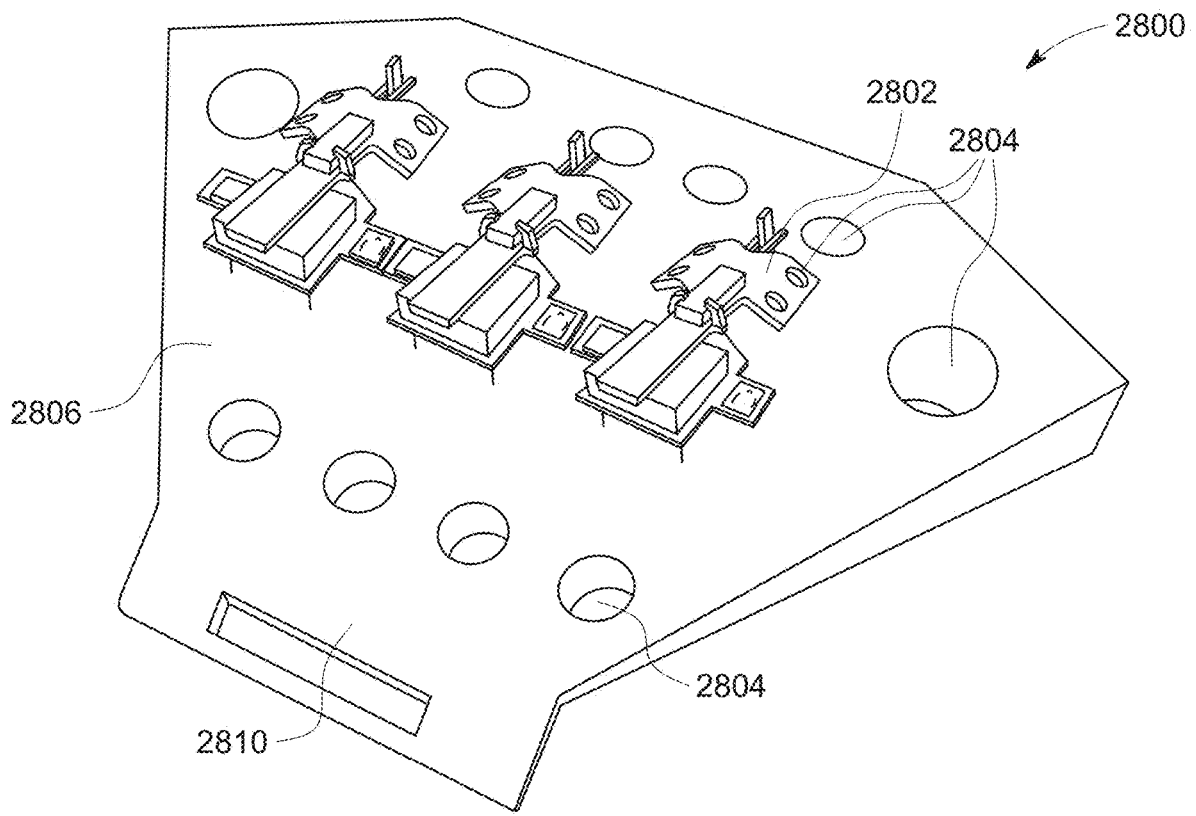
FIGS. 62A-B illustrate perspective views of an example portable drone carrier embodiment for use, for example, in a hospital or medical environment.
Figure 62B:
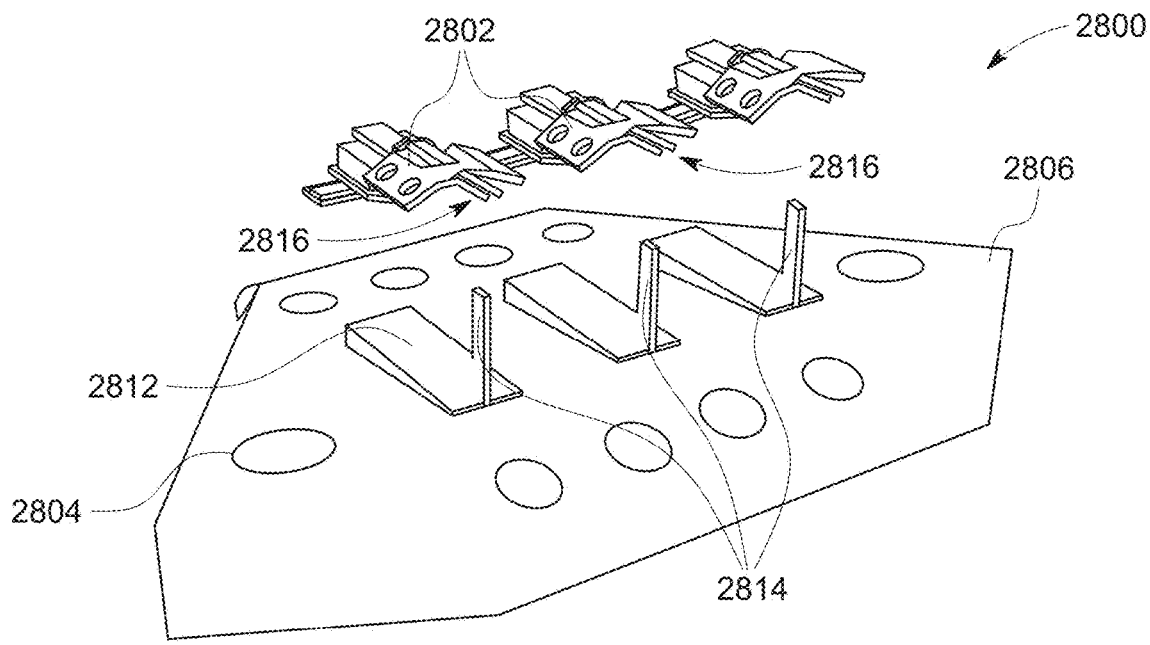

Referring to FIGS. 62A-B, another example drone carrier 2800 is described. FIGS. 62A-B schematically illustrate an example drone carrier 2800 (e.g., a larger/mother drone or carrier) configured to hold and carrier one or more drones 2802 (e.g., a smaller/satellite/child drones). The drones 2802 can be configured to similar to the drones 2704 or other drones described herein. The drones 2802 may be configured for the same or different functionalities. For example, each satellite drone can perform separate functions in the same or disparate locations. In some implementations, the drone carrier 2800 is configured to be manually handled. For example, the drone carrier 2800 includes a handle 2810 for manual gripping. Alternatively or in addition, the drone carrier 2800 is configured to be self-driven.

The drone carrier 2800 can include one or more propulsion devices 2804 located at desired locations in a body 2806 of the drone carrier 2800. The propulsion devices 2804 can be of various types, such as engines with propeller fans, and configured to propel, levitate, and/or hover the drone carrier 2800.

As illustrated in FIG. 62A, the child drones 2802 can be secured or mated onto the drone carrier 2800. In FIG. 62B, the child drones 2802 are separated from the drone carrier 2800. As illustrated in FIG. 62B, the drone carrier 2800 can include one or more drone support areas 2812 on which the child drones 2802 can rest. The drone carrier 2800 can further include one or more dock latches 2814 configured to mate with the child drones 2802. For example, similarly to the drones 2704, the child drones 2802 can have slots 2816 configured to engage with the dock latches 2814. Similarly to the drone carrier system 2700, the drone carrier 2800 can provide additional functions to the child drones 2802, such as charging, data communication, etc., through the connection between the dock latches 2814 and the slots 2816.

Figure 63A:
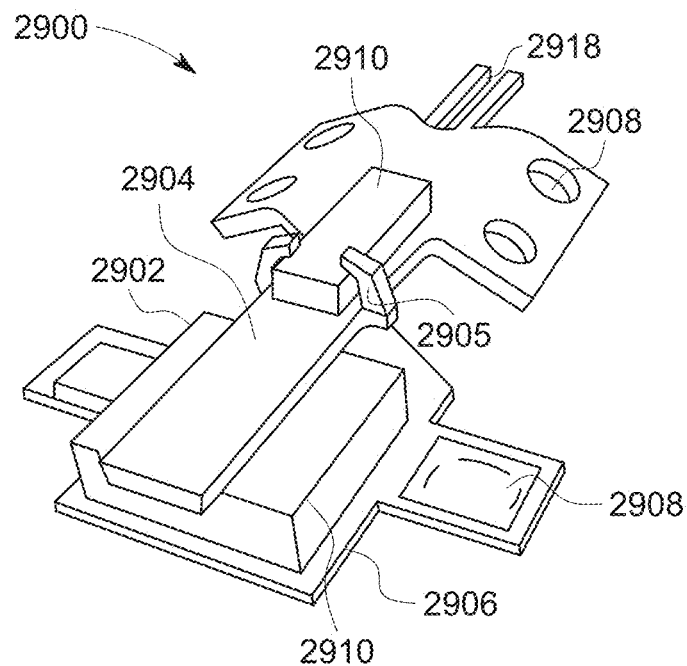
FIGS. 63A-C illustrate perspective views of example child satellite drones of FIGS. 62A-B.
Figure 63B:
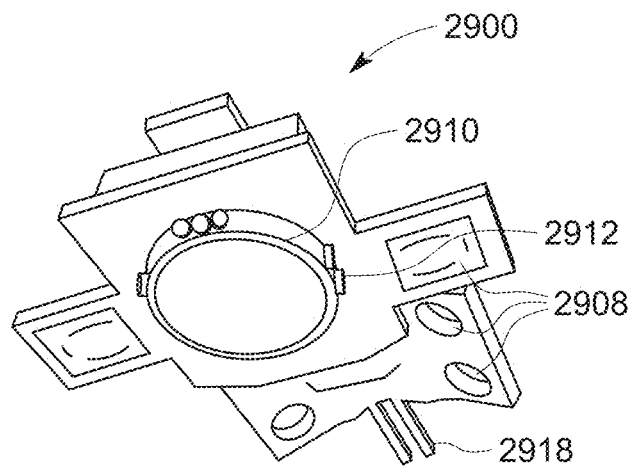
Figure 63C:
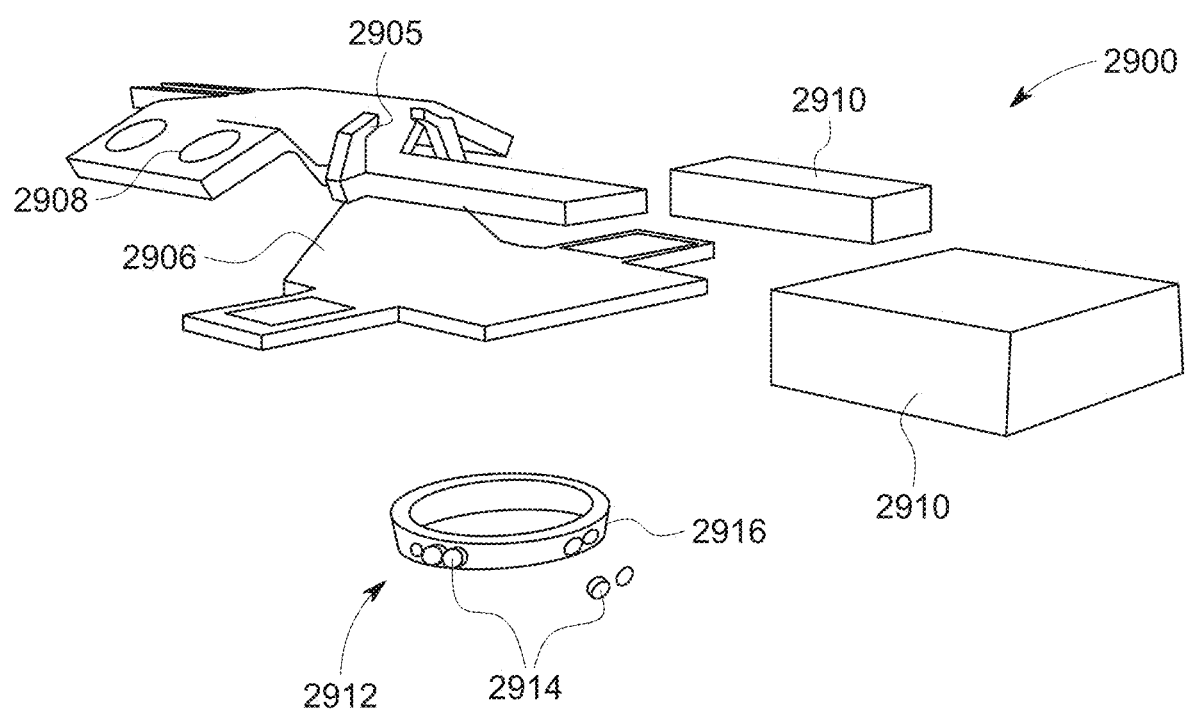

Referring to FIGS. 63A-C, an example drone 2900 is described, which can be used to implement the drones described herein, such as the drones 2704, 2802, and other drones illustrated above. The drone 2900 includes a body 2902 with an upper cargo compartment 2904 and a lower cargo compartment 2906. Example cargo packages 2910 can be held by the upper cargo compartment 2904 and the lower cargo compartment 2906. In some implementations, a package can be held onto the upper cargo compartment 2904 and secured by a cargo fastener 2905. In some implementations, a package can be held onto the lower cargo compartment 2904 by being engaged between the lower cargo compartment 2904 and the upper cargo compartment 2904.

The drone 2900 includes one or more propulsion devices 2908 provided in the body 2902. The propulsion devices 2908 can be of various types, such as engines with propeller fans, and configured to propel, levitate, and/or hover the drone 2900. The drone 2900 includes a control system 2910 and a sensor system 2912. The sensor system 2912 includes one or more sensors 2914 (e.g., optical sensors, light sensors, imaging sensors, photon sensors, position sensors, angle sensors, displacement sensors, distance sensors, speed sensors, acceleration sensors, acoustic sensors, sound sensors, vibration sensors, or other sensors for desired purposes). For example, the sensor system 2912 can include cameras and/or sonar sensors. The sensor system 2912 is attached to the body 2902 so that the sensors are arranged in desired directions and orientations. For example, the sensors 2914 can be arranged around a circular rim 2916 attached to the body 2902, so that the sensors are arranged for multi-directional sensing. The control system 2910 is configured to receive sensor signals from the sensor system 2912 and control the components of the drone 2900 for operating the drone 2900 based at least part on the signals. The drone 2900 can include slots 2918 configured to engage a docking extension of another structure, such as the vertical docking extension 2706, the dock latches 2814, or other suitable structures for mating, charging, data communication, and other suitable functions.

Referring now to FIGS. 64-82, various embodiments of drones are described.

FIG. 64 schematically illustrates an example drone 3100 with one or more foldable wings. For example, as shown in Scene 1, the drone 3100 includes a stabilizer 3102 and lift wings 3104. The lift wings 3104 include lift propulsion devices 3106 (e.g., engines with propellers). The drone 3100 can include a foldable undercarriage wing 3108. The drone 3100 can include other foldable wings. In Scene 2, the undercarriage wing 3108 is in a folded configuration. In Scene 3, the undercarriage wing 3108 is unfolding. In Scene 4, the undercarriage wing 3108 is fully unfolded. The wing can be made from various materials, such as rigid materials, cloth, or other suitable materials.

In some implementations, the foldable wings can include a plurality of pieces coupled movably coupled together. The wings can be retracted by folding one or more of the pieces, and extended by unfolding the pieces.

The foldable wings and other structures, described with reference to this Figure and other Figures herein, can be made of various materials. Example materials for the foldable wings and other structures include shape memory alloys, which remember their original shape and can return to their original shape after deformation under a stimulus. Examples of shape memory alloys include a gold-cadmium alloy (bent when cool and return to its original shape when heated), a nickel-titanium alloy (or nitinol), etc. In some implementations, some example shape memory alloys can return to a shape different from their original shape under a stimulus, thus holding two different shapes. Examples of shape memory alloys are further described in P. K. Kumar, et al., *"Introduction to shape memory alloys,"* In: Shape Memory Alloys. Springer, Boston, Mass. (2008); Ogawa et al., Science, 353 (2016), 368. DOI: 10.1126/science.aaf6524; Raj Suhail, et al., *Potential Applications of Shape Memory Alloys in Seismic Retrofitting of an Exterior Reinforced Concrete Beam-column Joint*, SECED 2015 Conference: Earthquake Risk and Engineering towards a Resilient World, 9-10 Jul. 2015, Cambridge UK; and Canadinc et al., *Scripta Materialia*, 158 (2019), 83. The disclosures of these references are incorporated herein by reference.

Figure 65A:
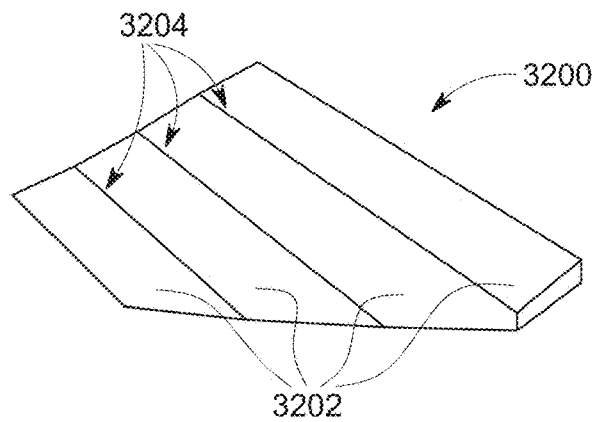
FIGS. 65A-C illustrate perspective views of an alternative example for a foldable wing of an aerial drone carrier.
Figure 65B:
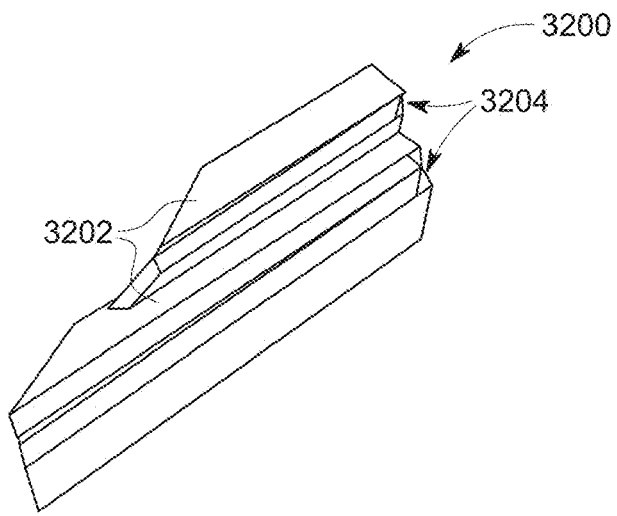
Figure 65C:
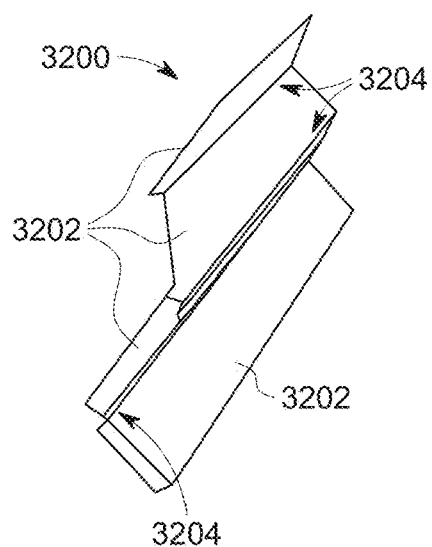

FIGS. 65A-C schematically illustrate an example foldable wing 3200 which can be used with a drone. Illustrated are three stages in FIGS. 65A-C. The wing 3200 includes multiple segments 3202 that are coupled at hinges 3204. The wing 3200 is in a folded mode (FIG. 65A), in the process of folding (FIG. 65B), and completely folded (FIG. 65C).

Figure 66B:
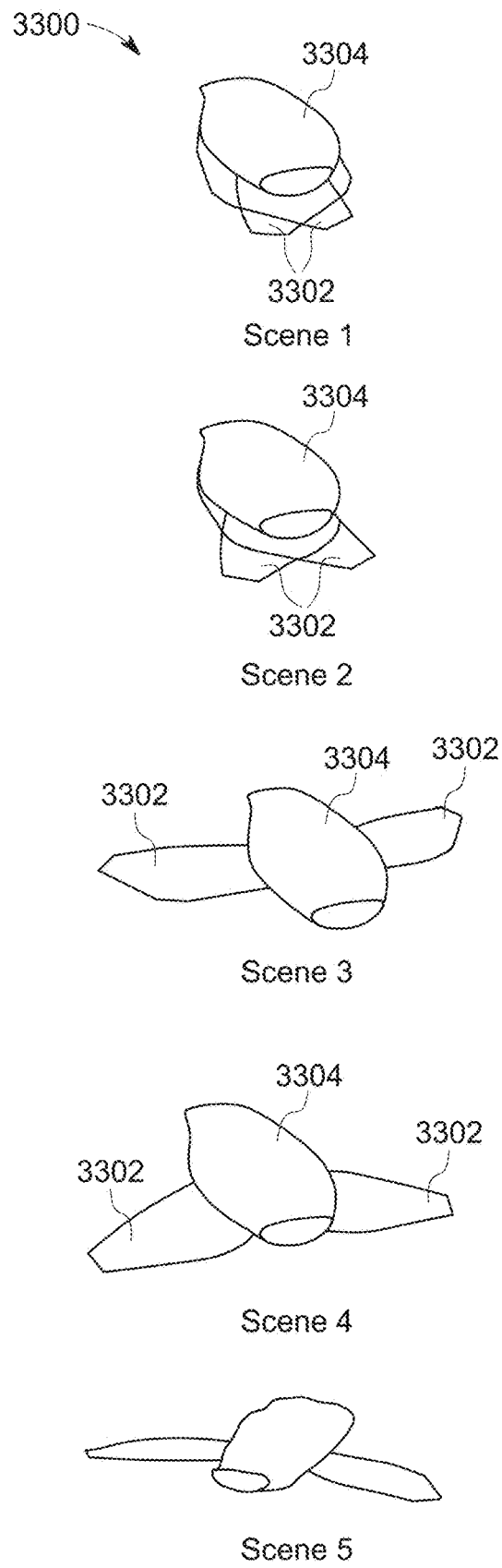
Figure 67A:
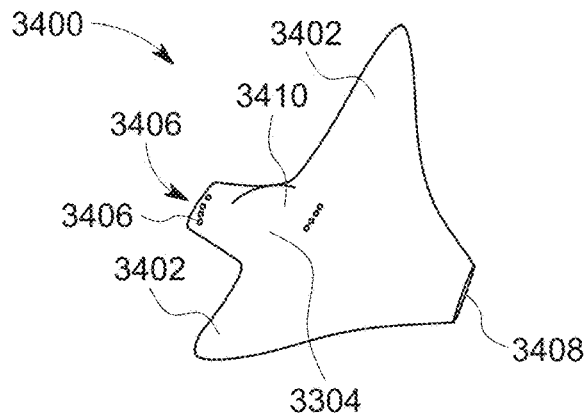
FIGS. 67A-D illustrate perspective views of an example drone aircraft embodiment with deformable wings for use, for example, in medical delivery applications.
Figure 67B:
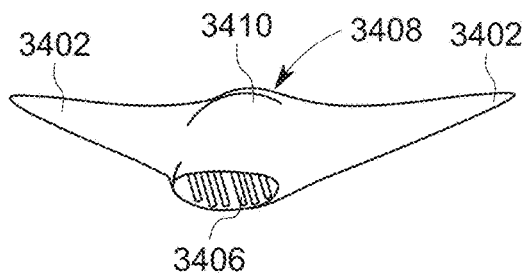
Figure 67C:
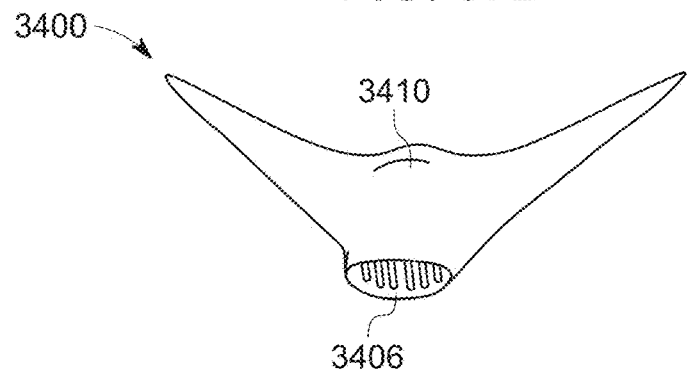
Figure 67D:
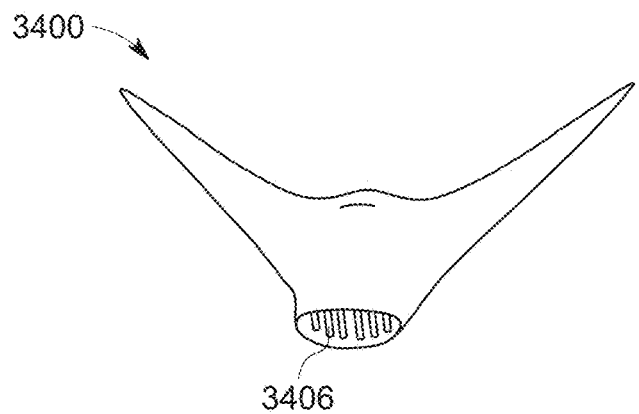

FIGS. 66A-C schematically example drones with nestled wings. As illustrated in FIG. 66A (a front perspective view) and FIG. 66B (a rear perspective view), an example drone 3300 includes wings 3302 that can be selectively retracted into or extended from a body 3304 of the drone 3300. The wings 3302 can be arranged on a desired portion (e.g., an upper portion, a lower portion, sides, etc.) of the body 3304. In FIGS. 66A-B, the wings 3302 move gradually from a compacted position to an expanded position (from Scene 1 to Scene 4 in FIG. 66A, and from Scene 1 to Scene 5 in FIG. 66B).

As illustrated in FIG. 66C, another example drone 3330 includes wings 3332 that can be selectively retracted into or extended from a body 3334 of the drone 3330. The wings 3332 can be arranged on a desired portion (e.g., an upper portion, a lower portion, sides, etc.) of the body 3334. In FIG. 66C, the wings 3332 move gradually from a compacted position to an expanded position (from Scene 1 to Scene 3).

Dependent on scaling factors, drones described herein can be used achieve guidance and/or lift via propeller action (rotary on top of craft, flapping action (laterally positioned) or static airfoil type lift).

FIGS. 67A-D schematically illustrate a drone 3400 with deformable wings 3402. For example, the wings 3402 include flexible wings that can adjust to various weather/wind conditions and a midline airflow path. Such flexible wings 3402 can be made from flexible or deformable materials, such as flexible cloth, nitinol, or other material suitable materials. In addition to the example shape memory alloys described above, other example shape memory alloys, which can be used for the wings, are described in, for example, J. K. Strelec, et al., *Design and Implementation of a Shape Memory Alloy Actuated Reconfigurable Airfoil*, Journal of Intelligent Material System, Vol 14, Issue 4-5, 2003, the disclosure of which is incorporated herein by reference.

In some implementations, the drone 3400 can include a body 3404 with an airflow intake 3406 into which air is drawn, and a rear exhaust 3408 from which the air is discharged. The drone 340 can include a cargo space 3410 configured to hold and carry a package.

Figure 68:
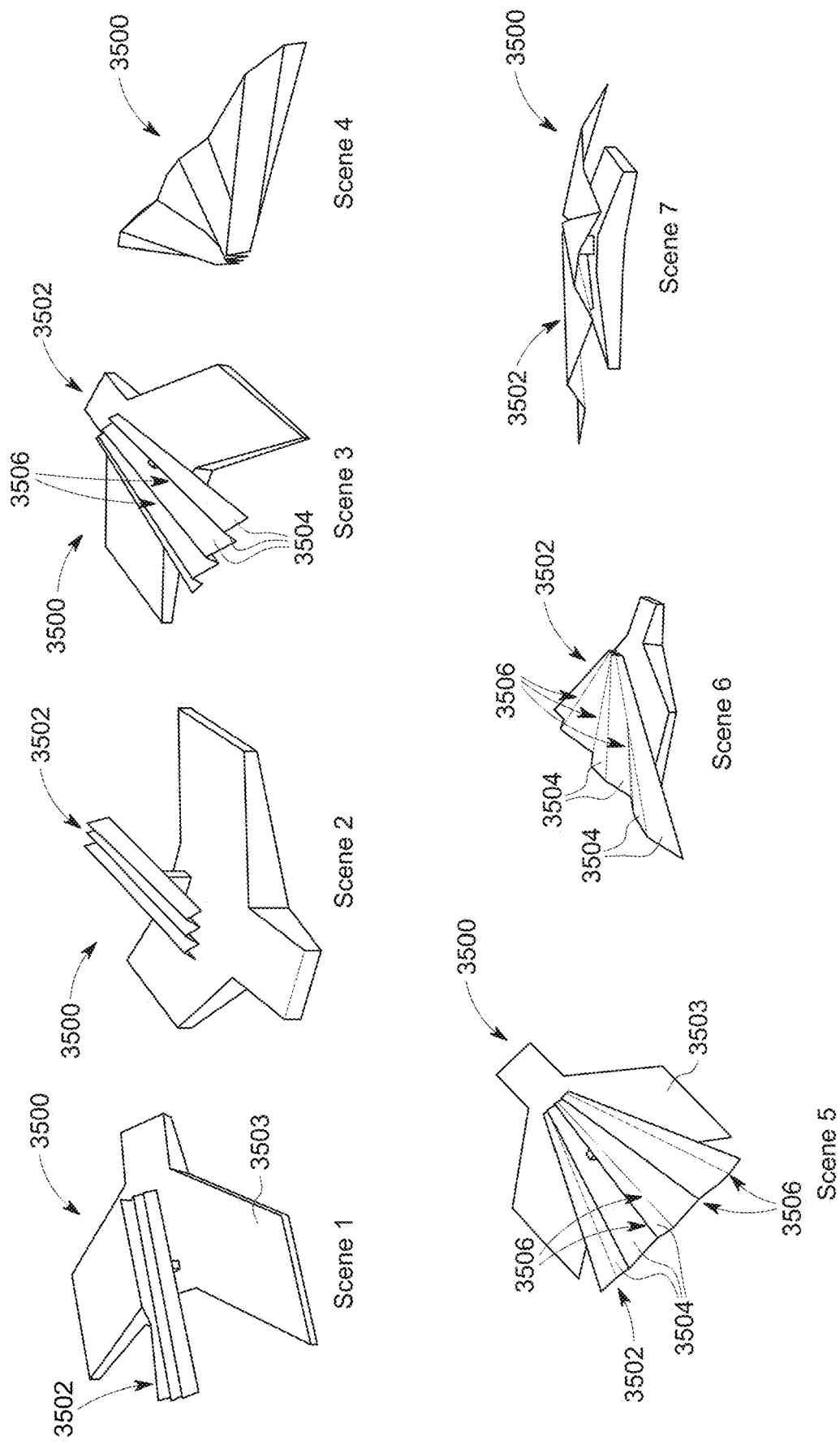
FIG. 68 illustrates perspective views of an example small vehicle drone with an expandable low-cost glider for use, for example, in medical delivery applications.

FIG. 68 schematically illustrates a small drone 3500 with an expandable low-cost glider (or flapper) 3502 mounted to a body 3503. For example, the glider 3502 can include multiple segments 3504 that are coupled together at hinges 3506. The segments 3504 can be hinged or folded/unfolded so that the glider 3502 can move between a collapsed position and an expanded position. For example, Scenes 1 and 2 illustrate side and frontal-oblique views of the drone 3500 with the glider 3502 in a folded position. Scene 3 captures the glider in the process of unfolding. Scene 4 illustrates the glider is unfolded (i.e. extended). Scenes 5-7 illustrate the drone with the extended flapper (top view, front view, and rear view).

Figure 69A:
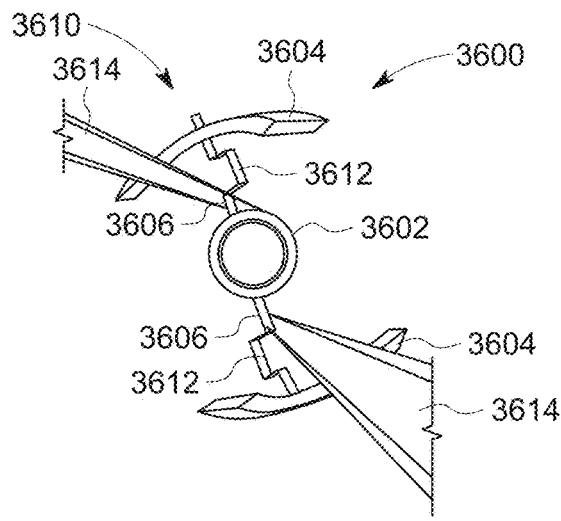
FIGS. 69A-C illustrate perspective views of an example pole/wire guided drone embodiment for use, for example, in medical delivery applications.
Figure 69B:
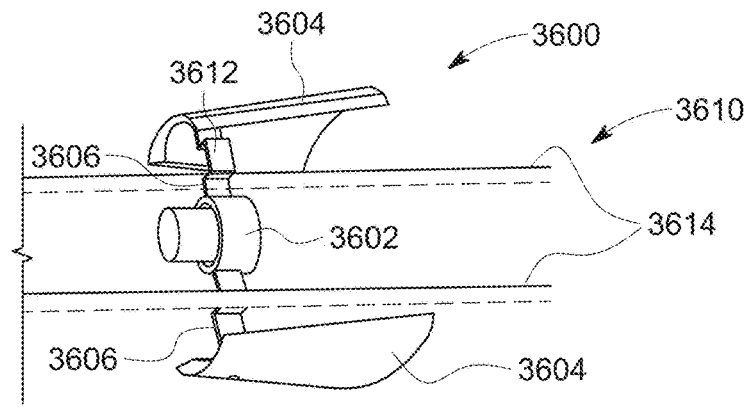
Figure 69C:
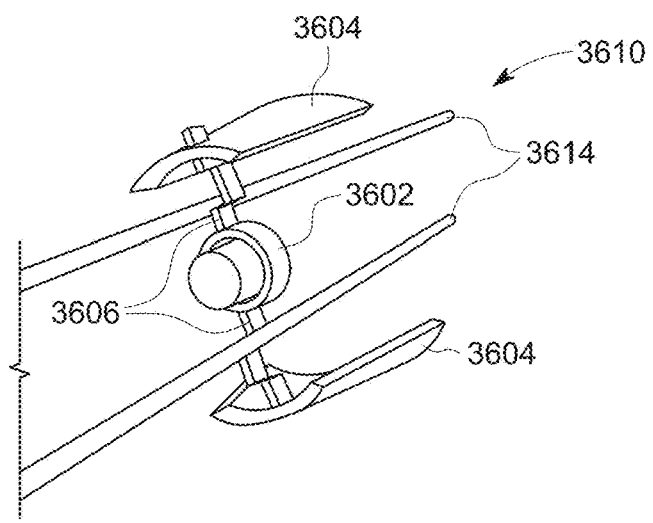

FIGS. 69A-C schematically illustrate an example drone 3600 that can be guided by guide rails (e.g., polls or wires). In this example, the drone 3600 includes a body 3602 and wings 3604 configured to be selectively extendable. For example, the wings 3604 can be collapsed toward the body 3602, or extended from the body 3602 for navigating the drone 3600. The drone 3600 can further include guide extensions 3606 extending from the body 3602 and configured to engage a guidance rail system 3610. For example, the guide extensions 3606 include recessed portions 3612 that may receive rails (wires or poles) 3614 of the guidance rail system 3610, independently or simultaneously. In some implementations, the recessed portions 3612 are arranged such that their open sides that receive rails face in the opposite direction (as illustrated in FIGS. 69A-C) or in the same direction. The guidance rail system 3610 can be routed in various configurations. Examples of the guidance rail system 3610 include the guidance rail systems described above. The guidance rail system 3610 can provide guidance by permitting the drone to physically contact the rails as it moves. Alternatively, the guidance rail system 3610 can provide contactless guidance rails using for example electromagnetism. The drone 3600 can be further configured to take off from the guidance rail system 3610 and fly on its own.

Figure 70:
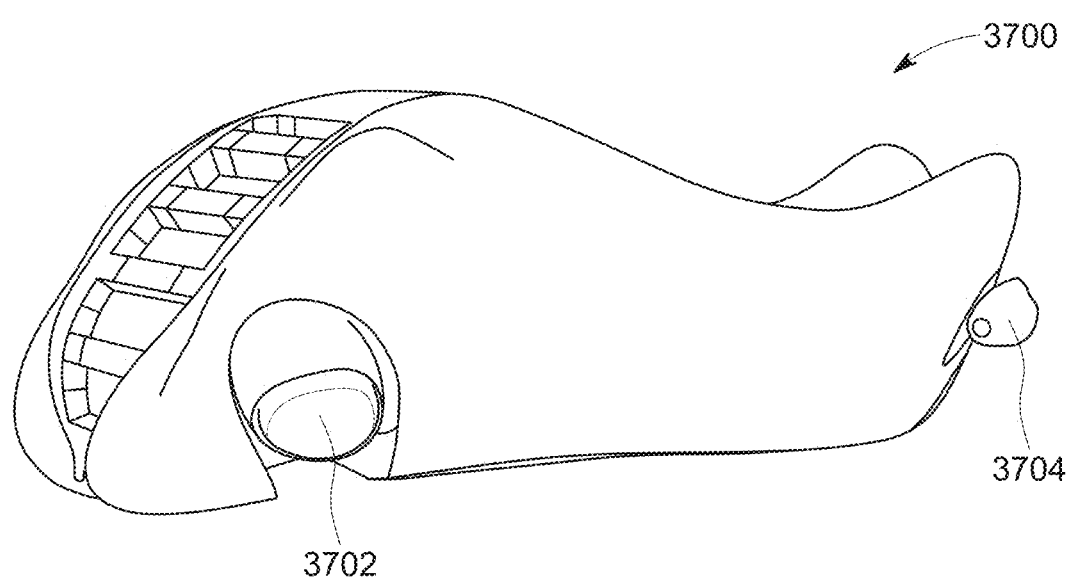
FIG. 70 illustrates a perspective view of an example land ambulette vehicle, which may optionally be connected in tandem style (e.g., train), for use, for example, in medical delivery applications.

FIG. 70 schematically illustrates an example land ambulette vehicle 3700. The vehicle 3700 can move freely on the ground, or move in tandem style (similarly to a train on tracks). The vehicle 3700 includes a propulsion system 3702 (e.g., using traction, mating, propellant or any combination thereof), and a rotatable thruster assembly 3704.

Figure 71A:
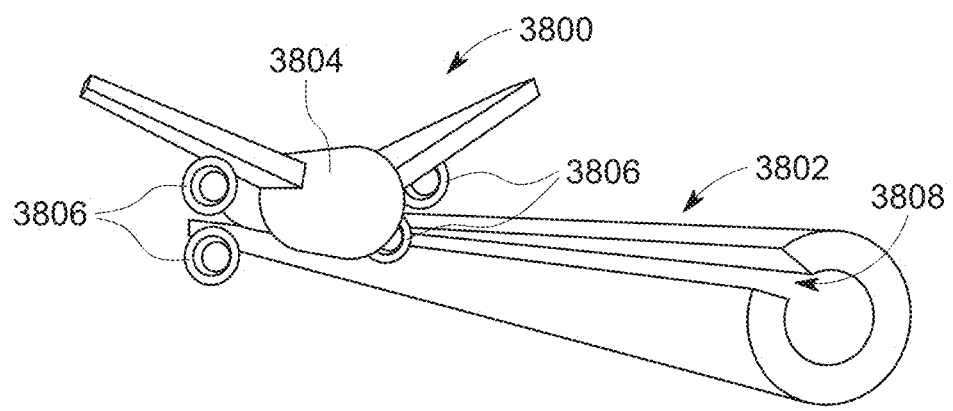
FIGS. 71A-D illustrate perspective views of an example Hybrid flight/train vehicle that can be assisted by tubular propulsion for use, for example, in medical delivery applications.
Figure 71B:
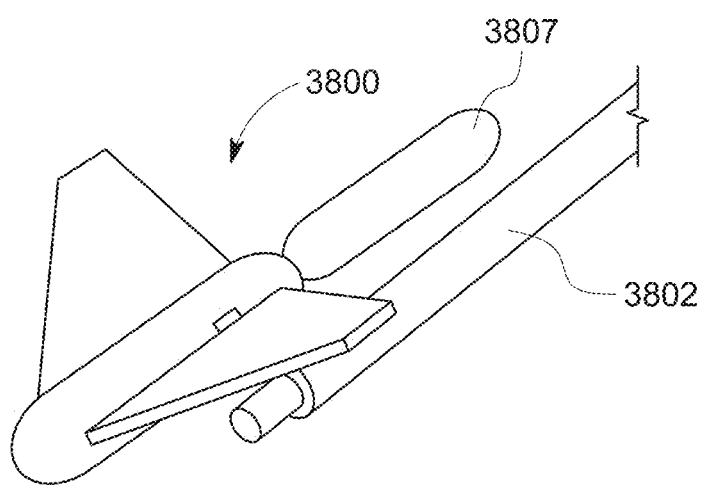
Figure 71C:
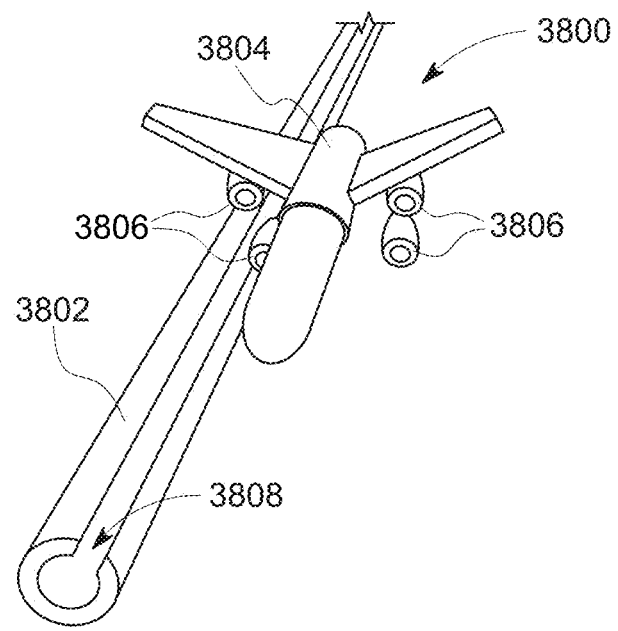
Figure 71D:
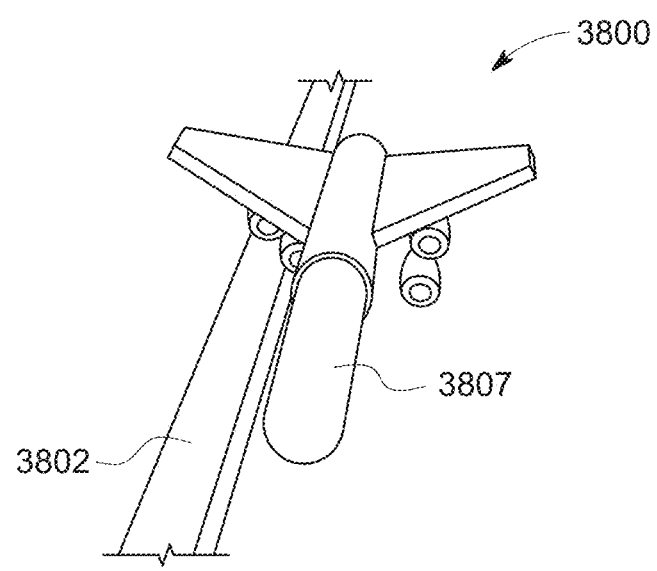

FIGS. 71A-D schematically illustrate an example hybrid flight/train vehicle (e.g., drone) 3800. The vehicle 3800 can fly while assisted by a track system 3802 (e.g., a tubular propulsion). In particular, FIGS. 71A-B illustrate front views of the vehicle 3800 with the track system 3802, and FIGS. 71C-D illustrate rear views thereof.

The vehicle 3800 includes a body 3804 and one or more propulsion devices 3806, such as a thrust/exhaust fan or engine assembly. The vehicle can further include a cargo (or payload capture) 3807 that is removably attached to, or carried by, the body 3804. One or more of the propulsion devices 3806 of the vehicle 3800 can be engaged with the track system 3802, and the vehicle 3800 can move along the track system 3802 with the one or more of the propulsion devices 3806 sliding along the track system 3802. For example, the track system 3802 includes a tubular track that includes an open portion 3808. When the one or more of the propulsion devices 3806 are engaged within the track system 3802, the rest of the vehicle 3800 is arranged next to the track system 3802 through the open portion 3808. The track system 3802 can use various propulsion or momentum delivery mechanisms which can further assist propulsion of the vehicle 3800 in addition or alternatively to the vehicle's own propulsion devices 3806. Examples of such propulsion delivery mechanisms can use mechanical propulsion delivery schemes (e.g., using partially enclosed suction effect), electrical propulsion delivery schemes (e.g., using electric current), and/or magnetic propulsion delivery (e.g., using magnetic or electromagnetic effects).

Figure 72A:
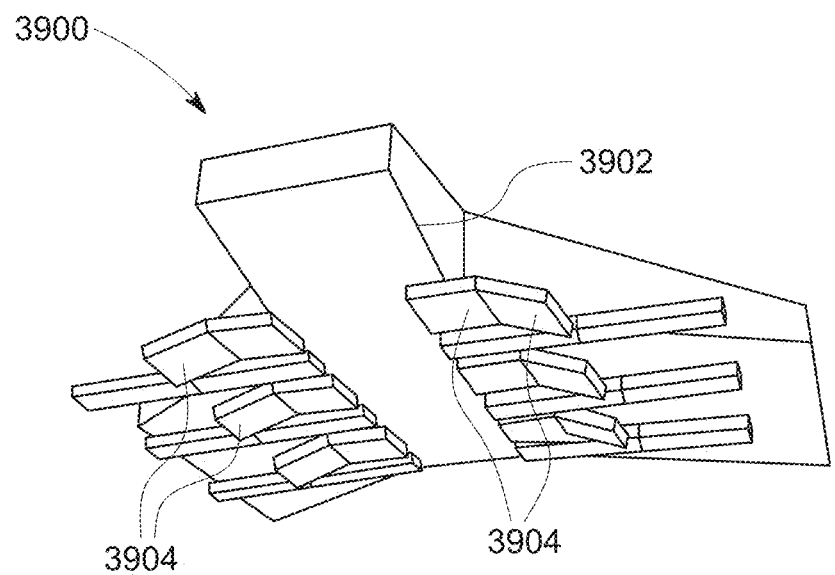
FIGS. 72A-B illustrate perspective views of an example combined land-air vehicle (drone) embodiment for use, for example, in medical delivery applications.
Figure 72B:
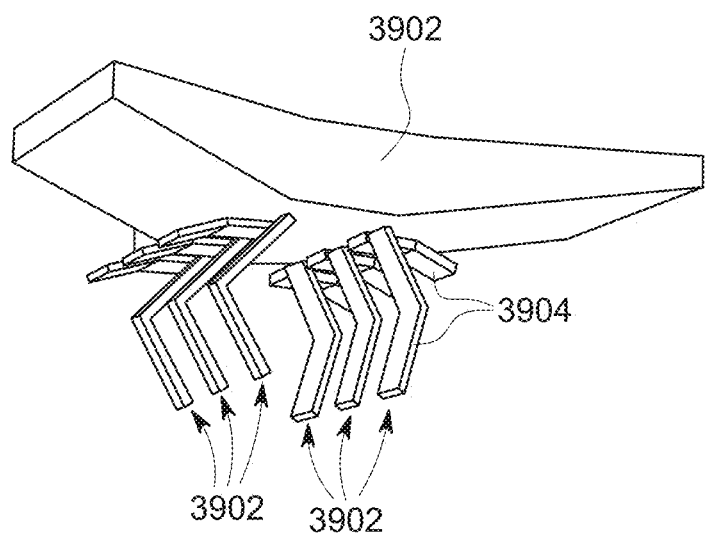

FIGS. 72A-B schematically illustrate an example combined land-air vehicle (e.g., drone) 3900. The vehicle 3900 includes a body 3902 and a plurality of clasping legs 3904 extending from the body 3902 (e.g., a bottom of the body 3902). The clasping legs 3904 are arranged in two opposing rows so that they can move to grasp or release an object. Each clasping leg 3904 can include a plurality of segments 3906 that are movably (e.g., pivotally) coupled to adjust the shape of the leg for clasping or releasing. For example, in FIG. 72A (a bottom-oblique view), the clasping undercarriage segmented legs 3904 are in an extended (no-clasping) position. In FIG. 72B, the segmented legs 3904 are in a clasping position.

Figure 73:
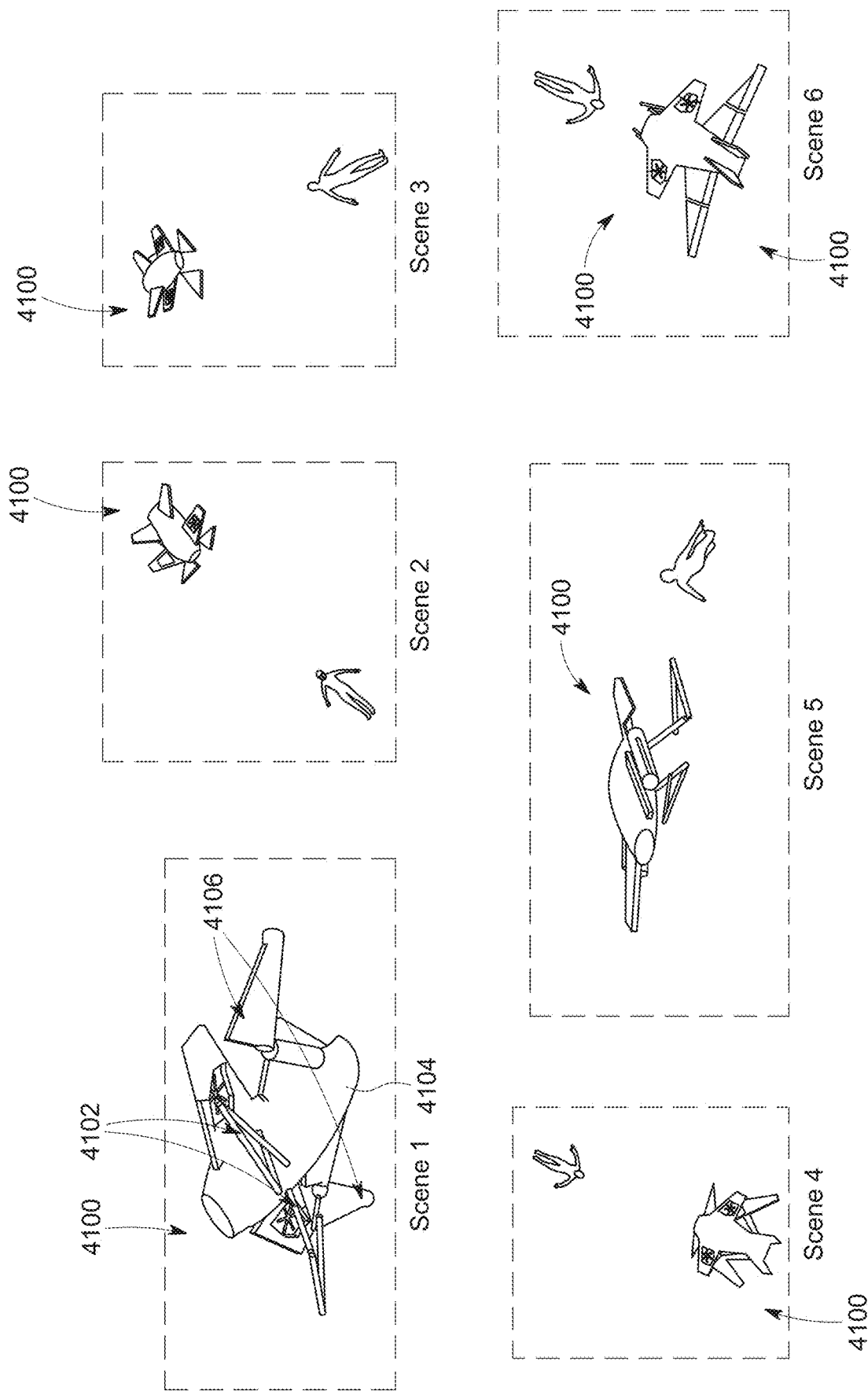
FIG. 73 illustrates perspective views of an example winged drone embodiment with extendable arms for engaging in person rescue and transport.
Figure 74:
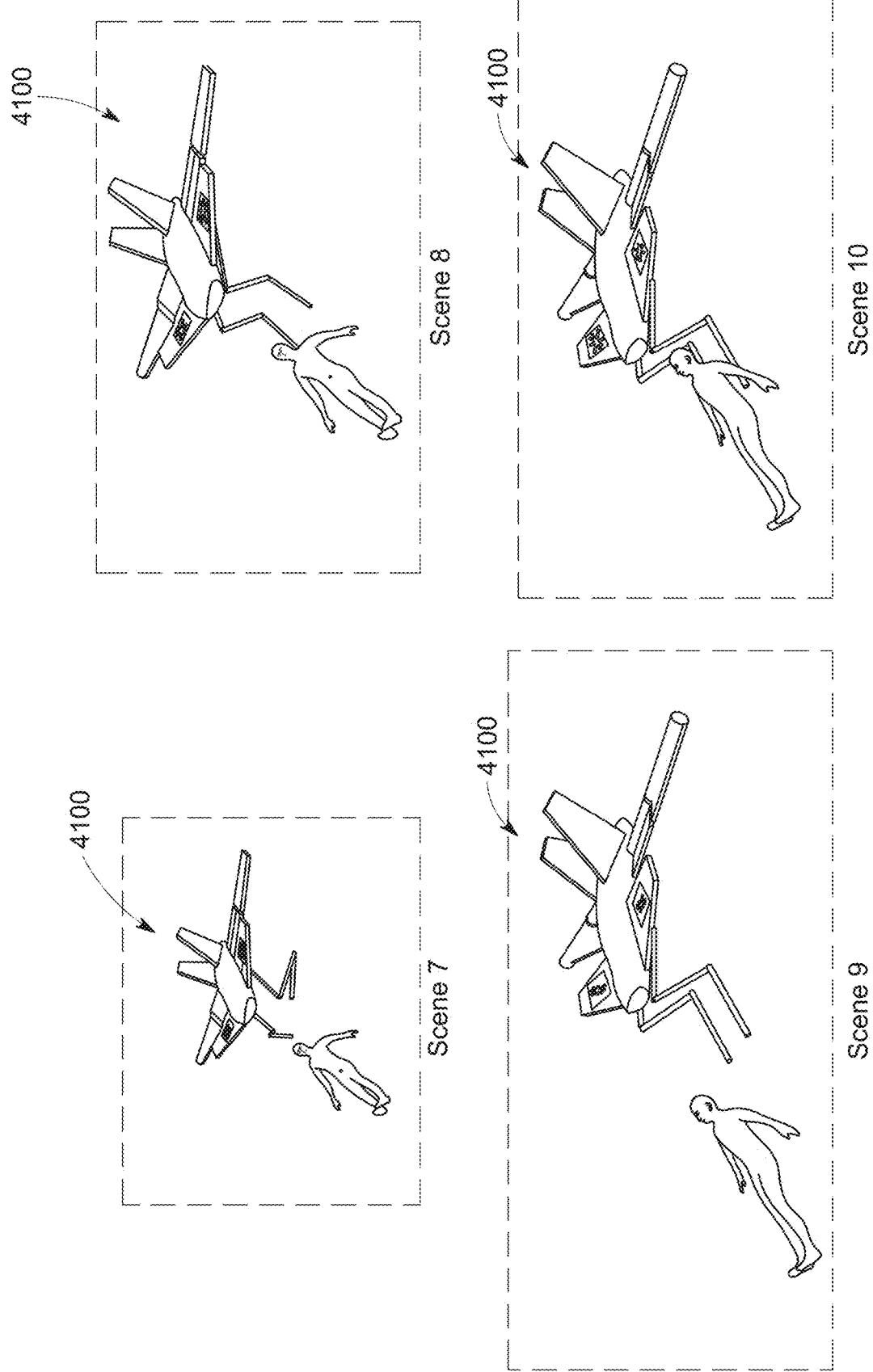
FIG. 74 illustrates additional perspective views of the example of the winged drone embodiment with extendable arms of FIG. 73.
Figure 75:
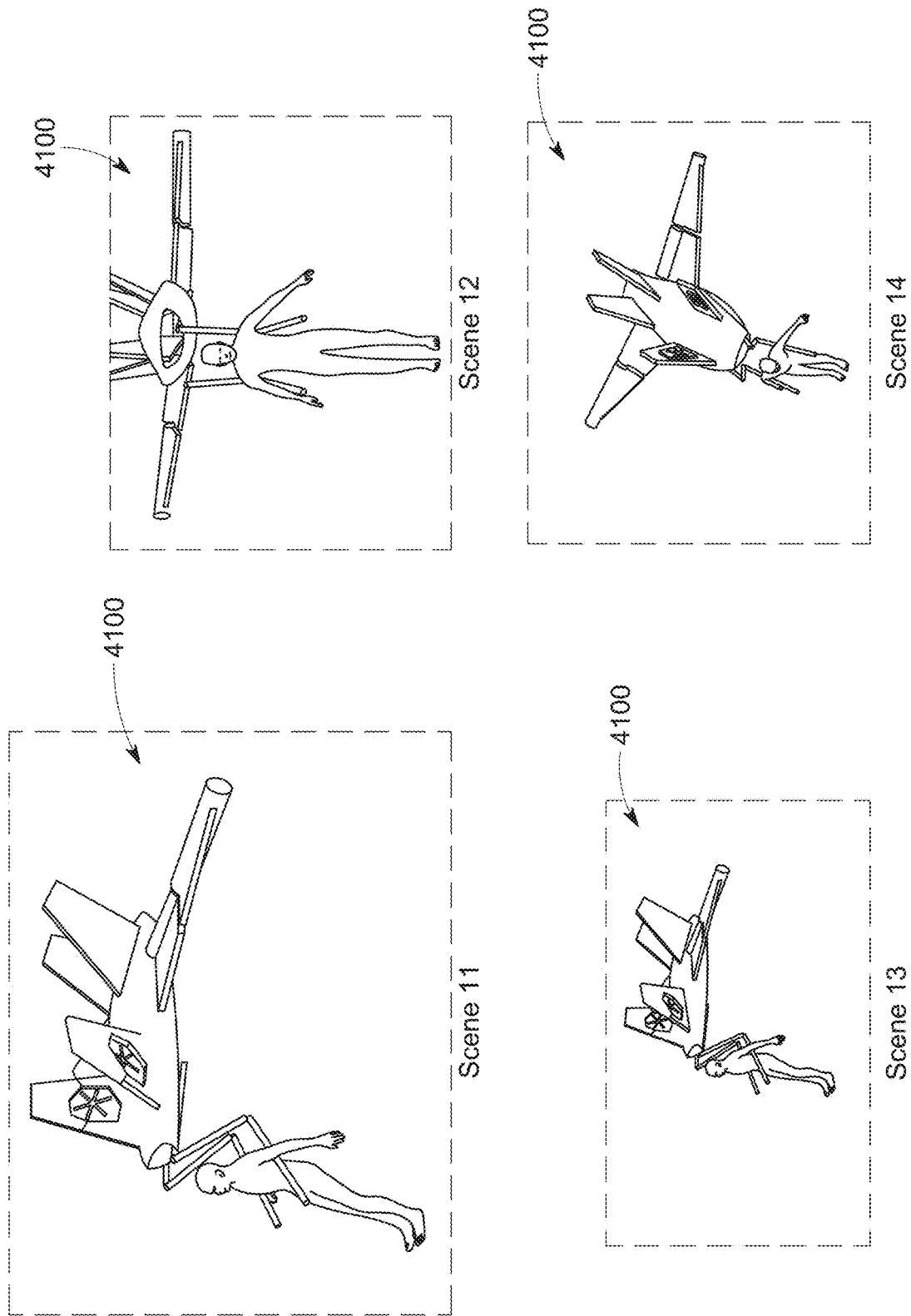
FIG. 75 illustrates additional perspective views of the example of the winged drone embodiment with extendable arms of FIG. 73.

FIGS. 73-75 schematically illustrate an example winged drone 4100 with extendable arms 4102 configured to engage in a person rescue. The arms 4102 are configured to be foldable into, and extendable from, a body 4104 of the drone 4100. The arms 4102 can be configured with multiple links to provide multiple configurations and grasping functionality. The drone 4100 can perform a rescue process with minimal arm extension. The drone 4100 can further include wings 4106 which may be foldable.

In Scene 1 (a bottom view), the drone 4100 has the arms 4102 being folded, and the wings 4106 being folded, while the drone 4100 can move. In Scenes 2 and 3, the drone 4100 is approaching a person to be rescued. In Scene 4, the drone 4100 has the arms 4102 being gradually extending, and/or the wings 4106 unfolding as necessary for navigational or physical requirements. In Scene 5, the arms 4102 are lowered but with its ends still withheld. In Scene 6, the drone 4100 is being reoriented for optimal contact with the person being rescued. For example, the wings 4106 can be extended to achieve desired lift or glide assistance during flight. The wings 4106 may or may not be retracted during specified segments of the operation.

In Scenes 7-8, the drone 4100 has the arms 4102 gradually extending to approach the person. In Scene 9, the drone 4100 is ready to engage the person with the extended arms 4102. In Scene 10, the drone 4100 has the arms 4102 cradling the undersurface of the person as it engages for removal from scene.

In Scenes 11-14, the drone 4100 has the arms 4102 engaging with the person in maximal arm extension and contacting the person under his/her limbs (e.g., arms).

Figure 76:
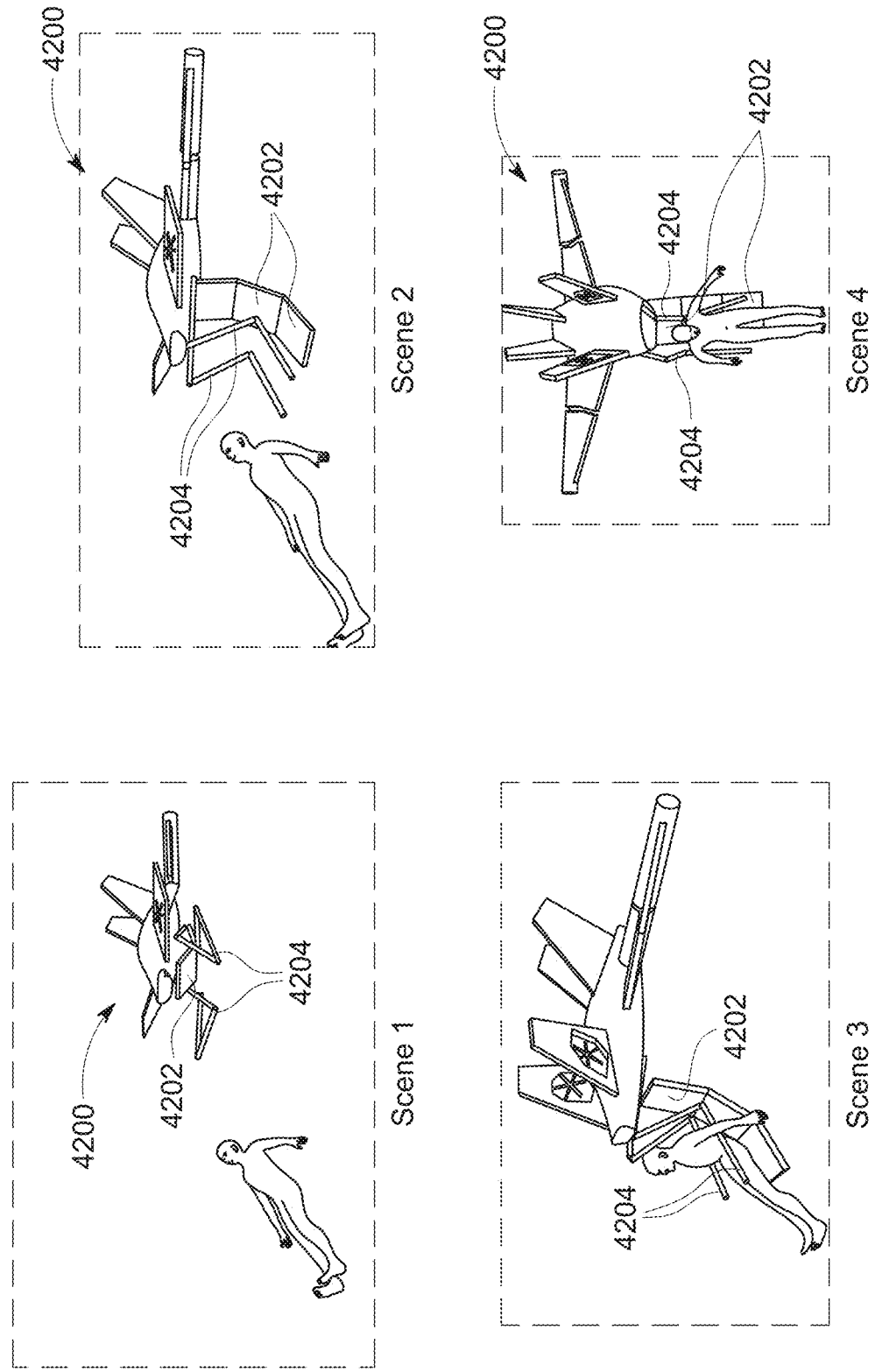
FIG. 76 illustrates perspective views of an example winged drone embodiment with back/seat support for engaging in person rescue and transport.

FIG. 76 schematically illustrates an example winged drone 4200. The drone 4200 is configured similarly to the drone 4100 and further includes an object support panel 4202 (e.g., back and/or seat support) configured to support a person being rescued. The object support panel 4202 is selectively collapsible for storage or expandable for usage. For example, the object support panel 4202 can include multiple segments movably coupled so that different positions of such segments provide different configurations of the object support panel 4202. The object support panel 4202 is configured to change its shape to support the person with or without extended arms 4204 from the drone 4200. For example, in Scene 1, the drone 4200 is approaching a patient with the object support panel 4202 being compacted. In Scene 2, the drone 4202 is approaching with the arms 4204 and the object support panel 4202 both being extended. In Scene 3, the drone 4200 is engaging the patient's body with the extended arms 4204 beneath patient arms, and the extended object support panel 4202 positioning it underneath the patient. In Scene 4, the drone 4200 is in flight safely transporting the patient to the desired location for treatment.

Figure 77:
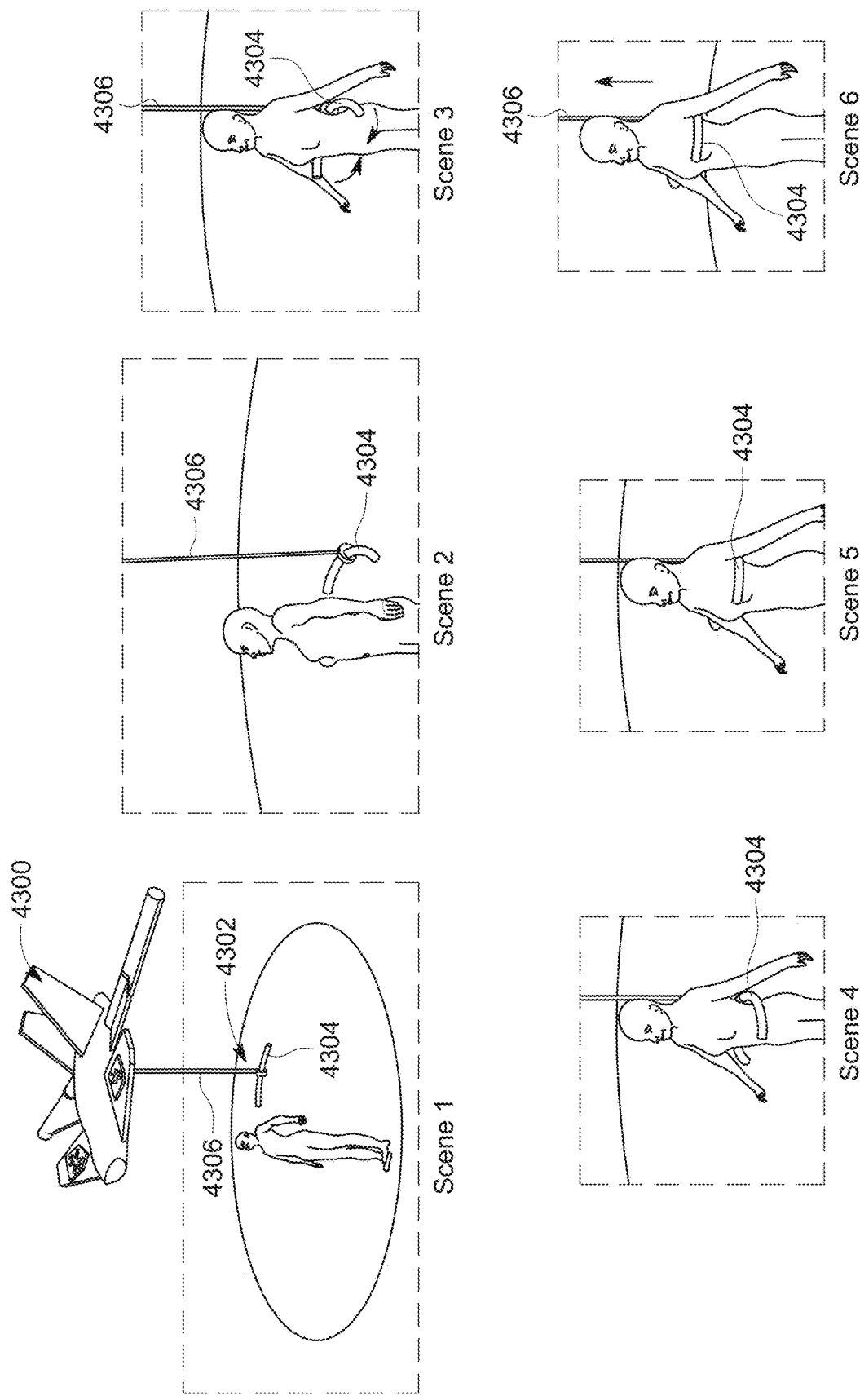
FIG. 77 illustrates perspective views of an example winged drone embodiment using a robotic flexible buoy for engaging in patient rescue and transport.

FIG. 77 schematically illustrates an example winged drone 4300 that includes a robotic flexible buoy assembly 4302 for engaging in patient rescue. The buoy assembly 4302 can be used to hold and remove a person from a water, fluid, or other entrapping bodies around the person. The buoy assembly 4302 can include a flexible buoy 4304 and a retractable extension 4306 (e.g., wire, telescoping body, etc.) for connecting the flexible buoy 4304 to a body of the drone 4300. In Scene 1, the drone 4300 moves on site and the flexible buoy 4304 is approaching a person to be rescued from an entrapping body (e.g., water). In Scene 2, the flexible buoy 4304 starts deforming on approach to the person. In Scene 3, the flexible buoy 4304 is deforming around the person. In Scenes 4 and 5, the flexible buoy 4304 is in an enclosed position around the person. In Scene 6, the drone 4300 is lifting the person held by the flexible buoy 4304. The flexible buoy 4304 can be remotely controlled to change its shapes (e.g., flexed in and out). Alternatively, the buoy assembly 4302 includes a controller that automatically controls the shape of the buoy.

Figure 78A:
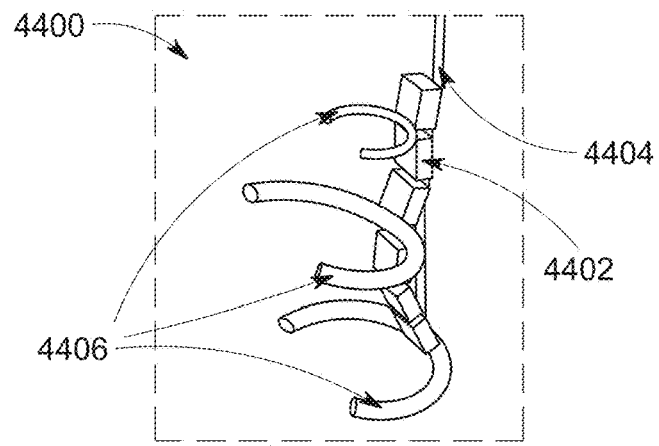
FIGS. 78A-C illustrate perspective views of an alternative robotic flexible buoy with back support mechanisms.
Figure 78B:
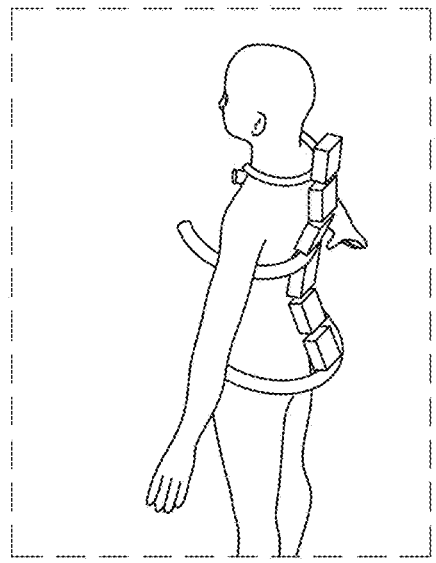
Figure 78C:
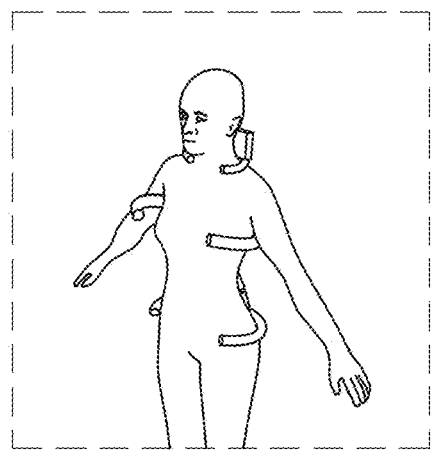

FIGS. 78A-C schematically illustrate an example robotic flexible buoy assembly 4400 with a back support mechanism 4402. Similarly to the buoy 4304, the buoy assembly 4400 can be connected to a drone using a retractable extension 4404. The body assembly 4400 can include one or more buoys 4406 that may be arranged vertically to improve holding of a person. Similarly to the buoy 4304, the buoys 4406 can be remotely controlled to change their shapes. Alternatively, the buoy assembly 4400 includes a controller that automatically controls the shape of the buoy. Multiple buoys 4406 can be controlled individually or in coordination.

The back support mechanism 4402 can include a plurality of panels 4408 connected in series using flexible connectors which can be controlled to change the overall shape of the back support mechanism 4402 so that the back support mechanism 4402 can comply with the contour of the person's body being supported by the mechanism. Optionally, there may be provided a minimal harness with controlled personal back/spine support.

Figure 79A:
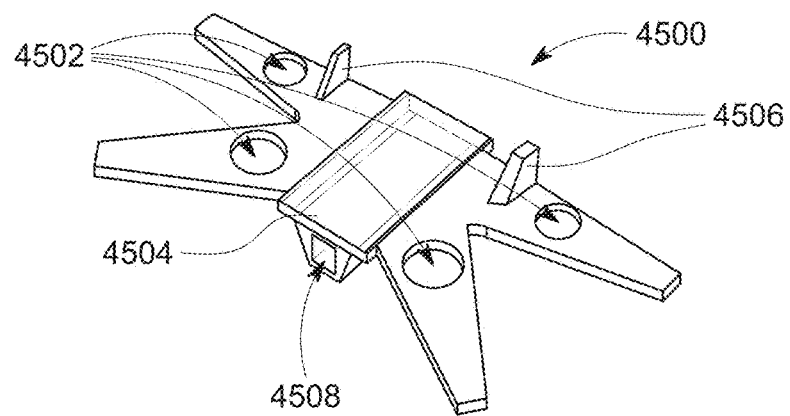
FIGS. 79A-C illustrate perspective views of an example standing personal conveyer drone for use, for example, in medical delivery applications.
Figure 79B:
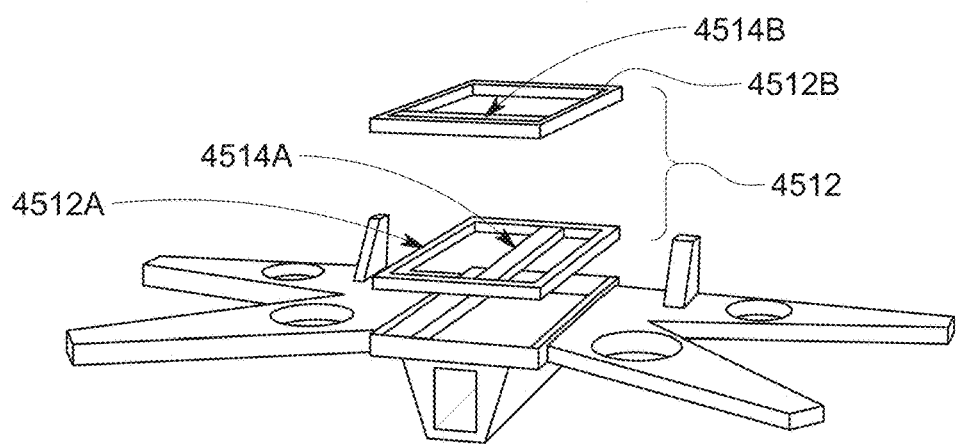
Figure 79C:
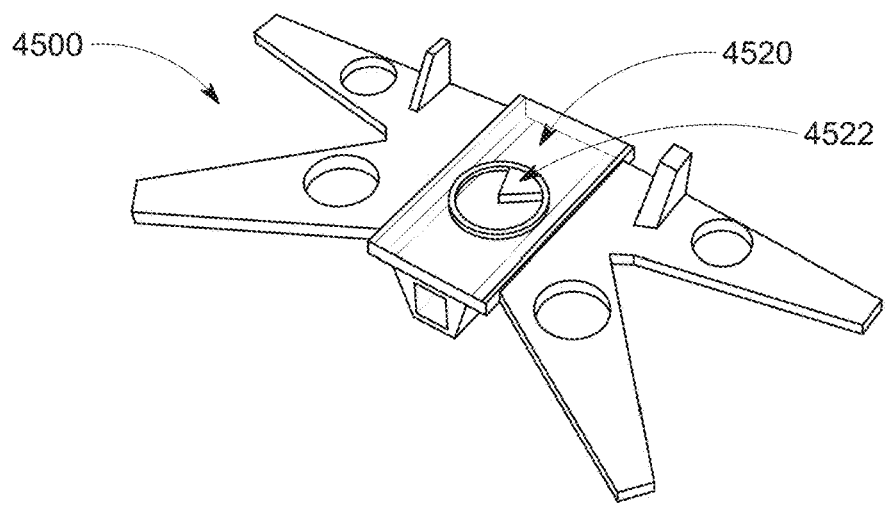

FIGS. 79A-C schematically illustrate an example drone 4500 for carrying an object thereon. The drone 4500 can be configured as a standing personal conveyer drone. The drone 4500 can include one or more slots 4502 for propulsion devices, such as propulsion fans for guidance, vertical lift, etc. The drone 4500 can further include an object support platform 4504 (e.g., a personal standing platform), vertical stabilizers 4506, and a section 4508 for one or more horizontal propulsive devices which can be modular, interchangeable or dual function.

As illustrated in FIG. 79B, the drone 4500 can include a weight adjustment assembly 4510. The weight adjustment assembly 4510 can include one or more electronic and/or mechanical rectilinear weight adjustment structures 4512 for either of counterbalance, stabilization, or heading/direction adjustment (exploded view). In the illustrated example, a first weight adjustment structure 4512A includes a bar weight 4514A that is adjustable along a first axis (e.g., left-right axis). A second weight adjustment structure 4512B includes a bar weight 4514B that is adjustable along a second axis (e.g., front-rear axis). In some embodiments, the second axis is perpendicular to the first axis. In other embodiments, the second axis is angled (other than 90 degrees) relative to the first axis.

As illustrated in FIG. 79C, the drone 4500 can include a cylindrical counterbalance/navigational weight adjustment assembly 4520, which can include a cylindrical adjustable weight 4522.

Figure 80A:
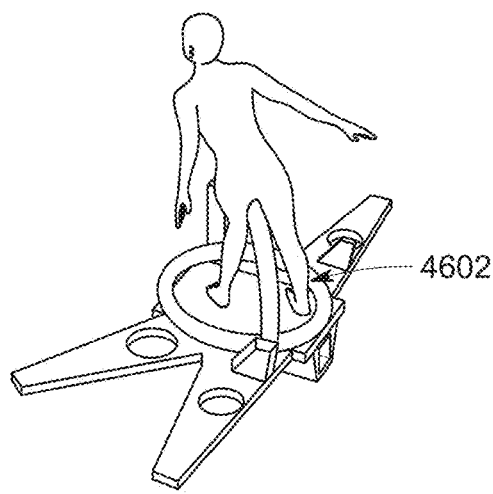
FIGS. 80A-C illustrate perspective views of an example electromechanical gimbal drone embodiment that can be used for steering/navigation and contact/strap with passenger, for example, in medical delivery applications.
Figure 80B:
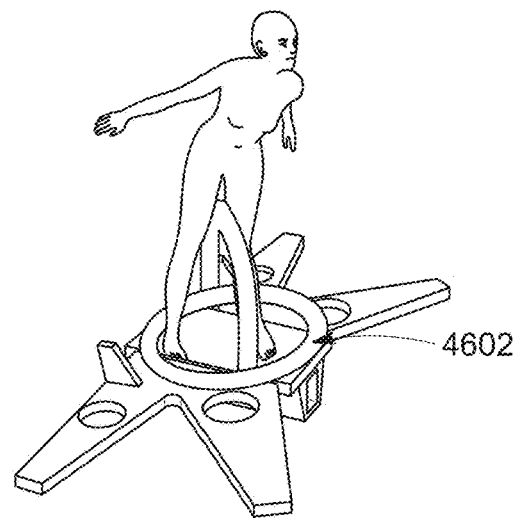
Figure 80C:
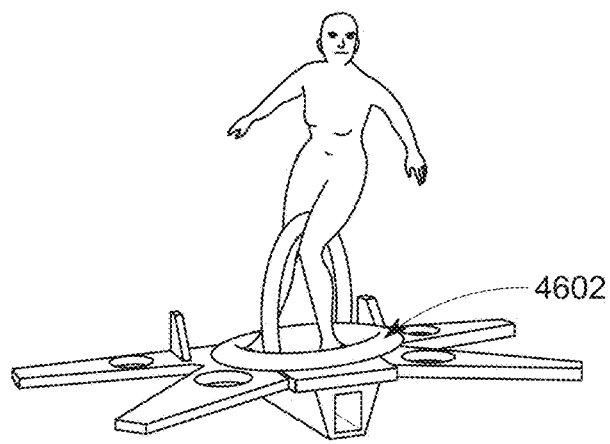

FIGS. 80A-C illustrate an example drone 4600 that includes an electromechanical gimbal assembly 4602 configured to steer and navigate the drone 4600. The gimbal assembly 4602 can also be configured to support (e.g., contact, strap, etc.) a passenger of the drone. The drone 4600 permits for a passenger to be in a posterior oblique position (FIG. 80A), an anterior oblique position (FIG. 80B) and a lateral oblique position (FIG. 80C).

Figure 81:
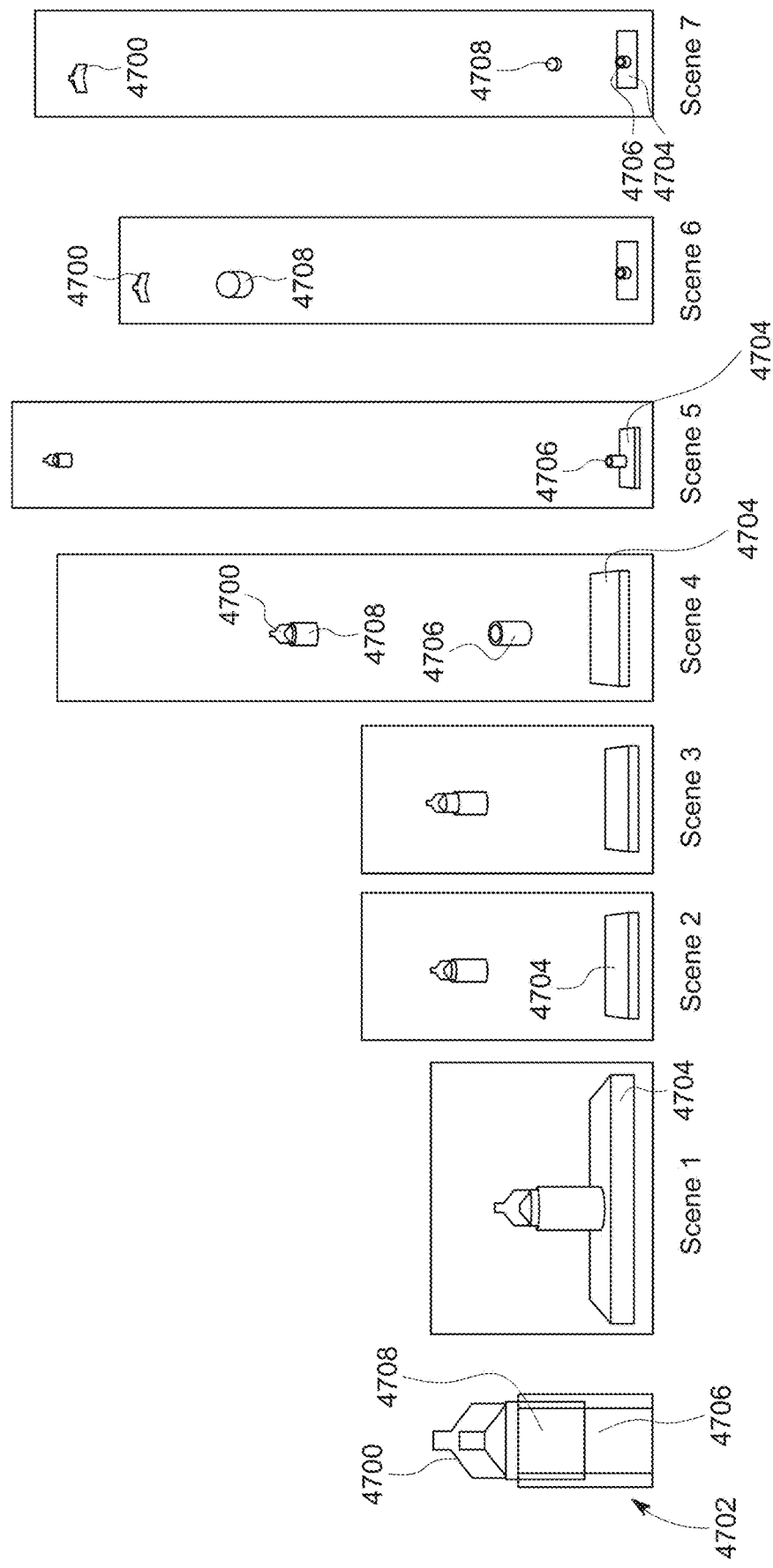
FIG. 81 illustrates perspective views of an example assisted/catapult vertical drone launch, which may include multiple stages that are returnable.

FIG. 81 illustrates an example operation of launching a drone 4700 using a launcher assembly 4702. The launcher assembly 4702 can be configured to assist and/or catapult the drone therefrom. This Figure schematically depict multiple stages that are returnable (Scenes 1-7). In this example operation, the drone can be launched without requiring continuous power or electrical charge. Depending on various material abilities, some embodiments of the launcher can remain grounded or powered through an extendable cord. In some implementations, the launcher can be re-arranged to propel vehicles along the horizontal. Due to convenience and lesser gravitational considerations, the horizontal launchers may be guided by rail.

The launcher assembly 4702 can be configured as a concentric/returnable ballistic launcher. For example, the launcher assembly 4702 can include the drone 4700, an inner thruster 4708, an outer launcher 4706, and a ground or base 4704.

Illustrated are progressing stages of the drone projection. A base 4704 is configured to propel an outer launcher 4706, which at a later stage propels an inner thruster 4708, which in turn propels the drone 4700. Scene 1 depicts a prelaunch configuration. Scene 2 depicts a full launch assembly. Scene 3 depicts that the outer launcher 4706 is separating. The outer launcher 4706 can be aimed ejection back to the ground and/or the base 4704. Scene 4 depicts the outer launcher 4706 has been fully separated. Scene 5 depicts the outer launcher 4706 is fully returned. The inner thruster 4708 continues on a programmed trajectory. Scene 6 depicts the inner thruster 4708 has separated from the projectile vehicle (the drone 4700) and is ejected to be returned to the ground base 4704 in a guided manner. Scene 7 depicts the projectile vehicle (the drone 4700) is continuing on course using its guidance/thrust.

Figure 82:
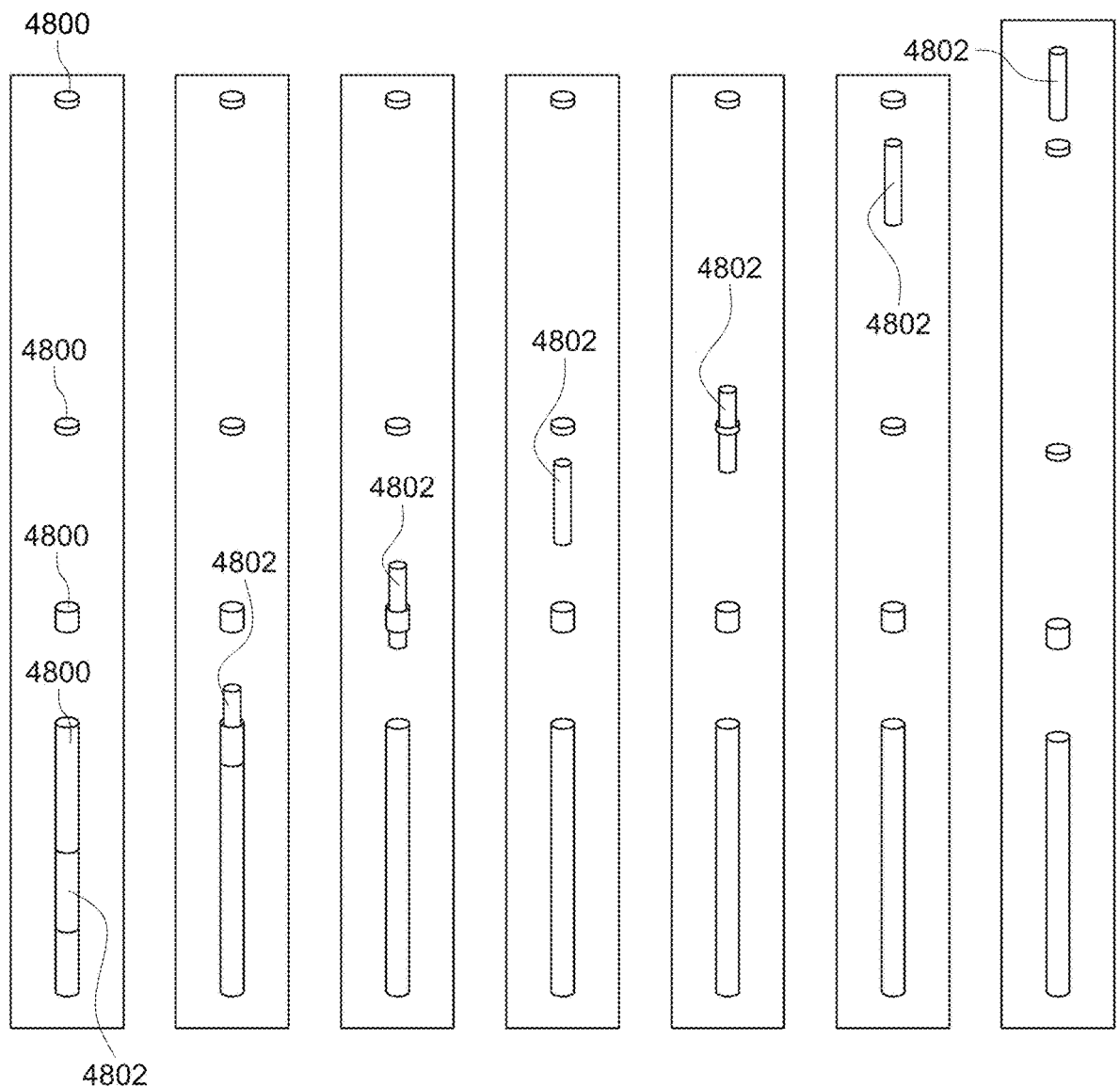
FIG. 82 illustrates perspective views of an example vertical or horizontal launcher with fixed stages acting as a catapult to a projectile.

FIG. 82 schematically illustrates an example vertical or horizontal launcher 4800 with fixed stages 4802 acting as catapult to projectile. Such fixed projection stages 4802 can impart further momentum or catapulting onto a projected launch vehicle 4804, thereby reducing necessary onboard energy reserves.

Figure 83A:
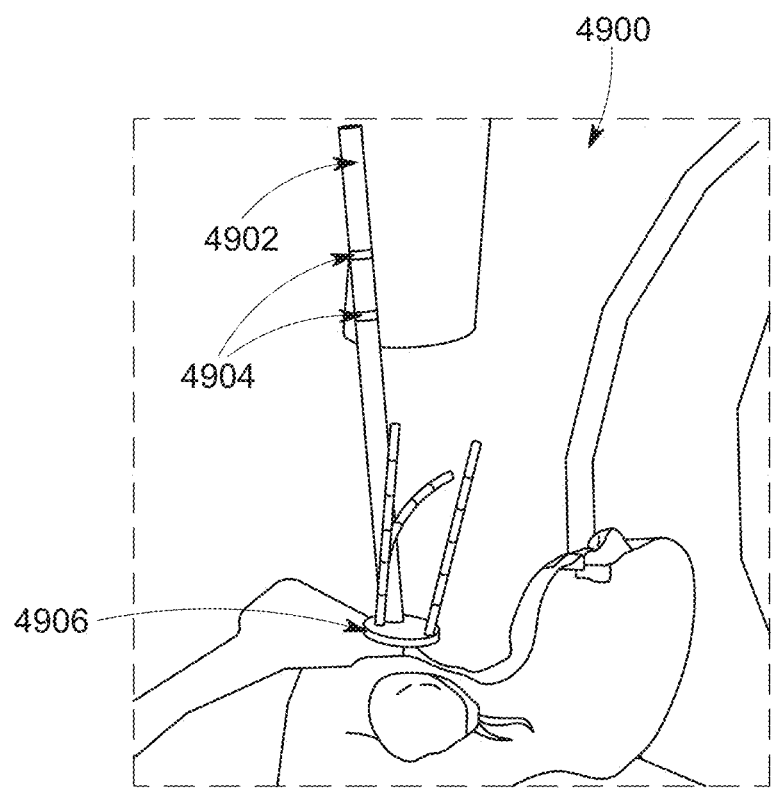
FIGS. 83A-B illustrate an example robotic system for controlling and placing an instrument.
Figure 83B:
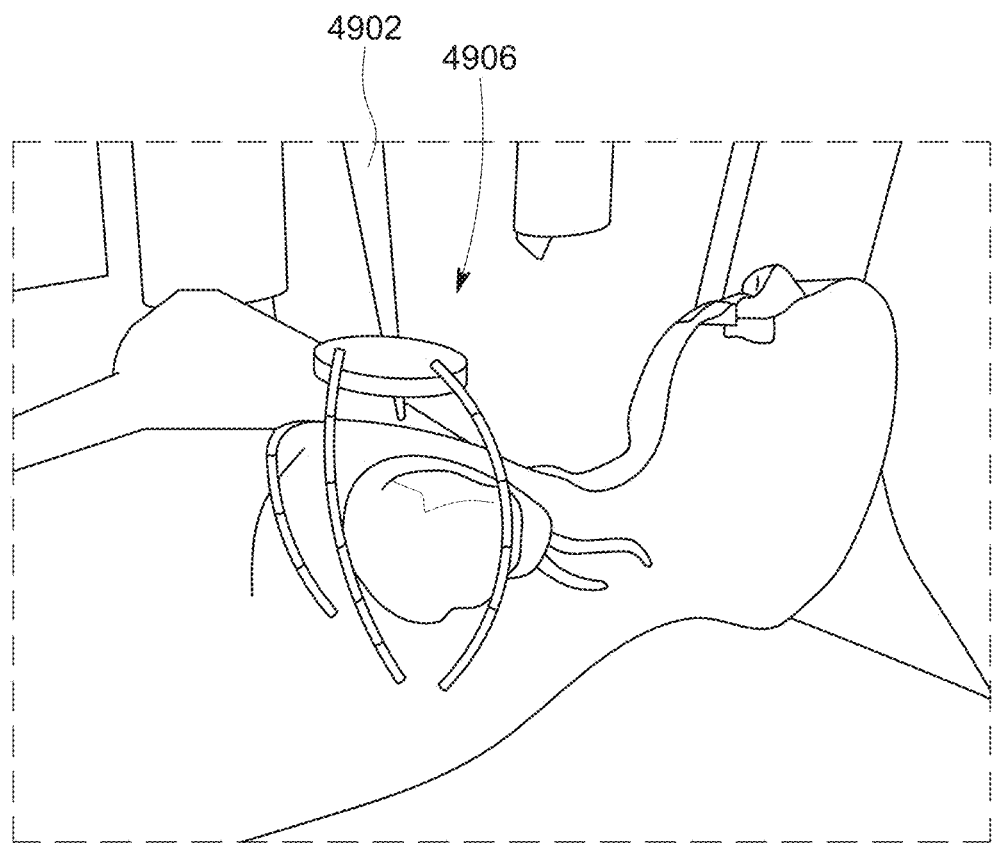

FIGS. 83A-B schematically illustrate an example robotic system 4900 for controlling and placing an instrument. The system 4900 can include an instrument extension 4902 (e.g., radiation, layer, imaging device, etc.) that includes one or more notches 4904 that mate with corresponding structures of a robot so that the robot can grip the instrument extension 4902. The instrument extension 4902 has a distal end configured to engage an instrument, such as a modular multi jointed electronic manipulator 4906. In FIG. 83A, the manipulator 4906 is in an inactive position. In FIG. 83B, the manipulator 4906 is in an active position where the manipulator 4906 is emulating or performing operations against an internal organ in a patient.

Figure 84:
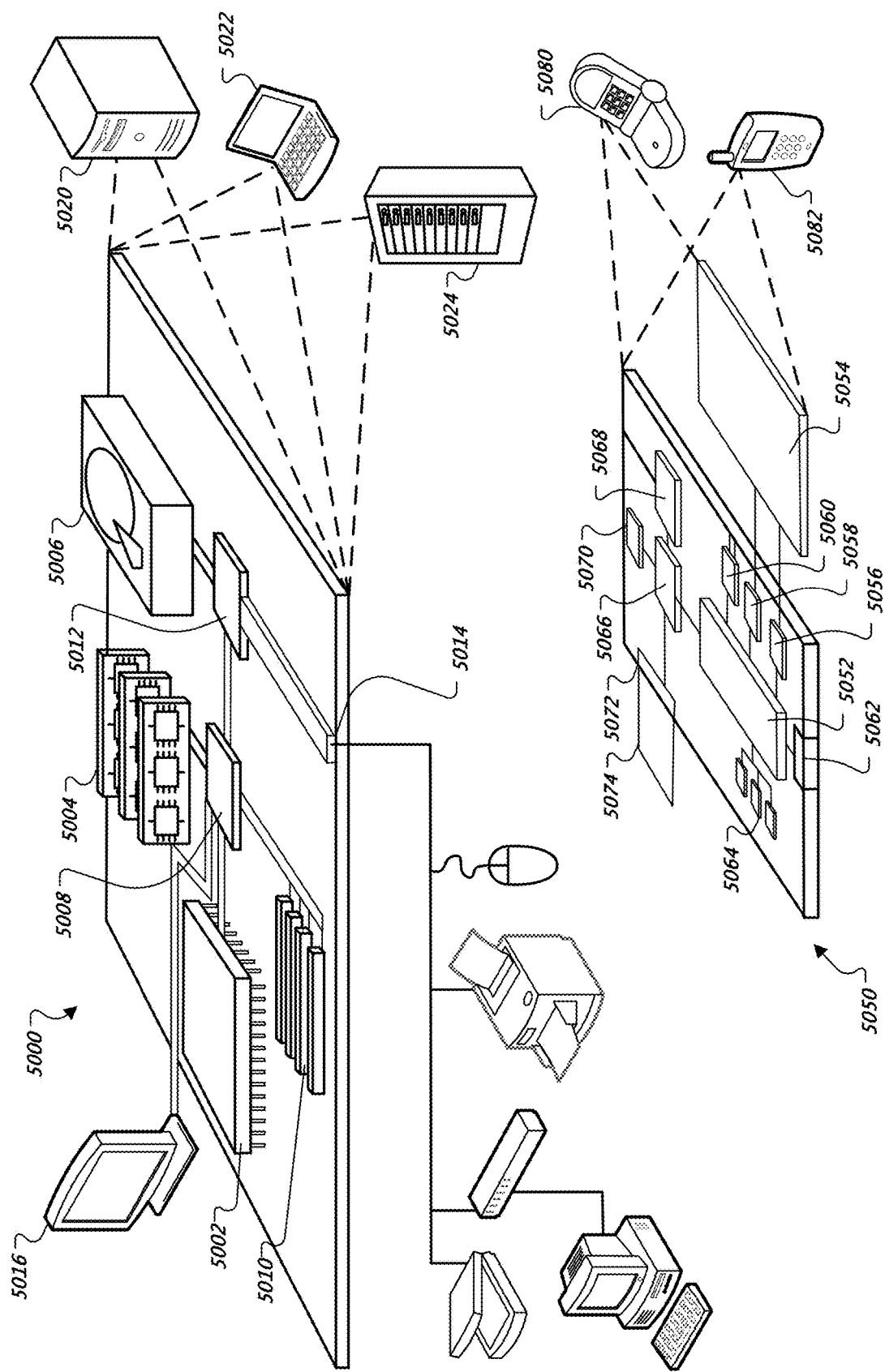
FIG. 84 is a block diagram of computing devices that may be used to implement the systems and methods described in this document, as either a client or as a server or plurality of servers.

FIG. 84 is a block diagram of computing devices 5000, 5050 that may be used to implement the devices, systems and methods described in this document, as either a client or as a server or plurality of servers. Computing device 5000 is intended to represent various forms of digital computers, such as laptops, desktops, workstations, personal digital assistants, servers, blade servers, mainframes, and other appropriate computers. Computing device 5050 is intended to represent various forms of mobile devices, such as personal digital assistants, cellular telephones, smartphones, and other similar computing devices. The components shown here, their connections and relationships, and their functions, are meant to be examples only, and are not meant to limit implementations described and/or claimed in this document. One or more components described in this Figure can be used to implement the systems, devices, elements, components, controllers, parts, objects, etc. that are described herein.

Computing device 5000 includes a processor 5002, memory 5004, a storage device 5006, a high-speed interface 5008 connecting to memory 5004 and high-speed expansion ports 5010, and a low speed interface 5012 connecting to low speed bus 5014 and storage device 5006. Each of the components 5002, 5004, 5006, 5008, 5010, and 5012, are interconnected using various busses, and may be mounted on a common motherboard or in other manners as appropriate. The processor 5002 can process instructions for execution within the computing device 5000, including instructions stored in the memory 5004 or on the storage device 5006 to display graphical information for a GUI on an external input/output device, such as display 5016 coupled to high-speed interface 5008. In other implementations, multiple processors and/or multiple buses may be used, as appropriate, along with multiple memories and types of memory. Also, multiple computing devices 5000 may be connected, with each device providing portions of the necessary operations (e.g., as a server bank, a group of blade servers, or a multi-processor system).

The memory 5004 stores information within the computing device 5000. In one implementation, the memory 5004 is a volatile memory unit or units. In another implementation, the memory 5004 is a non-volatile memory unit or units. The memory 5004 may also be another form of computer-readable medium, such as a magnetic or optical disk.

The storage device 5006 is capable of providing mass storage for the computing device 5000. In one implementation, the storage device 5006 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 5004, the storage device 5006, or memory on processor 5002.

The high-speed controller 5008 manages bandwidth-intensive operations for the computing device 5000, while the low speed controller 5012 manages lower bandwidth-intensive operations. Such allocation of functions is an example only. In one implementation, the high-speed controller 5008 is coupled to memory 5004, display 5016 (e.g., through a graphics processor or accelerator), and to high-speed expansion ports 5010, which may accept various expansion cards (not shown). In the implementation, low-speed controller 5012 is coupled to storage device 5006 and low-speed expansion port 5014. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 5000 may be implemented in a number of different forms, as shown in the figure. For example, it may be implemented as a standard server 5020, or multiple times in a group of such servers. It may also be implemented as part of a rack server system 5024. In addition, it may be implemented in a personal computer such as a laptop computer 5022. Alternatively, components from computing device 5000 may be combined with other components in a mobile device (not shown), such as device 5050. Each of such devices may contain one or more of computing device 5000, 5050, and an entire system may be made up of multiple computing devices 5000, 5050 communicating with each other.

Computing device 5050 includes a processor 5052, memory 5064, an input/output device such as a display 5054, a communication interface 5066, and a transceiver 5068, among other components. The device 5050 may also be provided with a storage device, such as a microdrive or other device, to provide additional storage. Each of the components 5050, 5052, 5064, 5054, 5066, and 5068, are interconnected using various buses, and several of the components may be mounted on a common motherboard or in other manners as appropriate.

The processor 5052 can execute instructions within the computing device 5050, including instructions stored in the memory 5064. The processor may be implemented as a chipset of chips that include separate and multiple analog and digital processors. Additionally, the processor may be implemented using any of a number of architectures. For example, the processor may be a CISC (Complex Instruction Set Computers) processor, a RISC (Reduced Instruction Set Computer) processor, or a MISC (Minimal Instruction Set Computer) processor. The processor may provide, for example, for coordination of the other components of the device 5050, such as control of user interfaces, applications run by device 5050, and wireless communication by device 5050.

Processor 5052 may communicate with a user through control interface 5058 and display interface 5056 coupled to a display 5054. The display 5054 may be, for example, a TFT (Thin-Film-Transistor Liquid Crystal Display) display or an OLED (Organic Light Emitting Diode) display, or other appropriate display technology. The display interface 5056 may comprise appropriate circuitry for driving the display 5054 to present graphical and other information to a user. The control interface 5058 may receive commands from a user and convert them for submission to the processor 5052. In addition, an external interface 5062 may be provide in communication with processor 5052, so as to enable near area communication of device 5050 with other devices. External interface 5062 may provided, for example, for wired communication in some implementations, or for wireless communication in other implementations, and multiple interfaces may also be used.

The memory 5064 stores information within the computing device 5050. The memory 5064 can be implemented as one or more of a computer-readable medium or media, a volatile memory unit or units, or a non-volatile memory unit or units. Expansion memory 5074 may also be provided and connected to device 5050 through expansion interface 5072, which may include, for example, a SIMM (Single In Line Memory Module) card interface. Such expansion memory 5074 may provide extra storage space for device 5050, or may also store applications or other information for device 5050. Specifically, expansion memory 5074 may include instructions to carry out or supplement the processes described above, and may include secure information also.

Thus, for example, expansion memory 5074 may be provide as a security module for device 5050, and may be programmed with instructions that permit secure use of device 5050. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 5064, expansion memory 5074, or memory on processor 5052 that may be received, for example, over transceiver 5068 or external interface 5062.

Device 5050 may communicate wirelessly through communication interface 5066, which may include digital signal processing circuitry where necessary. Communication interface 5066 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 5068. In addition, short-range communication may occur, such as using a Bluetooth, WiFi, or other such transceiver (not shown). In addition, GPS (Global Positioning System) receiver module 5070 may provide additional navigation- and location-related wireless data to device 5050, which may be used as appropriate by applications running on device 5050.

Device 5050 may also communicate audibly using audio codec 5060, which may receive spoken information from a user and convert it to usable digital information. Audio codec 5060 may likewise generate audible sound for a user, such as through a speaker, e.g., in a handset of device 5050. Such sound may include sound from voice telephone calls, may include recorded sound (e.g., voice messages, music files, etc.) and may also include sound generated by applications operating on device 5050.

The computing device 5050 may be implemented in a number of different forms, as shown in the figure. For example, it may be implemented as a cellular telephone 5080. It may also be implemented as part of a smartphone 5082, personal digital assistant, or other similar mobile device.

Additionally computing device 5000 or 5050 can include Universal Serial Bus (USB) flash drives. The USB flash drives may store operating systems and other applications. The USB flash drives can include input/output components, such as a wireless transmitter or USB connector that may be inserted into a USB port of another computing device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system can include clients and servers. A client and server are generally remote from each other and typically interact through a communication network. The relationship of client and server arises by virtue of computer programs running on the respective computers and having a client-server relationship to each other.

As described herein, the embodiments described in the present disclosure can include one or more of the following features.

An example robotic surgical system can include one or more surgical robots with multiple arms which can navigate 3-Dimensional space; and one or more real-time image devices to provide real-time visual monitoring of the one or more surgical robots.

In the system described herein, the one or more robots are configured to provide totally autonomous robotic surgery (TARS).

An example robotic surgical system can include one or more autonomously movable operating room tables to selectively position a patient's body and or limbs.

The system described herein can further include one or more surgical robots with multiple arms which can navigate 3-Dimensional space to operate on the patient.

The system described herein can further include one or more real-time image devices to provide real-time visual monitoring of the one or more surgical robots.

In the system described herein, the one or more robots are configured to provide totally autonomous robotic surgery (TARS).

The system described herein can further include one or more self-driving gurneys to provide transport for the patient.

The system described herein can further include one or more carriages coupled to driverless autonomous self-driving vehicles to provide transport for the patient.

The system described herein can further include one or more person rescue drones for transportation and delivery to a health care facility.

An example robotic surgical system can include one or more person rescue drones configured to engage in multiple autonomous movements proximate to a targeted person.

An example totally autonomous robotic surgery (TARS) system can be integrated with autonomous-assisted intraoperative real-time single modality and/or multi-modality fusion imaging. The system can further be integrated with autonomous-assisted intraoperative body/limb positioning, and integrated with autonomous-assisted land and unmanned aerial vehicular patient/equipment/supply transport systems.

An example totally autonomous robotic surgery (TARS) system can include Integrated Delta Robots and C-arms.

An example totally autonomous robotic surgery (TARS) system can include Mobile Robotic Doctor (MRD).

An example totally autonomous robotic surgery (TARS) system can include Robotic articulated linkage arms Array (RALAA).

An example totally autonomous robotic surgery (TARS) system can include cylinder arms.

An example totally autonomous robotic surgery (TARS) system can include truss arms truss-arms.

An example totally autonomous robotic surgery (TARS) system can be configured for system modularity and patient intake.

An example totally autonomous robotic surgery (TARS) system can include patient carts that can be automatically driven either independently or with a mobile table mover.

An example totally autonomous robotic surgery (TARS) system can include robotic accordion arm (RAA) instruments.

An example cooperative totally autonomous robotic surgery (TARS) method can include using a Mobile Robotic Doctor (MRD) and robotic accordion arm (RAA) instruments to perform different phases of an operative preparation and procedure.

An example totally autonomous robotic surgery (TARS) system can include a Gimble-Telescoping arm (GTA).

An example cooperative totally autonomous robotic surgery (TARS) method can include using a Gimble-Telescoping arm (GTA) with robotic accordion arm (RAA) instruments.

An example totally autonomous robotic surgery (TARS) system can include autonomous limb positioner (ALP) embodiment that can work synergistically with any of the TARS embodiments.

An example totally autonomous robotic surgery (TARS) system can include autonomous limb positioner (ALP) embodiment utilizing voxelated sensor/actuator components.

An example totally autonomous robotic surgery (TARS) system can include Multi-Functional Compaction Arch (MFCA) that includes a Foldable/Compactable Combination Actuation/Manipulation Device.

An example method can include a MFCA autonomously positioning itself over a patient.

An example totally autonomous robotic surgery (TARS) system can include Self-Organizing Modular Robot (SOMR) with ARUs and DBJs.

An example totally autonomous robotic surgery (TARS) system can include a T-jointed version of an ARU.

An example totally autonomous robotic surgery (TARS) system can include wing-shaped ARUs to assist in non-ground locomotion or other propulsive mechanisms.

An example totally autonomous robotic surgery (TARS) system can include different configurations of ARUs in re-configurable states of: arachnid, humanoid, and praying mantis.

An example totally autonomous robotic surgery (TARS) system can include modular robotic systems self-aggregation and learning system.

An example totally autonomous robotic surgery (TARS) system can include artificial Intelligent (AI) system for diagnosis and surgical procedure.

An example totally autonomous robotic surgery (TARS) system can include AI Robotic based diagnosis.

An example totally autonomous robotic surgery (TARS) system can include an AI/Robotic algorithm.

An example totally autonomous robotic surgery (TARS) method can include an artificial intelligence (AI) robotic instrument interacting with a human.

An example totally autonomous robotic surgery (TARS) system can include a communication structure over distances.

An example totally autonomous robotic surgery (TARS) system can include an Automated Patient Delivery System (APDS) utilizing a transport carriage.

An example totally autonomous robotic surgery (TARS) system can include drones within a hospital setting to, optionally, aerially deliver patients and or equipment to hospitals for treatment and surgery.

An example medical delivery system can include a free-travelling drone latching on to guidance rails.

An example medical delivery method can include a drone autonomously transferring from its safer travel lanes to the people.

An example robotic surgical method can include disabling a set of robotic devices when an MRI system is activated.

An example medical delivery method within a hospital corridor, comprising: utilizing multi-purpose guidance rails that are above the general human height level.

An example Hybrid Drone Electromagnetic Guidance Rail/Propulsion System can be integrated into a hospital corridor.

The system described herein can include a Hybrid Drone Guidance and self-propulsion system.

The system described herein can include an indoor-rail-based drone system as used in a hospital.

The system described herein can include one or more drones with rail guidance and bypass capacities with separate rails, either physical or virtual (markers, electronic elements such as magnets, lasers etc.).

The system described herein can include a drone capable of entering a room, traversing the U-shaped rail to access individual patient or doctor necessities on both sides of the room.

The system described herein can include a mechanism/operation of drones choosing a room bypass track.

The system described herein can include drone claspers reorienting to follow the opposing non-bypass route and enter the patient room.

An example medical delivery method within a hospital corridor can include ACU to ACU handoff of cargo.

An example medical delivery system can include granulated magnetic wallpaper for guiding drones along path in a medical environment without necessity for rail-guidance.

The system described herein can include an aerial "vertical" carrier drone which can pick up or mate with smaller child/satellite drones with the help of its mating slot that can additionally function as a charging/communication mechanism.

The system described herein can include aerial drone carrier embodiment with various propulsion devices fixed to carrier to propel the carrier.

The system described herein can include a larger "carrier" (mother) drone that houses three "satellite" (child) drones.

The system described herein can provide the ability to integrate MRIs with other electronic devices enabling co-usage of magnetic instrumentation with other surgical tools in every TARS embodiment presented.

The system described herein can include an unfoldable endoscopic screen (UES).

The system described herein can include modular robotic self-aggregation and learning systems.

The system described herein can include a manual (portable) drone carrier embodiment.

The system described herein can include a drone with foldable wings.

The system described herein can include a foldable wing on a drone.

The system described herein can include drone vehicles with "nestled" wings that can be compacted to above or below the vehicle body.

The system described herein can include a drone aircraft with deformable wings.

The system described herein can include a small vehicle drone with an expandable low-cost glider.

The system described herein can include a pole/wire guided drone.

The system described herein can include a land ambulette vehicle that can be used in tandem style as well (i.e. train).

The system described herein can include a hybrid flight/train vehicle that can be assisted by tubular propulsion.

The system described herein can include a combined land-air vehicle (drone).

The system described herein can include a winged drone with extendable arms engaging in person rescue (minimal arm extension)

The system described herein can include a winged drone with extendable arms engaging in person rescue (maximal arm extension).

The system described herein can include a winged drone with extendable arms engaging in person rescue (maximal arm extension) contacting refugee under his/her arms.

The system described herein can include a winged drone with back/seat support engaging person rescue.

The system described herein can include a winged drone using robotic flexible buoy engaging in patient rescue.

The system described herein can include a robotic flexible buoy with back support mechanisms.

The system described herein can include a standing personal conveyer drone.

The system described herein can include an electromechanical gimbal drone that can be used either/or steering/navigation and contact/strap with passenger.

The system described herein can include an assisted/catapult vertical drone launch with multiple stages that are returnable.

The system described herein can include a vertical or horizontal drone launcher with fixed stages acting as catapult to projectile.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A robotic surgical system comprising:
one or more surgical robots including a first surgical robot and a second surgical robot;
a plurality of arms movably coupled to the one or more surgical robots and configured to navigate three dimensional space, the plurality of arms including (i) a first C-arm coupled to the first surgical robot and (ii) a second C-arm that is coupled to the second surgical robot and is independently movable from the first C-arm, the first C-arm being configured to move within a first surgical area relative to a patient, and the second C-arm being configured to move within a second surgical area relative to the patient that does not overlap with the first surgical area; and
one or more real-time imaging devices disposed in one or more of the plurality of arms and configured to provide real-time visual monitoring of the one or more surgical robots,
wherein the one or more surgical robots includes:
a top portion operatively coupled to at least one of the plurality of arms to allow the one or more surgical robots to move relative to the at least one of the plurality of arms,
a bottom portion configured to attach a surgical instrument,
a plurality of upper linkages having first upper ends and second upper ends opposite to the first upper ends, the first upper ends being pivotably coupled to the top portion,
a plurality of lower linkages having first lower ends and second lower ends opposite to the first lower ends, the second lower ends being pivotably coupled to the bottom portion, and
one or more sensors including one or more visual monitoring sensors that are embedded in the plurality of upper linkages and the plurality of lower linkages,
wherein the second upper ends of the plurality of upper linkages are pivotably coupled to the first lower ends of the plurality of lower linkages, respectively, between the top portion and the bottom portion, and
wherein the one or more surgical robots are configured to:
receive image data from the one or more real-time imaging devices, the image data produced from the real-time visual monitoring;
determine a first position of the one or more surgical robots relative to a patient; and
autonomously adjust a position of the surgical instrument relative to the patient by automatically moving to a second position relative to an arm of the plurality of arms, the automatically moving to the second position being based at least in part on the received image data,
wherein receiving the image data, determining the first position, and the autonomously adjusting the position of the surgical instrument are performed for the first and second surgical robots, independently.

2. The system of claim 1, wherein the one or more surgical robots are configured to be autonomously operated.

3. The system of claim 1, wherein the one or more surgical robots are configured to provide autonomous robotic surgery.

4. The system of claim 1, wherein the one or more surgical robots comprise integrated delta robots.

5. The system of claim 1, wherein the plurality of arms comprises C-arms.

6. The system of claim 1, wherein the one or more surgical robots include a base being autonomously movable and configured to operatively couple to the plurality of arms, the plurality of arms being coupled in humanoid form and including autonomous elements.

7. The system of claim 1, further comprising:
an autonomous limb positioner (ALP) including a robotic arm with a planar kinematic chain with linkages and configured to position an involuntary patient or limbs.

8. The system of claim 1, further comprising:
a plurality of autonomous robotic units (ARUs), each including a body and electronics contained in the body and configured to perform desired functionality; and
one or more double ball joints (DBJs), each configured to movably interlock with an end of one ARU and an end of another ARU.

9. The system of claim 1, further comprising:
one or more operating room tables configured to be autonomously movable and selectively position a patient's body or limbs thereon.

10. The system of claim 1, further comprising:
one or more self-driving gurneys to provide transport for the patient.

11. The system of claim 1, and further comprising one or more controllers configured to receive the image data from the one or more real-time imaging devices in real-time, and to continually adjust a position of the one or more surgical robots based on the image data received in real-time.

12. The system of claim 1, and further comprising one or more controllers configured to determine the first position of the one or more surgical robots based at least in part on data received from the one or more sensors.

13. The system of claim 12, wherein the one or more controllers are configured to control movement of the one or more surgical robots using a closed control loop.

14. The system of claim 13, wherein the one or more controllers are configured to control movement of the one or more surgical robots based at least in part on one or more user inputs.

15. The system of claim 1, wherein automatically moving relative to the arm of the plurality of arms to a second position further comprises dynamically repositioning the one or more surgical robots relative to the patient.

16. The system of claim 15, wherein the arm of the plurality of arms is a C-arm, and wherein automatically moving relative to the arm comprises moving along a track in the C-arm.

17. The system of claim 1, wherein the bottom portion of the one or more surgical robots is configured to be attached to a surgical instrument comprising one of an imager, a therapeutic radiation tool and an ultrasound tool.

18. The system of claim 1, wherein the bottom portion of the one or more surgical robots is configured to be attached to a surgical instrument comprising one of a clamp, an occlude, a needle driver, a retractor, a distractor, or a mechanical cutting tool.

19. The system of claim 1, wherein a surgical instrument of the first surgical robot is different from a surgical instrument of the second surgical robot.

20. The system of claim 1, wherein autonomously adjusting the position of the surgical instrument for the first surgical robot is not based on receiving the image data and determining the first position for the second surgical robot.

* * * * *